United States Patent
Kotula et al.

(10) Patent No.: US 10,907,221 B2
(45) Date of Patent: *Feb. 2, 2021

(54) ENGINEERED GENETIC ENTERIC SENSOR BACTERIA AND USES THEREOF

(71) Applicant: PRESIDENT AND FELLOWS OF HARVARD COLLEGE, Cambridge, MA (US)

(72) Inventors: Jonathan Kotula, Somerville, MA (US); Scott Jordan Kerns, West Roxbury, MA (US); Jeffrey Charles Way, Cambridge, MA (US); Pamela A. Silver, Cambridge, MA (US); Lev Shaket, Orange Park, FL (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 290 days.

This patent is subject to a terminal disclaimer.

(21) Appl. No.: 16/000,185

(22) Filed: Jun. 5, 2018

(65) Prior Publication Data

US 2019/0024192 A1    Jan. 24, 2019

Related U.S. Application Data

(63) Continuation of application No. 15/103,372, filed as application No. PCT/US2014/071672 on Dec. 19, 2014, now Pat. No. 10,047,405.

(60) Provisional application No. 61/919,257, filed on Dec. 20, 2013.

(51) Int. Cl.
*C12Q 1/6897* (2018.01)
*C12N 15/73* (2006.01)

(52) U.S. Cl.
CPC ........... *C12Q 1/6897* (2013.01); *C12N 15/73* (2013.01)

(58) Field of Classification Search
None
See application file for complete search history.

(56) References Cited

U.S. PATENT DOCUMENTS

| 10,047,405 B2 * | 8/2018 | Kotula .................. C12N 15/73 |
| 2003/0049799 A1 | 3/2003 | Schwartz et al. |
| 2003/0166191 A1 | 9/2003 | Gardner et al. |
| 2012/0321718 A1 | 12/2012 | Manzo et al. |

FOREIGN PATENT DOCUMENTS

| WO | 2006079790 A2 | 8/2006 |
| WO | 2009126719 A2 | 10/2009 |
| WO | 2011066541 A2 | 6/2011 |

OTHER PUBLICATIONS

Gardner et al., "Construction of a genetic toggle switch in *Escherichia coli*", Nature, 403(6767):339-42 (2000).
Hasty et al. :Engineered gene circuits Nature 420:224-230 (2002).
Kotula et al., "Programmable bacteria detect and record an environmental signal in the mammalian gut," PNAS USA, 111(13):4838-43 (2014).
Schubert et al., "Role in the Cl-Cro bistable switch is critical for lambda's transition from lysogeny to lytic development," Genes Dev., 21(19):2461-2472 (2007).
Zabeau et al., "Enhanced expression of cro-beta-galactosidase fusion proteins under the control of the PR promoter of baceteriophase lamda," EMBO J, 1(10):1217-24 (1982).

* cited by examiner

*Primary Examiner* — Nancy J Leith
(74) *Attorney, Agent, or Firm* — Nixon Peabody LLP

(57) ABSTRACT

The disclosure relates to genetic engineered bacteria having a genetic memory circuit, compositions thereof, formulations thereof, methods of analyses and method of treatment of conditions related to the gastrointestinal tract including the mouth and the stomach.

10 Claims, 109 Drawing Sheets

Specification includes a Sequence Listing.

FIG. 1A
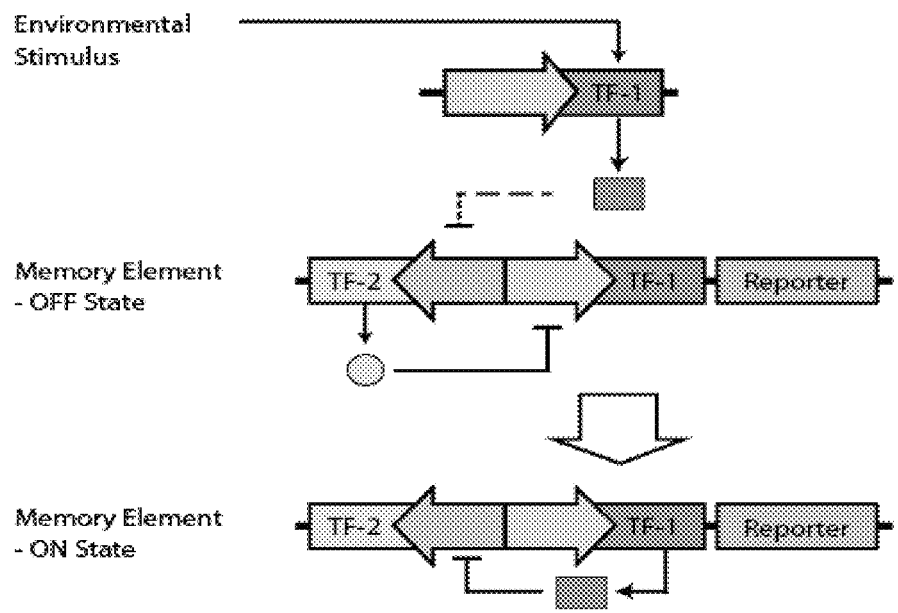
FIG. 1B
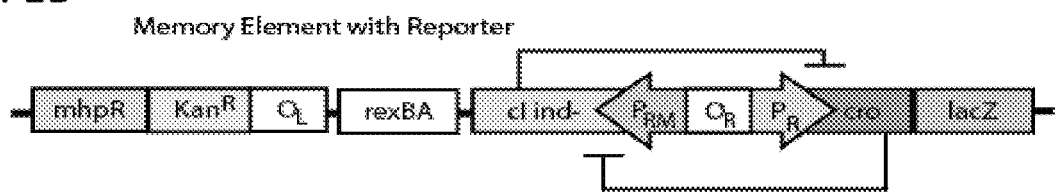
FIG. 1C
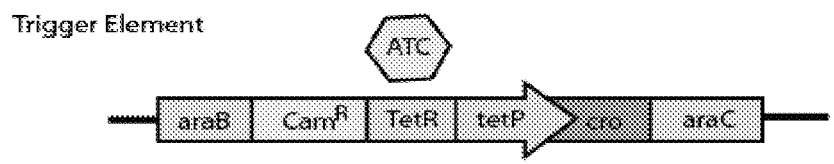
FIG. 1D

```
   gttagcctcccgccccggtgatgactatcaactggcacggaaccgttaaagctgg aagccattctggcg
   ----+----|----+----|----+----|----+----|----+----|----+----|----+----|    70
                                     mhpR cgcgcgcgcaaagagggttacggacagaactaccggctgggatcaggaggagaa gatcgcctctatcg
   ----+----|----+----|----+----|----+----|----+----|----+----|----+----|   140
                                     mhpR ccgtaccgctgcgcagtgaacaacgggtgattggctgtctgaatctggtgtgta tggcgagcgcaatgac
   ----+----|----+----|----+----|----+----|----+----|----+----|----+----|   210
                                     mhpR cattgaacaggcagcggaaaagcatctccggcgctacaacgggtagcaaacaga tcgaagaagggtt
   ----+----|----+----|----+----|----+----|----+----|----+----|----+----|   280
                                     mhpR gaatcgcaggctattctggtggccgaaggcgaagcggcatgcattacgttgaca ccatcgttagaaga
   ----+----|----+----|----+----|----+----|----+----|----+----|----+----|   350
                     mhpR                                    Kanam..ette actcgtcaagaaggcgatagaaggcgatgcgctgcgaatcggagcggcgataccgtaaagcacgaggaa
   ----+----|----+----|----+----|----+----|----+----|----+----|----+----|   420
                             Kanamycin Resistance Cassette
```

Figure 6A

```
5' gcggtcagccattcgccggccaagctcttcagcaatatcacgggtagccaacgctatgtcctgatagcgg 490
     Kanamycin Resistance Cassette 5' tccgccacaccagccggccacagtcgatgaatccagaaaagcggccattttccaccatgatattcggca 560
     Kanamycin Resistance Cassette 5' agcaggcatcgccatgggtcacgacgagatcctcgccgtcgggcatgcgcgccttgagcctggcgaacag 630
     Kanamycin Resistance Cassette 5' ttcggctggcgcgagcccctgatgctcttcgtccagatcatcctgatcgacaagaccggcttccatccga 700
     Kanamycin Resistance Cassette 5' gtacgtgctcgctcgatgcgatgtttcgcttggtggtcgaatgggcaggtagccggatcaagcgtatgca 770
     Kanamycin Resistance Cassette 5' gccgccgcattgcatcagccatgatggatactttctcggcaggagcaaggtgagatgacaggagatcctg 840
     Kanamycin Resistance Cassette
```

Figure 6A (cont.)

```
cccggcacttcgcccaatagcagccagtccttcccgcttcagtgacaacgtcgagcacagtgcgcaa    910
                         Kanamycin Resistance Cassette ggaacgcccgtcgtggccagccacgatagccgcgctgcctcgtcctgcagttcattcagggcaccggaca    980
                         Kanamycin Resistance Cassette ggtcggtcttgacaaaagaaccgggcgcccctgcgctgacagccggaacacggcggcatcagagcagcc   1050
                         Kanamycin Resistance Cassette gattgtcgttgtgcccagtcatagccgaatagcctctccacccaagcggccggagaacctgcgtgcaat   1120
                         Kanamycin Resistance Cassette ccatcttgttcaatcatgcgaaacgatcctcatcctgtctcttgatcagatcttgatccctgcgccatc   1190
                         Kanamycin Resistance Cassette agatccttggcggcaagaaagccatccagtttactttgcagggcttcccaaccttaccagagggcgccc   1260
                         Kanamycin Resistance Cassette
```

Figure 6A (cont.)

```
    agctggcaattccggttcgcttgctgtcctgcatagtggtcagtgcctgctgatgtgctcagtatcaccg
 50 +---------+---------+---------+---------+---------+---------+---------+ 1330
                                                                    <──OL── ccagtggtatttatgtcaacacacgccagagataattatcaccgcagatggttatctgtatgttttttat
 50 +---------+---------+---------+---------+---------+---------+---------+ 1400
         Kanamycin Resistance Cassette              ┌─────OL─────┐ atgaatttattttttgcaggggggcattgtttggtaggtgagagatctgaattgctatgtttagtgagtt
 50 +---------+---------+---------+---------+---------+---------+---------+ 1470 gtatctattattttcaataatacaattggttatgtgttttgggggcgatcgtgaggcaaagaaaacc
 50 +---------+---------+---------+---------+---------+---------+---------+ 1540 cggcgctgaggccgggttattctctgttctctcttggtcaaattatatagttggaaacaaggatgcatatatg
 50 +---------+---------+---------+---------+---------+---------+---------+ 1610 aatgaacgatgcagaggcaatgccgatagtgggtatcatgtagccgcttatgctgaaagaagc
 50 +---------+---------+---------+---------+---------+---------+---------+ 1680 aataaccgcagaaaacaaagctccaagctcaacaaactaaggcatagacaataactaccgatgtca
 50 +---------+---------+---------+---------+---------+---------+---------+ 1750 tataccatactctctaatcttggccagtcggcgcgttctgcttccgattagaaacgtcaaggcagcaat
 50 +---------+---------+---------+---------+---------+---------+---------+ 1820
```

Figure 6A (cont.)

```
caggattgcaatcatgttcctgtcatatgatgacaatgtcgcccaagaccatctctatgagctgaaaaa  1890
gaaacaccaggaatgtagtggcggaaaaggagatagcaaatgcttacgataacgtaaggaattattacta  1960
tgtaaacaccaggcatgattctgttccgcataattactcctgataattaatcctaacttttgcccacctg  2030
cctttaaaacattccagtatatcactttccattcttgcgtagcaatatgccatctcttcagctatctca  2100
gcattggtgaccttgttcagaggcgctgagatggcctttttctgatagataatgtctgttaaaatat    2170
ctccggcctcatctttgcccgcaggctaatgtctgaaaattgaggtgacgggttaaaaataatatccct  2240
ggcaacctttttatatccctttaaatttggcttaatgactatatccaatgagtcaaaaagctcccct   2310
tcaatatctgttgccctaagactttaatatatcgccaaatacaggtagcttggcttctaccttcaccg   2380
ttgttcggccgatgaaatgcataacatcgtctttggtggttccctcatcagtggctctatctg       2450
```

Figure 6A (cont.)

```
aacgcgctctccactgcttaatgacattcctttcccgattaaaaatctgtcagatcgatgtggtcggc   2520
ccgaaaacagttctggcaaaaccaatggtgtcgcttcaacaacaaaaagatgggaatcccaatgatt    2590
cgtcatctgcgagctgtttcttaatatcttcaactgaagctttagagcgattatctttctgaccagact 2660
cttgtcattgtttttggtaaagagaaaagtttttccatcgattttatgaatatacaaataattggagcca 2730
acctgcaggtgatgattatcagccagcagagaattaaggaaaacagacaggtttattgagcgcttatctt 2800
tcccttatttttgctgcggtaagtcgcataaaaaccattcttcataattcgatgaagataatcatatgttat 2870
gttctgaggggagtgaaaattcccctaattcgatgaagattcttgctcaattgttatcagctatgccgcg  2940
accagaacaccttgccgatcagccactgactagcgataactttcccacaacg                   3010
                                                              <---cI857
```

Figure 6A (cont.)

```
gaacaactctcattgcatggatcattgggtactgtggttgtaaaacacctgaccgctat   3080
                              cI857 ccctgatcagtttcttgaaggtaaactcatcaccccaagtctgctatgcagaaatcacctggctcaac   3150
                              cI857 agcctgctgtcaagggtcaacgagaattaacattccgtcaggaaagcttggcttggagcctgttggtgcggtc   3220
                              cI857 atggaattaccttcaacctcaagccagaatgcagaatcactggcttttttggttgtgtgcttaccatctct   3290
                              cI857 ccgcatcaccttttggtaaaggttctaagcttagtgagaacatccctgcctgaacatgagaaaaacagg   3360
                              cI857 gtactcatactcacttctaagtgacggctgcatactaaccgcttcatacatctcgtagatttctgtggcg   3430
                              cI857
```

Figure 6A (cont.)

```
5'  gggaaaacctggcgttaccccaacttaatcgccttgcagcacatccccctttcgccagctggcgtaatag  4200
         |----+----|----+----|----+----|----+----|----+----|----+----|----+----|
                                   lacZ 5'  cgaagaggcccgcaccgatcgcccttcccaacagttgcgcagcctgaatggcgaatggcgctttgcctgg  4270
         |----+----|----+----|----+----|----+----|----+----|----+----|----+----|
                                   lacZ 5'  tttccggcaccagaagcggtgccggaaagctggctggagtgcgatcttcctgaggccgatactgtcgtcg  4340
         |----+----|----+----|----+----|----+----|----+----|----+----|----+----|
                                   lacZ 5'  tcccctcaaactggcagatgcacggttacgatgcgcccatctacaccaacgtgacctatcccattacggt  4410
         |----+----|----+----|----+----|----+----|----+----|----+----|----+----|
                                   lacZ 5'  caatccgccg  4420
         |----+
          lacZ ⇒
```

Figure 6A (cont.)

```
gttagcctcccgccccggtgatgactatcaactggcacggaaccgttaaagctggaagccattctggcg    70
                                    mhpR cgcgcgcgcaaagagggttacggacagaactaccggctgggatcaggaggagaagatcgcctctatcg   140
                                    mhpR ccgtaccgctgcgcagtgaacaacgggtgattggctgtctgaatctggtgtatgcgagcgcaatgac   210
                                    mhpR cattgaacaggcaggaaaagcatcttccggcgctacaacgggtagcaaacagatcgaagaagggtt    280
                                    mhpR gaatcgcaggctattctggtggccgaaggcgaagcggcattgcattacgttgacaccatcgttagaaga  350
                                    mhpR                    Kanam...ette
                                                              ⇑ actcgtcaagaaggcgatagaaggcgctgcgaatcggagcggcgataccgtaaagcacgaggaa       420
                              Kanamycin Resistance Cassette
```

Figure 6B

```
5'  gcggtcagccattcgccgccaagctcttcagcaatatcacgggtagccaacgctatgtcctgatagcgg  490
                        Kanamycin Resistance Cassette 5'  tccgccacacccagccggccacagtcgatgaatccagaaaagcggccattttccaccatgatattcggca  560
                        Kanamycin Resistance Cassette 5'  agcaggcatcgccatgggtcacgacgagatcctcgcgcgtcgggcatgcgcgccttgagcctggcgaacag  630
                        Kanamycin Resistance Cassette 5'  ttcggctggcgcgagccccctgatgctcttcgtccagatcatcctgatcgacaagaccggcttccatccga  700
                        Kanamycin Resistance Cassette 5'  gtacgtgctcgctcgatgcgatgtttcgcttggtggtcgaatgggcaggtagccggatcaagcgtatgca  770
                        Kanamycin Resistance Cassette 5'  gccgccgcattgcatcagccatgatggatactttctcggcaggagcaaggtgagatgacaggagatcctg  840
                        Kanamycin Resistance Cassette
```

Figure 6B (cont.)

```
5' cccgggcacttcgcccaatagcagccagtccccttcccgcttcagtgacaacgtcgagcacagctgcgcaa   910
   ――――――――――――――――――――――――――――――――――――――――
   Kanamycin Resistance Cassette 5' ggaacgcccgtcgtggccagccacgatagccgcgctgcctcgtcctgcagttcattcagggcaccggaca    980
   ――――――――――――――――――――――――――――――――――――――――
   Kanamycin Resistance Cassette 5' ggtcggtcttgacaaaaagaaccggcgccctgcgctgacagccggaacacggcggcatcagagcagcc     1050
   ――――――――――――――――――――――――――――――――――――――――
   Kanamycin Resistance Cassette 5' gattgtctgttgtgcccagtcatagccgaatagcctctccacccaagcggccggagaacctgcgtgcaat   1120
   ――――――――――――――――――――――――――――――――――――――――
   Kanamycin Resistance Cassette 5' ccatcttgttcaatcatgcgaaacgatcctcatcctgtctcttgatcagatcttgatccctgcgccatc   1190
   ――――――――――――――――――――――――――――――――――――――――
   Kanamycin Resistance Cassette 5' agatccttggcgggcaagaaagccatccagtttactttgcagggcttcccaaccttaccagagggcgcccc  1260
   ――――――――――――――――――――――――――――――――――――――――
   Kanamycin Resistance Cassette
```

Figure 6B (cont.)

```
agctggcaattccggttcgcttgctgtcgtcgtccatagtggtcagtgcgtcctgctgatgtgctcagtatcaccg    1330
                    ╔══════════════════════════════════
                    ║  Kanamycin Resistance Cassette
ccagtggtatttatgtcaacacaccgccagagataattatcaccgcagatggttatctgtatgtttttat    1400
     ┌─────────────────────────────
     │  OL
atgaatttattttttgcaggggggcattgtttggtaggtgagagatctgaattgctatgtttagtgagtt    1470
gtatctatttatttttcaataaatacaattggttatgtgtttggggcgatcgtgaggcaaagaaaacc    1540
cggcgctgaggccgggttattccttgttctctgttcctctggtcaaattatatagttggaaaacaaggatgcatatatg    1610
aatgaacgatgcagagaggcaatgccgatgcgatagtgggtatcatgtagccgcttatgctgaaagaagc    1680
aataaccgcagaaaaacaaagctccaagctcaacaaaactaagggcataagacaataactaccgatgtca    1750
tataccatactctctaatcttggccagtcggcgcgttcctgcttccgattagaaacgtcaaggcagcaat    1820
```

Figure 6B (cont.)

```
  5' caggattgcaatcatgttcctgcatatgatgacaatgtcgcccaagaccatctctatgagctgaaaaa 1890
  5' gaaacaccaggaatgtagtggcggaaaaggagatagcaaatgcttacgataacgtaaggaattactta 1960
  5' tgtaaacaccaggcatgattctgttccgcataattactcctgataattaatccttaactttgcccacctg 2030
  5' cctttaaaacattccagtatatcactttcattcttgcgtagcaatatgccatctcttcagctatctca 2100
  5' gcattggtgacttgttcagaggcgctgagagatggcctttttctgatagataatgttctgttaaaatat 2170
  5' ctccggcctcatctttgcccgcaggctaatgtctgaaaattgaggtgacgggttaaaaataatatccct 2240
  5' ggcaacctttttatatccctttaaattttggcttaatgactatatccaatgagtcaaaagctcccct 2310
  5' tcaatatctgttgccctaagacctttaatatatcgccaaatacaggtagcttggcttctaccttcaccg 2380
  5' ttgttcggccgatgaaatgcataacatcgtctttggtggttccctcatcagtggctctatctg 2450
```

Figure 6B (cont.)

```
     aacgcgctctccactgcttaatgacattccttcccgattaaaaatctgtcagatcggatgtggtcggc    2520
     ccgaaaacagttctggcaaaaccaatggtgtcgccttcaacaaacaaaagatgggaatcccaatgatt    2590
     cgtcatctgcgaggctgttcttaatatcttcaactgaagcttagagcgattatcttctgaaccagact    2660
     cttgtcattgtttggtaaagagaaaagttttccatcgatttatgaatatacaaataattggagcca    2730
     acctgcaggtgatgattatcagccagcagagaattaaggaaaacagacaggtttattgagcgcttatctt    2800
     tccctttattttgctgcggtaagtcgcataaaaccattcttcataattcattcattactatgttat    2870
     gttctgaggggagtgaaaattcccctaattcgatgaagattccttgctcaattgttatcagctatgccg    2940
     accagaacccttgccgatcagccaaacgtctcttcaggccactgactagcgataactttccccacaacg    3010
```

<--- ci+ ind-

Figure 6B (cont.)

```
5' gaacaactctcattgcatggatcattgggtactgtggttgtaaaaacacctgaccgctat   3080
   ------------------------------------------------------------
                            cI+ ind- 5' ccctgatcagtttcttgaaggtaaactcatcaccccaagtctgctatgcagaaatcacctgctcaac   3150
   -----------------------------------------------------------------
                            cI+ ind- 5' agcctgctcagggtcaacgagaattaacattccgtcaggaaagcttggcttggagcctgttggtgcggtc   3220
   ---------------------------------------------------------------------
                            cI+ ind- 5' atggaattaccttcaacctcaagccagaatgcagaatcactggctttttggttgtgcttaccatctct   3290
   --------------------------------------------------------------------
                            cI+ ind- 5' ccgcatcacctttggtaaaggttctaagcttagtgagaacatccctgcctgaacatgagaaaaacagg   3360
   -------------------------------------------------------------------
                            cI+ ind- 5' gtactcatactcacttctaagtgacggctgcatactaaccgcttcatacatctcgtagatttctggcg   3430
   -------------------------------------------------------------------
                            cI+ ind-
```

```
                                                                                        4270
5' cgaagaggcccgcaccgatgcgccttcccaacagttgcgcagcctgaatggcgaatggcgctttgcctgg
                                  ──────────────────lacZ──────────────────

4340
5' tttccggcaccagaaagcgggtgccggaaagtggctggagtgcgatcttcctgaggccgatactgtcg
                                  ──────────────────lacZ──────────────────

4410
5' tcccctcaaactggcagatgcacggttacgatgcgcccatctacaccaacgtgacctatcccattacggt
                                  ──────────────────lacZ──────────────────

4420
5' caatccgccg
   ═══▶ lacZ
```

Figure 6B (cont.)

```
      gttagcctcccgccccggtgatgactatcaactggcacggaaccgttaaagctggaagccattctggcg   70
                                        mhpR cgcgcgcaaagagggttacggacagaactaccggctgggatcaggaggagaagatcgcctctatcg     140
                                        mhpR ccgtaccgctgcgcagtgaacaacgggtgattggctgtctgaatctggtgtatggcgagcgcaatgac   210
                                        mhpR cattgaacaggcagcggaaaagcatcttccggcgctacaacgggtagcaaacagatcgaagaagggtt   280
                                        mhpR gaatcgcaggctattctggtggccggaaggcgaaggcgcatgcattacgttgacaccatcgttagaaga  350
                                        mhpR                    Kanam...ette actcgtcaagaaggcgataagaaggcgatgcgctgcgaatcgggagcggcgataccgtaaagcacgaggaa 420
                              Kanamycin Resistance Cassette
```

Figure 6C

```
gcggtcagccattcgccgccaagctcttcagcaatatcacgggtagccaacgctatgtcctgatagcgg   490
tccgccacacccagccggccacagtcgatgaatccagaaaagcggccattttccaccatgatattcggca  560
agcaggcatcgccatgggtcacgacgagatcctcgccgtcgggcatgcgcgccttgagcctggcgaacag  630
ttcggctggcgcgagcccctgatgctcttcgtccagatcatcctgatcgacaagaccggcttccatccga  700
gtacgtgctcgctcgatgcgatgtttcgcttggtggtcgaatgggcaggtagccggatcaagcgtatgca  770
gccgccgcattgcatcagccatgatggatactttctcggcaggagcaaggtgagatgacaggagatcctg  840
```

Figure 6C (cont.)

```
5'  cccggcacttcgcccaatagcagccagtcccttcccgcttcagtgacaacgtcgagcacagctgcgcaa  910
        ----+----+----+----+----+----+----+----+----+----+----+----+----+----
        ═══════════════════════════════════════════════════════════════════════
                                  Kanamycin Resistance Cassette 5'  ggaacgcccgtcgtggccagccacgatagccgcgctgcctcgtcctgcagttcattcagggcaccggaca  980
        ----+----+----+----+----+----+----+----+----+----+----+----+----+----
        ═══════════════════════════════════════════════════════════════════════
                                  Kanamycin Resistance Cassette 5'  ggtcggtcttgacaaaaagaaccgggcgcccctgcgctgacagccgaacacggcggcatcagagcagcc  1050
        ----+----+----+----+----+----+----+----+----+----+----+----+----+----
        ═══════════════════════════════════════════════════════════════════════
                                  Kanamycin Resistance Cassette 5'  gattgtctgtgtgccagtcatagccgaatagcctctccacccaagcggccggagaacctgcgtgcaat  1120
        ----+----+----+----+----+----+----+----+----+----+----+----+----+----
        ═══════════════════════════════════════════════════════════════════════
                                  Kanamycin Resistance Cassette 5'  ccatcttgttcaatcatgcgaaacgatcctcatcctgtctcttgatcagatcttgatccctgcgccatc  1190
        ----+----+----+----+----+----+----+----+----+----+----+----+----+----
        ═══════════════════════════════════════════════════════════════════════
                                  Kanamycin Resistance Cassette 5'  agatccttggcgggcaagaaagccatccagtttactttgcagggcttcccaaccttaccagagggcgccc  1260
        ----+----+----+----+----+----+----+----+----+----+----+----+----+----
        ═══════════════════════════════════════════════════════════════════════
                                  Kanamycin Resistance Cassette
```

Figure 6C (cont.)

```
                                                                                             1330
agctggcaattccggttcgcttgctgtcctgctgatgtgctcagtgtcaccg
                                                      ─────▷
                                                        OL
                                                                                             1400
ccagtggtatttatgtcaacaccgccagataattatcaccgcagatggttatctgtatgttttat
         ┌──────────────────────────┐
         │ Kanamycin Resistance Cassette │
         └──────────────────────────┘
                                                                                             1470
atgaatttattttttgcaggggggcattgtttggtaggtgagagatctgaattgctatgtttagtgagtt
 ┌────┐
 │ OL │
 └────┘
                                                                                             1540
gtatctatttttttcaataaatacaattggttatgtgtttgggggcgatcgtgaggcaaagaaaacc
                                                                                             1610
cggcgctgaggccggttattcttgtctctggtcaaattatatagttgaaaacaaggatgcatatatg
                                                                                             1680
aatgaacgatgcagaggcaatgccgatggcgatagtgggtatcatgtagccgcttatgctgaaagaagc
                                                                                             1750
aataacccgcagaaaacaaagtccaagctccaacaaactaaggcatagacaataactaccgatgtca
                                                                                             1820
tataccatactctctaatcttggccagtcggcgcgttcttccgattagaaacgtcaaggcagcaat
```

Figure 6C (cont.)

```
caggattgcaatcatgatgatgacaatgtcgcccaagaccatctctatgagctgaaaaa    1890
gaaacaccaggaatgtagtggcggaaaaggagatagcaaatgcttacgataacgtaaggaattacta  1960
tgtaaacaccaggcatgattctgttccgcataattactcctgataattaatccttaactttgcccacctg  2030
cctttaaaacattccagtatatcacttttcattcttgcgtagcaatatgccatctcttcagctatctca  2100
gcattggtgacttgttcagaggcgctgagagatggcctttttctgatagataatgttctgttaaaatat  2170
ctccggcctcatctttgcccgcaggctaatgtctgaaaattgaggtgacgggttaaaaataatatcctt  2240
ggcaacctttttatatccctttaaatttggcttaatgactatatccaatgagtcaaaagtcccct      2310
tcaatatctgttgccctaagacctttaatatatcgccaaatacaggtagcttggcttctacctttcaccg  2380
ttgttcggccgatgaaatgcataacatcgtctttggtggttcccctcatcagtggctctatctg       2450
```

Figure 6C (cont.)

```
aacgcgctctccactgcttaatgacattcctttcccgattaaaaatctgtcagatcgatgtggtcggc    2520
ccgaaaacagttctggcaaaaccaatggtgtcgccttcaacaacaaaaagatgggaatcccaatgatt    2590
cgtcatctgcgaggctgtcttcttaatatcttcaactgaagcttagagcgattatcttctgaccagact  2660
cttgtcattgtttggtaaagagaaaagtttttccatcgattttatgaatatacaaataattggagcca   2730
acctgcaggtgatgattcagccagcagagaattaaggaaaacagacaggtttattgagcgcttatctt   2800
tccctttattttgctgcggtaagtcgcataaaaccattcttcataattcattccattcattatgttat   2870
gttctgaggggagtgaaattcccctaattcgatgaagattcttgctcaattgttatcagctatgcgccg 2940
accagaacaccttgccgatcagccaaacgtctcttcaggccactgactagcgataactttccccacaacg 3010
                                                          <--------- cI857
```

Figure 6C (cont.)

```
gaacaactctcattgcatggatcattgggtactgtggttgtaaaacacctgaccgctat      3080
                                 c1857 cctgatcagtttcttgaaggtaaactcatcaccccaagtctgctatgcagaaatcacctgctcaac 3150
                                 c1857 agcctgctcagggtcaacgagaattaacattccgtcaggaaagcttggcttggagcctgttggtgcggtc 3220
                                 c1857 atgaattaccttcaacctcaagccagaatcactggctttttggttgtgtgcttaccatctct 3290
                                 c1857 ccgcatcacctttggtaaaggttctaagcttagtgagaacatccctgcctgaacatgagaaaaacagg 3360
                                 c1857 gtactcatactcacttctaagtgacggctgcatactaaccgcttcatacatctcgtagattctctggcg 3430
                                 c1857
```

```
5'  gttagcctcccgcccggtgatgactatcaactggcacggaaccgttaaagctggaagccattctggcg  70
            mhpR 5'  cgcgcgcgcaaagagggttacggacagaactaccggcgctgggatcaggaggagaagatcgcctatcg  140
            mhpR 5'  ccgtaccgctgcgcagtgaacaacgggtgattggctgtctgaatctggtgtatgcgagcgcaatgac  210
            mhpR 5'  cattgaacaggcaggaaaagcatcttccggcgctacaacgggtagcaaacagatcgaagaagggtt  280
            mhpR 5'  gaatcgcaggctattctggtggccggaaggcgaagcggcgaagcgcattgcattacgttgacaccatcgttagaaga  350
            mhpR                                                    Kan R...sette 5'  actcgtcaagaaggcgatagaaggcgatgcgctgcgaatcgggagcgcgatacggtaaagcacgagga  420
            Kan Resistance Cassette
```

Figure 6D

```
5'  gcggtcagccattcgccgccaagctcttcagcaatatcacgggtagccaacgctatgtcctgatatagcgg  490
                                    Kan Resistance Cassette 5'  tccgccacacccagccggccacagtcgatgaatccagaaaagcggccattttccaccatgatattcggca  560
                                    Kan Resistance Cassette 5'  agcaggcatcgccatgggtcacgacgagatcctcgcgtcgggcatgcgcgccttgagcctggcgaacag  630
                                    Kan Resistance Cassette 5'  ttcggctggcgcgagccccctgatgctcttcgtccagatcatcctgatcgacaagaccggcttccatccga  700
                                    Kan Resistance Cassette 5'  gtacgtgctcgctcgatgcgatgtttcgcttggtggtcgaatgggcaggtagccggatcaagcgtatgca  770
                                    Kan Resistance Cassette 5'  gccgccgcattgcatcagccatgatggatactttctcggcaggagcaaggtgagatgacaggagatcctg  840
                                    Kan Resistance Cassette
```

Figure 6D (cont.)

```
5'  cccgggcacttcgcccaatagcagccagtccctcccgcttcagtgacaacgtcgagcacagctgcgcaa     910
    ──────────────────────────────────────────────────────────────────────
                              Kan Resistance Cassette 5'  ggaacgcgccgtcgtggccagccacgatagccgcgctgcctcgtcctgcagttcattcagggcaccggaca   980
    ──────────────────────────────────────────────────────────────────────
                              Kan Resistance Cassette 5'  ggtcggtcttgacaaaaagaaccgggcgcccctgcgctgacagccggaacacggcggcatcagagcagcc    1050
    ──────────────────────────────────────────────────────────────────────
                              Kan Resistance Cassette 5'  gattgtctgttgtgcccagtcatagccgaatagcctctccaccaagcggccggagaacctgcgtgcaat    1120
    ──────────────────────────────────────────────────────────────────────
                              Kan Resistance Cassette 5'  ccatcttgttcaatcatgcgaaacgatcctcatcctgtctcttgatcagatcttgatccctgcgccatc    1190
    ──────────────────────────────────────────────────────────────────────
                              Kan Resistance Cassette 5'  agatcccttggcgggcaagaaagccatccagtttactttgcagggcttcccaaccttaccagagggcgcccc  1260
    ──────────────────────────────────────────────────────────────────────
                              Kan Resistance Cassette
```

Figure 6D (cont.)

```
     agctggcaattccggttcgcttgctgtcccatagtggtcagtgctccatcctgctgatgtgctcagtatcacg     1330
                                                           ─────OL────▷ ccagtggtatttatgtcaacacaccgccagagataattatcaccgcagatggttatctgtatgtttttat      1400
     ────────Kan Resistance Cassette────
                                          ──────OL────── atgaatttattttttgcaggggggcattgtttggtaggtgagagatctgaattgctatgttttagtgagtt      1470 gtatctatttattttcaataaatacaattggttatgtgttttgggggcgatcgtgaggcaaagaaaacc        1540 cggcgctgaggccggttattcttgttctctggtcaaattatatagttggaaaacaaggatgcatatatg        1610 aatgaacgatgcagagaggcaatgccgatgcgatagtggtatcatgtagccgcttatgctgaagaagc        1680 aataacccgcagaaaaacaaagtccaagctccaacaaactaagggcatagacaataactaccgatgtca       1750 tataccatactctctaatcttggccagtcggcgcgttcctgcttccgattagaaacgtcaaggcagcaat     1820
```

Figure 6D (cont.)

```
caggattgcaatcatgttcctgcatatgatgacaatgtcgcccaagaccatctctatgagctgaaaaa  1890
gaaacaccaggaatgtagtggcggaaaaggagatagcaaatgcttacgataacgtaaggaattacta  1960
tgtaaacaccaggcatgattctgttccgcataattactcctgataattcctaacttttgccacctg  2030
cctttaaaacattccagtatatcactttcattcttgcgtagcaatatgccatctcttcagctatctca 2100
gcattggtgacttgttcagaggcgctgagatggccttttctgatagataatgttctgttaaatat  2170
ctccggcctcatctttgcccgcaggctaatgtctgaaaattgaggtgacgggttaaaataatatccttt 2240
ggcaacctttttatatccctttaaatttggcttaatgactatatccaatgagtcaaaagtccccct 2310
tcaatatctgttgcccctaagacctttaatatatcgccaaatacaggtagcttggcttctaccttcaccg 2380
ttgttcggccgatgaaatgcatatgcataacatcgtctttggtggttcccctcatcagtggctctatctg 2450
```

Figure 6D (cont.)

```
      aacgcgctctccactgcttaatgacattcctttcccgattaaaaatctgtcagatcgatgtggtcggc
   5'  ----+----|----+----|----+----|----+----|----+----|----+----|----+----|  2520
      ccgaaaacagttctggcaaaaccaatggtgtcgccttcaacaaacaaaaagatgggaatcccaatgatt
   5'  ----+----|----+----|----+----|----+----|----+----|----+----|----+----|  2590
      cgtcatctgcgaggctgttcttaatatcttcaactgaagcttagagcgattatcttctgaaccagact
   5'  ----+----|----+----|----+----|----+----|----+----|----+----|----+----|  2660
      cttgtcattgtttggtaaagagaaaagttttccatcgatttatgaatatacaaataattggagcca
   5'  ----+----|----+----|----+----|----+----|----+----|----+----|----+----|  2730
      acctgcaggtgatgattatcagccagcagagaattaaggaaaacagacaggtttattgagcgcttatctt
   5'  ----+----|----+----|----+----|----+----|----+----|----+----|----+----|  2800
      tccctttatttttgctgcggtaagtcgcataaaaaccattcttcataattcattcattactatgttat
   5'  ----+----|----+----|----+----|----+----|----+----|----+----|----+----|  2870
      gttctgagggggagtgaaaattcccctaattcgatgaagattcttgctcaattgttatcagctatgccg
   5'  ----+----|----+----|----+----|----+----|----+----|----+----|----+----|  2940
      accagaacaccttgccgatcagcaaacgtctcttcaggccactgactagcgataactttcccacaacg
   5'  ----+----|----+----|----+----|----+----|----+----|----+----|----+----|  3010
                                                        cI+ ind-
                                                   ═══════════════▷
```

Figure 6D (cont.)

```
gaacaactctcattgcattggatcattgggtactgtggttgtaaaacacctgaccgctat     3080
           cI+ ind-ccctgatcagtttcttgaaggtaaactcatcaccccaagtctgctatgcagaaatcacctgctcaac     3150
           cI+ ind-agcctgctcagggtcaacgagaattaacattccgtcaggaaagcttggcttggagcctgttggtgcggtc     3220
           cI+ indatggaattaccttcaacctcaagccagaatgcagaatcactggctttttggttgtgtgcttaccatctct     3290
           cI+ indccgcatcaccttttggtaaaggttctaagcttagtgagaacatccctgcctgaacatgagaaaaacagg     3360
           cI+ indgtactcatactcacttctaagtgacggctgcatactaaccgcttcatacatctcgtagattctctggcg     3430
           cI+ ind-
```

Figure 6D (cont.)

```
5'  accactctacgctggtggcgatctcttcacgcggtagcgcagtccacgcgccaagctcgcacagaatcact
        ----+----+----+----+----+----+----+----+----+----+----+----+----+----   70
3'  tggtgagatgcgaccaccgctagagaagtggccatcgcgtcaggtggcggttcgagcgtgtcttagtga
                    <——————————————————————————————————————————————————————
                                                araB 5'  gccaaatcgaggccaattgcaatcgccatcgtttcactcgttcactccaaaaaacggtatggagaaacagt
        ----+----+----+----+----+----+----+----+----+----+----+----+----+----   140
3'  cggttttagctcggttaacgttagcggtagcaaagtgagcaaagtgaggttttttgccatacctctttgtca
    ——————————————————————————————————————————————————————————————————|▽P..D
                araB 5'  agagagttgcgataaaaagcgtcaggtcaggatccgctaatcttatggataaaaatgctatggcatagcaa
        ----+----+----+----+----+----+----+----+----+----+----+----+----+----   210
3'  tctctcaacgctattttcgcagtccagtcctaggcgattagaatacctattttacgataccgtatcgtt
                        |————————|
                         P-BAD 5'  agtgtgaaccagcaataagcggtatattcgccgataaattgctggaccgggactggctgctggcccagcttaa
        ----+----+----+----+----+----+----+----+----+----+----+----+----+----   280
3'  tcacacttggtcgttatcgccatataagcggctatttaacgacctgccctgaccgacgaccgggtcgaatt
                                                        ▽|—————————————————————
                                                          chloramphenicol resistance cassette 5'  tgctttcgaattctgccattcatccgcttattcacttattcaggcgtagcaccaggcgtttaagggc
        ----+----+----+----+----+----+----+----+----+----+----+----+----+----   350
3'  acgaaagcttaagacggtaagtaggcgaataagtgaataagtccatcgtggtccgcaaattcccg
    ——————————————————————————————————————————————————————————————————————
                        chloramphenicol resistance cassette
```

Figure 6E

```
accaataactgccttaaaaaattacgccccgccctgccactcatcgcagtactgttgtaattcattaag    420
tggttattgacggaattttttaatgcggggcgggacggtgagtagcgtcatgacaacattaagtaattc
                                    chloramphenicol resistance cassette cattctgccgacatgaagagccatcacagacggcatgatgaacctgaatcgccagcggcatcagcacctg    490
gtaagacggctgtactcggtagtgtctgcctactcttagcggtcgcgtagtcgtgtggaac
                                    chloramphenicol resistance cassette tcgccttgcgtatatatttgcccatggtgaaaacgggggcgaagaagttgtccatattggccacgttta    560
agcggaacgcattataaacgggtaccactttgccccgcttcttcaacaggtataaccggtgcaaat
                                    chloramphenicol resistance cassette aatcaaaactggtgaaactcaccaggattggctgagacgaaaaacatattctcaataaccctttagg    630
ttagttttgaccactttgatgggtccctaaccgactctgcttttgtataagagttattgggaaatcc
                                    chloramphenicol resistance cassette gaaataggccaggtttcaccgtaacacgccacatcttgcgaatatatgtgtagaaactgccggaaatcg    700
ctttatccggtccaaagtggcattgtgcggtgtagaacgcttatatacacatctttgacggcctttagc
                                    chloramphenicol resistance cassette
```

Figure 6E (cont.)

```
5'  tcgtggtattcactccagagcgatgaaacgttcagtttgctcatggaaaaacgttgtaacaaggggtgaa  770
        ||||||||||||||||||||||||||||||||||||||||||||||||||||||||||||||||||||
3'  agcaccataagtgaggtctcgctactttgcaaagtcaaacgagtaccttttgccacattgttccactt
    ─────────────────────────── chloramphenicol resistance cassette ───────────────────────────

5'  cactatccatatcaccagtcaccgtctttcattgccatacggaattccggatgagcattcatcaggcg  840
        ||||||||||||||||||||||||||||||||||||||||||||||||||||||||||||||||||||
3'  gtgataggtagtgttggtgtcgagtggcagaaagtaacggtatgccttaaggcctactcgtaagtagtccgc
    ─────────────────────────── chloramphenicol resistance cassette ───────────────────────────

5'  ggcaagaatgtgaataaaggccggataaaacttgtgcttattttctttacggtctttaaaaaggccgta  910
        ||||||||||||||||||||||||||||||||||||||||||||||||||||||||||||||||||||
3'  ccgttcttacacttattccggcctattttgaacacgaataaaagaaatgccagaaatttttccggcat
    ─────────────────────────── chloramphenicol resistance cassette ───────────────────────────

5'  atatccagctgaacggtctggttataggtacattgagcaactgactgaaatgcctcaaaatgttctttac  980
        ||||||||||||||||||||||||||||||||||||||||||||||||||||||||||||||||||||
3'  tataggtcgacttgccagaccaatatccatgtaactcgttgactgactttacgagttacaagaaatg
    ─────────────────────────── chloramphenicol resistance cassette ───────────────────────────

5'  gatgccattgggatatatcaacggtggtatatccagtgatttttctccatttagcttccttagctcc  1050
        ||||||||||||||||||||||||||||||||||||||||||||||||||||||||||||||||||||
3'  ctacggtaaccctatatagttgccaccatatagttcactaaaaagaggtaaaatcgaaggaatcgagg
    ─────────────────────────── chloramphenicol resistance cassette ───────────────────────────
```

Figure 6E (cont.)

```
                                                                                        1120
5'  tgaaaatctcgataactcaaaaatacgcccggtagtgatcttattcattatggtgaaagttggaacct
3'  actttagctattgagttttttatgcgggccatcactagaataaagtaatacccacttcaacctga
                          ─────────────────────────────────────
                                chloramphenicol resistance cassette 1190
5'  cttacgtgccgatcaacgtctcatttcgccaaaagttggccagggcttcccgtatcaacaggacac
3'  gaatgcacggctagttgcagagtaaagcggttttcaaccggtcccgaagggccatagttgtccctgtg
                          ─────────────────────────────────────
                                chloramphenicol resistance cassette 1260
5'  caggatttattattctgcgaagtgatcttccgtcacattaagaccccacttcacacattagttgttttt
3'  gtcctaaataataagacgcttcactagaaggcagtgtaattctgggtgaaagtgtaaattcaacaaaaa
                          ─────────────────────────────────────
                                chloramphenicol resistance cassette
                                                              ◁─── tetR 1330
5'  ctaatccgcatatgatcaattcaaggccgaataagaaggctggctctgcaccttggtgatcaataattc
3'  gattaggcgtatactagttaagttccggcttattctccgaccgagacgtggaaccactagttattaag
                                              ───────────
                                                  tetR 1400
5'  gatagcttgtcgtaataatggcgcatactcagtagtggtgttcccttcttttagcgacttga
3'  ctatcgaacagcattattaccgcgtatgatagtcatcagtagtcatccacaaggaaagaaatcgctgaact
                                              ───────────
                                                  tetR
```

Figure 6E (cont.)

```
                                                                        1470
5' tgtcttgatcttccaatacgcaacctaagtaaaatgcccacagcgctgagtgcatataatgcattct
3' acgagaactagaaggttatgcgttggattcatttacggggtgtcgcgactcacgtatattacgtaaga
                                    tetR 1540
5' ctagtgaaaaaccttgtttggcataaaaaggctaattgattttcgagagtttcatactgttttctgtagg
3' gatcacttttttggaacaaaccgtatttttccgattaactaaaagctctcaaagtatgacaaaagacatcc
                                    tetR 1610
5' ccgtgtacctaaatgtactttttgctccatcgcgatgactagtaaagcacatctaaaactttagcgtta
3' ggcacatggatttacatgaaaaacgaggtagcgctactgatcatttcgtgtagatttttgaaaatcgcaat
                                    tetR 1680
5' ttacgtaaaaatccttgccagtttcccctcctaaagggcaaaagtgagtatggtgcctatctaacatct
3' aatgcattttttaggaacggtcgaaaggggagattcccgtttcactcatacccacggatagattgtaga
                                    tetR 1750
5' caatggctaaggcgtcgagcagctttgagcaaagcccgcttatttttacatgccaatacaatgtaggctgctctacacc
3' gttaccgattccgcagctcgtcgaaactcgtttcgggcgaataaaaaatgtacggttatgttacatccgacgagatgtgg
                                    tetR
```

Figure 6E (cont.)

```
                                                                                    1820
5'  tagcttctggggcgagttacgggttgttaaaccttcgacctcattaagcagctctaatgcctg
    ++++++++++++++++++++++++++++++++++++++++++++++++++++++++++++++++
3'  atcgaagaccccgctcaatgcccaacaatttggaagctaaggctggagtaattgtcgagattacgcgac
                                    tetR 1890
5'  ttaatcactttacttttatctagacatcattaattcctaatttttgttgacactctatcattgat
    ++++++++++++++++++++++++++++++++++++++++++++++++++++++++++++++++
3'  aattagtgaaatgaaaatagattagatctgtagtaattaaggattaaaaacaactgtgagatagtaacta
                 tetR                              tetA promoter element 1960
5'  agagttatttaccactccctatcagtgatagagaaaagtgaaatgtactaaggaggttgtatggaacaa
    ++++++++++++++++++++++++++++++++++++++++++++++++++++++++++++++++
3'  tctcaataaatggtgagggatagtcactatctcttttcactttacatgattcctccaacatacccttgtt
              tetA promoter element                cro 2030
5'  cgcataaccctgaaagattatgcaatgcgctttgggcaaaccaagacagctaaagaCctcggcgtatatc
    ++++++++++++++++++++++++++++++++++++++++++++++++++++++++++++++++
3'  gcgtattgggactttctaatacgttacgcgaaaccgtttggttctgtcgattctGgagccgcatatag
                                  cro 2100
5'  aaagcgcgatcaacaaggccattcatgcaggccgaaagattttttaactataaacgctgatggaagcgt
    ++++++++++++++++++++++++++++++++++++++++++++++++++++++++++++++++
3'  tttcgcgctagttgttccggtaagtacgtccggctttctaaaaaattgatatttgcgactaccttcgca
                                  cro
```

```
5' tgaggccaacggttatctcgatt
   ++++++++++++++++++++++
3' actccggttgccaatagagctaa
   ────────araC────────▶
```

```
  5  acgcgggttagatccgcagacacccttgttgtcgaagccacgccgctcgaagcagatgccttacgccgc     70
        |----+----|----+----|----+----|----+----|----+----|----+----|----+----|
                                        yheL 5  gaactcgccaactacgatgttattttgaggcgtttgaggtttatgctgcacacattacatcgctcaccc   140
     |----+----|----+----|----+----|----+----|----+----|----+----|----+----|
                                        yheL 5  tggctgacggattttgctgcgtctgctgctgctcagtgaaggagacgaactgctattattgcaagatg   210
     |----+----|----+----|----+----|----+----|----+----|----+----|----+----|
                                        yheL 5  gcgtaactgccgcagttgacggtaaccgctacttgaaagtctgcgtaatgccccattaaggtctatgc   280
     |----+----|----+----|----+----|----+----|----+----|----+----|----+----|
                                        yheL 5  cctgaacgaagaccttattgcccgcgggtttgactggtcaaatttcgaacgacatcattctcattgactat 350
     |----+----|----+----|----+----|----+----|----+----|----+----|----+----|
                                        yheL 5  actgatttcgtcagacttacggttaagcaccccagccagatggcctggtgatgggcgggatcgttgtatat 420
     |----+----|----+----|----+----|----+----|----+----|----+----|----+----|
                                        yheL
```

Figure 8

```
                                                              490
ttcctgacacctttcggcatcgcgccctaaaattcggcgtcctcatatgtgtgaggacgtttattacgt 560
gttacgaagcaaaagctaaaaccaggagctatttaatggcaacagttaaccagctggtacgcaaaccac
                                                                   ┌──────
                                                                   │ rpsL 630
gtgctccgcaaagttgcgaaaagcaacgtgcctgcgctgaagcatgcccgcaaaacgtggcgtatgtac
───────────────────────────────────────────────────────────────────────
                              rpsL 700
tcgtgtatactaccactcctagaaaaccgaactccgcgctgcgtaaagtatgccgtgttcgtctgact
───────────────────────────────────────────────────────────────────────
                              rpsL 770
aacggtttcgaagtgactcctacatcggtggtgaaggtcacaacctgcaggagcactccgtgatcctga
───────────────────────────────────────────────────────────────────────
                              rpsL 840
tccgtggcggtcgtgttaagacctcccgggtgttaccacacgtacgtggtgcgttgactgctc
───────────────────────────────────────────────────────────────────────
                              rpsL
```

Figure 8 (cont.)

```
                                                                910
cggcgttaagagaccgtaagcaggctcgttccaagtatggcgtgaagcgtcctaaggcttaatggttctcc
     +----+----+----+----+----+----+----+----+----+----+----+----+----+
                              ──────▷
                               rpsL
                                                                980
gttaagtaaggccaaacgtttaacttaaatgtcaaactcgtagagttttggacaatcctgaatt
     +----+----+----+----+----+----+----+----+----+----+----+----+----+
                                                                1050
aacaacggagtattccatgccacgtcgtcgcgtcattggtcagcgtaaaattctgccggatccgaagtt
     +----+----+----+----+----+----+----+----+----+----+----+----+----+
                                                    ┌──
                                                    rpsG
                                                                1120
cggatcagaactgctggctaaatttgtaaatatcctgatggtagatggtaaaaaatctactgctgaatct
     +----+----+----+----+----+----+----+----+----+----+----+----+----+
                                                      rpsG
                                                                1190
atcgtatacagcggcgctggagacccctggctcagcgtctggtaaatctgaactggaagcattcgaagtag
     +----+----+----+----+----+----+----+----+----+----+----+----+----+
                                                      rpsG
                                                                1260
ctctcgaaaacgtgcgcccgactgtagaagttaagtctccgccgcgttggtggttctacttatcaggtacc
     +----+----+----+----+----+----+----+----+----+----+----+----+----+
                                                      rpsG
```

5' agttgaagtccgtccggttcgtcgtaatgctctggcaatgcgttggatcgttgaagctgc rpsG

```
5' ttatagagtcgaacggcctgggcagcctgtgccggggcggaagttggaagatagtgttgttcggcgtc
                                                                        70
   <---------------------------- araB truncated 5' atcgcccattgctgatagcggcgataaagctgttcaaagcgttgtgctgctcgctgcacggttgcaggg
                                                                        140
   araB truncated 5' ttttctctaccgcactggccattttttgctgagctgatgggatgtctgcgtgcactttcgcggcgacggc
                                                                        210
   araB truncated 5' agcaaaatcgccgcaccgagcgcacagcactggtcagaggcaacaatttgcagcgggcgattcagcacg
                                                                        280
   araB truncated 5' tcgcagcaggcctgcataatgacctggttttccgcgcgatgccgcccagtgccatcacgttattaacgg
                                                                        350
   araB truncated 5' cgatcccctgatcggtaaagcactccatgattgcgcgtgcgccaaaggcggtggcagcaatcaaacgcc
                                                                        420
   araB truncated 5' gaacagcagcggagcgtcggtagcgaggttaagatcggtaatcaccctttcaggcgttggttagcgttc
                                                                        490
   araB truncated 5' ggtgtgcggcggccgttaaaccagtcgagcaccaccggcaggtgatccagagacggattttggcccatg
                                                                        560
   araB truncated 5' cttcggtcagcgccggaagcagttgtttctggctggcgttgatttgcgttttcagttccggatgctggc
                                                                        630
   araB truncated 5' ggcaagctgttccagcggccagcgagtacgcgaccaaaccaggcgtagatatcaccaaacgccgattgg
                                                                        700
   araB truncated 5' cctgcttccagaccgataaatccaggcaccacgctgccatcaacctgaccgcaaataccttttaatgccc
                                                                        770
   araB truncated 5' gctcgccaacgctctgtttgtcggcaatcagaatgtcgcaggtggaagtaccgataactttttaccagtgc
                                                                        840
   araB truncated
```

Figure 15 Continue

```
5'  gttaggctgtgcgctgcgccaactgcgcccatatggcagtcaaacgcgccgccggaaatcaccacgctt
                                                                                910
                              araB truncated 5'  tcaggcaggccgagacgctgcgcccattccgggcataaggtgcccaccggaatatcggcagtccaagtgt
                                                                                980
                              araB truncated 5'  cagtgaacagcggggaaggcaaatggcgattgaggatcgggtccagctcatcaaagaaactggctggcgg
                                                                                1050
                              araB truncated 5'  caggccgccacagctttcgtgccacagagatttatgcccggcgctgcaacgtccgcgacgaatatcctgc
                                                                                1120
                              araB truncated 5'  gggcgggtggtaccggaaagcagagctggcacccagtcgcacagctcaatccacgatgcggcagattgcg
                                                                                1190
                              araB truncated 5'  ccacggcgctgtcctggcgagtcacatgcaggatttttgcccagaaccattcgctggaataaataccacc
                                                                                1260
                              araB truncated 5'  aatgtagcgggagtagtcaacgttgcccggcgcgtggcacaaacgggtaatctcttccgcttcttcaacc
                                                                                1330
                              araB truncated 5'  gcagtgtggtctttccacaatacgaacatcgcgttcgggttttcggcaaactcggggcgcagcgccagca
                                                                                1400
                              araB truncated 5'  cgtttccgtcggatcaatcggtgcgggcgtcgagccggtactgtcaacgccaatccgaccacagctgc
                                                                                1470
                              araB truncated 5'  gcgctgttcgacgctaagctctgcaagcacggttttcagtgccgcttccattgactcaatgtagtcacgc
                                                                                1540
                              araB truncated 5'  ggatgatgacggaactggttattcggggcatcacaaaattgcccttctgccaacggggataccactcta
                                                                                1610
                              araB truncated 5'  cgctggtggcgatctcttcaccggtagcgcagtccacgccaaagctcgcacagaatcactgccaaaatc
                                                                                1680
                              araB truncated
```

Figure 15 Continue

```
5'  gaggccaattgcaaaccagcaatagacataagcggctatttaacgaccctgccctgaaccgacgaccggg
                                                                              1750
3'

5'  tcgaatttgctttcgaatttctgccattcatccgcttattatcacttattcaggcgtagcaccaggcgtt
                                                                              1820
3'

5'  taagggcaccaataactgccttaaaaaaattacgccccgccctgccactcatcgcagtactgttgtaatt
                                                                              1890
3'

5'  cattaagcattctgccgacatggaagccatcacagacggcatgatgaacctgaatcgccagcggcatcag
                                                                              1960
3'

5'  caccttgtcgccttgcgtataatatttgcccatggtgaaaacggggcgaagaagttgtccatattggcc
                                                                              2030
3'

5'  acgtttaaatcaaaactggtgaaactcacccaggattggctgagacgaaaaacatattctcaataaacc
                                                                              2100
3'

5'  ctttagggaataggccaggttttcaccgtaacacgccacatcttgcgaatatatgtgtagaaactgccg
                                                                              2170
3'

5'  gaaatcgtcgtggtattcactccagagcgatgaaaacgtttcagttgctcatggaaaacggtgtaacaa
                                                                              2240
3'

5'  gggtgaacactatcccatatcaccagctcacgtctttcattgccatacggaattccggatgagcattca
                                                                              2310
3'

5'  tcaggcggcaagaatgtgaataaaggccggataaaacttgtgcttatttttctttacggtctttaaaaa
                                                                              2380
3'

5'  ggccgtaatatccagctgaacggtctggttataggtacattgagcaactgactgaaatgcctcaaaatgt
                                                                              2450
3'

5'  tctttacgatgccattgggatatatcaacggtggtatatccagtgatttttttctccattttagcttcct
                                                                              2520
3'

5'  tagctcctgaaaatctcgataactcaaaaatacgcccggtagtgatcttatttcattatggtgaaagtt
                                                                              2590
3'

5'  ggaacctcttacgtgccgatcaacgtctcatttcgccaaaagttggcccaggcttccggtatcaaca
                                                                              2660
3'

5'  gggacaccaggatttatttattctgcgaagtgatcttccgtcaaatcatggctcatacgttgttcgtatt
                                                                              2730
3'

5'  ctggtctctggcgaggccattttttcgaaacgctaatcagttccgccaggctacggcctgcatttttt
                                                                              2800
3'
```

Figure 15 Continue

```
5' ccatgactctggcgcggtgcacctctacggtacgcaccgcgatattcatcgcttccgcaatttcacggtt
                                                                                    2870
                                           tnR 5' cataaatccttttgccaccaggctggccagctcacgctctttcggcgtcaactgctggtaacacagtata
                                                                                    2940
                                           tnR 5' atctcacgacgcgccaccgctgccgatgaaaccgtcagcgcacgctccagcgccggctgtagcggtttta
                                                                                    3010
                                           tnR 5' ccgataccggttttttgcagaaaatcgacggcgccgcgtttcatctgctccacggccatcggtacatcgcc
                                                                                    3080
                                           tnR 5' atgcccggtaagaaaacaaccgccagggtacttccgcactggcgcaacgatcatgaacgccctgccca
                                                                                    3150
                                           tnR 5' tccagtaccggcattcgcatatccagtaatacgaccccggcctgataacagactggcctgcgccaaaaat
                                                                                    3220
                                           tnR 5' ccgccccctgcgtccagcattttacgtcatatcccagactttccagtaaaaacgcgcacgcgttagtgac
                                                                                    3290
                                           tnR 5' cgccgtatcatcatccagtagatgaattgtcgccatccctgccccattttcatgtaagaaatgtatcgt
                                                                                    3360
                                           tnR
                                     ←————tnS————

5' aaccacgttcccgacagaccgtcggcgcggtctggttcctgatgctgatatcgccccgcccataccgc
                                                                                    3430
                                           tnS 5' accagccgctggcaaatcgccagccctaagcccatccctctttacgggtggtcataaacggctgaaacg
                                                                                    3500
                                           tnS 5' cctgacgtaatagcgcctcatcgattccccggcgttatcctgtaaaacaatactgatgccgttttcagt
                                                                                    3570
                                           tnS
```

Figure 15 Continue

```
gcgttcagcaacgatccataatggtggcgcccgcctgagccgcattaagaatgatattcgccagcacc
                                                                      3640 tgttccagcagcactgacggcagcgttacgcgcagcgcagcgctaacctggtatgcagagtcactgtcg
                                                                      3710 gaaactgttgcgccatacgcaacaattgccagacatgatcaatcgctcgcgaatggctatggcttcca
                                                                      3780 cgcttcggttagcaacgggttgccctgcgcctggctgacccagtgacgcaggttacgcagagtatccgca
                                                                      3850 ccgcgttgcgcctgctggtcaatctgctccagcgccggcagcaagggatgctgttcatctgcagcgcgca
                                                                      3920 gtcgaatcaggcaccctgggcataatgtcgaatcgcggaaagcggctgattaagctcatgggcaaaccc
                                                                      3990 ggaggtcatttcacccaacacgctcatttgccggggcggtttccagcgcccgctcatgctgatgaagaact
                                                                      4060 acgctattacgttccagttgctttccacgtcgacgcaccagcagcatgacccaaatataattgagcgtga
                                                                      4130 gcaacaagaacgccagaatcacgccgccgaccattagctggtgctggattaaccaacttttgacatccag
                                                                      4200 ccacagtcgacgctgctgagggtgctgacgaacatcacgcagcaaggcttccacctgactggtggacgca
                                                                      4270 ggcgcgcccagtgaaatgacgcggcggcgggcgcgttgaatagcgctcgcgttacgcgatccgccagcg
                                                                      4340 catcgcttaccgcaggtagcgccgcgaacgaccagtcaggatataacggcgtactggttaagcaaggcag
                                                                      4410
```

Figure 15 Continue

```
5' gggcgtcggtcgggaagcagcgcgataaagtccttttattaatcatccttcctgacccatattttct
                                                                                        4480
                                    ttrS 5' aacaggcacactggcacaattgccgcctgcaccgcttttttcgcgcagcatatagactaaggcatcgccag
                                                                                        4550
                                    ttrS 5' gaaatccggtaaaacggagatgaaaatcgcgctccgggcgtaagccgcgtcgctgagcgctttatagcc
                                                                                        4620
                                    ttrS 5' taataaatagccgccaaacgcctgagcatcaatcgcgccgacggtcttaccgatgagatcatgcgccgtg
                                                                                        4690
                                    ttrS 5' gtgatgccgctatcgcgccgggtcaaatcacgctgccaataacattactcaccgcttcccatcgcgcg
                                                                                        4760
                                    ttrS 5' tggagcgcaggaagctaaccagcgcagcggcgcatggctgttcagttggacaaattgcgccgggttggt
                                                                                        4830
                                    ttrS 5' tatcacaaactgcacggttccctggttaacggctcctgcatttgatgcagatccagcggctggatgtga
                                                                                        4900
                                    ttrS 5' aaggtttcgcctggaagctgttggcttaatgtctttgccaacggttgccagtggctacgcgtagacgcct
                                                                                        4970
                                    ttrS 5' cgccgcgcatggccaaaatacgatattccacgtccctgccacgcgccatgacaaagtagcctactgc
                                                                                        5040
                                    ttrS 5' cgccaacaccgccaggcgccttacggtttacctctcaccccaatatccctgtcaattatgttgttttag
                                                                                        5110
                                    ttrS    | ttrS - ttrB intergenic region 5' atcaacaacaagccgggtatgtggttaaccacaatagagcgcacccgcctcgatttttacactgtaaat
                                                                                        5180
                                    ttrS - ttrB intergenic region 5' catcgacattttttattcattacacatgaaccaacatcgtgacaaatgtttcattgttggcaatgtggac
                                                                                        5250
                                    ttrS - ttrB intergenic region
```

```
5' accactctacgctggtggcgatctcttcaccggtagcgcagtccaccgccaaagctcgcacagaatcact
                                                                              70
3' tggtgagatgcgaccaccgctagagaagtggccatcgcgtcaggtggcggtttcgagcgtgtcttagtga
   ←──────────────────────────── araB ────────────────────────────

5' gccaaaatcgaggccaattgcaatcgccatcgtttcactccatccaaaaaaacgggtatggagaaacagt
                                                                              140
3' cggttttagctccggttaacgttagcggtagcaaagtgaggtaggttttttgcccatacctctttgtca
   ──── araB ────

5' agagagttgcgataaaaagcgtcaggtaggatccgctaatcttatggataaaaatgctatggcatagcaa
                                                                              210
3' tctctcaacgctattttcgcagtccatcctaggcgattagaatacctattttacgataccgtatcgtt 5' agtgtgaaccagcaatagacataagcggctatttaacgaccctgccctgaaccgacgaccgggtcgaatt
                                                                              280
3' tcacacttggtcgttatctgtattcgccgataaattgctgggacgggacttggctgctggcccagcttaa
                        ←──── chloramphenicol resistance cassette 5' tgctttcgaatttctgccattcatccgcttattatcacttattcaggcgtagcaccaggcgtttaaggc
                                                                              350
3' acgaaagcttaaagacggtaagtaggcgaataatagtgaataagtccgcatcgtggtccgcaaattccg
                        chloramphenicol resistance cassette 5' accaataactgccttaaaaaaattacgccccgccctgccactcatcgcagtactgttgtaattcattaag
                                                                              420
3' tggttattgacggaatttttttaatgcggggcgggacggtgagtagcgtcatgacaacattaagtaattc
                        chloramphenicol resistance cassette 5' cattctgccgacatggaagccatcacagacggcatgatgaacctgaatcgccagcggcatcagcaccttg
                                                                              490
3' gtaagacggctgtacctcggtagtgtctgccgtactacttggacttagcggtcgccgtagtcgtggaac
                        chloramphenicol resistance cassette 5' tcgccttgcgtataatatttgcccatggtgaaaacgggggcgaagaagttgtccatattggccacgttta
                                                                              560
3' agcggaacgcatattataaacgggtaccactttgccccccgcttcttcaacaggtataaccggtgcaaat
                        chloramphenicol resistance cassette 5' aatcaaaactggtgaaactcacccagggattggctgagacgaaaaacatattctcaataaaccctttagg
                                                                              630
3' ttagttttgaccactttgagtgggtccctaaccgactctgcttttgtataagagttatttgggaaatcc
                        chloramphenicol resistance cassette 5' gaaataggccaggttttcaccgtaacacgccacatcttgcgaatatatgtgtagaaactgccggaaatcg
                                                                              700
3' ctttatccggtccaaaagtggcattgtgcggtgtagaacgcttatatacacatctttgacggcctttagc
                        chloramphenicol resistance cassette
```

Figure 16 Continue

```
5'  tcgtggtattcactccagagcgatgaaaacgtttcagtttgctcatggaaaacggtgtaacaaggtgaa
                                                                                    770
3'  agcaccataagtgaggtctcgctacttttgcaaagtcaaacgagtaccttttgccacattgttccactt
    ─────────────────────── chloramphenicol resistance cassette ───────────────────────

5'  cactatcccatatcaccagctcaccgtctttcattgccatacggaattccggatgagcattcatcaggcg
                                                                                    840
3'  gtgatagggtatagtggtcgagtggcagaaagtaacggtatgccttaaggcctactcgtaagtagtccgc
    ─────────────────────── chloramphenicol resistance cassette ───────────────────────

5'  ggcaagaatgtgaataaaggccggataaaacttgtgcttatttttctttacggtctttaaaaggccgta
                                                                                    910
3'  ccgttcttacacttatttccggcctattttgaacacgaataaaaagaaatgccagaaattttccggcat
    ─────────────────────── chloramphenicol resistance cassette ───────────────────────

5'  atatccagctgaacggtctggttataggtacattgagcaactgactgaaatgcctcaaaatgttctttac
                                                                                    980
3'  tataggtcgacttgccagaccaatatccatgtaactcgttgactgactttacggagttttacaagaaatg
    ─────────────────────── chloramphenicol resistance cassette ───────────────────────

5'  gatgccattgggatatatcaacggtggtatatccagtgatttttttctccatttagcttccttagctcc
                                                                                    1050
3'  ctacggtaaccctatatagttgccaccatataggtcactaaaaaagaggtaaatcgaaggaatcgagg
    ─────────────────────── chloramphenicol resistance cassette ───────────────────────

5'  tgaaaatctcgataactcaaaaaatacgcccggtagtgatcttatttcattatggtgaaagttggaacct
                                                                                    1120
3'  acttttagagctattgagttttttatgcgggccatcactagaataaagtaataccactttcaaccttgga
    ─────────────────────── chloramphenicol resistance cassette ───────────────────────

5'  cttacgtgccgatcaacgtctcatttttcgccaaagttggcccagggcttcccggtatcaacagggacac
                                                                                    1190
3'  gaatgcacggctagttgcagagtaaaagcggtttcaaccgggtcccgaagggccatagttgtccctgtg
    ─────────────────────── chloramphenicol resistance cassette ───────────────────────

5'  caggatttatttattctgcgaagtgatcttccgtcacaTGCTGCAATAATAAGAAAAAATCAGCCCCGAC
                                                                                    1260
3'  gtcctaaataataagacgcttcactagaaggcagtgtACGACGTTATTATTCTTTTTTAGTCGGGGCTG
    ── chloramphenicol resistance cassette ──────────── PaiA ────────────

5'  GATTCACCTGTCGGGGCTGGACGCCATTTCAAGCCTGATAAACTGCTTAACAAATCAGCATAACTCATT
                                                                                    1330
3'  CTAAGTGGACAGCCCCGACCTGCGGTAAAGTTCGGACTATTTGACGAATTGTTTAGTCGTATTGAGTAA
    ────────────────────────────── PaiA ──────────────────────────────

5'  AATAACATAAGAGAATGCGATGGCTTGCAAAAGTAATTCATTGCCTGAATAATATAAATTATATATAAAT
                                                                                    1400
3'  TTATTGTATTCTCTTACGCTACCGAACGTTTTCATTAAGTAACGGACTTATTATATTTAATATATATTTA
    ────────────────────────────── PaiA ──────────────────────────────
```

Figure 16 Continue

```
5'  TTACGAAAAGTACGGCATTGATAATCATTTCAATATCATTTAATTAACTATAATGAACCAACTGCTTAC
    ++++++++++++++++++++++++++++++++++++++++++++++++++++++++++++++++++++  1470
3'  AATGCTTTTCATGCCGTAACTATTAGTAAAGTTATAGTAAATTAATTGATATTACTTGGTTGACGAATG
                                    PsodA 5'  GCGGCATTAACAATCGGCCGCCCGACAATACTGCAGATGAAtgtactaaggaggttgtatggaacaac
    ++++++++++++++++++++++++++++++++++++++++++++++++++++++++++++++++++++  1540
3'  CGCCGTAATTGTTAGCCGGCGGGCTGTTATGACCTCTACTTAcatgattcctccaacataccttgttg
                        PsodA                            cro 5'  gcataaccctgaagattatgcaatgcgctttggycaaaccaagacagctaagaCctggcgtatatca
    ++++++++++++++++++++++++++++++++++++++++++++++++++++++++++++++++++++  1610
3'  cgtattgggactttctaatacgttacgcgaaaccgtttggttctgtcgatttctGgagccgcatatagt
                                      cro 5'  aagcgcgatcaacaaggccattcatgcaggccgaaagatttttttaactataaacgctgatggaagcgtt
    ++++++++++++++++++++++++++++++++++++++++++++++++++++++++++++++++++++  1680
3'  ttcgcgctagttgttccggtaagtacgtccggctttctaaaaaattgatatttgcgactaccttcgcaa
                                      cro 5'  tatgcggaagaggtaaagcccttcccgagtaacaaaaaacaacagcataacgccgtgcaaataatcaat
    ++++++++++++++++++++++++++++++++++++++++++++++++++++++++++++++++++++  1750
3'  atacgccttctccatttcgggaagggctcattgttttttgttgtcgtattgcggcacgtttattagtta
                          cro →

5'  gtggacttttctgccgtgattatagacacttttgttacgcgttttgtcatggctttggtcccgctttgt
    ++++++++++++++++++++++++++++++++++++++++++++++++++++++++++++++++++++  1820
3'  cacctgaaaagacggcactaatatctgtgaaaacaatgcgcaaaacagtaccgaaaccagggcgaaaca 5'  tacagaatgcttttaataagcggggttaccggttgggttagcgagaagagccagtaaaagacgcagtgac
    ++++++++++++++++++++++++++++++++++++++++++++++++++++++++++++++++++++  1890
3'  atgtcttacgaaaattattcgccccaatggccaacccaatcgctcttctcggtcattttctgcgtcactg 5'  ggcaatgtctgatgcaatatggacaattggtttcttctctgaatggtgggagtatgaaaagtatggctga
    ++++++++++++++++++++++++++++++++++++++++++++++++++++++++++++++++++++  1960
3'  ccgttacagactacgttatacctgttaaccaaagaagagacttaccaccctcatactttcataccgact
                                                                  araC 5'  agcgcaaaatgatccctgctgccgggatactcgtttaacgccatctggtggcgggtttaacgccgatt
    ++++++++++++++++++++++++++++++++++++++++++++++++++++++++++++++++++++  2030
3'  tcgcgttttactagggacgacggccctatgagcaaattgcgggtagaccaccgcccaaattgcggctaa
                                      araC 5'  gaggccaacggttatctcgatt
    ++++++++++++++++++++++  2052
3'  ctccggttgccaatagagctaa
        araC →
```

```
5' TGGTGTATATCGTAACGGTAACACTTTAAAAGGGAGCTGAGATatgtactaaggagg ttgtatggaacaa
                                                                              1400
3' ACCACATATAGCATTGCCATTGTGAAATTTTCCCTCGACTCTAtacatgattcctccaacataccttgtt
   [cstG promoter]                                                [cro]

5' cgcataacctgaaagattatgcaatgcgctttggcaaaccaagacagctaaagaCctcggcgtatatc
                                                                              1470
3' gcgtattgggactttctaatacgttacgcgaaaccgtttggttctgtcgatttcGgagccgcatatag
   [cro]

5' aaagcgcgatcaacaaggccattcatgcaggccgaaagatttttttaactataaacgctgatggaagcgt
                                                                              1540
3' tttcgcgctagttgttccggtaagtacgtccggctttctaaaaaaattgatatttgcgactaccttcgca
   [cro]

5' ttatgcggaagaggtaaagcccttcccgagtaacaaaaaacaacagcataaagccgtgcaaataatcaa
                                                                              1610
3' aatacgccttctccatttcgggaaggcctcattgttttttgttgtcgtattcggcacgtttattagtt
   [cro →]

5' tgtggactttttctgccgtgattatagacaactttgttacgcgtttttgtcatggctttggtcccgctttg
                                                                              1680
3' acacctgaaaagacggcactaatatctgtgaaaacaatgcgcaaaaacagtaccgaaaccagggcgaaac
                           [P.araC →]

5' ttacagaatgcttttaataagcggggttaccggttgggttagcgagaagagccagtaaaagacgcagtga
                                                                              1750
3' aatgtcttacgaaaattattcgcccaatggccaacccaatcgctcttctcggtcattttctgcgtcact 5' cggcaatgtctgatgcaatatggacaattggtttcttctctgaatggtgggagtatgaaaagtatggctg
                                                                              1820
3' gccgttacagactacgttatacctgttaaccaaagaagagacttaccaccctcatacttttcataccgac
                                                                     [araC]

5' aagcgcaaaatgatcccctgctgccgggatactcgtttaacgccatctggtggcgggtttaacgccgat
                                                                              1890
3' ttcgcgttttactaggggacgacggccctatgagcaaattgcgggtagaccaccgcccaaattgcggcta
                                    [araC]

5' tgaggccaacggttatctcgatt
                                                                              1913
3' actccggttgccaatagagctaa
   [araC →]
```

Figure 19

```
5' accactctacgctggtggcgatctcttcacggtagcgcagtccaccgccaaagctcgcacagaatcact
                                                                                    70
                                        ← araB 5' gccaaaatcgaggccaattgcaatcgccatcgtttcactccatccaaaaaacgggtatggagaaacagt
                                                                                    140
        araB 5' agagagttgcgataaaaagcgtcaggtaggatccgctaatcttatggataaaaatgctatggcatagcaa
                                                                                    210

5' agtgtgaaccagcaatagacataagcggctatttaacgaccctgccctgaaccgacgacgggtcgaatt
                                                                                    280
                    ← chloramphenicol resistance cassette 5' tgcttttcgaatttctgccattcatccgcttattatcacttattcaggcgtagcaccaggcgtttaaggc
                                                                                    350
                        chloramphenicol resistance cassette 5' accaataactgccttaaaaaaattacgccccgccctgccactcatcgcagtactgttgtaattcattaag
                                                                                    420
                        chloramphenicol resistance cassette 5' cattctgccgacatggaagccatcacagacggcatgatgaacctgaatcgccagcggcatcagcaccttg
                                                                                    490
                        chloramphenicol resistance cassette 5' tcgccttgcgtataatatttgcccatggtgaaaacgggggcgaagaagttgtccatattggccacgttta
                                                                                    560
                        chloramphenicol resistance cassette 5' aatcaaaactggtgaaactcacccaggattggctgagacgaaaaacatattctcaataaaccctttagg
                                                                                    630
                        chloramphenicol resistance cassette 5' gaaataggccaggttttcaccgtaacacgccacatcttgcgaatatatgtgtagaaactgccggaaatcg
                                                                                    700
                        chloramphenicol resistance cassette 5' tcgtggtattcactccagagcgatgaaaacgtttcagtttgctcatggaaaacggtgtaacaagggtgaa
                                                                                    770
                        chloramphenicol resistance cassette 5' cactatccccatatcaccagctcaccgtctttcattgccatacggaattccggatgagcattcatcaggcg
                                                                                    840
                        chloramphenicol resistance cassette
```

```
5' caatggctaaggcgtcgagcaaagccgcttatttttacatgcaatacaatgtaggctgctctacacc
                                                                              1750
     ─────────────────────────────── tetR ───────────────────────────────

5' tagcttctgggcgagtttacgggttgttaaaccttcgattccgacctcattaagcagctctaatgcgctg
                                                                              1820
     ─────────────────────────────── tetR ───────────────────────────────

5' ttaatcacttacttttatctaatctagacatcattaattcctaatttttgttgacactctatcattgat
                                                                              1890
     ──────────── tetR ────────────┤├──────── tetA promoter element ────────

5' agagttattttaccactccctatcagtgatagagaaaagtgaaatgagcacaaaaaagaaaccattaaca
                                                                              1960
     ──── tetA promoter element ────▶├───────────── sIDN ─────────────

5' caGgaAcagcttgaAgaTgcacgtcgcctGaaGgcGatttaCgaaaGaaAaaGaatgaacttggcttaA
                                                                              2030
     ─────────────────────────────── sIDN ───────────────────────────────

5' GccaggaAGCgtGgcGgaTaagatgggCatgggCcagAGCggcgtGggCgcGCtGtttaatggcatTaa
                                                                              2100
     ─────────────────────────────── sIDN ───────────────────────────────

5' ggcGCtGaatgcGtataacgccgcaCtgctGgcGaaaattctGaaagttagcgttgaagaattttCGccG
                                                                              2170
     ─────────────────────────────── sIDN ───────────────────────────────

5' tcaatTgccCgCgaaatctcagaAatgtacgaagcggttagtatgcagccgtcacttcgtagtgagtatg
                                                                              2240
     ─────────────────────────────── sIDN ───────────────────────────────

5' agtaccggttttttctcatgttcaggcagAgatgttctcacctgagcttcgtacctttaccaaaggtga
                                                                              2310
     ─────────────────────────────── sIDN ───────────────────────────────

5' tgcGgagcgttgggtaagcacaaccaaaaagccagtgattctgcattctggcttgaggttgaaggtaat
                                                                              2380
     ─────────────────────────────── sIDN ───────────────────────────────

5' tccatgaccgcaccaactggctccaagccaagTttttcctgacggaatgttaattctcgttgaccctgagc
                                                                              2450
     ─────────────────────────────── sIDN ───────────────────────────────

5' aggctgttgagccaggtgatttctgcattgcccgtcttggggtgatgagtttaccttcaagaaactgat
                                                                              2520
     ─────────────────────────────── sIDN ───────────────────────────────
```

Figure 20 continue

Figure 20 continue

```
5' TTGGGTCACGCGAACCACCGTGCGCGATACCGGCTCCGGCAGGCTTATCGACGTATCCCCCACGAGCTCT
   +---+---+---+---+---+---+---+---+---+---+---+---+---+---+   4550
```

```
5' AAATGAACATCCAATGGCGCACCGAGAGCATCCTGTTTGGTGCGTAGATTATTAATGGTACTGGTCAGTG
   +---+---+---+---+---+---+---+---+---+---+---+---+---+---+   4620
```

```
5' CGATAGGCAGCGAGTCGCCGAGTGCTGGGCTGCTAGGTGGCGCACAAAGCGGCGTGCCTCTGCAAGGCT
   +---+---+---+---+---+---+---+---+---+---+---+---+---+---+   4690
```

```
5' GTCAGAGGCTTGGGTTTCGATCACGCTGAGTTGCTGTGCCACATCTTCAATTTCACCTTTATCGAGGCGG
   +---+---+---+---+---+---+---+---+---+---+---+---+---+---+   4760
```

```
5' CCGTGTGCGGCGCGTGCCAAGATTACGATGGAACTCAATCCTTGGGCAACTGTGTCATGGATCTCGCAG
   +---+---+---+---+---+---+---+---+---+---+---+---+---+---+   4830
```

```
5' AGAGCCGCTCGCGCTCCTCGAGCCGGCCTGCCTGATGTTCAGAGGTGGCGAGATCCTGCTGGGCTGCAAG
   +---+---+---+---+---+---+---+---+---+---+---+---+---+---+   4900
```

```
5' CAACTCTGCCGCTAGTTGGCGGTAATGTTGGGCATCGTTGCGCAAGGTGGTGTAGCTATAAAAATCACC
   +---+---+---+---+---+---+---+---+---+---+---+---+---+---+   4970
```

```
5' GTGGAAAACGCGGCACCCATCGTTGGGCCCATGGCCTGTGCGGGCATCCACTCATCTGGCGTGTGGCTA
   +---+---+---+---+---+---+---+---+---+---+---+---+---+---+   5040
```

```
5' GGGGAATTGCGATGGCGATGGCAAGGAGTAAGGCAACGCCCAAGATGCCACGAATGCCCTGCTTGAGATG
   +---+---+---+---+---+---+---+---+---+---+---+---+---+---+   5110
```

```
5' CAACATTACAAATACGAGTGGAACATCAGCCACAGGAAATAGCCGGAGGCACCTACGAGGAAAGCCCAG
   +---+---+---+---+---+---+---+---+---+---+---+---+---+---+   5180
```

```
5' AGAGCAACAATAATCACGAGCCACACGGGACTGAGTATCCCCGGGGTCCGGGATGTCGTCGCCACGCGCGA
   +---+---+---+---+---+---+---+---+---+---+---+---+---+---+   5250
```

```
5' AACGATTTTCCCATGCGGTGCCGATCATGTAGAAAATTCCCAGCGTGATTGCTGCGGCGATAGCAATATT
   +---+---+---+---+---+---+---+---+---+---+---+---+---+---+   5320
```

Figure 20 continue

```
5'  GTTTGCATCGGTTGGAACTGTTGGAAGCTCGAGATAATAACGTACGATTCCAAAAATGAGCAGACCAGCG
                                                                                              5390
                                              chrB 5'  AACATTACATGCAGGCTGACACGCATGACGGTGAGAATTTGAATCACATGAGGCTTCACACTAGCGAGCA
                                                                                              5460
                                              chrB 5'  TAAAAGATCTCCTGCGCCTGTGATGGATTGGAAGGAAAGTTCGCTTAATTGAAGCCTATGTTGCATAGGA
                                                                                              5530
                                          chrBA Promoter 5'  GCAAATTAGGCTATACCTTTTAATGAGCGGTTGATGTGGTGAGGTCGATCGCTCGGTGAGTGGAAGAATC
                                                                                              5600
                  chrBA Promoter                              humD Promoter 5'  AACTATCTGGTTGATGTGAGGGGAACCTAACCTAAGTATCTTCTAGGTTATTGATCAAAACGCACGATGT
                                                                                              5670
                                          humD Promoter 5'  GTCCATACGAAAGGTTTTCTTCATCTatggaacaacgcataaccctgaagattatgcaatgcgctttgg
                                                                                              5740
            humD Promoter                                cro 5'  gcaaaccaagacagctaaagaCctcggcgtatatcaaagcgcgatcaacaaggccattcatgcaggcga
                                                                                              5810
                                              cro 5'  aagattttttaactataaacgctgatggaagcgtttatgcggaagaggtaaagccottcccgagtaaca
                                                                                              5880
                                              cro 5'  aaaaacaacagcataaaagcgcaaaatgatccctgctgccgggatactcgtttaacgcccatctggtg
                                                                                              5950
                          cro                           araC truncated 5'  gcgggtttaacgccgattgaggccaacggttatctcgatttttttatcgaccgaccgctgggaatgaaag
                                                                                              6020
                                          araC truncated 5'  gttatattctcaatctcaccattcgcggtcaggggtggtgaaaatcaggacgagaattcgtctgccg
                                                                                              6090
                                          araC truncated 5'  accgggtgatatttttgctgttccgccaggagagattcatcactaaggtcgtcatccggaggctcgcgaa
                                                                                              6160
                                          araC truncated
```

Figure 20 continue

```
5' tggtatcaccagtgggtttactttcgtccgcgcgcctactggcatgaatggcttaactggccgtcaatat
                                                                              6230
                                araC truncated 5' ttgccaatacgggtttcttccgccgatgaagcgcaccagccgcatttcagcgacctgtttggycaaat
                                                                              6300
                                araC truncated 5' cattaacgccggcaagggaaggccgctattcggagctgctggcgataaatctgcttgagcaattgtta
                                                                              6370
                                araC truncated 5' ctgcggcgcatggaagcgattaacgagtcgctccatccaccgatggataatcgggtacgcgaggcttgtc
                                                                              6440
                                araC truncated 5' agtacatcagcgatcacctggcagacagcaattttgatatcgccagcgtcgcacagcatgtttgcttgtc
                                                                              6510
                                araC truncated 5' gccgtcgcgtctgtcacatcttttccgccagccagttagggattagcgtcttaagctggcgcgaggaccaa
                                                                              6580
                                araC truncated 5' cgcattagtcaggcgaagctgcttttgagcactacccggatgcctatcgccaccgtcggtcgcaatgttg
                                                                              6650
                                araC truncated 5' gttttgacgatcaactctatttctcgcgagtatttaaaaaatgcaccggggccagccgagcgagtttcg
                                                                              6720
                                araC truncated 5' tgccggttgtgaagaaaagtgaatgatgtagccgtcaagttgtcataa
                                                                              6769
                                araC truncated →
```

Figure 21

```
ttatagagtcgaacggcctgggcagcctgtgccggggcggaagttggaagatagtgttgttcggcgctc                    70
                    ←──── araB truncated atcgccattgctgatagcggcgataaagctgttcaaagcgttgtgcctgctgctgcacggttgcaggg                   140
                         araB truncated ttttctctaccgcactggccattttttgctgagctgatggatgtctgcgtgcactttcgggcgacggc                   210
                         araB truncated agcaaaaatcgcgcaccgagcgcacagcactggtcagaggcaacaatttgcagcgggcgattcagcacg                  280
                         araB truncated tcgcagcaggctgcataatgacctggttttccgcgcgatgccgcccagtgccatcacgttattaacgg                   350
                         araB truncated cgatccctgatcggtaaagcactccatgattgcgcgtgcgccaaaggcggtggcagcaatcaaaccgcc                  420
                         araB truncated gaacagcagcggagcgtcggtagcgaggtaagatcggtaatcaccctttcaggcgttggttagcgttc                   490
                         araB truncated ggtgtgcggcggccgttaaaccagtcgagcaccacggcaggtgatccagagacggatttttggcccatg                  560
                         araB truncated cttcggtcagcgccggaagcagttgtttctggctggcgttgatttgcgttttcagttccggatgctggc                  630
                         araB truncated ggcaagctgttccagcggccagccgagtacgcgaccaaaccaggcgtagatatcaccaaacgccgattgg                 700
                         araB truncated cctgcttccagaccgataaatccaggcaccacgctgccatcaacctgaccgcaaatacctttaactgccc                 770
                         araB truncated gctcgccaacgctctgtttgtcggcaatcagaatgtcgcaggtggaagtaccgataactttaccagtgc                  840
                         araB truncated
```

Figure 21 continue

```
    gttaggctgtgcgctgcgccaactgcgcccatatggcagtcaaacgcggcggccggaaatcaccacgctt
5'  ├────┼────┼────┼────┼────┼────┼────┼────┼────┼────┼────┼────┼────┼────┤  910
                                    araB truncated tcaggcaggccgagacgctgcgcccattccgggcataaggtgccacggaatatcggcagtccaagtgt
5'  ├────┼────┼────┼────┼────┼────┼────┼────┼────┼────┼────┼────┼────┼────┤  980
                                    araB truncated cagtgaacagcggggaaggcaaatggcgattgaggatcgggtccagtcatcaaagaaactggctggcgg
5'  ├────┼────┼────┼────┼────┼────┼────┼────┼────┼────┼────┼────┼────┼────┤  1050
                                    araB truncated caggccgcccagctttcgtgccacagagatttatgcccggcgctgcaacgtccgcgacgaatatcctgc
5'  ├────┼────┼────┼────┼────┼────┼────┼────┼────┼────┼────┼────┼────┼────┤  1120
                                    araB truncated gggcgggtggtaccggaaagcagagctggcacccagtcgcacagtcaatccacgatgcggcagattgcg
5'  ├────┼────┼────┼────┼────┼────┼────┼────┼────┼────┼────┼────┼────┼────┤  1190
                                    araB truncated ccacggcgctgtcctggcgagtcacatgcaggatttttgcccagaaccattcgctggaataaataccac
5'  ├────┼────┼────┼────┼────┼────┼────┼────┼────┼────┼────┼────┼────┼────┤  1260
                                    araB truncated aatgtagcgggagtagtcaacgttgcccggcgcgtggcacaaacgggtaatctcttccgcttcttcaacc
5'  ├────┼────┼────┼────┼────┼────┼────┼────┼────┼────┼────┼────┼────┼────┤  1330
                                    araB truncated gcagtgtggtctttccacaatacgaacatcgcgttcgggttttcggcaaactcggggcagcgccagca
5'  ├────┼────┼────┼────┼────┼────┼────┼────┼────┼────┼────┼────┼────┼────┤  1400
                                    araB truncated cgtttccgtcggcatcaatcggtgcggcgtcgagccggtactgtcaacgccaatccgaccacagctgc
5'  ├────┼────┼────┼────┼────┼────┼────┼────┼────┼────┼────┼────┼────┼────┤  1470
                                    araB truncated gcgctgttcgacgctaagctctgcaagcacggttttcagtgccgcttccattgactcaatgtagtcacgc
5'  ├────┼────┼────┼────┼────┼────┼────┼────┼────┼────┼────┼────┼────┼────┤  1540
                                    araB truncated ggatgatgacggaactggttattcggggcatcacaaaattgcccttctgccaacggggataccactcta
5'  ├────┼────┼────┼────┼────┼────┼────┼────┼────┼────┼────┼────┼────┼────┤  1610
                                    araB truncated cgctggtggcgatctcttcaccggtagcgcagtccaccgccaaagctcgcacagaatcactgccaaaatc
5'  ├────┼────┼────┼────┼────┼────┼────┼────┼────┼────┼────┼────┼────┼────┤  1680
                                    araB truncated
```

Figure 21 continue

Figure 21 continue

```
5' GATCGGACAGTAGCGGCCGGATCAGGGCATAGCCGACACCGGAGAGGAAACGCATGGCCTGGAGTTCGGC  2870
5' GCGACAGTCGGCACAGACATGCGCCAGTTCGAGCAGGCGCGGATCAGAGGACGGGAAGTCCTCGGCGTCG  2940
5' CGGATCAGGGCTTCGAGTCCGAGATCGGGATCGCCCTCGGGGCGCAGGGCGCGAAGGTTGCACGCAGAC   3010
5' AGTCGAGGACAGTCAGCAGGACATCCTGGTTGGGCGGTTTGTCCAGGATGCGCGCCATGGTCTTGAGATA  3080
5' ACCCTGACCGGCAGGCGTATGGAGTCGCACCAACAGGTGCGCGACCGGATCATCAGCGTTCGCCGGAGAC  3150
5' CTCAGCCGATTCAGGGCGTGCGCGGGCCGGCGCCGGCTCGGGCCAGTCGTCGAACCGGCACACAGAAACC  3220
5' CCGCCAGCCAGGCGGGCCTGCGCGCCGCGCGCGTCCAGAGATCGCGGCCGCCGTTCGTCGTCGAGCAGTCC 3290
5' AGGGTGCAGGATCAGCCGCACACTCTCAATCATTGCCTCCGAGTCGGTCTCGAACGGCAGATACTGGAGC  3360
5' AGATACTCGGCCAGGACCGGCCCCATGCGTCCGTCGCGACGCGCGGATTGGCCAGCATCCGGCGCGCGT   3430
5' TGCCGGCGTCCTCCATCACCCACCAGGCGCGGCGTGCCAGCTCGTCGGTCAGTCCAGGCGAGCCGACGGC  3500
5' GGCGACCACGGCTTCCGGTTCGCCGAGCCGGCAGCAGTTGCGCCAGACTCTCGTCGGCATCTGACCCAGA  3570
5' CGGGTCCAGCGGCTGAGATAGACCGGATACCCACCGGGCGAGCCAAGCACATGCCCGGAGATGAGTTCGC  3640
```

```
5' aatgttggttttgacgatcaactctattrctcgcgagtatttaaaaaatgcaccggggccagcccgagcg
                                                                                    5390
                               araC truncated 5' agtttcgtgccggttgtgaagaaaaagtgaatgatgtagccgtcaagttgtcataa
                                                                                    5446
                               araC truncated
```

```
5' TTGCTTGATGTTAGGTGCTTATTTCGCCATTCCGCAATAATCTTAAAAGTTCCCTTGCATTTACATTTT
                                                                                            2870
                                        PompC 5' GAAACATCTATAGCGATAAATGAAACATCTTAAAAGTTTTAGTATCATATTCGTGTTGGATTATTCTGCA
                                                                                            2940
                                        PompC 5' TTTTTGGGGAGAATGGACTTGCCGACTGATTAATGAGGGTTAATCAGTATGCAGTGGCATAAAAAGCAA
                                                                                            3010
                                        PompC 5' ATAAAGGCATATAACAGAGGGTTAATAACatggaacaacgcataaccctgaagattatgcaatgcgctt
                                                                                            3080
                            PompC                    →              cro 5' tggcaaaccaagacagctaaagaCctcggcgtatatcaaagcgcgatcaacaaggccattcatgcaggc
                                                                                            3150
                                        cro 5' cgaaagattttttaactataaacgctgatggaagcgtttatgcggaagaggtaaagcccttcccgagta
                                                                                            3220
                                        cro 5' acaaaaaacaacagcataaaagcgcaaaatgatccctgctgccgggatactcgtttaacgcccatctg
                                                                                            3290
                            cro           →              araC truncated 5' gtggcgggtttaacgccgattgaggccaacggttatctcgattttttttatcgaccgaccgctgggaatga
                                                                                            3360
                                        araC truncated 5' aaggttatattctcaatctcaccattcgcggtcagggggtggtgaaaaatcagggacgagaatttgtctg
                                                                                            3430
                                        araC truncated 5' ccgaccgggtgatattttgctgtcccgccaggagagattcatcactacggtcgtcatccggaggctcgc
                                                                                            3500
                                        araC truncated 5' gaatggtatcaccagtgggttactttcgtccgcgcgcctactggcatgaatggcttaactggccgtcaa
                                                                                            3570
                                        araC truncated 5' tatttgccaataacgggttcctttcgcccggatgaagcgcaccagccgcatttcagcgacctgtttggca
                                                                                            3640
                                        araC truncated
```

Figure 22 continue

SEQUENCE LISTING

<160> NUMBER OF SEQ ID NOS: 20

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccagccagat ggcctgg                                                        17

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacgcgacga cgtggc                                                         16

<210> SEQ ID NO 3
<211> LENGTH: 4420
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gttagcctcc cgccccggtg atgactatca actggcacgg gaaccgttaa agctggaagc         60
cattctggcg cgcgcgcgca aagagggtta cggacagaac taccgcggct gggatcagga        120
ggagaagatc gcctctatcg ccgtaccgct gcgcagtgaa caacgggtga ttggctgtct        180
gaatctggtg tatatggcga gcgcaatgac cattgaacag gcagcggaaa agcatcttcc        240
ggcgctacaa cgggtagcaa aacagatcga agaaggggtt gaatcgcagg ctattctggt        300
ggccggaagg cgaagcggca tgcatttacg ttgacaccat cgttagaaga actcgtcaag        360
aaggcgatag aaggcgatgc gctgcgaatc gggagcggcg ataccgtaaa gcacgaggaa        420
gcggtcagcc cattcgccgc caagctcttc agcaatatca cgggtagcca acgctatgtc        480
ctgatagcgg tccgccacac ccagccggcc acagtcgatg aatccagaaa agcggccatt        540
ttccaccatg atattcggca agcaggcatc gccatgggtc acgacgagat cctcgccgtc        600
gggcatgcgc gccttgagcc tggcgaacag ttcggctggc gcgagcccct gatgctcttc        660
gtccagatca tcctgatcga caagaccggc ttccatccga gtacgtgctc gctcgatgcg        720
atgtttcgct tggtggtcga atgggcaggt agccggatca gcgtatgca gccgccgcat        780 tgcatcagcc atgatggata cttctctggc aggagcaagg tgagatgaca ggagatcctg        840
ccccggcact tcgcccaata gcagccagtc ccttcccgct tcagtgacaa cgtcgagcac        900
agctgcgcaa ggaacgcccg tcgtggccag ccacgatagc cgcgctgcct cgtcctgcag        960
ttcattcagg gcaccggaca ggtcggtctt gacaaaaaga accgggcgcc cctgcgctga       1020
cagccggaac acgcggcat cagagcagcc gattgtctgt tgtgcccagt catagccgaa        1080
tagcctctcc acccaagcgg ccggagaacc tgcgtgcaat ccatcttgtt caatcatgcg       1140
aaacgatcct catcctgtct cttgatcaga tcttgatccc ctgcgccatc agatccttgg      1200

```
cggcaagaaa gccatccagt ttactttgca gggcttccca accttaccag agggcgcccc     1260
agctggcaat tccggttcgc ttgctgtcca tagtggtcag tgcgtcctgc tgatgtgctc     1320
agtatcaccg ccagtggtat ttatgtcaac accgccagag ataatttatc accgcagatg     1380
gttatctgta tgttttttat atgaatttat tttttgcagg ggggcattgt ttggtaggtg     1440
agagatctga attgctatgt ttagtgagtt gtatctattt attttcaat aaatacaatt     1500 ggttatgtgt tttgggggcg atcgtgaggc aaagaaaacc cggcgctgag gccgggttat     1560
tcttgttctc tggtcaaatt atatagttgg aaaacaagga tgcatatatg aatgaacgat     1620
gcagaggcaa tgccgatggc gatagtgggt atcatgtagc cgcttatgct ggaaagaagc     1680
aataacccgc agaaaaacaa agctccaagc tcaacaaaac taagggcata gacaataact     1740
accgatgtca tacccata ctctctaatc ttggccagtc ggcgcgttct gcttccgatt       1800
agaaacgtca aggcagcaat caggattgca atcatggttc ctgcatatga tgacaatgtc     1860
gccccaagac catctctatg agctgaaaaa gaaacaccag gaatgtagtg gcggaaaagg     1920
agatagcaaa tgcttacgat aacgtaagga attattacta tgtaaacacc aggcatgatt     1980
ctgttccgca taattactcc tgataattaa tccttaactt tgcccacctg ccttttaaaa     2040
cattccagta tatcactttt cattcttgcg tagcaatatg ccatctcttc agctatctca     2100
gcattggtga ccttgttcag aggcgctgag agatggcctt tttctgatag ataatgttct     2160
gttaaaatat ctccggcctc atcttttgcc cgcaggctaa tgtctgaaaa ttgaggtgac     2220
gggttaaaaa taatatcctt ggcaacctt tttatatccc tttaaattt tggcttaatg      2280 actatatcca atgagtcaaa agctcccct tcaatatctg ttgcccctaa gacctttaat     2340
atatcgccaa atacaggtag cttggcttct accttcaccg ttgttcggcc gatgaaatgc     2400
atatgcataa catcgtcttt ggtggttccc ctcatcagtg gctctatctg aacgcgctct     2460
ccactgctta atgacattcc tttcccgatt aaaaaatctg tcagatcgga tgtggtcggc     2520
ccgaaaacag ttctggcaaa accaatggtg tcgccttcaa caaacaaaaa agatgggaat     2580
cccaatgatt cgtcatctgc gaggctgttc ttaatatctt caactgaagc tttagagcga     2640
tttatcttct gaaccagact cttgtcattt gttttggtaa agagaaaagt ttttccatcg     2700
attttatgaa tatacaaata attggagcca acctgcaggt gatgattatc agccagcaga     2760
gaattaagga aaacagacag gtttattgag cgcttatctt tcccttatt tttgctgcgg      2820 taagtcgcat aaaaaccatt cttcataatt caatccattt actatgttat gttctgaggg     2880
gagtgaaaat tccctaatt cgatgaagat tcttgctcaa ttgttatcag ctatgcgccg      2940
accagaacac cttgccgatc agccaaacgt ctcttcaggc cactgactag cgataacttt     3000
ccccacaacg gaacaactct cattgcatgg gatcattggg tactgtgggt ttagtggttg     3060
taaaaacacc tgaccgctat ccctgatcag tttcttgaag gtaaactcat cacccccaag     3120
tctggctatg cagaaatcac ctggctcaac agcctgctca gggtcaacga gaattaacat     3180
tccgtcagga aagcttggct tggagcctgt tggtgcggtc atggaattac cttcaacctc     3240
aagccagaat gcagaatcac tggcttttt ggttgtgctt acccatctct ccgcatcacc      3300
tttggtaaag gttctaagct taggtgagaa catccctgcc tgaacatgag aaaaaacagg     3360
gtactcatac tcacttctaa gtgacggctg catactaacc gcttcataca tctcgtagat     3420
ttctctggcg attgaagggc taaattcttc aacgctaact tgagaatttt tgtaagcaa      3480 tgcggcgtta taagcattta atgcattgat gccattaaat aaagcaccaa cgcctgactg     3540
ccccatcccc atcttgtctg cgacagattc ctgggataag ccaagttcat ttttcttttt     3600
```

```
ttcataaatt gctttaaggc gacgtgcgtc ctcaagctgc tcttgtgtta atggtttctt    3660
ttttgtgctc atacgttaaa tctatcaccg caagggataa atatctaaca ccgtgcgtgt    3720
tgactatttt acctctggcg gtgataatgg ttgcatgtac taaggaggtt gtatggaaca    3780
acgcataacc ctgaaagatt atgcaatgcg ctttgggcaa accaagacag ctaaagatct    3840
cggcgtatat caaagcgcga tcaacaaggc cattcatgca ggccgaaaga ttttttttaac   3900 tataaacgct gatggaagcg tttatgcgga agaggtaaag ccttcccga gtaacaaaaa    3960 aacaacagca taaataaccc cgctcttaca cattccagcc ctgaaaaagg gcatcaaatt    4020
aaaccacacc tatggtgtat gcatttattt gcatacattc aatcaattgt tatctaagga    4080
aatgaccatg attacggatt cactggccgt cgttttacaa cgtcgtgact gggaaaaccc    4140
tggcgttacc caacttaatc gccttgcagc acatccccct ttcgccagct ggcgtaatag    4200
cgaagaggcc cgcaccgatc gcccttccca acagttgcgc agcctgaatg gcgaatggcg    4260
ctttgcctgg tttccggcac cagaagcggt gccggaaagc tggctggagt gcgatcttcc    4320
tgaggccgat actgtcgtcg tcccctcaaa ctggcagatg cacggttacg atgcgcccat    4380
ctacaccaac gtgacctatc ccattacggt caatccgccg                         4420

<210> SEQ ID NO 4
<211> LENGTH: 4420
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gttagcctcc cgccccggtg atgactatca actggcacgg gaaccgttaa agctggaagc      60
cattctggcg cgcgcgcgca aagagggtta cggacagaac taccgcggct gggatcagga    120
ggagaagatc gcctctatcg ccgtaccgct gcgcagtgaa caacgggtga ttggctgtct    180
gaatctggtg tatatggcga gcgcaatgac cattgaacag gcagcggaaa agcatcttcc    240
ggcgctacaa cgggtagcaa aacagatcga agaaggggtt gaatcgcagg ctattctggt    300
ggccggaagg cgaagcggca tgcatttacg ttgacaccat cgttagaaga actcgtcaag    360
aaggcgatag aaggcgatgc gctgcgaatc gggagcggcg ataccgtaaa gcacgaggaa    420
gcggtcagcc cattcgccgc caagctcttc agcaatatca cgggtagcca acgctatgtc    480
ctgatagcgg tccgccacac ccagccggcc acagtcgatg aatccagaaa agcggccatt    540
ttccaccatg atattcggca agcaggcatc gccatgggtc acgacgagat cctcgccgtc    600
gggcatgcgc gccttgagcc tggcgaacag ttcggctggc gcgagcccct gatgctcttc    660
gtccagatca tcctgatcga caagaccggc ttccatccga gtacgtgctc gctcgatgcg    720
atgtttcgct tggtggtcga atgggcaggt agccggatca gcgtatgca gccgccgcat    780 tgcatcagcc atgatggata ctttctcggc aggagcaagg tgagatgaca ggagatcctg    840
ccccggcact tcgcccaata gcagccagtc ccttcccgct tcagtgacaa cgtcgagcac    900
agctgcgcaa ggaacgcccg tcgtggccag ccacgatagc cgcgctgcct cgtcctgcag    960
ttcattcagg gcaccggaca ggtcggtctt gacaaaaaga accgggcgcc cctgcgctga   1020
cagccggaac acggcggcat cagagcagcc gattgtctgt tgtgcccagt catagccgaa   1080
tagcctctcc acccaagcgg ccggagaacc tgcgtgcaat ccatcttgtt caatcatgcg   1140
aaacgatcct catcctgtct cttgatcaga tcttgatccc ctgcgccatc agatccttgg   1200
```

```
cggcaagaaa gccatccagt ttactttgca gggcttccca accttaccag agggcgcccc   1260
agctggcaat tccggttcgc ttgctgtcca tagtggtcag tgcgtcctgc tgatgtgctc   1320
agtatcaccg ccagtggtat ttatgtcaac accgccagag ataatttatc accgcagatg   1380
gttatctgta tgtttttat atgaatttat tttttgcagg ggggcattgt ttggtaggtg    1440
agagatctga attgctatgt ttagtgagtt gtatctattt attttcaat aaatacaatt    1500 ggttatgtgt tttggggcg atcgtgaggc aaagaaaacc cggcgctgag gccgggttat    1560
tcttgttctc tggtcaaatt atatagttgg aaaacaagga tgcatatatg aatgaacgat   1620
gcagaggcaa tgccgatggc gatagtgggt atcatgtagc cgcttatgct ggaaagaagc   1680
aataacccgc agaaaaacaa agctccaagc tcaacaaaac taagggcata gacaataact   1740
accgatgtca tacccata ctctctaatc ttggccagtc ggcgcgttct gcttccgatt     1800
agaaacgtca aggcagcaat caggattgca atcatggttc ctgcatatga tgacaatgtc   1860
gccccaagac catctctatg agctgaaaaa gaaacaccag gaatgtagtg gcggaaaagg   1920
agatagcaaa tgcttacgat aacgtaagga attattacta tgtaaacacc aggcatgatt   1980
ctgttccgca taattactcc tgataattaa tccttaactt tgcccacctg ccttttaaaa   2040
cattccagta tatcactttt cattcttgcg tagcaatatg ccatctcttc agctatctca   2100
gcattggtga ccttgttcag aggcgctgag agatggcctt tttctgatag ataatgttct   2160
gttaaaatat ctccggcctc atcttttgcc cgcaggctaa tgtctgaaaa ttgaggtgac   2220
gggttaaaaa taatatcctt ggcaacctt tttatatccc ttttaaattt tggcttaatg    2280
actatatcca atgagtcaaa agctccccct tcaatatctg ttgcccctaa gacctttaat   2340
atatcgccaa atacaggtag cttggcttct accttcaccg ttgttcggcc gatgaaatgc   2400
atatgcataa catcgtcttt ggtggttccc ctcatcagtg gctctatctg aacgcgctct   2460
ccactgctta atgacattcc tttcccgatt aaaaaatctg tcagatcgga tgtggtcggc   2520
ccgaaaacag ttctggcaaa accaatggtg tcgccttcaa caaacaaaaa agatgggaat   2580
cccaatgatt cgtcatctgc gaggctgttc ttaatatctt caactgaagc tttagagcga   2640
tttatcttct gaaccagact cttgtcattt gttttggtaa agagaaaagt ttttccatcg   2700
attttatgaa tatacaaata attggagcca acctgcaggt gatgattatc agccagcaga   2760
gaattaagga aaacagacag gtttattgag cgcttatctt tcccttattt tttgctgcgg   2820
taagtcgcat aaaaaccatt cttcataatt caatccattt actatgttat gttctgaggg   2880
gagtgaaaat tccctaatt cgatgaagat tcttgctcaa ttgttatcag ctatgcgccg    2940
accagaacac cttgccgatc agccaaacgt ctcttcaggc cactgactag cgataacttt   3000
ccccacaacg gaacaactct cattgcatgg gatcattggg tactgtgggt ttagtggttg   3060
taaaaacacc tgaccgctat ccctgatcag tttcttgaag gtaaactcat cacccccaag   3120
tctggctatg cagaaatcac ctggctcaac agcctgctca gggtcaacga gaattaacat   3180
tccgtcagga aagcttggct tggagcctgt tggtgcggtc atggaattac cttcaacctc   3240
aagccagaat gcagaatcac tggcttttt ggttgtgctt acccatctct ccgcatcacc    3300
tttggtaaag gttctaagct taggtgagaa catccctgcc tgaacatgag aaaaaacagg   3360
gtactcatac tcacttctaa gtgacggctg catactaacc gcttcataca tctcgtagat   3420
ttctctggcg attgaagggc taaattcttc aacgctaact ttgagaattt ttgcaagcaa   3480
tgcggcgtta taagcattta atgcattgat gccattaaat aaagcaccaa cgcctgactg   3540
```

| | |
|---|---|
| ccccatcccc atcttgtctg cgacagattc ctgggataag ccaagttcat tttctttttt | 3600 |
| ttcataaatt gctttaaggc gacgtgcgtc ctcaagctgc tcttgtgtta atggtttctt | 3660 |
| ttttgtgctc atacgttaaa tctatcaccg caagggataa atatctaaca ccgtgcgtgt | 3720 |
| tgactatttt acctctggcg gtgataatgg ttgcatgtac taaggaggtt gtatggaaca | 3780 |
| acgcataacc ctgaaagatt atgcaatgcg ctttgggcaa accaagacag ctaaagatct | 3840 |
| cggcgtatat caaagcgcga tcaacaaggc cattcatgca ggccgaaaga ttttttaac | 3900 |
| tataaacgct gatggaagcg tttatgcgga agaggtaaag cccttcccga gtaacaaaaa | 3960 |
| aacaacagca taataaccc cgctcttaca cattccagcc ctgaaaaagg gcatcaaatt | 4020 |
| aaaccacacc tatggtgtat gcatttattt gcatacattc aatcaattgt tatctaagga | 4080 |
| aatgaccatg attacggatt cactggccgt cgttttacaa cgtcgtgact gggaaaaccc | 4140 |
| tggcgttacc caacttaatc gccttgcagc acatcccct ttcgccagct ggcgtaatag | 4200 |
| cgaagaggcc cgcaccgatc gcccttccca cagttgcgc agcctgaatg gcgaatggcg | 4260 |
| ctttgcctgg tttccggcac cagaagcggt gccggaaagc tggctggagt gcgatcttcc | 4320 |
| tgaggccgat actgtcgtcg tccctcaaa ctggcagatg cacggttacg atgcgcccat | 4380 |
| ctacaccaac gtgacctatc ccattacggt caatccgccg | 4420 |

<210> SEQ ID NO 5
<211> LENGTH: 4312
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| | |
|---|---|
| gttagcctcc cgccccggtg atgactatca actggcacgg gaaccgttaa agctggaagc | 60 |
| cattctggcg cgcgcgcgca aagagggtta cggacagaac taccgcggct gggatcagga | 120 |
| ggagaagatc gcctctatcg ccgtaccgct gcgcagtgaa caacgggtga ttggctgtct | 180 |
| gaatctggtg tatatggcga gcgcaatgac cattgaacag gcagcggaaa agcatcttcc | 240 |
| ggcgctacaa cgggtagcaa aacagatcga agaaggggtt gaatcgcagg ctattctggt | 300 |
| ggccggaagg cgaagcggca tgcatttacg ttgacaccat cgttagaaga actcgtcaag | 360 |
| aaggcgatag aaggcgatgc gctgcgaatc gggagcggcg ataccgtaaa gcacgaggaa | 420 |
| gcggtcagcc cattcgccgc caagctcttc agcaatatca cgggtagcca acgctatgtc | 480 |
| ctgatagcgg tccgccacac ccagccggcc acagtcgatg aatccagaaa agcggccatt | 540 |
| ttccaccatg atattcggca agcaggcatc gccatgggtc acgacgagat cctcgccgtc | 600 |
| gggcatgcgc gccttgagcc tggcgaacag ttcggctggc gcgagcccct gatgctcttc | 660 |
| gtccagatca tcctgatcga caagaccggc ttccatccga gtacgtgctc gctcgatgcg | 720 |
| atgtttcgct tggtggtcga atgggcaggt agccggatca gcgtatgca gccgccgcat | 780 |
| tgcatcagcc atgatggata ctttctcggc aggagcaagg tgagatgaca ggagatcctg | 840 |
| ccccggcact tcgcccaata gcagccagtc ccttcccgct tcagtgacaa cgtcgagcac | 900 |
| agctgcgcaa ggaacgcccg tcgtggccag ccacgatagc cgcgctgcct cgtcctgcag | 960 |
| ttcattcagg gcaccggaca ggtcggtctt gacaaaaaga accgggcgcc cctgcgctga | 1020 |
| cagccggaac acgcggcat cagagcagcc gattgtctgt tgtgcccagt catagccgaa | 1080 |
| tagcctctcc acccaagcgg ccggagaacc tgcgtgcaat ccatcttgtt caatcatgcg | 1140 |

```
aaacgatcct catcctgtct cttgatcaga tcttgatccc ctgcgccatc agatccttgg    1200
cggcaagaaa gccatccagt ttactttgca gggcttccca accttaccag agggcgcccc    1260
agctggcaat tccggttcgc ttgctgtcca tagtggtcag tgcgtcctgc tgatgtgctc    1320
agtatcaccg ccagtggtat ttatgtcaac accgccagag ataatttatc accgcagatg    1380
gttatctgta tgttttttat atgaatttat tttttgcagg ggggcattgt ttggtaggtg    1440
agagatctga attgctatgt ttagtgagtt gtatctattt attttcaat aaatacaatt    1500 ggttatgtgt tttgggggcg atcgtgaggc aaagaaaacc cggcgctgag gccgggttat    1560
tcttgttctc tggtcaaatt atatagttgg aaaacaagga tgcatatatg aatgaacgat    1620
gcagaggcaa tgccgatggc gatagtgggt atcatgtagc cgcttatgct ggaaagaagc    1680
aataacccgc agaaaaacaa agctccaagc tcaacaaaac taagggcata gacaataact    1740
accgatgtca tacccata ctctctaatc ttggccagtc ggcgcgttct gcttccgatt    1800
agaaacgtca aggcagcaat caggattgca atcatggttc ctgcatatga tgacaatgtc    1860
gccccaagac catctctatg agctgaaaaa gaaacaccag gaatgtagtg gcggaaaagg    1920
agatagcaaa tgcttacgat aacgtaagga attattacta tgtaaacacc aggcatgatt    1980
ctgttccgca taattactcc tgataattaa tccttaactt tgcccacctg ccttttaaaa    2040
cattccagta tatcactttt cattcttgcg tagcaatatg ccatctcttc agctatctca    2100
gcattggtga ccttgttcag aggcgctgag agatggcctt tttctgatag ataatgttct    2160
gttaaaatat ctccggcctc atctttgcc cgcaggctaa tgtctgaaaa ttgaggtgac    2220
gggttaaaaa taatatcctt ggcaaccttt tttatatccc ttttaaattt tggcttaatg    2280
actatatcca atgagtcaaa agctcccct tcaatatctg ttgcccctaa gacctttaat    2340
atatcgccaa atacaggtag cttggcttct accttcaccg ttgttcggcc gatgaaatgc    2400
atatgcataa catcgtcttt ggtggttccc ctcatcagtg gctctatctg aacgcgctct    2460
ccactgctta atgacattcc tttcccgatt aaaaaatctg tcagatcgga tgtggtcggc    2520
ccgaaaacag ttctggcaaa accaatggtg tcgccttcaa caaacaaaaa agatgggaat    2580
cccaatgatt cgtcatctgc gaggctgttc ttaatatctt caactgaagc tttagagcga    2640
tttatcttct gaaccagact cttgtcattt gttttggtaa agagaaaagt ttttccatcg    2700
attttatgaa tatacaaata attggagcca acctgcaggt gatgattatc agccagcaga    2760
gaattaagga aaacagacag gtttattgag cgcttatctt tccctttatt tttgctgcgg    2820
taagtcgcat aaaaaccatt cttcataatt caatccattt actatgttat gttctgaggg    2880
gagtgaaaat tcccctaatt cgatgaagat tcttgctcaa ttgttatcag ctatgcgccg    2940
accagaacac cttgccgatc agccaaacgt ctcttcaggc cactgactag cgataacttt    3000
ccccacaacg gaacaactct cattgcatgg gatcattggg tactgtgggt ttagtggttg    3060
taaaaacacc tgaccgctat ccctgatcag tttcttgaag gtaaactcat cacccccaag    3120
tctggctatg cagaaatcac ctggctcaac agcctgctca gggtcaacga gaattaacat    3180
tccgtcagga aagcttggct tggagcctgt tggtgcggtc atggaattac cttcaacctc    3240
aagccagaat gcagaatcac tggctttttt ggttgtgctt acccatctct ccgcatcacc    3300
tttggtaaag gttctaagct taggtgagaa catccctgcc tgaacatgag aaaaaacagg    3360
gtactcatac tcacttctaa gtgacggctg catactaacc gcttcataca tctcgtagat    3420
ttctctggcg attgaagggc taaattcttc aacgctaact ttgagaattt ttgtaagcaa    3480
tgcggcgtta taagcatttta atgcattgat gccattaaat aaagcaccaa cgcctgactg    3540
```

```
ccccatcccc atcttgtctg cgacagattc ctgggataag ccaagttcat ttttcttttt    3600
ttcataaatt gctttaaggc gacgtgcgtc ctcaagctgc tcttgtgtta atggtttctt    3660
ttttgtgctc atacgttaaa tctatcaccg caagggataa atatctaaca ccgtgcgtgt    3720
tgactatttt acctctggcg gtgataatgg ttgcatgtac taaggaggtt gtatggaaca    3780
acgcataacc ctgaaagatt atgcaatgcg ctttgggcaa accaagacag ctaaagatct    3840
cggcgtatat caaagcgcga tcaacaaggc cattcatgca ggccgaaaga ttttttttaac   3900 tataaacgct gatggaagcg tttatgcgga agaggtaaag cccttcccga gtaacaaaaa    3960
aacaacagca taaatgacca tgattacgga ttcactggcc gtcgttttac aacgtcgtga    4020
ctgggaaaac cctggcgtta cccaacttaa tcgccttgca gcacatcccc ctttcgccag    4080
ctggcgtaat agcgaagagg cccgcaccga tcgcccttcc caacagttgc gcagcctgaa    4140
tggcgaatgg cgctttgcct ggtttccggc accagaagcg gtgccggaaa gctggctgga    4200
gtgcgatctt cctgaggccg atactgtcgt cgtcccctca aactggcaga tgcacggtta    4260
cgatgcgccc atctacacca acgtgaccta tcccattacg gtcaatccgc cg            4312
```

```
<210> SEQ ID NO 6
<211> LENGTH: 4312
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
```

```
gttagcctcc cgccccggtg atgactatca actggcacgg gaaccgttaa agctggaagc      60
cattctggcg cgcgcgcgca aagagggtta cggacagaac taccgcggct gggatcagga     120
ggagaagatc gcctctatcg ccgtaccgct gcgcagtgaa caacgggtga ttggctgtct     180
gaatctggtg tatatggcga gcgcaatgac cattgaacag gcagcggaaa agcatcttcc     240
ggcgctacaa cgggtagcaa aacagatcga agaaggggtt gaatcgcagg ctattctggt     300
ggccggaagg cgaagcggca tgcatttacg ttgacaccat cgttagaaga actcgtcaag     360
aaggcgatag aaggcgatgc gctgcgaatc gggagcggcg ataccgtaaa gcacgaggaa     420
gcggtcagcc cattcgccgc caagctcttc agcaatatca cgggtagcca acgctatgtc     480
ctgatagcgg tccgccacac ccagccggcc acagtcgatg aatccagaaa agcggccatt     540
ttccaccatg atattcggca agcaggcatc gccatgggtc acgacgagat cctcgccgtc     600
gggcatgcgc gccttgagcc tggcgaacag ttcggctggc gcgagcccct gatgctcttc     660
gtccagatca tcctgatcga caagaccggc ttccatccga gtacgtgctc gctcgatgcg     720
atgtttcgct tggtggtcga atgggcaggt agccggatca agcgtatgca gccgccgcat     780
tgcatcagcc atgatggata ctttctcggc aggagcaagg tgagatgaca ggagatcctg     840
ccccggcact tcgcccaata gcagccagtc ccttcccgct tcagtgacaa cgtcgagcac     900
agctgcgcaa ggaacgcccg tcgtggccag ccacgatagc cgcgctgcct cgtcctgcag     960
ttcattcagg gcaccggaca ggtcggtctt gacaaaaaga accgggcgcc cctgcgctga    1020
cagccggaac acggcggcat cagagcagcc gattgtctgt tgtgcccagt catagccgaa    1080
tagcctctcc acccaagcgg ccggagaacc tgcgtgcaat ccatcttgtt caatcatgcg    1140
aaacgatcct catcctgtct cttgatcaga tcttgatccc ctgcgccatc agatccttgg    1200
cggcaagaaa gccatccagt ttactttgca gggcttccca accttaccag agggcgcccc    1260
```

```
agctggcaat tccggttcgc ttgctgtcca tagtggtcag tgcgtcctgc tgatgtgctc    1320
agtatcaccg ccagtggtat ttatgtcaac accgccagag ataatttatc accgcagatg    1380
gttatctgta tgtttttat atgaatttat ttttgcagg ggggcattgt ttggtaggtg     1440
agagatctga attgctatgt ttagtgagtt gtatctattt atttttcaat aaatacaatt    1500
ggttatgtgt tttggggcg atcgtgaggc aaagaaaacc cggcgctgag gccgggttat    1560
tcttgttctc tggtcaaatt atatagttgg aaaacaagga tgcatatatg aatgaacgat    1620
gcagaggcaa tgccgatggc gatagtgggt atcatgtagc cgcttatgct ggaaagaagc    1680
aataacccgc agaaaaacaa agctccaagc tcaacaaaac taagggcata gacaataact    1740
accgatgtca tacccata ctctctaatc ttggccagtc ggcgcgttct gcttccgatt      1800
agaaacgtca aggcagcaat caggattgca atcatggttc ctgcatatga tgacaatgtc    1860
gccccaagac catctctatg agctgaaaaa gaaacaccag gaatgtagtg gcggaaaagg    1920
agatagcaaa tgcttacgat aacgtaagga attattacta tgtaaacacc aggcatgatt    1980
ctgttccgca taattactcc tgataattaa tccttaactt tgcccacctg ccttttaaaa    2040
cattccagta tatcactttt cattcttgcg tagcaatatg ccatctcttc agctatctca    2100
gcattggtga ccttgttcag aggcgctgag agatggcctt tttctgatag ataatgttct    2160
gttaaaatat ctccggcctc atcttttgcc cgcaggctaa tgtctgaaaa ttgaggtgac    2220
gggttaaaaa taatatcctt ggcaaccttt tttatatccc ttttaaattt tggcttaatg    2280
actatatcca atgagtcaaa aagctcccct tcaatatctg ttgcccctaa gacctttaat    2340
atatcgccaa atacaggtag cttggcttct accttcaccg ttgttcggcc gatgaaatgc    2400
atatgcataa catcgtcttt ggtggttccc ctcatcagtg gctctatctg aacgcgctct    2460
ccactgctta atgacattcc tttcccgatt aaaaaatctg tcagatcgga tgtggtcggc    2520
ccgaaaacag ttctggcaaa accaatggtg tcgccttcaa caaacaaaaa agatgggaat    2580
cccaatgatt cgtcatctgc gaggctgttc ttaatatctt caactgaagc tttagagcga    2640
tttatcttct gaaccagact cttgtcattt gttttggtaa agagaaaagt ttttccatcg    2700
attttatgaa tatacaaata attggagcca acctgcaggt gatgattatc agccagcaga    2760
gaattaagga aaacagacag gtttattgag cgcttatctt tccctttatt tttgctgcgg    2820
taagtcgcat aaaaaccatt cttcataatt caatccattt actatgttat gttctgaggg    2880
gagtgaaaat tcccctaatt cgatgaagat tcttgctcaa ttgttatcag ctatgcgccg    2940
accagaacac cttgccgatc agccaaacgt ctcttcaggc cactgactag cgataacttt    3000
ccccacaacg gaacaactct cattgcatgg gatcattggg tactgtgggt ttagtggttg    3060
taaaaacacc tgaccgctat ccctgatcag tttcttgaag gtaaactcat caccccaag    3120 tctggctatg cagaaatcac ctggctcaac agcctgctca gggtcaacga gaattaacat    3180
tccgtcagga aagcttggct tggagcctgt tggtgcggtc atggaattac cttcaacctc    3240
aagccagaat gcagaatcac tggctttttt ggttgtgctt acccatctct ccgcatcacc    3300
tttggtaaag gttctaagct taggtgagaa catccctgcc tgaacatgag aaaaaacagg    3360
gtactcatac tcacttctaa gtgacggctg catactaacc gcttcataca tctcgtagat    3420
ttctctggcg attgaagggc taaattcttc aacgctaact tgagaatttt tgcaagcaa    3480 tgcggcgtta taagcatttta atgcattgat gccattaaat aaagcaccaa cgcctgactg    3540
ccccatcccc atcttgtctg cgacagattc ctgggataag ccaagttcat ttttcttttt    3600
```

```
ttcataaatt gctttaaggc gacgtgcgtc ctcaagctgc tcttgtgtta atggtttctt    3660
ttttgtgctc atacgttaaa tctatcaccg caagggataa atatctaaca ccgtgcgtgt    3720
tgactatttt acctctggcg gtgataatgg ttgcatgtac taaggaggtt gtatggaaca    3780
acgcataacc ctgaaagatt atgcaatgcg ctttgggcaa accaagacag ctaaagatct    3840
cggcgtatat caaagcgcga tcaacaaggc cattcatgca ggccgaaaga ttttttttaac   3900
tataaacgct gatggaagcg tttatgcgga agaggtaaag cccttcccga gtaacaaaaa    3960
aacaacagca taaatgacca tgattacgga ttcactggcc gtcgttttac aacgtcgtga    4020
ctgggaaaac cctggcgtta cccaacttaa tcgccttgca gcacatcccc ctttcgccag    4080
ctggcgtaat agcgaagagg cccgcaccga tcgcccttcc caacagttgc gcagcctgaa    4140
tggcgaatgg cgctttgcct ggtttccggc accagaagcg gtgccggaaa gctggctgga    4200
gtgcgatctt cctgaggccg atactgtcgt cgtcccctca aactggcaga tgcacggtta    4260
cgatgcgccc atctacacca acgtgaccta tcccattacg gtcaatccgc cg           4312
```

<210> SEQ ID NO 7
<211> LENGTH: 2473
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 7

```
accactctac gctggtggcg atctcttcac cggtagcgca gtccaccgcc aaagctcgca      60
cagaatcact gccaaaatcg aggccaattg caatcgccat cgtttcactc catccaaaaa     120
aacgggtatg gagaaacagt agagagttgc gataaaaagc gtcaggtagg atccgctaat     180
cttatggata aaaatgctat ggcatagcaa agtgtgaacc agcaatagac ataagcggct     240
atttaacgac cctgccctga accgacgacc gggtcgaatt tgctttcgaa tttctgccat     300
tcatccgctt attatcactt attcaggcgt agcaccaggc gtttaagggc accaataact     360
gccttaaaaa aattacgccc cgccctgcca ctcatcgcag tactgttgta attcattaag     420
cattctgccg acatggaagc catcacagac ggcatgatga acctgaatcg ccagcggcat     480
cagcaccttg tcgccttgcg tataatattt gcccatggtg aaaacggggg cgaagaagtt     540
gtccatattg gccacgttta atcaaaact ggtgaaactc acccagggat tggctgagac     600
gaaaaacata ttctcaataa acccttaagg gaaataggcc aggttttcac cgtaacacgc     660
cacatcttgc gaatatatgt gtagaaactg ccggaaatcg tcgtggtatt cactccagag     720
cgatgaaaac gtttcagttt gctcatggaa acggtgtaaa caagggtgaa cactatccca    780
tatcaccagc tcaccgtctt tcattgccat acgaattcc ggatgagcat tcatcaggcg    840
ggcaagaatg tgaataaagg ccggataaaa cttgtgctta ttttcttta cggtcttaa    900
aaaggccgta atatccagct gaacggtctg gttataggta cattgagcaa ctgactgaaa    960
tgcctcaaaa tgttctttac gatgccattg ggatatatca acggtggtat atccagtgat   1020
ttttttctcc attttagctt ccttagctcg tgaaatctc gataactcaa aaatacgcc     1080
cggtagtgat cttatttcat tatggtgaaa gttggaacct cttacgtgcc gatcaacgtc   1140
tcattttcgc caaaagttgg cccagggctt cccggtatca acagggacac caggatttat   1200
ttattctgcg aagtgatctt ccgtcacatt aagacccact ttcacattta agttgttttt   1260
ctaatccgca tatgatcaat tcaaggccga ataagaaggc tggctctgca ccttggtgat   1320
```

```
caaataattc gatagcttgt cgtaataatg gcggcatact atcagtagta ggtgttccc      1380 tttcttcttt agcgacttga tgctcttgat cttccaatac gcaacctaaa gtaaaatgcc     1440
ccacagcgct gagtgcatat aatgcattct ctagtgaaaa accttgttgg cataaaaagg     1500
ctaattgatt ttcgagagtt tcatactgtt tttctgtagg ccgtgtacct aaatgtactt     1560
ttgctccatc gcgatgactt agtaaagcac atctaaaact tttagcgtta ttacgtaaaa     1620
aatcttgcca gctttcccct tctaaagggc aaaagtgagt atggtgccta tctaacatct     1680
caatggctaa ggcgtcgagc aaagcccgct tatttttac atgccaatac aatgtaggct      1740
gctctacacc tagcttctgg gcgagtttac gggttgttaa accttcgatt ccgacctcat     1800
taagcagctc taatgcgctg ttaatcactt tacttttatc taatctagac atcattaatt    1860
cctaattttt gttgacactc tatcattgat agagttattt taccactccc tatcagtgat    1920
agagaaaagt gaaatgtact aaggaggttg tatggaacaa cgcataaccc tgaaagatta    1980
tgcaatgcgc tttgggcaaa ccaagacagc taaagacctc ggcgtatatc aaagcgcgat    2040
caacaaggcc attcatgcag gccgaaagat ttttttaact ataaacgctg atggaagcgt    2100
ttatgcggaa gaggtaaagc ccttcccgag taacaaaaaa acaacagcat aacgccgtgc    2160
aaataatcaa tgtggacttt tctgccgtga ttatagacac ttttgttacg cgttttgtc     2220 atggctttgg tcccgctttg ttacagaatg cttttaataa gcggggttac cggttgggtt    2280
agcgagaaga gccagtaaaa gacgcagtga cggcaatgtc tgatgcaata tggacaattg    2340
gtttcttctc tgaatggtgg gagtatgaaa agtatggctg aagcgcaaaa tgatcccctg    2400
ctgccgggat actcgtttaa cgcccatctg gtggcgggtt taacgccgat tgaggccaac    2460
ggttatctcg att                                                       2473
```

<210> SEQ ID NO 8
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
acgcgggtta gatccgcaga caccctttgt tgtcgaagcc acgccgctcg aagcagatgc       60
cttacgccgc gaactcgcca actacgatgt tattttgagg ttttgaggcg tttatgctgc      120
acacattaca tcgctcaccc tggctgacgg attttgctgc gctgctgcgt ctgctcagtg      180
aaggagacga actgctatta ttgcaagatg gcgtaactgc cgcagttgac ggtaaccgct      240
accttgaaag tctgcgtaat gcccccatta aggtctatgc cctgaacgaa gaccttattg      300
cccgcggttt gactggtcaa atttcgaacg acatcattct cattgactat actgatttcg      360
tcagacttac ggttaagcac cccagccaga tggcctggtg atggcgggat cgttgtatat      420
ttcttgacac cttttcggca tcgccctaaa attcggcgtc ctcatattgt gtgaggacgt      480
tttattacgt gtttacgaag caaaagctaa aaccaggagc tatttaatgg caacagttaa      540
ccagctggta cgcaaaccac gtgctcgcaa agttgcgaaa agcaacgtgc ctgcgctgga      600
agcatgcccg caaaaacgtg gcgtatgtac tcgtgtatat actaccactc ctagaaaacc      660
gaactccgcg ctgcgtaaag tatgccgtgt tcgtctgact aacggtttcg aagtgacttc      720
ctacatcggt ggtgaaggtc acaacctgca ggagcactcc gtgatcctga tccgtggcgg      780
tcgtgttaaa gacctcccgg gtgttcgtta ccacaccgta cgtggtgcgc ttgactgctc      840
```

```
cggcgttaaa gaccgtaagc aggctcgttc caagtatggc gtgaagcgtc ctaaggctta    900
atggttctcc gttaagtaag gccaaacgtt ttaacttaaa tgtcaaacta aactcgtaga    960
gttttggaca atcctgaatt aacaacggag tatttccatg ccacgtcgtc gcgtcattgg   1020
tcagcgtaaa attctgccgg atccgaagtt cggatcagaa ctgctggcta aatttgtaaa   1080
tatcctgatg gtagatggta aaaaatctac tgctgaatct atcgtataca gcgcgctgga   1140
gaccctggct cagcgctctg gtaaatctga actggaagca ttcgaagtag ctctcgaaaa   1200
cgtgcgcccg actgtagaag ttaagtctcg ccgcgttggt ggttctactt atcaggtacc   1260
agttgaagtc cgtccggttc gtcgtaatgc tctggcaatg cgttggatcg ttgaagctgc   1320
```

<210> SEQ ID NO 9
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: May or may not be present
<220> FEATURE:
<221> NAME/KEY: modified_base
<222> LOCATION: (6)..(10)
<223> OTHER INFORMATION: May or may not be present
<220> FEATURE:
<221> NAME/KEY: modified_base
<222> LOCATION: (1428)..(1500)
<223> OTHER INFORMATION: May or may not be present

<400> SEQUENCE: 9

```
ggcrgsmsyw acacatgcag tcgaacggta acaggaagca gcttgcttct ttgctgacga     60
gtggcggacg ggtgagtaat gtctgggaaa ctgcctgatg gaggggggata actactggaa    120 acggtagcta ataccgcata acgtcgcaag accaaagagg gggaccttcg ggcctcttgc    180
catcggatgt gcccagatgg gattagctag taggtggggt aacggctcac ctaggcgacg    240
atccctagct ggtctgagag gatgaccagc cacactggaa ctgagacacg gtccagactc    300
ctacgggagg cagcagtggg gaatattgca caatgggcgc aagcctgatg cagccatgcc    360
gcgtgtatga agaaggcctt cgggttgtaa agtactttca gcggggagga agggagtaaa    420
gttaatacct ttgctcattg acgttacccg cagaagaagc accggctaac tccgtgccag    480
cagccgcggt aatacggagg gtgcaagcgt taatcggaat tactgggcgt aaagcgcacg    540
caggcggttt gttaagtcag atgtgaaatc cccgggctca acctgggaac tgcatctgat    600
actggcaagc ttgagtctcg tagaggggggg tagaattcca ggtgtagcgg tgaaatgcgt    660
agagatctgg aggaataccg gtggcgaagg cggcccctg gacgaagact gacgctcagg    720
tgcgaaagcg tggggagcaa acaggattag ataccctggt agtccacgcc gtaaacgatg    780
tcgacttgga ggttgtgccc ttgaggcgtg gcttccggag ctaacgcgtt aagtcgaccg    840
cctggggagt acggccgcaa ggttaaaact caaatgaatt gacgggggcc cgcacaagcg    900
gtggagcatg tggtttaatt cgatgcaacg cgaagaacct tacctggtct tgacatccac    960
ggaagttttc agagatgaga atgtgccttc gggaaccgtg agacaggtgc tgcatggctg   1020
tcgtcagctc gtgttgtgaa atgttgggtt aagtcccgca acgagcgcaa cccttatcct   1080
ttgttgccag cggtccggcc gggaactcaa aggagactgc cagtgataaa ctggaggaag   1140
gtggggatga cgtcaagtca tcatggccct tacgaccagg gctacacacg tgctacaatg   1200
```

```
gcgcatacaa agagaagcga cctcgcgaga gcaagcggac ctcataaagt gcgtcgtagt    1260
ccggattgga gtctgcaact cgactccatg aagtcggaat cgctagtaat cgtggatcag    1320
aatgccacgg tgaatacgtt cccgggcctt gtacacaccg cccgtcacac catgggagtg    1380
ggttgcaaaa gaagtaggta gcttaacctt cgggagggcg ctaccacttt gtgattcatg    1440
actggggtga agtcgtaaca aggtaaccgt aggggaacct gcggttggat cacctcctta    1500
```

<210> SEQ ID NO 10
<211> LENGTH: 1542
<212> TYPE: DNA
<213> ORGANISM: Escherichia coli

<400> SEQUENCE: 10

```
aaattgaaga gtttgatcat ggctcagatt gaacgctggc ggcaggccta acacatgcaa      60
gtcgaacggt aacaggaaga gcttgcttc tttgctgacg agtggcggac gggtgagtaa     120
tgtctgggaa actgcctgat ggagggggat aactactgga aacggtagct aataccgcat     180
aacgtcgcaa gaccaaagag ggggaccttc gggcctcttg ccatcggatg tgcccagatg     240
ggattagcta gtaggtgggg taacggctca cctaggcgac gatccctagc tggtctgaga     300
ggatgaccag ccacactgga actgagacac ggtccagact cctacgggag gcagcagtgg     360
ggaatattgc acaatgggcg caagcctgat gcagccatgc cgcgtgtatg aagaaggcct     420
tcgggttgta agtactttc agcggggagg aaggagtaa agttaatacc tttgctcatt     480
gacgttaccc gcagaagaag caccggctaa ctccgtgcca gcagccgcgg taatacggag     540
ggtgcaagcg ttaatcggaa ttactgggcg taaagcgcac gcaggcggtt tgttaagtca     600
gatgtgaaat ccccgggctc aacctggaa ctgcatctga tactggcaag cttgagtctc     660
gtagaggggg gtagaattcc aggtgtagcg gtgaaatgcg tagagatctg gaggaatacc     720
ggtggcgaag gcggcccct ggacgaagac tgacgctcag gtgcgaaagc gtggggagca     780
aacaggatta gataccctgg tagtccacgc cgtaaacgat gtcgacttgg aggttgtgcc     840
cttgaggcgt ggcttccgga gctaacgcgt taagtcgacc gcctggggag tacggccgca     900
aggttaaaac tcaaatgaat tgacggggc ccgcacaagc ggtggagcat gtggtttaat     960
tcgatgcaac gcgaagaacc ttacctggtc ttgacatcca gaactttc cagagatgga    1020 ttggtgcctt cgggaactgt gagacaggtg ctgcatggct gtcgtcagct cgtgttgtga    1080
aatgttgggt taagtcccgc aacgagcgca acccttatct tttgttgcca gcggtccggc    1140
cgggaactca aaggagactg ccagtgataa actggaggaa ggtgggggatg acgtcaagtc    1200 atcatggccc ttacgaccag ggctacacac gtgctacaat ggcgcataca aagagaagcg    1260
acctcgcgag agcaagcgga cctcataaag tgcgtcgtag tccggattgg agtctgcaac    1320
tcgactccat gaagtcggaa tcgctagtaa tcgtggatca gaatgccacg gtgaatacgt    1380
tcccgggcct tgtacacacc gcccgtcaca ccatgggagt gggttgcaaa agaagtaggt    1440
agcttaacct tcgggagggc gcttaccact ttgtgattca tgactggggt gaagtcgtaa    1500
caaggtaacc gtaggggaac tgcggttgga tcacctcct ta                         1542
```

<210> SEQ ID NO 11
<211> LENGTH: 1428
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
ggcggcagct acacatgcag tcgaacggta acaggaagca gcttgcttct ttgctgacga      60
gtggcggacg ggtgagtaat gtctgggaaa ctgcctgatg gaggggggata actactggaa    120
acggtagcta ataccgcata acgtcgcaag accaaagagg gggaccttcg ggcctcttgc    180
catcggatgt gcccagatgg gattagctag taggtggggt aacggctcac ctaggcgacg    240
atccctagct ggtctgagag gatgaccagc cacactggaa ctgagacacg gtccagactc    300
ctacgggagg cagcagtggg gaatattgca caatgggcgc aagcctgatg cagccatgcc    360
gcgtgtatga agaaggcctt cgggttgtaa agtactttca gcgggggagga agggagtaaa    420
gttaatacct ttgctcattg acgttacccg cagaagaagc accggctaac tccgtgccag    480
cagccgcggt aatacggagg gtgcaagcgt taatcggaat tactgggcgt aaagcgcacg    540
caggcggttt gttaagtcag atgtgaaatc cccgggctca acctgggaac tgcatctgat    600
actggcaagc ttgagtctcg tagagggggg tagaattcca ggtgtagcgg tgaaatgcgt    660
agagatctgg aggaataccg gtgggcgaag gcggcccccct ggacgaagac tgacgctcag    720
gtgcgaaagc gtggggagca aacaggatta gataccctgg tagtccacgc cgtaaacgat    780
gtcgacttgg aggttgtgcc cttgaggcgt ggcttccgga gctaacgcgt taagtcgacc    840
gcctggggag tacggccgca aggttaaaac tcaaatgaat tgacggggcc cgcacaagc    900
ggtggagcat gtggtttaat tcgatgcaac gcgaagaacc ttacctggtc ttgacatcca    960
cggaagtttt cagagatgag aatgtgcctt cgggaaccgt gagacaggtg ctgcatggct   1020
gtcgtcagct cgtgttgtga atgttgggt taagtcccgc aacgagcgca accttatcc    1080
tttgttgcca gcggtccggc cgggaactca aggagactg ccagtgataa actggaggaa    1140
ggtggggatg acgtcaagtc atcatggccc ttacgaccag ggctacacac gtgctacaat    1200
ggcgcataca agagaagcg acctcgcgag agcaagcgga cctcataaag tgcgtcgtag    1260
tccggattgg agtctgcaac tcgactccat gaagtcggaa tcgctagtaa tcgtggatca    1320
gaatgccacg gtgaatacgt tcccgggcct tgtacacacc gcccgtcaca ccatgggagt    1380
gggttgcaaa agaagtaggt agcttaacct tcgggagggc gctaccac                 1428
```

<210> SEQ ID NO 12
<211> LENGTH: 1390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
aagcagcttg ctgctttgct gacgagtggc ggacgggtga gtaatgtctg ggaaactgcc      60
tgatggaggg ggataactac tggaaacggt agctaatacc gcataacgtc gcaagaccaa    120
agaggggggac cttcgggcct cttgccatcg gatgtgccca gatgggatta gctagtaggt    180
ggggtaaagg ctcacctagg cgacgatccc tagctggtct gagaggatga ccagccacac    240
tggaactgag acacggtcca gactcctacg ggaggcagca gtggggaata ttgcacaatg    300
ggcgcaagcc tgatgcagcc atgccgcgtg tatgaagaag gccttcgggt tgtaaagtac    360
tttcagcggg gaggaaggga gtaaagttaa taccttgct cattgacgtt acccgcagaa    420
gaagcaccgg ctaactccgt gccagcagcc gcggtaatac ggagggtgca agcgttaatc    480
ggaattactg ggcgtaaagc gcacgcaggc ggtttgttaa gtcagatgtg aaatccccgg    540
```

```
gctcaacctg ggaactgcat ctgatactgg caagcttgag tctcgtagag ggggggtaga      600
attccaggtg tagcggtgaa atgcgtagag atctggagga ataccggtgg cgaaggcggc      660
cccctggacg aagactgacg ctcaggtgcg aaagcgtggg gagcaaacag gattagatac      720
cctggtagtc cacgccgtaa acgatgtcga cttggaggtt gtgcccttga ggcgtggctt      780
ccggagctaa cgcgttaagt cgaccgcctg gggagtacgg ccgcaaggtt aaaactcaaa      840
tgaattgacg gggcccgca caagcggtgg agcatgtggt ttaattcgat gcaacgcgaa      900
gaaccttacc tggtcttgac atccacggaa gttttcagag atgagaatgt gccttcggga      960
accgtgagac aggtgctgca tggctgtcgt cagctcgtgt tgtgaaatgt tgggttaagt     1020
cccgcaacga gcgcaaccct tatcctttgt tgccagcggt ccggccggga actcaaagga     1080
gactgccagt gataaactgg aggaaggtgg ggatgacgtc aagtcatcat ggcccttacg     1140
accagggcta cacacgtgct acaatggcgc atacaaagag aagcgacctc gcgagagcaa     1200
gcggacctca taaagtgcgt cgtagtccgg attggagtct gcaactcgac tccatgaagt     1260
cggaatcgct agtaatcgtg gatcagaatg ccacggtgaa tacgttcccg ggccttgtac     1320
acaccgcccg tcacaccatg ggagtgggtt gcaaagaag taggtagctt aaccttcggg     1380
agggcgctac                                                            1390

<210> SEQ ID NO 13
<211> LENGTH: 6333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ttatagagtc gcaacggcct gggcagcctg tgccggggcg gaagttggaa gatagtgttg       60
ttcggcgctc atcgcccatt gctgatagcg gcgataaagc tgttcaaagc gttgtgcctg      120
ctcgctgcac ggttgcaggg ttttctctac cgcactggcc attttttgct gagctgatgg      180
gatgtctgcg tgcactttcg cggcgacggc agcaaaaatc gccgcaccga gcgcacagca      240
ctggtcagag gcaacaattt gcagcgggcg attcagcacg tcgcagcagg cctgcataat      300
gacctggttt ttccgcgcga tgccgcccag tgccatcacg ttattaacgg cgatcccctg      360
atcggtaaag cactccatga ttgcgcgtgc gccaaaggcg gtggcagcaa tcaaaccgcc      420
gaacagcagc ggagcgtcgg tagcgaggtt aagatcggta atcaccccctt tcaggcgttg      480 gttagcgttc ggtgtgcggc ggccgttaaa ccagtcgagc accaccggca ggtgatccag      540
agacggattt ttggcccatg cttcggtcag cgccggaagc agttgtttct ggctggcgtt      600
gatttgcgtt ttcagttccg gatgctgggc ggcaagctgt tccagcggcc agccgagtac      660
gcgaccaaac caggcgtaga tatcaccaaa cgccgattgg cctgcttcca gaccgataaa      720
tccaggcacc acgctgccat caacctgacc gcaaatacct ttaactgccc gctcgccaac      780
gctctgtttg tcggcaatca gaatgtcgca ggtggaagta ccgataactt ttaccagtgc      840
gttaggctgt gcgcctgcgc caactgcgcc catatggcag tcaaacgcgc gccggaaat      900 caccacgctt tcaggcaggc cgagacgctg cgcccattcc gggcataagg tgcccaccgg      960
aatatcggca gtccaagtgt cagtgaacag cggggaaggc aaatggcgat tgaggatcgg     1020
gtccagctca tcaaagaaac tggctggcgg caggccgccc cagctttcgt gccacagaga     1080
tttatgcccg gcgctgcaac gtccgcgacg aatatcctgc gggcgggtgg taccggaaag     1140
```

-continued

```
cagagctggc acccagtcgc acagctcaat ccacgatgcg gcagattgcg ccacggcgct    1200
gtcctggcga gtcacatgca ggattttttgc ccagaaccat tcgctggaat aaataccacc   1260
aatgtagcgg gagtagtcaa cgttgcccgg cgcgtggcac aaacgggtaa tctcttccgc    1320
ttcttcaacc gcagtgtggt ctttccacaa tacgaacatc gcgttcgggt tttcggcaaa    1380
ctccgggcgc agcgccagca cgtttccgtc ggcatcaatc ggtgcgggcg tcgagccggt    1440
actgtcaacg ccaatcccga ccacagctgc gcgctgttcg acgctaagct ctgcaagcac    1500
ggttttcagt gccgcttcca ttgactcaat gtagtcacgc ggatgatgac ggaactggtt    1560
attcggggca tcacaaaatt gccctttctg ccaacgggga taccactcta cgctggtggc    1620
gatctcttca ccggtagcgc agtccaccgc caaagctcgc acagaatcac tgccaaaatc    1680
gaggccaatt gcaaaccagc aatagacata agcggctatt taacgaccct gccctgaacc    1740
gacgaccggg tcgaatttgc tttcgaattt ctgccattca tccgcttatt atcacttatt    1800
caggcgtagc accaggcgtt taagggcacc aataactgcc ttaaaaaaat tacgccccgc    1860
cctgccactc atcgcagtac tgttgtaatt cattaagcat tctgccgaca tggaagccat    1920
cacagacggc atgatgaacc tgaatcgcca gcggcatcag caccttgtcg ccttgcgtat    1980
aatatttgcc catggtgaaa acgggggcga agaagttgtc catattggcc acgtttaaat    2040
caaaactggt gaaactcacc cagggattgg ctgagacgaa aaacatattc tcaataaacc    2100
ctttagggaa ataggccagg ttttcaccgt aacacgccac atcttgcgaa tatatgtgta    2160
gaaactgccg gaaatcgtcg tggtattcac tccagagcga tgaaaacgtt tcagtttgct    2220
catggaaaac ggtgtaacaa gggtgaacac tatcccatat caccagctca ccgtctttca    2280
ttgccatacg gaattccgga tgagcattca tcaggcgggc aagaatgtga ataaaggccg    2340
gataaaactt gtgcttattt ttcttttacgg tcttttaaaaa ggccgtaata tccagctgaa    2400
cggtctggtt ataggtacat tgagcaactg actgaaatgc ctcaaaatgt tctttacgat    2460
gccattggga tatatcaacg gtggtatatc cagtgatttt tttctccatt ttagcttcct    2520
tagctcctga aaatctcgat aactcaaaaa atacgcccgg tagtgatctt atttcattat    2580
ggtgaaagtt ggaaccctct tacgtgccgat caacgtctca ttttcgccaa aagttggccc    2640
agggcttccc ggtatcaaca gggacaccag gatttattta ttctgcgaag tgatcttccg    2700
tcacatcatg gctcatacgt tgttcgtatt ctggtctctg gcgaggccat tttttcgaaa    2760
cgcctaatca gttccgccag gctaccggcc tgcattttttt ccatgactct ggcgcggtgc    2820
acctctacgg tacgcaccgc gatattcatc gcttccgcaa tttcacggtt cataaatcct    2880
tttgccacca ggctggccag ctcacgctct tcggcgtca actgctggta acacagtata    2940
atctcacgac gcgccaccgc tgccgatgaa accgtcagcg cacgctccag cgccgcctgt    3000
agcggtttta ccgataccgg ttttttgcaga aaatcgacgg cgccgcgttt catctgctcc    3060
acggccatcg gtacatcgcc atgcccggta agaaaaacaa ccgccagggt acttccgcac    3120
tggcgcaacg catcatgaac gccctgccca tccagtaccg gcattcgcat atccagtaat    3180
acgaccccgg cctgatacag actggcctgc gccaaaaaat ccgcccctg cgtccagcat    3240 tttacgtcat atcccagact ttccagtaaa acgcgcacg cgttagtgac cgccgtatca    3300
tcatccagta gatgaattgt cgccatccct gcccccattt tcatgtaaga aatgtatcgt    3360
aaccaccgtt cccgacagac cgtccggcgc ggtctggttc ctgatgctga tatcgccccg    3420
cccataccgc accagccgct ggcaaatcgc cagcccaag cccatcccct ctttacgggt    3480
ggtcataaac ggctgaaacg cctgacgtaa tagcgcctca tcgattcccc cggcgttatc    3540
```

```
ctgtaaaaca atactgatgc cgttttcagt gcgttcagca acgatccata aatgggtggc   3600
gcccgcctga gccgcattaa gaatgatatt cgccagcacc tgttccagca gcactgacgg   3660
cagcgttacg cgcagcgcag cgctaacctc ggtatgcaga gtcactgtcg gaaactgttg   3720
cgccatacgc aacaattgcc agacatgatc aatcgcctcg cgaatggcta tggccttcca   3780
cgcttcggtt agcaccgggt tgccctgcgc ctggctgacc cagtgacgca ggttacgcag   3840
agtatccgca ccgcgttgcg cctgctggtc aatctgctcc agcgccggca gcaagggatg   3900
ctgttcatct gcagcgcgca gtcgaatcag gcacccctgg gcataatgtc gaatcgcgga   3960
aagcggctga ttaagctcat gggcaaaccc ggaggtcatt tcacccaaca cgctcatttg   4020
ccgggcggtt ccagcgcccg gctcatgctg atgaagaact acgctattac gttccagttg   4080
cttcccacgt cgacgcacca gcagcatgac ccaaatataa ttgagcgtga gcaacaagaa   4140
cgccagaatc acgccgccga ccattagctg gtgctggatt aaccaacttt tgacatccag   4200
ccacagtcga cgctgctgag ggtgctgacg aacatcacgc agcaaggctt ccacctgact   4260
ggtggacgca ggcgcgcccc agtgaaatga cgcggcggcg ggcgcgttga atagcgctcg   4320
cgttacgcga tccgccagcg catcgcttac cgcaggtagc gccgcgaacg accagtcagg   4380
atataacggc gtactggtta agcaaggcag gggcgtcggt cgggaaagca gcgcgataaa   4440 gtcctttta ttaatcaatc cttcctgatc catattttct aacaggcaca ctggcacaat   4500
tgccgcctgc accgcttttt cgcgcagcat atagactaag gcatcgccag gaaatccggt   4560
aaaacggaga tgaaaatcgc gctccgggcg taagcccgcg tcgctgagcg ctttatagcc   4620
taataaatag ccgccaaacg cctgagcatc aatcgcgccg acggtcttac cgatgagatc   4680
atgcgccgtg gtgatgccgc tatcgcgccg ggtcaaaatc acgctgccaa taacattact   4740
caccgctttc ccatcgcgcg tggagcgcag ggaagctaac cagcgcagcg gcgcatggct   4800
gttcagttgg acaaattgcg ccgggttggt tatcacaaac tgcacggttc cctggttaac   4860
ggcctcctgc atttgatgca gatccagcgg ctggatgtga aggtttcgc ctggaagctg    4920 ttggcttaat gtctttgcca acggttgcca gtgctacgc gtagacgcct cgccgcgcat   4980
ggccaaaata ccgatattcc acgtccctgc ccacgcgcca tgacaaagta gccctactgc   5040
cgccaacacc gccaggcgcc ttacggtttt acctctcacc ccaatatccc tgtcaattat   5100
gttgttttag atcaacaaca agccgggtat gtggttaacc acaatagagc gcaccccgcc   5160 tcgatttta cactgtaaat catcgacatt ttttattcat tacacatgaa ccaacatcgt   5220
gacaaatgtt tcattgttgg caatgtggac gggagtcaat atggaacaac gcataaccct   5280
gaaagattat gcaatgcgct ttgggcaaac caagacagct aaagacctcg gcgtatatca   5340
aagcgcgatc aacaaggcca ttcatgcagg ccgaaagatt tttttaacta taaacgctga   5400
tggaagcgtt tatgcggaag aggtaaagcc cttcccgagt aacaaaaaaa caacagcata   5460
aaagcgcaaa atgatcccct gctgccggga tactcgttta acgcccatct ggtggcgggt   5520
ttaacgccga ttgaggccaa cggttatctc gattttttta tcgaccgacc gctgggaatg   5580
aaaggttata ttctcaatct caccattcgc ggtcagggg tggtgaaaaa tcagggacga    5640
gaatttgtct gccgaccggg tgatatttg ctgttcccgc caggagagat tcatcactac    5700
ggtcgtcatc cggaggctcg cgaatggtat caccagtggg tttacttcg tccgcgcgcc   5760 tactggcatg aatggcttaa ctggccgtca atatttgcca atacgggttt ctttcgcccg   5820
gatgaagcgc accagccgca tttcagcgac ctgtttgggc aaatcattaa cgccgggcaa   5880
```

| | |
|---|---|
| ggggaagggc gctattcgga gctgctggcg ataaatctgc ttgagcaatt gttactgcgg | 5940 |
| cgcatggaag cgattaacga gtcgctccat ccaccgatgg ataatcgggt acgcgaggct | 6000 |
| tgtcagtaca tcagcgatca cctggcagac agcaattttg atatcgccag cgtcgcacag | 6060 |
| catgtttgct tgtcgccgtc gcgtctgtca catcttttcc gccagcagtt agggattagc | 6120 |
| gtcttaagct ggcgcgagga ccaacgcatt agtcaggcga agctgctttt gagcactacc | 6180 |
| cggatgccta tcgccaccgt cggtcgcaat gttggttttg acgatcaact ctatttctcg | 6240 |
| cgagtattta aaaaatgcac cggggccagc ccgagcgagt tcgtgccgg ttgtgaagaa | 6300 |
| aaagtgaatg atgtagccgt caagttgtca taa | 6333 |

<210> SEQ ID NO 14
<211> LENGTH: 2008
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

| | |
|---|---|
| accactctac gctggtggcg atctcttcac cggtagcgca gtccaccgcc aaagctcgca | 60 |
| cagaatcact gccaaaatcg aggccaattg caatcgccat cgtttcactc catccaaaaa | 120 |
| acgggtatg gagaaacagt agagagttgc gataaaaagc gtcaggtagg atccgctaat | 180 |
| cttatggata aaaatgctat ggcatagcaa agtgtgaacc agcaatagac ataagcggct | 240 |
| atttaacgac cctgccctga accgacgacc gggtcgaatt tgctttcgaa tttctgccat | 300 |
| tcatccgctt attatcactt attcaggcgt agcaccaggc gtttaagggc accaataact | 360 |
| gccttaaaaa aattacgccc cgccctgcca ctcatcgcag tactgttgta attcattaag | 420 |
| cattctgccg acatggaagc catcacagac ggcatgatga acctgaatcg ccagcggcat | 480 |
| cagcaccttg tcgccttgcg tataatattt gcccatggtg aaaacggggg cgaagaagtt | 540 |
| gtccatattg gccacgttta atcaaaaact ggtgaaactc acccagggat tggctgagac | 600 |
| gaaaaacata ttctcaataa acccttagg gaaataggcc aggttttcac cgtaacacgc | 660 |
| cacatcttgc gaatatatgt gtagaaactg ccggaaatcg tcgtggtatt cactccagag | 720 |
| cgatgaaaac gtttcagttt gctcatggaa aacggtgtaa caagggtgaa cactatccca | 780 |
| tatcaccagc tcaccgtctt tcattgccat acggaattcc ggatgagcat tcatcaggcg | 840 |
| ggcaagaatg tgaataaagg ccggataaaa cttgtgctta ttttctttta cggtctttaa | 900 |
| aaaggccgta atatccagct gaacggtctg gttataggta cattgagcaa ctgactgaaa | 960 |
| tgcctcaaaa tgttctttac gatgccattg gatatatca acggtggtat atccagtgat | 1020 |
| ttttttctcc attttagctt ccttagctcc tgaaaatctc gataactcaa aaaatacgcc | 1080 |
| cggtagtgat cttatttcat tatggtgaaa gttggaacct cttacgtgcc gatcaacgtc | 1140 |
| tcattttcgc caaagttgg cccagggctt cccggtatca acaggacac caggatttat | 1200 |
| ttattctgcg aagtgatctt ccgtcacatg ctgcaataat aagaaaaaat cagccccgac | 1260 |
| gattcacctg tcggggctgg acgccatttc aagcctgata aaactgctta acaaatcagc | 1320 |
| ataactcatt aataacataa gagaatgcga tggcttgcaa agtaattca ttgcctgaat | 1380 |
| aatataaatt atatataaat cttatttatg tgatagtttg aattatcatt ataaatgata | 1440 |
| ctcactctca ggggcgttgc ggtttactat gtactaagga ggttgtatgg aacaacgcat | 1500 |
| aaccctgaaa gattatgcaa tgcgctttgg gcaaaccaag acagctaaag acctcggcgt | 1560 |

```
atatcaaagc gcgatcaaca aggccattca tgcaggccga aagattttt taactataaa    1620 cgctgatgga agcgtttatg cggaagaggt aaagcccttc ccgagtaaca aaaaaacaac    1680
agcataacgc cgtgcaaata atcaatgtgg acttttctgc cgtgattata gacactttg    1740 ttacgcgttt ttgtcatggc tttggtcccg ctttgttaca gaatgctttt aataagcggg    1800
gttaccggtt gggttagcga gaagagccag taaaagacgc agtgacggca atgtctgatg    1860
caatatggac aattggtttc ttctctgaat ggtgggagta tgaaaagtat ggctgaagcg    1920
caaaatgatc ccctgctgcc gggatactcg tttaacgccc atctggtggc gggtttaacg    1980
ccgattgagg ccaacggtta tctcgatt                                       2008
```

<210> SEQ ID NO 15
<211> LENGTH: 2052
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
accactctac gctggtggcg atctcttcac cggtagcgca gtccaccgcc aaagctcgca      60
cagaatcact gccaaaatcg aggccaattg caatcgccat cgtttcactc catccaaaaa     120
aacgggtatg gagaaacagt agagagttgc gataaaaagc gtcaggtagg atccgctaat     180
cttatggata aaaatgctat ggcatagcaa agtgtgaacc agcaatagac ataagcggct     240
atttaacgac cctgccctga accgacgacc gggtcgaatt tgctttcgaa tttctgccat     300
tcatccgctt attatcactt attcaggcgt agcaccaggc gtttaagggc accaataact     360
gccttaaaaa aattacgccc cgccctgcca ctcatcgcag tactgttgta attcattaag     420
cattctgccg acatggaagc catcacagac ggcatgatga acctgaatcg ccagcggcat     480
cagcaccttg tcgccttgcg tataatattt gcccatggtg aaaacggggg cgaagaagtt     540
gtccatattg gccacgttta atcaaaact ggtgaaactc acccagggat tggctgagac     600
gaaaaacata ttctcaataa acccttagg gaaataggcc aggttttcac cgtaacacgc     660
cacatcttgc gaatatatgt gtagaaactg ccggaaatcg tcgtggtatt cactccagag     720
cgatgaaaac gtttcagttt gctcatggaa aacggtgtaa caagggtgaa cactatccca     780
tatcaccagc tcaccgtctt tcattgccat acggaattcc ggatgagcat tcatcaggcg     840
ggcaagaatg tgaataaagg ccggataaaa cttgtgctta ttttcttta cggtctttaa     900 aaaggccgta atatccagct gaacggtctg gttataggta cattgagcaa ctgactgaaa     960
tgcctcaaaa tgttctttac gatgccattg gatatatca acggtggtat atccagtgat    1020
ttttttctcc atttttagctt ccttagctcc tgaaaatctc gataactcaa aaaatacgcc    1080
cggtagtgat cttatttcat tatggtgaaa gttggaacct cttacgtgcc gatcaacgtc    1140
tcattttcgc caaagttggg cccagggctt cccggtatca acaggggacac caggatttat    1200 ttattctgcg aagtgatctt ccgtcacact tcttatcctc atcattttc gtcgcgtcac    1260 atctccgacg agatgagtgt aaaaatcgtg ctgtcgatta acctttcgcc tgttgccgcc    1320
gttgtcgatt tactggcaat cacggcatta agtgggtgat tgcttcaca tctcgggcat    1380 tttcctgcaa aaccataccc ttacgaaaag tacggcattg ataatcattt tcaatatcat    1440
ttaattaact ataatgaacc aactgcttac gcggcattaa caatcggccg cccgacaata    1500
ctggagatga atatgtacta aggaggttgt atggaacaac gcataaccct gaaagattat    1560
```

```
gcaatgcgct ttgggcaaac caagacagct aaagacctcg gcgtatatca aagcgcgatc      1620
aacaaggcca ttcatgcagg ccgaaagatt tttttaacta taaacgctga tggaagcgtt      1680
tatgcggaag aggtaaagcc cttcccgagt aacaaaaaaa caacagcata acgccgtgca      1740
aataatcaat gtggactttt ctgccgtgat tatagacact tttgttacgc gttttttgtca     1800 tggctttggt cccgctttgt tacagaatgc ttttaataag cggggttacc ggttgggtta     1860
gcgagaagag ccagtaaaag acgcagtgac ggcaatgtct gatgcaatat ggacaattgg     1920
tttcttctct gaatggtggg agtatgaaaa gtatggctga agcgcaaaat gatccctgc      1980 tgccgggata ctcgtttaac gcccatctgg tggcgggttt aacgccgatt gaggccaacg     2040
gttatctcga tt                                                          2052

<210> SEQ ID NO 16
<211> LENGTH: 1913
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
accactctac gctggtggcg atctcttcac cggtagcgca gtccaccgcc aaagctcgca        60
cagaatcact gccaaaatcg aggccaattg caatcgccat cgtttcactc catccaaaaa       120
aacgggtatg gagaaacagt agagagttgc gataaaaagc gtcaggtagg atccgctaat       180
cttatggata aaaatgctat ggcatagcaa agtgtgaacc agcaatagac ataagcggct       240
atttaacgac cctgccctga accgacgacc gggtcgaatt tgctttcgaa tttctgccat       300
tcatccgctt attatcactt attcaggcgt agcaccaggc gtttaagggc accaataact       360
gccttaaaaa aattacgccc cgccctgcca ctcatcgcag tactgttgta attcattaag       420
cattctgccg acatggaagc catcacagac ggcatgatga acctgaatcg ccagcggcat       480
cagcaccttg tcgccttgcg tataatattt gcccatggtg aaaacggggg cgaagaagtt       540
gtccatattg ccacgtttta aatcaaaact ggtgaaactc acccagggat tggctgagac       600
gaaaaacata ttctcaataa accctttagg gaaataggcc aggttttcac cgtaacacgc       660
cacatcttgc gaatatatgt gtagaaactg ccggaaatcg tcgtggtatt cactccagag       720
cgatgaaaac gtttcagttt gctcatggaa aacggtgtaa caaggtgaaa cactatccca       780
tatcaccagc tcaccgtctt tcattgccat acggaattcc ggatgagcat tcatcaggcg       840
ggcaagaatg tgaataaagg ccggataaaa cttgtgctta ttttttcttta cggtctttaa       900 aaaggccgta atatccagct gaacggtctg gttataggta cattgagcaa ctgactgaaa       960
tgcctcaaaa tgttctttac gatgccattg gatatatca acgtggtat atccagtgat     1020 ttttttctcc atttagctt ccttagctcc tgaaatctc gataactcaa aaaatacgcc      1080
cggtagtgat cttatttcat tatggtgaaa gttggaacct cttacgtgcc gatcaacgtc      1140 tcatttcgc caaaagttgg cccagggctt cccggtatca cagggacac caggatttat       1200 ttattctgcg aagtgatctt ccgtcacaag ctttattaca actcatattg atctacatct      1260
ctgtaactaa aaatataaaa ggtattagct atcgaatctg tggattaatt caactatatc      1320
tatttgctcc tggtgtatat cgtaacggta acactttaaa agggagctga gatatgtact      1380
aaggaggttg tatggaacaa cgcataaccc tgaaagatta tgcaatgcgc tttgggcaaa      1440
ccaagacagc taaagacctc ggcgtatatc aaagcgcgat caacaaggcc attcatgcag      1500
```

| | | |
|---|---|---|
| gccgaaagat tttttaact ataaacgctg atggaagcgt ttatgcggaa gaggtaaagc | 1560 | |
| ccttcccgag taacaaaaaa acaacagcat aacgccgtgc aaataatcaa tgtggacttt | 1620 | |
| tctgccgtga ttatagacac ttttgttacg cgttttgtc atggctttgg tcccgctttg | 1680 | |
| ttacagaatg cttttaataa gcggggttac cggttgggtt agcgagaaga gccagtaaaa | 1740 | |
| gacgcagtga cggcaatgtc tgatgcaata tggacaattg gtttcttctc tgaatggtgg | 1800 | |
| gagtatgaaa agtatggctg aagcgcaaaa tgatcccctg ctgccgggat actcgtttaa | 1860 | |
| cgcccatctg gtggcgggtt aacgccgat tgaggccaac ggttatctcg att | 1913 | |

<210> SEQ ID NO 17
<211> LENGTH: 2976
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

| | | |
|---|---|---|
| accactctac gctggtggcg atctcttcac cggtagcgca gtccaccgcc aaagctcgca | 60 | |
| cagaatcact gccaaaatcg aggccaattg caatcgccat cgtttcactc catccaaaaa | 120 | |
| aacgggtatg gagaaacagt agagagttgc gataaaaagc gtcaggtagg atccgctaat | 180 | |
| cttatggata aaaatgctat ggcatagcaa agtgtgaacc agcaatagac ataagcggct | 240 | |
| atttaacgac cctgccctga accgacgacc gggtcgaatt tgctttcgaa tttctgccat | 300 | |
| tcatccgctt attatcactt attcaggcgt agcaccaggc gtttaagggc accaataact | 360 | |
| gccttaaaaa aattacgccc cgccctgcca ctcatcgcag tactgttgta attcattaag | 420 | |
| cattctgccg acatggaagc catcacagac ggcatgatga acctgaatcg ccagcggcat | 480 | |
| cagcaccttg tcgccttgcg tataatattt gcccatggtg aaaacggggg cgaagaagtt | 540 | |
| gtccatattg ccacgtttta aatcaaaact ggtgaaactc acccagggat ggctgagac | 600 | |
| gaaaaacata ttctcaataa acccttagg gaaataggcc aggttttcac cgtaacacgc | 660 | |
| cacatcttgc gaatatatgt gtagaaactg ccggaaatcg tcgtggtatt cactccagag | 720 | |
| cgatgaaaac gtttcagttt gctcatggaa acggtgtaa caagggtgaa cactatccca | 780 | |
| tatcaccagc tcaccgtctt tcattgccat acggaattcc ggatgagcat tcatcaggcg | 840 | |
| ggcaagaatg tgaataaagg ccggataaaa cttgtgctta ttttcttta cggtcttaa | 900 | |
| aaaggccgta atatccagct gaacggtctg gttataggta cattgagcaa ctgactgaaa | 960 | |
| tgcctcaaaa tgttctttac gatgccattg ggatatatca acggtggtat atccagtgat | 1020 | |
| tttttctcc attttagctt ccttagctcc tgaaatctc gataactcaa aaaatacgcc | 1080 | |
| cggtagtgat cttatttcat tatggtgaaa gttggaacct cttacgtgcc gatcaacgtc | 1140 | |
| tcattttcgc caaaagttgg cccagggctt cccggtatca acagggacac caggatttat | 1200 | |
| ttattctgcg aagtgatctt ccgtcacatt aagacccact ttcacattta agttgttttt | 1260 | |
| ctaatccgca tatgatcaat tcaaggccga ataagaaggc tggctctgca ccttggtgat | 1320 | |
| caaataattc gatagcttgt cgtaataatg gcggcatact atcagtagta ggtgtttccc | 1380 | |
| tttcttcttt agcgacttga tgctcttgat cttccaatac gcaacctaaa gtaaaatgcc | 1440 | |
| ccacagcgct gagtgcatat aatgcattct ctagtgaaaa accttgttgg cataaaaagg | 1500 | |
| ctaattgatt tcgagagtt tcatactgtt tttctgtagg ccgtgtacct aaatgtactt | 1560 | |
| ttgctccatc gcgatgactt agtaaagcac atctaaaact tttagcgtta ttacgtaaaa | 1620 | |

-continued

```
aatcttgcca gctttcccct tctaaagggc aaaagtgagt atggtgccta tctaacatct    1680
caatggctaa ggcgtcgagc aaagcccgct tattttttac atgccaatac aatgtaggct    1740
gctctacacc tagcttctgg gcgagtttac gggttgttaa accttcgatt ccgacctcat    1800
taagcagctc taatgcgctg ttaatcactt tacttttatc taatctagac atcattaatt    1860
cctaattttt gttgacactc tatcattgat agagttattt taccactccc tatcagtgat    1920
agagaaaagt gaaatgagca caaaaaagaa accattaaca caggaacagc ttgaagatgc    1980
acgtcgcctg aaggcgattt acgaaaagaa aaagaatgaa cttggcttaa gccaggagag    2040
cgtggcggat aagatgggca tgggccagag cggcgtgggc gcgctgttta atggcattaa    2100
ggcgctgaat gcgtataacg ccgcactgct ggcgaaaatt ctgaaagtta gcgttgaaga    2160
attttcgccg tcaattgccc gcgaaatcta cgaaatgtac gaagcggtta gtatgcagcc    2220
gtcacttcgt agtgagtatg agtaccctgt tttttctcat gttcaggcag agatgttctc    2280
acctgagctt cgtacctttta ccaaaggtga tgcggagcgt tgggtaagca caaccaaaaa    2340
agccagtgat tctgcattct ggcttgaggt tgaaggtaat tccatgaccg caccaactgg    2400
ctccaagcca agttttcctg acggaatgtt aattctcgtt gaccctgagc aggctgttga    2460
gccaggtgat ttctgcattg cccgtcttgg gggtgatgag tttaccttca agaaactgat    2520
ccgtgatagc ggtcaggtgt ttttacaacc actgaaccca cagtacccaa tgatcccatg    2580
caatgagagt tgttccgttg tggggaaagt tatcgctagt cagtggcctg aagagacgtt    2640
tggataatag gatcgcgccg tgcaaataat caatgtggac ttttctgccg tgattataga    2700
cacttttgtt acgcgttttt gtcatggctt tggtcccgct ttgttacaga atgcttttaa    2760
taagcggggt taccggttgg gttagcgaga agagccagta aaagacgcag tgacggcaat    2820
gtctgatgca atatggacaa ttggtttctt ctctgaatgg tgggagtatg aaaagtatgg    2880
ctgaagcgca aaatgatccc ctgctgccgg gatactcgtt taacgcccat ctggtggcgg    2940
gtttaacgcc gattgaggcc aacggttatc tcgatt                              2976
```

<210> SEQ ID NO 18
<211> LENGTH: 6769
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 18

```
ttatagagtc gcaacggcct gggcagcctg tgccggggcg gaagttggaa gatagtgttg      60
ttcggcgctc atcgcccatt gctgatagcg gcgataaagc tgttcaaagc gttgtgcctg     120
ctcgctgcac ggttgcaggg ttttctctac cgcactggcc attttttgct gagctgatgg     180
gatgtctgcg tgcactttcg cggcgacggc agcaaaaatc gccgcaccga gcgcacagca     240
ctggtcagag gcaacaattt gcagcgggcg attcagcacg tcgcagcagg cctgcataat     300
gacctggttt ttccgcgcga tgccgcccag tgccatcacg ttattaacgg cgatcccctg     360
atcggtaaag cactccatga ttgcgcgtgc gccaaaggcg gtggcagcaa tcaaaccgcc     420
gaacagcagc ggagcgtcgg tagcgaggtt aagatcggta atcacccctt tcaggcgttg     480
gttagcgttc ggtgtgcggc ggccgttaaa ccagtcgagc accaccggca ggtgatccag     540
agacggattt ttgccccatg cttcggtcag cgccggaagc agttgtttct ggctggcgtt     600
gatttgcgtt ttcagttccg gatgctgggc ggcaagctgt tccagcggcc agccgagtac     660
```

```
gcgaccaaac caggcgtaga tatcaccaaa cgccgattgg cctgcttcca gaccgataaa    720
tccaggcacc acgctgccat caacctgacc gcaaatacct ttaactgccc gctcgccaac    780
gctctgtttg tcggcaatca gaatgtcgca ggtggaagta ccgataactt ttaccagtgc    840
gttaggctgt gcgcctgcgc caactgcgcc catatggcag tcaaacgcgc cgccggaaat    900
caccacgctt tcaggcaggc cgagacgctg cgcccattcc gggcataagg tgcccaccgg    960
aatatcggca gtccaagtgt cagtgaacag cggggaaggc aaatggcgat tgaggatcgg   1020
gtccagctca tcaaagaaac tggctggcgg caggccgccc cagctttcgt gccacagaga   1080
tttatgcccg gcgctgcaac gtccgcgacg aatatcctgc gggcgggtgg taccggaaag   1140
cagagctggc acccagtcgc acagctcaat ccacgatgcg gcagattgcg ccacggcgct   1200
gtcctggcga gtcacatgca ggattttttgc ccagaaccat tcgctggaat aaataccacc   1260
aatgtagcgg gagtagtcaa cgttgcccgg cgcgtggcac aaacgggtaa tctcttccgc   1320
ttcttcaacc gcagtgtggt cttttccacaa tacgaacatc gcgttcgggt tttcggcaaa   1380
ctccgggcgc agcgccagca cgtttccgtc ggcatcaatc ggtgcgggcg tcgagccggt   1440
actgtcaacg ccaatcccga ccacagctgc gcgctgttcg acgctaagct ctgcaagcac   1500
ggttttcagt gccgcttcca ttgactcaat gtagtcacgc ggatgatgac ggaactggtt   1560
attcggggca tcacaaaatt gccctttctg ccaacgggga taccactcta cgctggtggc   1620
gatctcttca ccggtagcgc agtccaccgc caaagctcgc acagaatcac tgccaaaatc   1680
gaggccaatt gcaaaccagc aatagacata agcggctatt taacgaccct gccctgaacc   1740
gacgaccggg tcgaatttgc tttcgaattt ctgccattca tccgcttatt atcacttatt   1800
caggcgtagc accaggcgtt taagggcacc aataactgcc ttaaaaaaat tacgccccgc   1860
cctgccactc atcgcagtac tgttgtaatt cattaagcat tctgccgaca tggaagccat   1920
cacagacggc atgatgaacc tgaatcgcca gcggcatcag caccttgtcg ccttgcgtat   1980
aatatttgcc catggtgaaa acgggggcga agaagttgtc catattggcc acgtttaaat   2040
caaaactggt gaaactcacc cagggattgg ctgagacgaa aaacatattc tcaataaacc   2100
ctttagggaa ataggccagg ttttcaccgt aacacgccac atcttgcgaa tatatgtgta   2160
gaaactgccg gaaatcgtcg tggtattcac tccagagcga tgaaaacgtt tcagtttgct   2220
catggaaaac ggtgtaacaa gggtgaacac tatcccatat caccagctca ccgtctttca   2280
ttgccatacg gaattccgga tgagcattca tcaggcgggc aagaatgtga ataaaggccg   2340
gataaaactt gtgcttattt ttctttacgg tcttttaaaaa ggccgtaata tccagctgaa   2400
cggtctggtt ataggtacat tgagcaactg actgaaatgc ctcaaaatgt tctttacgat   2460
gccattggga tatatcaacg gtggtatatc cagtgatttt tttctccatt ttagcttcct   2520
tagctcctga aaatctcgat aactcaaaaa atacgcccgg tagtgatctt atttcattat   2580
ggtgaaagtt ggaaccctct acgtgccgat caacgtctca ttttcgccaa agttggcccc   2640
agggcttccc ggtatcaaca gggacaccag gatttattta ttctgcgaag tgatcttccg   2700
tcacatattt agagttcttc gatacgaata gtgtgggcca gatcatcgat aagttcgaca   2760
tcttttccat tgtggctcaa cgtgatgtgg ccgtctctat ctacaatttc aacttctgat   2820
ccaactcgga tatcagcatc gaggagctgt gtaaactgat ccgtttcaac ttggaagatt   2880
tcatttatct gaacaatgcg tactttgcgg ggcatactgg tggcagcgtc aataacgcga   2940
gttccgggga ctgccgcgtc agaattgcct acgccgagtt cgtcgagacc tggaattggg   3000
tttccgaagg gggaccgact gacatctttc aatactttca cgagcctgcg ttcaacttcg   3060
```

```
tcactcataa cgtgttccca gcggcaggct tcatcgtgaa ctttattgat atctaggcca   3120
atgatatcgg taagaaggcg ctcagctaag cgatgtttac gcataactgc agtcgctaaa   3180
gtgcggcctg tcggtgtcat ttgtagactg cggtctgagg cgacaacgac aagtccatcg   3240
cgctccatac gggcaacggt ttggctaact gtaggtccag attgttccag acgctcagcg   3300
atcctagcgc gaagaggggt gacaccctct tcttccagct catagatagt acgcaagtac   3360
atctctgtgg tatcgactaa gtccttcatt gtaagcctct ttccttatag tgccatggag   3420
actgttgtgt gctggtgatc aattcctatc aatctacaac gaattgtagc gtgaaaaata   3480
tggaatcgtt ttcttgttgc gttgtagtcc cgcagcgcgc ttttcgatga gactttaatt   3540
ataacgccta atctaaagat tgcttttaat aggcgtttat gtctttattg gtaggcatat   3600
ctaagcaaac gttaaatcag gcgttgctgg cgtgctgccg tgatggcggc ggtgcggtta   3660
tctacgccga gcttggagta gatgtgcacg aggtgagttt ttaccgttgc ctcggaaata   3720
aatagtttgg ctgcgagttg gcggttacta agtccttgtt ccaagttctg gaggatttcg   3780
atctcgcgag ccgagagtgc ctggcggggt ttgctcacac gttgcatgag ggcgttggcg   3840
accttggggg cgagggtgcg acggccttca aaggtggcga tcactgcatc gtgtagtgcc   3900
gattccggcg cgtctttgag caggtagccc atagcacctg cttcgactgc tgcgaggatg   3960
tctgcctcgg tgtcgtaggt ggtcaggatg agcactggag ggccgccggc gctggcgagt   4020
gcgcgggtta gggtgatgcc gtcggtgcct ggcatttgga tgtcggtgac aacaacgtcg   4080
atgcctttgg tgttgatgtt gctgccgtcg ctggcttcgg cgaccacggt gatgtcatcg   4140
aagctgtcca aaatggagcg cagtccggcg cggactacgg ggtggtcgtc gataagcatg   4200
acgcggatca tgaagtctcc cggcggctgg taagcggaat gcggcaagcg agtgcggtgc   4260
cgtatgtatc tgattcaatc acgagtgtgc caccaacggt atctacgcgc ttgcgaaggc   4320
catcaaggcc aaagccggag ctggtgccac gctcggtggt accgaggttg aacccgatcc   4380
cattgtccac cacgtcgagg ctgacctcgt cctcccacac gcccaatgtg accaccgctt   4440
ttgtggcatg agcatgttta accacattgt tgagcccttc ttgggtcacg cgaaccaccg   4500
tgcgcgatac cggctccggc aggcttatcg acgtatcccc cacgagctct aaatgaacat   4560
ccaatggcgc accgagagca tcctgttttgg tgcgtagatt attaatggta ctggtcagtg   4620
cgataggcag cgagtcgccc agtgctgggg ctgctaggtc gcgcacaaag cggcgtgcct   4680
ctgcaaggct gtcagaggct tgggtttcga tcacgctgag ttgctgtgcc acatcttcaa   4740
tttcacctttt atcgaggcgg ccgtgtgcgg cgcgtgccaa gattacgatg gaactcaatc   4800
cttgggcaac tgtgtcatgg atctcgcgag agagccgctc gcgctcctcg agccggcctg   4860
cctgatgttc agaggtggcg agatcctgct gggctgcaag caactctgcc gctagttggc   4920
ggtaatgttg ggcatcgttg cgcaaggtgg tgtagctata aaaatcaccc gtggaaaacg   4980
cggcacccat cgttgggccc atggcctgtg cgggcatcca ctcatctggg cgtgtggcta   5040
ggggaattgc gatggcgatg gcaaggagta aggcaacgcc caagatgcca cgaatgccct   5100
gcttgagatg caacattaca aatacgagtg ggaacatcag ccacaggaaa tagccggagg   5160
cacctacgag gaaagcccag agagcaacaa taatcacgag ccacacggga ctgagtatcc   5220
cggggtccgg gatgtcgtcg ccacgcgcga acgatttttc ccatgcggtg ccgatcatgt   5280
agaaaattcc cagcgtgatt gctgcggcga tagcaatatt gtttgcatcg gttgaactgc   5340
ttggaagctc gagataataa cgtacgattc caaaaatgag cagaccagcg aacattacat   5400
```

```
gcaggctgac acgcatgacg gtgagaattt gaatcacatg aggcttcaca ctagcgagca    5460
taaaagatct cctgcgcctg tgatggattg aaggaaagt tcgcttaatt gaagcctatg     5520
ttgcatagga gcaaattagg ctataccttt taatgagcgg ttgatgtggt gaggtcgatc    5580
gctcggtgag tggaagaatc aactatctgg ttgatgtgag gggaacctaa cctaagtatc    5640
ttctaggtta ttgatcaaaa cgcacgatgt gtccatacga aaggttttct tcatctatgg    5700
aacaacgcat aaccctgaaa gattatgcaa tgcgctttgg gcaaaccaag acagctaaag    5760
acctcggcgt atatcaaagc gcgatcaaca aggccattca tgcaggccga aagatttttt    5820
taactataaa cgctgatgga agcgtttatg cggaagaggt aaagcccttc ccgagtaaca    5880 aaaaacaac agcataaaag cgcaaaatga tccctgctg ccgggatact cgtttaacgc      5940
ccatctggtg gcgggtttaa cgccgattga ggccaacggt tatctcgatt tttttatcga    6000
ccgaccgctg ggaatgaaag gttatattct caatctcacc attcgcggtc aggggtggt    6060 gaaaaatcag ggacgagaat tgtctgccg accgggtgat attttgctgt tcccgccagg    6120
agagattcat cactacggtc gtcatccgga ggctcgcgaa tggtatcacc agtgggttta    6180
ctttcgtccg cgcgcctact ggcatgaatg gcttaactgg ccgtcaatat ttgccaatac    6240
gggtttcttt cgcccggatg aagcgcacca gccgcatttc agcgacctgt ttgggcaaat    6300
cattaacgcc gggcaagggg aagggcgcta ttcggagctg ctggcgataa atctgcttga    6360
gcaattgtta ctgcggcgca tggaagcgat taacgagtcg ctccatccac cgatggataa    6420
tcgggtacgc gaggcttgtc agtacatcag cgatcacctg gcagacagca attttgatat    6480
cgccagcgtc gcacagcatg tttgcttgtc gccgtcgcgt ctgtcacatc ttttccgcca    6540
gcagttaggg attagcgtct taagctggcg cgaggaccaa cgcattagtc aggcgaagct    6600
gcttttgagc actaccccgga tgcctatcgc caccgtcggt cgcaatgttg gttttgacga    6660
tcaactctat ttctcgcgag tatttaaaaa atgcaccggg gccagcccga gcgagtttcg    6720
tgccggttgt gaagaaaaag tgaatgatgt agccgtcaag ttgtcataa                6769
```

<210> SEQ ID NO 19
<211> LENGTH: 5446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
ttatagagtc gcaacggcct gggcagcctg tgccggggcg gaagttggaa gatagtgttg      60
ttcggcgctc atcgcccatt gctgatagcg gcgataaagc tgttcaaagc gttgtgcctg    120
ctcgctgcac ggttgcaggg ttttctctac cgcactggcc attttttgct gagctgatgg    180
gatgtctgcg tgcactttcg cggcgacggc agcaaaaatc gccgcaccga gcgcacagca    240
ctggtcagag gcaacaattt gcagcgggcg attcagcacg tcgcagcagg cctgcataat    300
gacctggttt ttccgcgcga tgccgcccag tgccatcacg ttattaacgg cgatcccctg    360
atcggtaaag cactccatga ttgcgcgtgc gccaaaggcg gtggcagcaa tcaaaccgcc    420
gaacagcagc ggagcgtcgg tagcgaggtt aagatcggta atcacccctt tcaggcgttg    480
gttagcgttc ggtgtgcggc ggccgttaaa ccagtcgagc accaccggca ggtgatccag    540
agacggattt ttgccccatg cttcggtcag cgccggaagc agttgtttct ggctggcgtt    600
gatttgcgtt ttcagttccg gatgctgggc ggcaagctgt tccagcggcc agccgagtac    660
```

```
gcgaccaaac caggcgtaga tatcaccaaa cgccgattgg cctgcttcca gaccgataaa    720
tccaggcacc acgctgccat caacctgacc gcaaatacct ttaactgccc gctcgccaac    780
gctctgtttg tcggcaatca gaatgtcgca ggtggaagta ccgataactt ttaccagtgc    840
gttaggctgt gcgcctgcgc caactgcgcc catatggcag tcaaacgcgc cgccggaaat    900
caccacgctt tcaggcaggc cgagacgctg cgcccattcc gggcataagg tgcccaccgg    960
aatatcggca gtccaagtgt cagtgaacag cggggaaggc aaatggcgat tgaggatcgg   1020
gtccagctca tcaaagaaac tggctggcgg caggccgccc cagctttcgt gccacagaga   1080
tttatgcccg cgcgctgcaac gtccgcgacg aatatcctgc gggcgggtgg taccggaaag   1140
cagagctggc acccagtcgc acagctcaat ccacgatgcg gcagattgcg ccacggcgct   1200
gtcctggcga gtcacatgca ggattttttgc ccagaaccat tcgctggaat aaataccacc   1260
aatgtagcgg gagtagtcaa cgttgcccgg cgcgtggcac aaacgggtaa tctcttccgc   1320
ttcttcaacc gcagtgtggt cttttccacaa tacgaacatc gcgttcgggt tttcggcaaa   1380
ctccgggcgc agcgccagca cgtttccgtc ggcatcaatc ggtgcgggcg tcgagccggt   1440
actgtcaacg ccaatcccga ccacagctgc gcgctgttcg acgctaagct ctgcaagcac   1500
ggttttcagt gccgcttcca ttgactcaat gtagtcacgc ggatgatgac ggaactggtt   1560
attcggggca tcacaaaatt gccctttctg ccaacgggga taccactcta cgctggtggc   1620
gatctcttca ccggtagcgc agtccaccgc caaagctcgc acagaatcac tgccaaaatc   1680
gaggccaatt gcaaaccagc aatagacata agcggctatt taacgaccct gccctgaacc   1740
gacgaccggg tcgaatttgc tttcgaattt ctgccattca tccgcttatt atcacttatt   1800
caggcgtagc accaggcgtt taagggcacc aataactgcc ttaaaaaaat tacgccccgc   1860
cctgccactc atcgcagtac tgttgtaatt cattaagcat tctgccgaca tggaagccat   1920
cacagacggc atgatgaacc tgaatcgcca gcggcatcag caccttgtcg ccttgcgtat   1980
aatatttgcc catggtgaaa acgggggcga agaagttgtc catattggcc acgtttaaat   2040
caaaactggt gaaactcacc cagggattgg ctgagacgaa aaacatattc tcaataaacc   2100
ctttagggaa ataggccagg ttttcaccgt aacacgccac atcttgcgaa tatatgtgta   2160
gaaactgccg gaaatcgtcg tggtattcac tccagagcga tgaaaacgtt tcagtttgct   2220
catggaaaac ggtgtaacaa gggtgaacac tatcccatat caccagctca ccgtcttcca   2280
ttgccatacg gaattccgga tgagcattca tcaggcgggc aagaatgtga ataaaggccg   2340
gataaaactt gtgcttattt ttctttacgg tcttaaaaa ggccgtaata tccagctgaa   2400
cggtctggtt ataggtacat tgagcaactg actgaaatgc ctcaaaatgt tctttacgat   2460
gccattggga tatatcaacg gtggtatatc cagtgatttt tttctccatt ttagcttcct   2520
tagctcctga aaatctcgat aactcaaaaa atacgcccgg tagtgatctt atttcattat   2580
ggtgaaagtt ggaaccctctt acgtgccgat caacgtctca ttttcgccaa aagttggccc   2640
agggcttccc ggtatcaaca gggacaccag gatttattta ttctgcgaag tgatcttccg   2700
tcacactaat cccggtccgc gatcaagcgt tcgatctggt tcgccatcgc tgtcagcacg   2760
ggggccagct gcggcgcat gagggtgccc tgggtggtcg gatcggacag tagcggccgg   2820
atcagggcat agccgacacc ggagaggaaa cgcatggcct ggagttcggc gcgacagtcg   2880
gcacagacat cgccagttc gagcaggcgc ggatcagagg acgggaagtc ctcggcgtcg   2940
cggatcaggg cttcgagtcc gagatcggga tcgcctcgg ggcgcagggg cgcgaaggtt   3000
gcacgcagac agtcgaggac agtcagcagg acatcctggt tgggcggttt gtccaggatg   3060
```

```
cgcgccatgg tcttgagata accctgaccg gcaggcgtat ggagtcgcac caacaggtgc    3120
gcgaccggat catcagcgtt cgccggagac ctcagcgatt cagggcgtgc gcgggccggc    3180
gccggctcgg gccagtcgtc gaacccggca cacagaaacc ccgccagcca ggccggcctg    3240
cgcgccgcgc gcgtccagag atcgcgccgc cgttcgtcgt cgagcagtcc agggtgcagg    3300
atcagccgca cactctcaat cattgcctcc gagtcggtct cgaacggcag atactggagc    3360
agatactcgg ccaggaccgg ccccatgcgt ccgtcgcgca cgcgcggatt ggccagcatc    3420
cggcgcgcgt tgccggcgtc ctccatcacc caccaggcgc ggcgtgccag ctcgtcggtc    3480
agtccaggcg agccgacggc ggcgaccacg gcttccggtt cgccgagccg cagcagttgc    3540
gccagactct cgtcgcgcat ctgacccaga cgggtccagc ggctgagata gaccggatac    3600
ccaccgggcg agccaagcac atgcccggag atgagttcgc gcacctggcg cagatagcgc    3660
tcgggcgcgg tattgggatt gagctggacg ctcgactcgc cgcgctcggt caggccctgg    3720
acccgcatcc ggtcttcgtc gatgcggatg ccagcggct gactggccag caggacgtgg    3780
agccgcagac tgtcctcgtg actgaggtcc atgatccgga cacgcgatca gccgccgctc    3840
ggcgggcgat aggtcggatc cctgggattg aggaagatga aatgaaactg ccccggctcc    3900
agttcgacat aatccagtgt cgtctggtcg agcagcgaaa catagtcggg cgcgatgacg    3960
atctccacgc cctcgctggt cagacggatg tcgtcctcgg tgaggtcgtc gaaccccatg    4020
cggtaatcga tgcttccatc gggattccgg ccggcggcca gacgcaggca catgccctcg    4080
gtaccgcctt gcttggccgc cttgaggact tgctcggcgg cggcgggtgt cagcttgaac    4140
atcatcagac cccttttgaa ccacgtccag cacgacaggc caacgaccg catcggcgac    4200 acggctcaat gtcgaaggtg aacagcgggc gcgcgcttg cggacagggg gaggcgcatc    4260
cggcacagca cggacgcgcc atgatcgaac gacaatccat cgcctcgggt cggacgccgc    4320
gcgcgaccga cccgagagcg cgatgactgg atttggatag ccacgaggtc tgcatggaac    4380
aacgcataac cctgaaagat tatgcaatgc gctttgggca aaccaagaca gctaaagacc    4440
tcggcgtata tcaaagcgcg atcaacaagg ccattcatgc aggccgaaag attttttttaa    4500 ctataaacgc tgatggaagc gtttatgcgg aagaggtaaa gcccttcccg agtaacaaaa    4560
aaacaacagc ataaaagcgc aaaatgatcc cctgctgccg ggatactcgt ttaacgccca    4620
tctggtggcg ggtttaacgc cgattgaggc caacggttat ctcgattttt ttatcgaccg    4680
accgctggga atgaaaggtt atattctcaa tctcaccatt cgcggtcagg gggtggtgaa    4740 aaaatcaggga cgagaatttg tctgccgacc gggtgatatt ttgctgttcc gccaggaga    4800 gattcatcac tacggtcgtc atccggaggc tcgcgaatgg tatcaccagt gggtttactt    4860
tcgtccgcgc gcctactggc atgaatggct taactggccg tcaatatttg ccaatacggg    4920
tttctttcgc ccggatgaag cgcaccagcc gcatttcagc gacctgtttg gcaaatcat    4980 taacgccggg caaggggaag ggcgctattc ggagctgctg gcgataaatc tgcttgagca    5040
attgttactg cggcgcatgg aagcgattaa cgagtcgctc catccaccga tggataatcg    5100
ggtacgcgag gcttgtcagt acatcagcga tcacctggca gacagcaatt ttgatatcgc    5160
cagcgtcgca cagcatgttt gcttgtcgcc gtcgcgtctg tcacatcttt tccgccagca    5220
gttagggatt agcgtcttaa gctggcgcga ggaccaacgc attagtcagg cgaagctgct    5280
tttgagcact acccgatgc ctatcgccac cgtcggtcgc aatgtggtt ttgacgatca    5340 actctatttc tcgcgagtat ttaaaaaatg caccggggcc agcccgagcg agtttcgtgc    5400
```

```
cggttgtgaa gaaaaagtga atgatgtagc cgtcaagttg tcataa              5446
```

<210> SEQ ID NO 20
<211> LENGTH: 4112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
ttatagagtc gcaacggcct gggcagcctg tgccggggcg aagttggaa gatagtgttg     60
ttcggcgctc atcgcccatt gctgatagcg gcgataaagc tgttcaaagc gttgtgcctg   120
ctcgctgcac ggttgcaggg tttttctctac cgcactggcc attttttgct gagctgatgg   180
gatgtctgcg tgcactttcg cggcgacggc agcaaaaatc gccgcaccga cgcacagca    240
ctggtcagag gcaacaattt gcagcgggcg attcagcacg tcgcagcagg cctgcataat   300
gacctggttt ttccgcgcga tgccgccag tgccatcacg ttattaacgg cgatcccctg    360
atcggtaaag cactccatga ttgcgcgtgc gccaaaggcg gtggcagcaa tcaaaccgcc   420
gaacagcagc ggagcgtcgg tagcgaggtt aagatcggta atcaccccctt tcaggcgttg  480
gttagcgttc ggtgtgcggc ggccgttaaa ccagtcgagc accaccggca ggtgatccag   540
agacggattt ttggcccatg cttcggtcag cgccggaagc agttgtttct ggctggcgtt   600
gatttgcgtt ttcagttccg gatgctgggc ggcaagctgt tccagcggcc agccgagtac   660
gcgaccaaac caggcgtaga tatcaccaaa cgccgattgg cctgcttcca gaccgataaa   720
tccaggcacc acgctgccat caacctgacc gcaaatacct ttaactgccc gctcgccaac   780
gctctgtttg tcggcaatca gaatgtcgca ggtggaagta ccgataactt ttaccagtgc   840
gttaggctgt gcgcctgcgc caactgcgcc catatggcag tcaaacgcgc cgccggaaat   900
caccacgctt tcaggcaggc cgagacgctg cgcccattcc gggcataagg tgcccaccgg   960
aatatcggca gtccaagtgt cagtgaacag cggggaaggc aaatggcgat tgaggatcgg  1020
gtccagctca tcaaagaaac tggctggcgg caggccgccc cagctttcgt gccacagaga  1080
tttatgcccg gcgctgcaac gtccgcgacg aatatcctgc gggcgggtgg taccggaaag  1140
cagagctggc acccagtcgc acagctcaat ccacgatgcg gcagattgcg ccacggcgct  1200
gtcctggcga gtcacatgca ggattttgc ccagaaccat tcgctggaat aaataccacc  1260
aatgtagcgg gagtagtcaa cgttgcccgg cgcgtggcac aaacgggtaa tctcttccgc  1320
ttcttcaacc gcagtgtggt cttttccacaa tacgaacatc gcgttcgggt tttcggcaaa  1380
ctccgggcgc agcgccagca cgtttccgtc ggcatcaatc ggtgcgggcg tcgagccggt  1440
actgtcaacg ccaatcccga ccacagctgc gcgctgttcg acgctaagct ctgcaagcac  1500
ggttttcagt gccgcttcca ttgactcaat gtagtcacgc ggatgatgac ggaactggtt  1560
attcggggca tcacaaaatt gccctttctg ccaacgggga taccactcta cgctggtggc  1620
gatctcttca ccggtagcgc agtccaccgc caaagctcgc acagaatcac tgccaaaatc  1680
gaggccaatt gcaaaccagc aatagacata agcggctatt taacgaccct gccctgaacc  1740
gacgaccggg tcgaatttgc tttcgaattt ctgccattca tccgcttatt atcacttatt  1800
caggcgtagc accaggcgtt taagggcacc aataactgcc ttaaaaaaat tacgccccgc  1860
cctgccactc atcgcagtac tgttgtaatt cattaagcat tctgccgaca tggaagccat  1920
cacagacggc atgatgaacc tgaatcgcca gcggcatcag caccttgtcg ccttgcgtat  1980
```

```
aatatttgcc catggtgaaa acgggggcga agaagttgtc catattggcc acgtttaaat    2040
caaaactggt gaaactcacc cagggattgg ctgagacgaa aaacatattc tcaataaacc    2100
ctttagggaa ataggccagg ttttcaccgt aacacgccac atcttgcgaa tatatgtgta    2160
gaaactgccg gaaatcgtcg tggtattcac tccagagcga tgaaaacgtt tcagtttgct    2220
catgaaaaac ggtgtaacaa gggtgaacac tatcccatat caccagctca ccgtctttca    2280
ttgccatacg gaattccgga tgagcattca tcaggcgggc aagaatgtga ataaaggccg    2340
gataaaactt gtgcttattt ttctttacgg tctttaaaaa ggccgtaata tccagctgaa    2400
cggtctggtt ataggtacat tgagcaactg actgaaatgc ctcaaaatgt tctttacgat    2460
gccattggga tatatcaacg gtggtatatc cagtgatttt tttctccatt ttagcttcct    2520
tagctcctga aaatctcgat aactcaaaaa atacgcccgg tagtgatctt atttcattat    2580
ggtgaaagtt ggaacctctt acgtgccgat caacgtctca ttttcgccaa aagttggccc    2640
agggcttccc ggtatcaaca gggacaccag gatttattta ttctgcgaag tgatcttccg    2700
tcacagggag ttattctagt tgcgagtgaa ggttttgttt tgacattcag tgctgtcaaa    2760
tacttaagaa taagttattg attttaacct tgaattatta ttgcttgatg ttaggtgctt    2820
atttcgccat tccgcaataa tcttaaaaag ttcccttgca tttacatttt gaaacatcta    2880
tagcgataaa tgaaacatct taaaagtttt agtatcatat tcgtgttgga ttattctgca    2940
tttttgggga aatggacttt gccgactgat taatgagggt taatcagtat gcagtggcat    3000
aaaaaagcaa ataaaggcat ataacagagg gttaataaca tggaacaacg cataaccctg    3060
aaagattatg caatgcgctt tgggcaaacc aagacagcta agacctcgg cgtatatcaa    3120 agcgcgatca acaaggccat tcatgcaggc cgaaagattt ttttaactat aaacgctgat    3180
ggaagcgttt atgcggaaga ggtaaagccc ttcccgagta acaaaaaaac aacagcataa    3240
aagcgcaaaa tgatcccctg ctgccgggat actcgtttaa cgcccatctg gtggcgggtt    3300
taacgccgat tgaggccaac ggttatctcg attttttttat cgaccgaccg ctgggaatga    3360
aaggttatat tctcaatctc accattcgcg gtcagggggt ggtgaaaaat cagggacgag    3420
aatttgtctg ccgaccgggt gatattttgc tgttcccgcc aggagagatt catcactacg    3480
gtcgtcatcc ggaggctcgc gaatggtatc accagtgggt ttactttcgt ccgcgcgcct    3540
actggcatga atggcttaac tggccgtcaa tatttgccaa tacgggtttc tttcgcccgg    3600
atgaagcgca ccagccgcat ttcagcgacc tgtttgggca aatcattaac gccgggcaag    3660
gggaagggcg ctattcggag ctgctggcga taaatctgct tgagcaattg ttactgcggc    3720
gcatggaagc gattaacgag tcgctccatc caccgatgga taatcgggta cgcgaggctt    3780
gtcagtacat cagcgatcac ctggcagaca gcaattttga tatcgccagc gtcgcacagc    3840
atgtttgctt gtcgccgtcg cgtctgtcac atcttttccg ccagcagtta gggattagcg    3900
tcttaagctg gcgcgaggac caacgcatta gtcaggcgaa gctgcttttg agcactaccc    3960
ggatgcctat cgccaccgtc ggtcgcaatg ttggttttga cgatcaactc tatttctcgc    4020
gagtatttaa aaaatgcacc ggggccagcc cgagcgagtt tcgtgccggt tgtgaagaaa    4080
aagtgaatga tgtagccgtc aagttgtcat aa                                  4112
```

ENGINEERED GENETIC ENTERIC SENSOR BACTERIA AND USES THEREOF

CROSS-REFERENCE TO RELATED APPLICATIONS

This application is a Continuation Application of U.S. application Ser. No. 15/103,372 filed on Jun. 10, 2016, now U.S. Pat. No. 10,047,405, which is a 35 U.S.C. § 371 National Phase Entry Application of International Application No. PCT/US2014/071672 filed on Dec. 19, 2014, which designates the U.S. and which claims benefit under 35 U.S.C. § 119(e) of U.S. Provisional Application No. 61/919,257 filed on Dec. 20, 2013, the contents of each of which are incorporated therein in their entirety.

GOVERNMENT SUPPORT

This invention was made with government support under N66001-11-C-4203 awarded by the Department of Defense. The Government has certain rights in the invention.

SEQUENCE LISTING

The instant application contains a Sequence Listing which has been submitted electronically in ASCII format and is hereby incorporated by reference in its entirety. Said ASCII copy, created on Jun. 5, 2018, is named 002806-079411-PCT_SL.txt and is 80,598 bytes in size.

FIELD

The disclosure relates to genetic engineered bacteria, compositions thereof, formulations thereof, methods of analyses and method of treatment of conditions related to the gastrointestinal tract including the mouth and the stomach.

BACKGROUND

The mammalian gastrointestinal tract is a complex heterogeneous and dynamic environment that hosts a community of symbiotic microbes, the microbiome. The gastrointestinal tract microbiome interacts closely with the host, impacting health, disease and metabolism; changes in its behavior can lead to liver disease, inflammatory/autoimmune disease, transfer of antibiotic resistance, obesity and diabetes, inflammatory bowel disease, pathogenic infections, and cancer. However, there is limited ability to non-destructively and/or non-invasively interrogate the gut. Novel non-destructive or non-invasive strategies are in demand.

SUMMARY

Embodiments of the present disclosure are based on genetic engineered *Escherichia coli* and gut coliform bacteria having genome integrated genetic memory circuits that can accurately senses specific environmental conditions in the gut long after the initial stimulus has been removed. For example, sensing antibiotic exposure. Therefore, specific genetic engineered bacteria can be designed for diagnostic/prognosis purposes, to monitor, indicate and/or report certain environmental conditions of interest in the gut without resorting to invasive endoscopy, colonoscopy and/or flexible sigmoidoscopy. Furthermore, specific genetic engineered bacteria can be designed for the delivery of therapeutics to the gut when certain environmental conditions of interest occur in the gut.

It is the objective of this disclosure to provide genetic engineered unicellular organism such as a bacterium having a genome-integrated genetic memory circuits for use in diagnostic, prognosis, and therapeutic purposes in the gastrointestinal tract of a mammal. The gastrointestinal tract would include the colon.

It is also the objective of this disclosure to provide methods of detecting environmental conditions of interest in the colon or the gastrointestinal tract using the genetic engineered unicellular organism such as engineered bacteria having genome integrated genetic memory circuits.

It is also the objective of this disclosure to provide methods of treating conditions of interest in the colon or the gastrointestinal tract using the genetic engineered unicellular organism such as engineered bacteria having genome integrated genetic memory circuits. For example, conditions such as colorectal cancer or colitis.

Accordingly, in one embodiment, provided herein is an engineered unicellular organism comprising a memory circuit comprising a bacteriophage-reporter element-based memory element comprising two antagonistic transcription factors or gene regulatory factors; and an inducible transcription factor-based trigger element which produces a triggering transcription factor upon induction, wherein the triggering transcription factor is operably linked to an inducible promoter, wherein the inducible promoter is responsive to a stimulus, and wherein the memory circuit is integrated into the genome of the organism. The reporter element of memory element comprises a reporter gene that is operably-linked to the one of the two antagonistic transcription factors of the memory element. In the absence of the stimulus that can induce the inducible transcription factor-based trigger element, the memory element is in the OFF state wherein the reporter element does not transcribe the reporter gene. In the presence of the stimulus, the inducible transcription factor-based trigger element is induced to produce the triggering transcription factor which turns the memory element to the ON state wherein the reporter element transcribes the reporter gene.

In one embodiment, the bacteriophage-reporter element-based memory element comprises two antagonistic transcription factors or gene regulatory factors and a reporter element. For example, the lambda phage-based cI/Cro. In one embodiment, each of the two antagonistic transcription factors or gene regulatory factors is operably linked to a respective promoter, wherein the function of each promoter is inhibited by the transcription factor or gene regulatory factor that is not operably-linked to it. In one embodiment, the reporter element comprises a reporter gene which is operably-linked to the one of the two antagonistic transcription factors of the memory element. In one embodiment, the triggering transcription factor is one of the two antagonistic transcription factors comprising the memory element.

In one embodiment, provided herein is a method of detecting a stimulus in a multicellular organism, the method comprising administering an engineered unicellular organism described herein to the subject, wherein the inducible promoter encompassed within the engineered unicellular organism described is responsive to the stimulus.

In one embodiment, provided herein is a method of detecting a stimulus in the subject, the method comprising (a) administering an engineered unicellular organism described herein to the subject, wherein the inducible promoter is responsive to the stimulus; (b) collecting a sample from the subject after a period of time after administering the engineered unicellular organism; and (c) measuring the expression or action of a reporter element to indicate the state of the memory element of the circuit in the engineered unicellular organism wherein the detectable expression or action of the reporter element encompassed within the engineered unicellular organism described indicates the presence of the stimulus and the presence of a condition caused by microbiota in the subject. In one embodiment, the organism is bacteria. In one embodiment, the sample is a fecal sample.

In one embodiment, provided herein is a method of detecting for cancer in the colon or the gastrointestinal tract in a subject in need thereof, the method comprising (a) administering an engineered unicellular organism described herein, wherein the inducible promoter encompassed within the engineered unicellular organism described is responsive a symptom or biomarker that is known to occur when colorectal cancer is present; (b) collecting a biological sample from the subject after a period of time after administering the engineered unicellular organism; and (c) measuring the expression of the reporter element from the memory element of the circuit in the engineered wherein the detectable expression or action of the reporter element indicates the presence of the a symptom or biomarker that is known to occur when colorectal cancer is present and the likelihood of cancer in the colon of the subject. In one embodiment, the biological sample is a fecal sample.

In one embodiment, provided herein is a method of detecting pathogenic bacterial infection in the colon or the gastrointestinal tract in a subject in need thereof, the method comprising (a) administering an engineered unicellular organism described herein, wherein the inducible promoter encompassed within the engineered unicellular organism described is responsive a symptom or biomarker that is known to occur when as an enteric pathogenic bacterium is present; (b) collecting a biological sample of from the subject after a period of time after administering the engineered unicellular organism; and (c) measuring the expression of or action of the reporter element indicating the state of the memory element of the circuit in the engineered organism wherein the detectable expression of the reporter element indicates the presence of the symptom or biomarker that is known to occur when as an enteric pathogenic bacterium is present and the presence of pathogenic bacterial infection in the colon of the subject. In one embodiment, the biological sample is a fecal sample.

In one embodiment, provided herein is a method of detecting inflammation in the colon or the gastrointestinal tract in a subject in need thereof, the method comprising (a) administering an engineered unicellular organism described herein, wherein the inducible promoter encompassed within the engineered unicellular organism described is responsive a symptom or biomarker that is known to occur when inflammation is present; (b) collecting a biological sample of from the subject after a period of time after administering the engineered unicellular organism; and (c) measuring the expression or action of the reporter element from the memory element of the circuit in the engineered unicellular organism wherein the detectable expression or action of the reporter element indicates the presence of the a symptom or biomarker that is known to occur when inflammation is present and the likelihood of inflammation in the colon of the subject. In one embodiment, the biological sample is a fecal sample.

In one embodiment, provided herein is a method of distinguishing colitis from Crohn's disease in the colon in a subject in need thereof, the method comprising (a) administering an engineered unicellular organism described herein to a subject, wherein the inducible promoter encompassed within the engineered unicellular organism described is responsive to a symptom or biomarker that is known to occur when inflammation is present; (b) administering a second engineered organism described herein to a subject, wherein the inducible promoter is responsive to a symptom or biomarker that is known to occur when a pathogenic bacteria in the colon; (c) collecting a biological sample from the subject after a period of time after the administration steps; and (d) measuring the expression or action of the reporter element from the memory element of the circuit in the first and second engineered unicellular organisms. In one embodiment, the biological sample is a fecal sample.

In one embodiment, provided herein is a method of monitoring the efficacy of a therapy for a colon or the gastrointestinal tract condition in a subject comprising (a) performing a method described herein comprising an engineered unicellular organism at a first time point; (b) performing a method described herein comprising an engineered organism at a second time point, wherein the method in the first time point and second time point are the same and the second time point is after administering at least one therapy; (c) comparing the expression or action of the reporter element from the first time point with that of the second time point, wherein a decrease in the expression or action of the reporter element encompassed within the engineered unicellular organism described is indication of effective therapy and wherein an increase or no change in the expression of the reporter element is indication of ineffective therapy. In one embodiment, the biological sample is a fecal sample.

In one embodiment, the unicellular organism is a bacterium. For example, *Escherichia coli*.

In one embodiment, the stimulus is an indicator of a condition in the subject. For example, tetrathionate and nitric oxide.

In one embodiment, the condition in the colon or the gastrointestinal tract is caused by the microbiota. For example, *Fusobacterium nucleatum, Bilophila wadsworthia*, pathogenic *E. coli*, and *Salmonella* sp.

In one embodiment, the method further comprises collecting a biological sample of matter from the subject after administering the engineered organism to the subject. In one embodiment, the biological sample is a fecal sample.

In one embodiment, the method further comprises measuring for the expression of the reporter element in the subject's biological sample wherein the expression or action of the reporter element indicates the presence of the stimulus and the presence of the corresponding condition in the subject.

In one embodiment, the method further comprises selecting a subject for detecting. In one embodiment, the subject has or is suspected of having a colon or the gastrointestinal tract condition described herein.

In one embodiment, the subject has or is at risk of developing a condition caused by the microbiota. For example, *Fusobacterium nucleatum, Bilophila wadsworthia*, pathogenic *E. coli*, and *Salmonella* sp.

In one embodiment, the two antagonistic transcription factors or gene regulatory factors are cI and Cro.

In one embodiment, the stimulus is a particular environmental condition or marker of interest in the gut of a subject. In one embodiment, the stimulus is the microbiota in the gut of the subject. In other embodiments, the stimulus includes but is not limited to small molecules such as tetracycline, tetrathionate, reactive oxygen species, calprotectin, lactoferrin, and hydrogen sulfide gas ($H_2S$)) or endogenous two-component systems or gene-regulatory networks.

In one embodiment, the stimulus is the inducer described in Table 3 or the target of interest in Table 4.

In one embodiment, provided herein is an engineered unicellular organism such as a bacterium comprising a memory circuit comprising a lambda phage-based cI/Cro-reporter gene-based memory element, and an inducible Cro-based or cI-based trigger element, wherein the lambda phage-based c I/Cro regulates a reporter gene within the memory element, wherein the reporter gene is operably linked to Cro expression in the memory element, wherein Cro or cI in the trigger element is operably linked to an inducible promoter, wherein the inducible promoter is responsive to a trigger agent, wherein the inducible Cro-based or cI-based trigger element produces the trigger transcription factor Cro or I in the presence of the trigger agent, and wherein the memory circuit is integrated into the genome of the bacteria. In one embodiment, the trigger agent is an indicator of a particular environmental condition of interest in the colon of a subject. In one embodiment, the subject is a mammal, for example, a primate mammal, a human.

In another embodiment, provided herein is a method of detecting a target in the colon or gastrointestinal tract in a subject, the method comprising administering any engineered unicellular organism described herein to the subject, wherein the inducible promoter encompassed within the engineered unicellular organism described is responsive to the target, collecting a sample of fecal matter from the subject after a period of time after the administration step; and measuring the expression of the reporter gene from the memory element of the circuit in the engineered unicellular organism wherein the detectable expression of the reporter gene indicates the presence of the target and the presence of a condition in the colon or gastrointestinal tract of the subject. In one embodiment, the presence of the target in the colon or gastrointestinal tract indicates a particular condition in the colon or gastrointestinal tract. For example, the target is the microbiota in the gut such as *F. nucleatum, B. wadsworthia*, pathogenic *E. coli*, and *Salmonella* sp. Presences of these bacteria indicate colon cancer.

In another embodiment, provided herein is a method of detecting cancer in the colon or gastrointestinal tract in a subject in need thereof, the method comprising administering any engineered unicellular organism described herein to a subject, wherein the inducible promoter encompassed within the engineered unicellular organism described is responsive to a symptom or biomarker that is known to occur when colorectal cancer is present; collecting a sample of fecal matter from the subject after a period of time after the administration step; and measuring the expression of the reporter gene from the memory element of the circuit in the engineered unicellular organism wherein the detectable expression of the reporter gene indicates the presence of a trigger agent and the likelihood of cancer in the colon of the subject.

In one embodiment of the method, the symptom or biomarker that is known to occur when colorectal cancer is present is selected from the group consisting of inflammation, an increase in $H_2S$ levels, the presence of *B. wadsworthia* and/or *F. nucleatum*, an increase in the sdiA antigen of a sdiA receptor, and an increase in the overall population of *Escherichia coli* or *Psuedomons* sp. in the colon or gastrointestinal tract.

In one embodiment of the method, more than one symptom or biomarker that is known to occur when colorectal cancer is present are monitored in order to determine the presence of cancer. In this embodiment, the method comprises more than one type of engineered bacteria, wherein each type of engineered unicellular organism is designed to be responsive to a symptom or biomarker described herein that is known to occur when colorectal cancer is present.

In one embodiment of any methods described, inflammation is detected by the presence of reactive oxygen species (ROS), or tetrathionate which is formed as a result of ROS. H2S can be detected by the dsrABEFHCMKLJOPNRS operon from *Allochromatium vinosum*. In one embodiment, an increase in $H_2S$ levels indicates the presence of *B. wadsworthia* or *F. nucleatum*, which correlate with colorectal cancer. sdiA is a reporter system in *E. coli* that senses the population levels of other *E. coli*. Because the population of *E. coli* in healthy people is steady, increases in *E. coli* population will trigger the sdiA response element in an sdiA inducible trigger element, which would indicate presence of a pathogenic strain.

In another embodiment, provided herein is a method of detecting enteric pathogenic bacterial infection in the colon or gastrointestinal tract in a subject in need thereof, the method comprising administering an engineered unicellular organism described herein to a subject, wherein the inducible promoter encompassed within the engineered unicellular organism described is responsive to a symptom or biomarker that is known to occur when a pathogenic bacteria in the colon or gastrointestinal tract; collecting a sample of fecal matter from the subject after a period of time after the administration step; and measuring the expression of the reporter gene from the memory element of the circuit in the engineered unicellular organism, wherein the symptom or biomarker that is known to occur when a pathogenic bacteria in the colon is inflammation, ROS, or tetrathionate, and wherein the detectable expression of the reporter gene indicates the presence of the trigger agent and the presence of pathogenic bacterial infection in the colon of the subject. In one embodiment, inflammation can be detected by the presence of ROS, or tetrathionate which is formed as a result of ROS.

In another embodiment, provided herein is a method of detecting inflammation in the colon or gastrointestinal tract in a subject in need thereof, the method comprising administering an engineered unicellular organism described herein to a subject, wherein the inducible promoter encompassed within the engineered unicellular organism described is responsive to a symptom or biomarker that is known to occur when inflammation is present; collecting a sample of fecal matter from the subject after a period of time after the administration step; and measuring the expression of the reporter gene from the memory element of the circuit in the engineered bacteria. wherein the symptom or biomarker that is known to occur when inflammation is present is ROS, NO, tetrathionate, H2S, calprotectin or lactoferrin, and wherein the detectable expression of the reporter gene indicates the presence of the trigger agent and the likelihood of inflammation in the colon of the subject. In some embodiments, the symptom or biomarker that is known to occur when inflammation is present include but are not limited to reactive oxygen species such as oxyRS and soxRS; tetrathionate, H2S, calprotectin and lactoferrin.

In another embodiment, provided herein is a method of distinguishing colitis from Crohn's disease in the colon or gastrointestinal tract in a subject in need thereof, the method comprising: administering a first engineered unicellular organism described herein to a subject, wherein the inducible promoter encompassed within the engineered unicellular organism described is responsive to a symptom or biomarker that is known to occur when inflammation is present; administering a second engineered unicellular organism described herein to a subject, wherein the inducible promoter is responsive to a symptom or biomarker that is known to occur when a pathogenic bacteria in the colon; collecting a sample of fecal matter from the subject after a period of time after the administration step; and measuring the expression of the reporter gene from the memory element of the circuit in the first and second engineered bacteria.

It is known that inflammation is present in both these diseases. In one embodiment, the detectable expression of the reporter genes from either the first and second engineered unicellular organism described indicates the presence of inflammation and therefore preliminarily indicates the possible presence of colitis or Crohn's disease. In one embodiment, the detectable expressions of the reporter genes from both the first and second engineered unicellular organism described, and/or the detectable presence of inflammation and the presence of specific bacteria distinguished between the two conditions, colitis or Crohn's disease, and/or other conditions that may cause inflammation.

In another embodiment, provided herein is a method of monitoring the efficacy of a therapy for a colon or gastrointestinal tract condition in a subject comprising performing a method comprising an engineered unicellular organism described herein at a first time point; performing a method comprising an engineered unicellular organism described herein at a second time point, wherein the method in the first time point and second time point are the same and the second time point is after administering at least one therapy; comparing the expression of the reporter gene from the first time point with that of the second time point, wherein a decrease in the expression of the reporter gene is indication of effective therapy and wherein an increase or no change in the expression of the reporter gene is indication of ineffective therapy.

In another embodiment, provided herein is a formulation comprising an engineered unicellular organism described herein.

In one aspect, this disclosure relates to the use of engineered unicellular organism described herein for detecting cancer in the colon or gastrointestinal tract in a subject.

In another aspect, this disclosure relates to the use of engineered unicellular organism described herein for detecting pathogenic bacterial infection in the colon or gastrointestinal tract in a subject.

In another aspect, this disclosure relates to the use of engineered unicellular organism described herein for detecting inflammation in the colon or gastrointestinal tract in a subject.

In another aspect, this disclosure relates to the use of engineered unicellular organism described herein for distinguishing colitis from Crohn's disease in the colon or gastrointestinal tract in a subject.

In another aspect, this disclosure relates to the use of engineered unicellular organism described herein for monitoring the efficacy of a therapy for a colon or gastrointestinal tract condition in a subject. For example, treatment of colitis and Crohn's disease.

In one embodiment, the engineered unicellular organism is an engineered bacterium. For example, *E. coli*.

In one embodiment of the engineered unicellular organism, the memory circuit in maintained in the unicellular organism without any antibiotic or metabolic selection.

In one embodiment of any engineered unicellular organism or bacterium described, the memory circuit comprises the lambda phage sequences of PL, OL, cI and Cro. In one embodiment of any engineered unicellular organism or bacterium described, the memory circuit further comprises the lambda phage sequences rexA and rexB. In one embodiment of any engineered unicellular organism or bacterium described, the memory circuit comprises the lambda phage sequences of PL, OL, rexA, rexB, cI and Cro. In one embodiment of any memory circuit in any engineered unicellular organism or bacterium described, the lambda phage PL, OL, rexA, rexB, cI and Cro sequences are arranged in the following order: PL, OL, rexA, rexB, cI and Cre. In one embodiment, PL, OL, rexA, rexB, cI and Cre sequences are arranged in the normal prophage orientation.

In one embodiment any methods described, any reporter gene that can be express and produces measurable or detectable signal readout can be used in the memory element. In one embodiment any methods described, the reporter gene encompassed within the bacteriophage-reporter element-based memory element is selected from a group consisting of β-galactosidase (LacZ), chloramphenicol acetyltransferase (CAT), neomycin phosphotransferase (G418), bacteria luciferase (LuxAB), a fluorescent protein (FP), alkaline phosphatase (PhoA), and p-glucuronidase (GUS), and leptin. In some embodiments, the FP is selected from green fluorescent protein, yellow fluorescent protein, red fluorescent protein, cyan fluorescent protein, blue fluorescent protein, Far-red fluorescent protein, true-red fluorescent protein, and infra-red fluorescent protein.

In one embodiment, the inducible promoter is responsive to a stimulus or a target.

In one embodiment, the inducible promoter is responsive to tetracycline. In other embodiments the inducible promoter is responsive to but not limited to tetrathionate, calprotectin, lactoferrin, hydrogen sulfide ($H_2S$), reactive oxygen species such as hydrogen peroxide, nitric oxide (NO), and superoxide, undesirable pathogenic bacteria such as *E. coli* NC101, *Salmonella typhimurium*, *B. wadswortia*, and *F. nucleatum*.

In another embodiment, provided herein is a method of detecting a target in the colon or gastrointestinal tract of a subject, the method comprising administering engineered bacteria described herein to the subject, wherein the inducible promoter encompassed within the engineered bacteria described is responsive to the target, and wherein the engineered bacteria described herein indicates the presence of the target in the colon. In other words, the engineered bacteria described herein "sense" the presence of the target in the colon and report the detected presence of the target via the regulated expression of the reporter gene encoded which in the memory element in the engineered bacteria.

In one embodiment, the target is an indicator of a condition in the colon or gastrointestinal tract. In some embodiments, several targets in combination indicate a condition in the colon. For example, the target can be $H_2S$, NO, super oxide or tetrathionate. All these targets individually indicate the presence of inflammation in the colon or gastrointestinal tract.

In one embodiment, more than one type of engineered bacteria described herein is administered to the subject in order to ascertain the presence or absence of a particular condition in the colon of the subject. In one embodiment, each type of engineered bacteria described herein indicates the presence or absence of a single target in the colon or gastrointestinal tract.

In one embodiment, the method further comprises collecting a sample of fecal matter from the subject after administering the engineered bacteria to the subject.

In one embodiment, the method further comprises measuring for the expression of the reporter gene in the sample of fecal matter wherein the detectable expression of the reporter gene indicates the presence of the target and the presence of the condition in the colon of the subject.

In one embodiment, the method further comprises selecting a subject for detecting.

In one embodiment, the subject has or is at risk of developing a colon condition.

In some embodiments, the target includes but is not limited tetrathionate, reactive oxygen species (ROS), $H_2S$, SdiA, bacteria enterotoxins, calprotectin and lactoferrin. Essentially anything that bacteria can detect through a two-component signaling system can serve as the target for detection. In some embodiments, the target includes the presence of metabolites such as amino acids, or other carbon sources such as arabinose.

In one embodiment, the colon condition is cancer, inflammation, pathogenic bacterial infection, inflammatory bowel disease (IBD) such as Crohn's disease, colitis, and diabetes. In one embodiment, the colon condition is detected and identified by detecting an increase in inflammation in the colon. Recent publications have indicated that disruptions to the balance of the microbiota and the immune system lead to increases in inflammation that lead to virtually every inflammation-based and over-active immune system-based disease. This includes diabetes, arthritis, and allergies. In another embodiment, the colon condition is detected and identified by detecting an increase in inflammation in the colon and the presence of at least one symptom of cancer, inflammation, pathogenic bacterial infection, inflammatory bowel disease (IBD) such as Crohn's disease, colitis, and diabetes.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, the term "comprising" or "comprises" is used in reference to methods, and respective component(s) thereof, that are essential to the invention, yet open to the inclusion of unspecified elements, whether essential or not. The use of "comprising" indicates inclusion rather than limitation.

As used herein, the term "gut" refers to the alimentary canal or gastrointestinal tract or a portion thereof, including the mouth, stomach, small intestine, large intestine, colon, rectum and anus.

As used herein, the term "pharmaceutically acceptable", and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. Each carrier must also be "acceptable" in the sense of being compatible with the other ingredients of the formulation. The preparation of a pharmacological composition that contains active ingredients dissolved or dispersed therein is well understood in the art and need not be limited based on formulation. The pharmaceutical formulation contains a compound of the invention in combination with one or more pharmaceutically acceptable ingredients. The carrier can be in the form of a solid, semi-solid or liquid diluent, cream or a capsule. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques. The phrase "pharmaceutically acceptable carrier or diluent" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. A pharmaceutically acceptable carrier will not promote the raising of an immune response to an agent with which it is admixed, unless so desired.

As used herein, "administered" refers to the placement of one or more type of engineered bacteria described herein, or a composition comprising into one or more type of engineered bacteria described here in a subject by a method or route which results in at least partial localization of the engineered bacteria to a desired site. In some embodiments, the desired site is anywhere along the gut. Modes of administration include injection, infusion, instillation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

As used herein, "operably linked" is intended to mean that a nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences).

As used herein, "a symptom or biomarker that is known to occur when colorectal cancer is present" includes but not limited to detect inflammation, anaerobic conditions, an increase in H2S levels, the presence of *B. wadsworthia* or *F. nucleatum*, an increase in the sdiA antigen of a sdiA receptor, and an increase in the overall population of *E. coli* in the colon, and secondary metabolites that may indicate the presence of a pro-tumor environment.

As used herein, "a symptom or biomarker that is known to occur when inflammation is present in the colon" includes but not limited to ROS, H2S, calprotectin or lactoferrin, hydrogen peroxide, nitric oxide, superoxide, and tetrathionate.

As used herein, "a symptom or biomarker that is known to occur when an enteric pathogen bacteria is present in the colon" includes but is not limited to inflammation, ROS, tetrathionate, species specific quorum signals and pathogen specific metabolites such as H2S.

As used herein, in one embodiment, the term "memory circuit" refers to a gene-based "device" comprising a (1) memory element and (2) a trigger element, wherein the memory element further comprises a (3) reporter element.

As used herein, in one embodiment, the term "memory element" refers to a genetic element comprising mutually exclusive, transcriptional auto-feedback loops defining distinct transcriptional states regulated by the expressions of antagonistic transcription factors.

As used herein, in one embodiment, the term "trigger element" refers to a genetic element comprising a stimulus-responsive promoter driving the expression of a trigger transcription factor that will induce the memory element to switch state from OFF to ON. In one embodiment, the trigger transcription factor from the trigger element is the trigger transcription factor that would upregulate the expression of the reporter gene encompassed within the memory element. In one embodiment, the trigger transcription factor from the trigger element is one of the antagonistic transcription factors comprising the memory element.

As used herein, in one embodiment, the term "reporter element" refers to a genetic element comprising promoters responsive to the state of the memory element, wherein the responsive promoters are operably linked to a reporter gene, and the reporter element produces a detectable signal that indicates the state of the memory element. In some embodiments, the detectable signal comprises a change in protein expression or DNA rearrangement. In some embodiments, the change in protein expression or DNA rearrangement is detected as a change in fluorescence over a reference level of fluorescence. In one embodiment, the reference level of fluorescence is the background level of fluorescence in the absence of protein expression or DNA rearrangement.

As used herein, in one embodiment, the term "genetic element" refers to elements comprising nucleic acid sequences, for example, deoxyribonucleic acid and ribonucleic acid.

As used herein, in one embodiment, the term "antagonistic transcription factors" refer to DNA binding proteins that act to upregulate self-expression and downregulate the expression of the competing transcription factor.

As used herein, in one embodiment, the term "stimulus" refers to a small molecule, protein, or environmental state that acts to upregulate transcription from a transcriptional promoter.

As used herein, "a stimulus-responsive promoter" is a promoter comprising at least one responsive element that is operably linked to drive the expression of a trigger transcription factor.

As used herein, in one embodiment, the phrase "a disease related to the microbiota" refers to a condition selected from the group consisting of cancer, inflammation, pathogenic bacterial infection, inflammatory bowel disease (IBD), Crohn's disease, colitis, rheumatoid arthritis, and diabetes.

As used herein, in one embodiment, the phrase "the expression or action of the reporter element" refers to the expression of the reporter gene encompassed within the reporter element.

As used herein, the term "microbiota" refers to the collection of the microorganisms of a particular site, habitat, or geological period. For example, gut microbiota (formerly called gut flora) is the name given today to the microbe population living in the intestine of a subject.

In one embodiment, as used herein, the term "detectable expression" or "detectable signal" when used in the context of the expression or action of reporter gene of the memory element to indicate the corresponding condition of the colon, gastrointestinal tract, target or stimulus means that the reporter expression level or action level is over the background level wherein the background expression or signal is that obtained in the absence of the any fecal matter or engineered unicellular organism when an appropriate detection method is used for assessing the expression or action of reporter gene or the background expression or signal is that obtained in healthy subjects having the engineered unicellular organisms. The protein expression is converted to a signal that can be measured and determined, e.g. a color precipitate or fluorescence. For example, if the signal is protein fluorescence, then "detectable expression" or "detectable signal" means fluorescence over that of background fluorescence reading in the absence of any fecal matter or engineered unicellular organism using the same fluorescence detection method.

In one embodiment, as used herein, the term "detectable expression" or "detectable signal" when used in the context of the expression or action of reporter gene in the memory element to indicate the corresponding condition of the colon, gastrointestinal tract, target or stimulus means that the reporter expression or action level is at least 2.5% increase over a reference level.

In one embodiment, the reference level is the background expression or signal obtained in the absence of the any fecal matter or engineered unicellular organism when an appropriate detection method is used for assessing the expression or action of reporter gene.

In one embodiment, the reference level is the background expression or signal obtained in healthy subjects having the engineered unicellular organisms when an appropriate detection method is used for assessing the expression or action of reporter gene. Healthy subjects would not have any inducers or biomarkers that would activate the trigger element.

In one embodiment, the reference level is the average background detectable expression or signal obtained in the absence of the any fecal matter or engineered unicellular organism or the average background expression or signal obtained in healthy subjects having the engineered unicellular organisms when an appropriate detection method is used for assessing the expression or action of reporter gene. The background is obtained by taking at least 10 separate and independent measurements (i.e., n>10) and the average background is calculated.

In one embodiment, the reference level is the average detectable expression or signal obtained from the fecal matter or engineered unicellular organisms obtained from healthy subjects known not to have condition of the colon, gastrointestinal tract, target or stimulus of interest. The average detectable expression or signal is obtained from a population of healthy subjects known not to have condition of the colon, gastrointestinal tract, target or stimulus of interest. For example, average detectable expression or signal is obtained from a population of at least 25 healthy subjects.

In some embodiments, as used herein, the term "detectable expression" or "detectable signal" when used in the context of the expression or action of reporter gene of the memory element to indicate the corresponding condition of the colon, gastrointestinal tract, target or stimulus means that the reporter expression or action level is least one or two standard deviation increase over a reference level, wherein the reference level is an average value from a collection of at least n>10 data points.

In some embodiments, the increase of the expression or action of reporter gene is by at least 2.5%, at least 5%, at least 7.5%, at least 10%, at least 20%, at least 30%, at least 40%, at least 50%, at least 60%, at least 70%, at least 80%, at least 90%, up to and including 100% over the reference level.

In some embodiments, the increase of the expression or action of reporter gene is by at least one standard deviation or at least two standard deviations over the average reference level.

BRIEF DESCRIPTION OF THE DRAWINGS

FIGS. 1A-1D show the representative schematic of a memory circuit and activation of such a circuit.

FIG. 1A shows an abstraction of the genetic circuit used in this study combining the elements of a trigger/memory system and a toggle switch10 (TF-1 and TF-2 symbolize generic antagonistic transcription factors). The chromosomally integrated memory element and trigger elements were constructed by a combination of commercial synthesis (GENSCRIPT, Inc.) and PCR amplification of component elements from source DNAs, and assembly in vitro through overlap extension PCR22, followed by introduction directly into *E. coli* TB1023 by recombineering without construction of plasmid intermediates[24]. A spontaneous high-level streptomycin-resistance mutation was isolated in MG1655 and confirmed to be rpsL(lys42arg)[25,26]. Memory and trigger elements and the rpsL mutation were moved between strains by P1vir transduction[27].

FIG. 1B shows one embodiment of the lambda cI/Cro-based transcriptional memory circuit. The construct integrated into the *E. coli* genome lacks sequences from the lad promoter up to the start codon for lacZ. These are replaced by phage sequences including $P_L$, $O_L$, rexB, rexA, cI and cro through the cro stop codon, such that lacZ is now transcribed from PR after cro.

FIG. 1C shows the tetP-cro trigger element used in this study. This element consists of a chloramphenicol-resistance cassette, a tetR-tetP segment from Tn10 that includes the divergent tetracycline promoters, and the Cro gene transcribed from the tetA promoter. This segment was inserted into the MG1655 genome between araB and araC promoters to minimize aberrant read-through from external promoters.

FIG. 1D shows the readout of the memory element using indicator plates. In the absence of ATC, the trigger element is 'OFF', the trigger transcription factor is not made, the memory element is in the cI state, cells are lac−, and colonies on M9 glucose X-gal plates are white, and on bromocresol purple (BCP)-containing MacConkey Lactose plates they are clear on a purple background. In the presence of ATC, the trigger element is 'ON', the trigger transcription factor is made, the memory element switches to the cro state, cells are lac+, and colonies on M9 glucose X-gal plates are blue, and on MacConkey Lactose plates they are yellow on a yellow background.

FIG. 2A shows the effects of PAS 132 grown in liquid culture in the presence of ATC (100 ng/ml) for 0-6 hrs. At the indicated times, aliquots were plated on M9 glucose X-gal plates to quantify cells that switched from the cI state to the cro state in response to ATC. To assess stability of the Cro-expressing memory state, cells that had been switched from the cI state to the cro state were transferred to −ATC media, and grown aerobically with shaking for up to 5 days with 1000-fold dilutions performed every 8 hours to maintain exponential growth. At the indicated times, aliquots were plated on M9 glucose X-gal plates to evaluate the percentage of cells that remained in the cro state after removal of ATC.

FIG. 2B shows the in vitro triggering of PAS 132. (circles) PAS 132 in +ATC media, (squares) PAS 132 in −ATC media.

FIG. 2C shows the in vitro memory of ATC exposure. (dark circles) cro state PAS 132 in −ATC media, (light circles) cro state PAS 132 in +ATC media (positive control), (squares) cI state PAS 132 in −ATC media (negative control).

FIG. 2D shows the effects of PAS 132 grown in liquid culture in the presence of ATC at the indicated concentration for 4 hours, then plated on M9 glucose X-gal plates to determine the minimum dose of ATC required to switch the cells from the cI state to the cro state. (circles) PAS 132 in +ATC media. For all panels, points represent the average of 3 or more individual cultures. Error bars represent standard deviation.

FIG. 3A shows that fecal samples were collected from acclimated female BALB/c mice (Charles River Laboratories) on the indicated days, weighed, and solubilized in 0.85% NaCl. Gut flora was analyzed by tittering solubilized fecal samples on the indicated days anaerobically on brain heart infusion (BHI) to determine total CFU, and aerobically on MacConkey lactose plates with and without streptomycin to measure total coliforms and engineered bacteria.

FIG. 3B shows that mice were given ATC 0.1 mg/ml) and streptomycin (0.5 mg/ml) in drinking water on day 8. PAS 132 cells were administered to the mice via oral gavage on day 9. Streptomycin and ATC were removed from the cage on days 10 and 11, respectively. (circles)+ATC mice, (squares)−ATC mice. Points represent the average from 4+ATC mice, and 4−ATC mice.

FIG. 3C shows that the total PAS 132 cells in the cI and cro states. Bars represent the average from 4+ATC mice, and 4−ATC mice.

FIG. 3D shows that (squares) PAS 132 and (circles) total culturable bacteria throughout the experiment. Points represent the average from 8 mice. For all panels, error bars represent standard deviation.

FIG. 4A shows that 16S ribosomal subunits of PAS132 and PAS 133 were sequenced and compared against known gut microbes28.

FIG. 4B shows the effects of PAS 133 grown in M9 glucose+casamino acids liquid medium+ATC (100 ng/ml), or −ATC for 0-6 hrs. PAS 133 was unable to grow in M9 glucose media, without casamino acids. At the indicated times, aliquots were titered on MacConkey Lactose plates to evaluate switching from the cI state to the cro state in response to ATC. (circles) PAS 133 in +ATC media, (squares) PAS 133 in −ATC media. Points represent the average of 3 individual cultures.

FIG. 4C shows the effects of PAS 133 administered by oral gavage to mice exposed to antibiotics, and gut flora were characterized following the same protocol as in FIG. 3. On day 11 the ATC was removed from the cage. (circles)+ATC mice, (squares)−ATC mice. Points represent the average from 4+ATC mice, and 4−ATC mice.

FIG. 4D shows the comparison of survival of PAS 133 and PAS 132, engineered E. coli K12 in the mouse gut. Shown are (black) PAS 132, (grey) PAS 133, and (white) total cultural gut flora counts on corresponding days. Bars represent the average from 8 mice administered PAS 132, and 8 mice administered PAS 133. For all panels, error bars represent standard deviation.

FIG. 5A shows that memory elements 11-14, which were integrated into strains PAS 129-PAS 132 respectively, and were evaluated for response to ATC. Element 12 failed to show a stable cro memory state when plated on Lac indicator plates without ATC. However, this element did express lacZ on plates with ATC, indicating that the cro state could be detected via read-through transcription of tR1, but that element 12 was unable to maintain the cro state in this plate assay. (Triangle) PAS 129, (square) PAS 130, (diamond) PAS 131, (circles) PAS 132.

FIG. 5B shows that memory 13 responded solely due to the increase in temperature. At t=0 there is a low level of switching from the cI state to the cro state, which was likely due to mutant cI instability. (diamond) PAS 131 in +ATC media at 37° C., (squares) PAS 131 in −ATC media at 37° C. For all panels, points represent the average of 3 individual cultures, and error bars represent standard deviation.

FIGS. 6A-6E show the engineered sequences for the embodiment of a memory circuit disclosed herein. The circuit consists of a kanamycin-resistance cassette transcribed away from cI and cro, and phage lambda sequences from 35561 to 38241 including the cIind1 mutation[29]. This DNA was inserted between bases 366802 and 365529 in the E. coli K12 MG1655 genome[30]. The resulting construct contains E. coli sequences including a potential terminator downstream of the mhp gene upstream of lacI, but lacks sequences from the lad promoter up to the start codon for lacZ. These are replaced by phage sequences including PL, OL, rexB, rexA, cI, and cro through the cro stop codon, such that lacZ is now transcribed from PR after cro.

FIG. 6A shows the memory element in PAS 129 (SEQ ID NO: 3).

FIG. 6B shows the memory element in PAS 130 (SEQ ID NO: 4).

FIG. 6C shows the memory element in PAS 131 (SEQ ID NO: 5).

FIG. 6D shows the memory element in PAS 132 (SEQ ID NO: 6).

FIG. 6E shows the tetP-Cro trigger element embodiment disclosed in the example section (SEQ ID NO: 7).

FIG. 8 shows the sequence of the rpsL mutation (SEQ ID NO: 8). The rpsL gene of PAS 132 and MG1655 was amplified using 5'-CCA GCC AGA TGG CCT GG-3' (SEQ ID NO: 1) and 5'-GAC GCG ACG ACG TGG C-3' (SEQ ID NO: 2) primers, then sequenced. The sequences were compared using Lasergene software to identify the A430G mutation that resulted in a Lys42Arg mutation.

FIG. 9A shows the recording of ATC in vivo exposure by engineered bacteria. PAS 132 cells were administered on day 9, and ATC was never removed from the drinking water. Nearly all of PAS 132 triggered into the cro state within 1 day of ATC exposure, and was displaced by the natural gut flora by day 18. (circles)+ATC mice, (squares)−ATC mice.

FIG. 9B shows the PAS 132 cells were administered on day 9. ATC (0.1 mg/ml) was added to the drinking water on day 10 after streptomycin was removed. ATC was removed from the drinking water on day 11. All PAS 132 cells triggered into the cro state within 1 day of ATC exposure, and remembered ATC exposure for more than 6 days. (circles)+ATC mice, (squares)−ATC mice. This indicates that PAS 132 that have colonized the gut are able to record changes in their environment. For all panels, points represent the average from 4+ATC mice, and 4−ATC mice, and error bars represent standard deviation.

FIG. 10A shows the in vivo experiment #1 corresponds to data presented in FIG. 7A. Mice were not weighed until day 8 before fasting for 24 hr, and the addition of streptomycin and ATC to their drinking water.

FIG. 10B shows the in vivo experiment #2 corresponds to data presented in FIG. 3.

FIG. 10C shows the in vivo experiment #3 corresponds to data presented in FIG. 7B.

FIG. 10D shows the in vivo experiment #4 corresponds to data presented in FIG. 4. Points represent the mass of an individual mouse on the specified day.

FIG. 11 shows the alignment of the 16S Sequence of PAS 132 (SEQ ID NO: 11) and PAS 133 (SEQ ID NO: 12) with MG1655 (SEQ ID NO: 10). The gene encoding the 16S ribosomal subunits of PAS 132 and PAS 133 were amplified by PCR, then sequenced[28][28]. The sequences were aligned against the reference sequence of MG1655 using Lasergene software. A phylogenetic tree was constructed comparing the reference sequences of the indicated bacteria using LASERGENE software. Figure discloses "Majority" sequence as SEQ ID NO: 9.

FIG. 12A shows the memory elements 11-14 were integrated into strains PAS129-PAS132, and the bacteria were evaluated for switching in response to ATC. For all panels, points represent the means±SD of 3 or more independent samples.

FIG. 12B shows PAS129-PAS132 were evaluated for switching in response to an incubation temperature of 42° C., without ATC. For all panels, points represent the means±SD of 3 or more independent samples.

Figure 14:
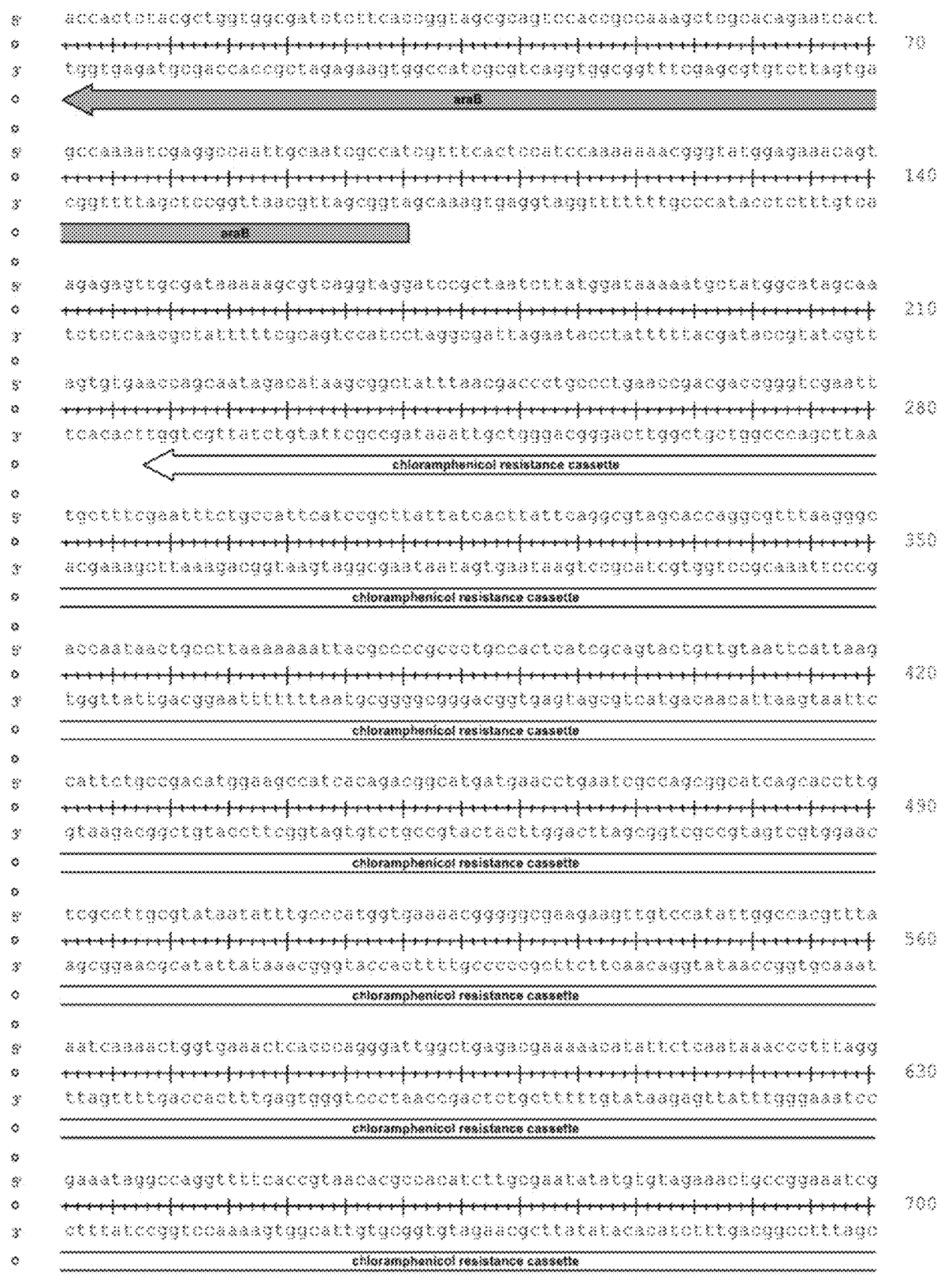
Figure 14:
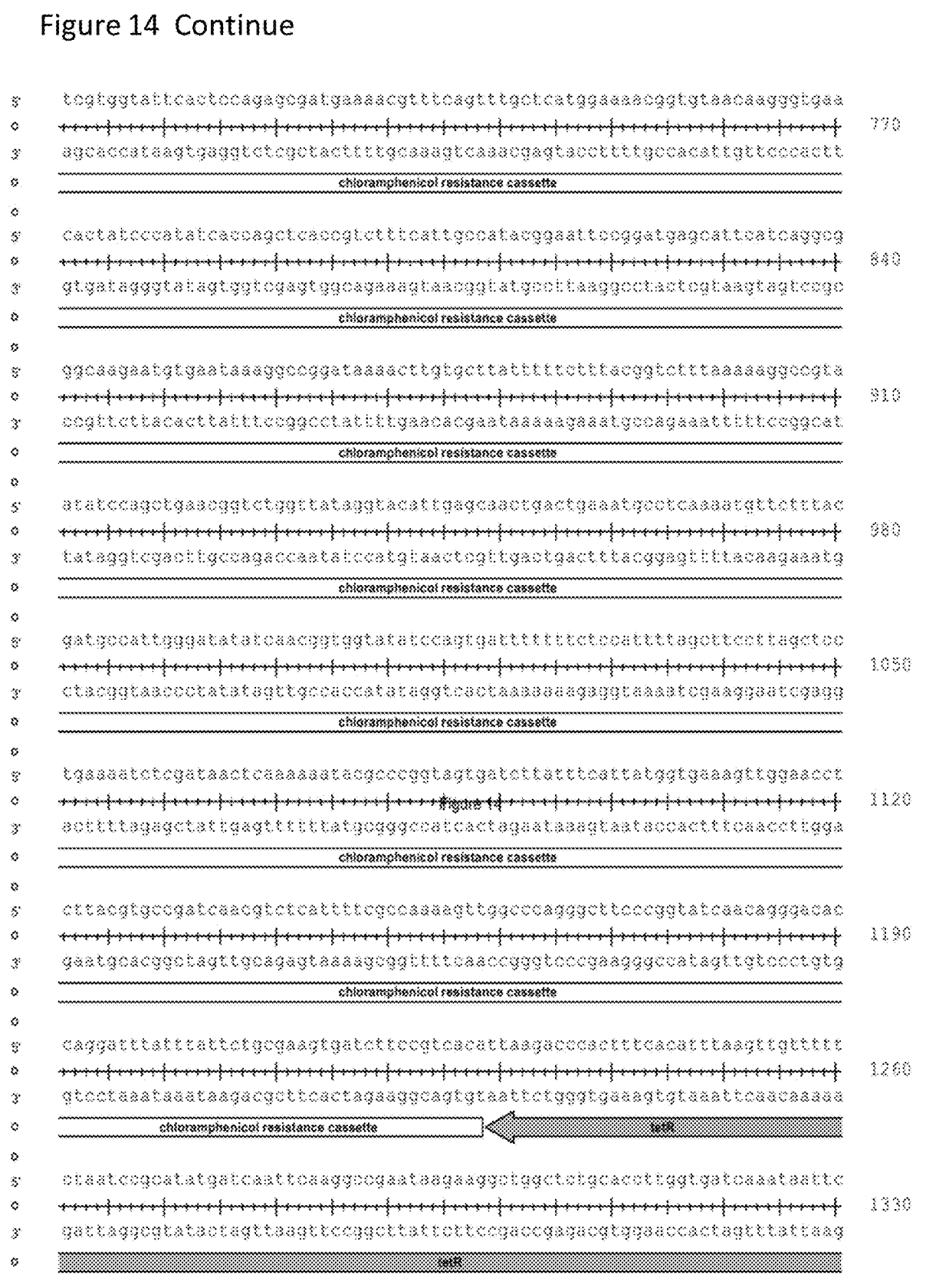
Figure 14:
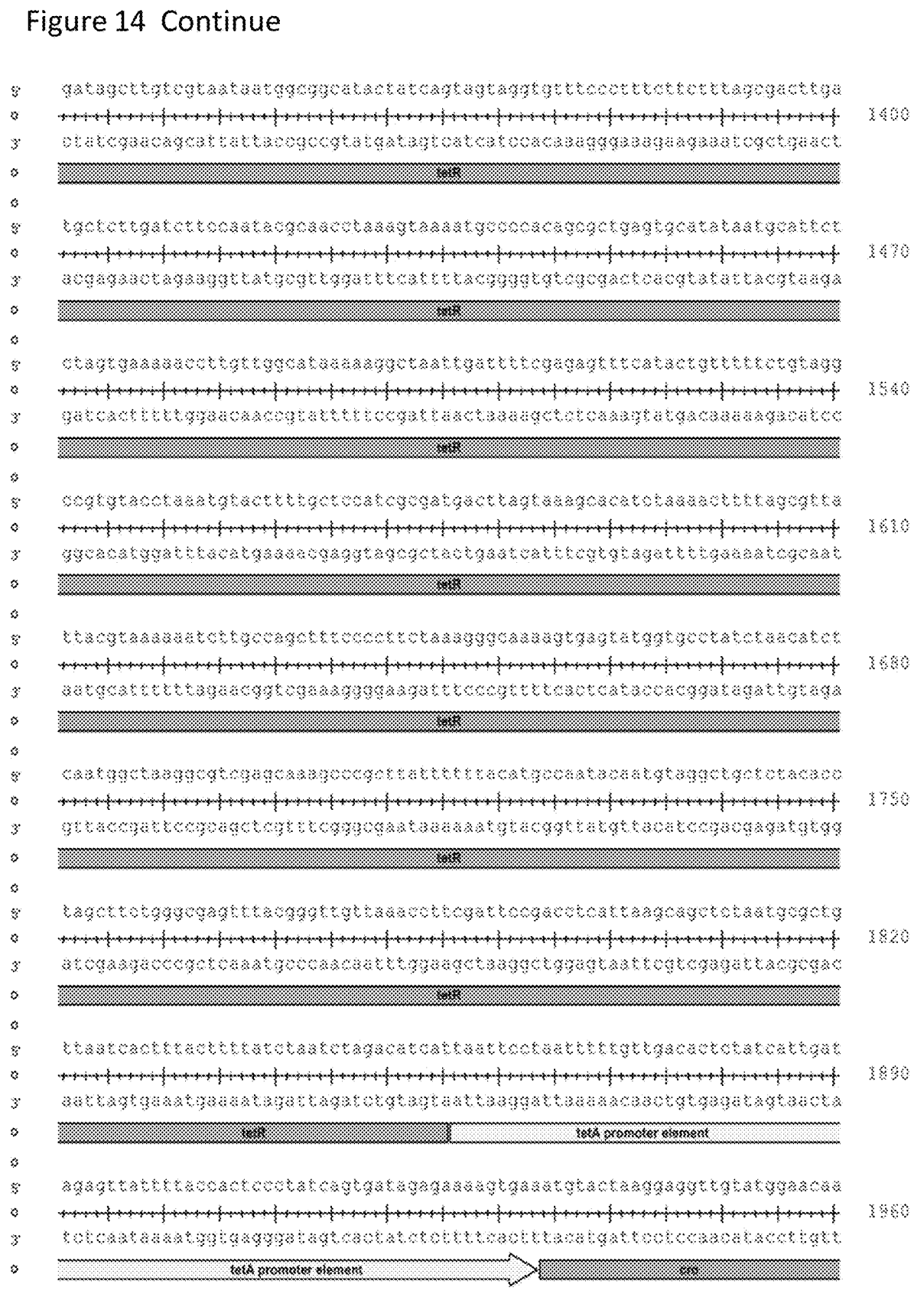
Figure 14:
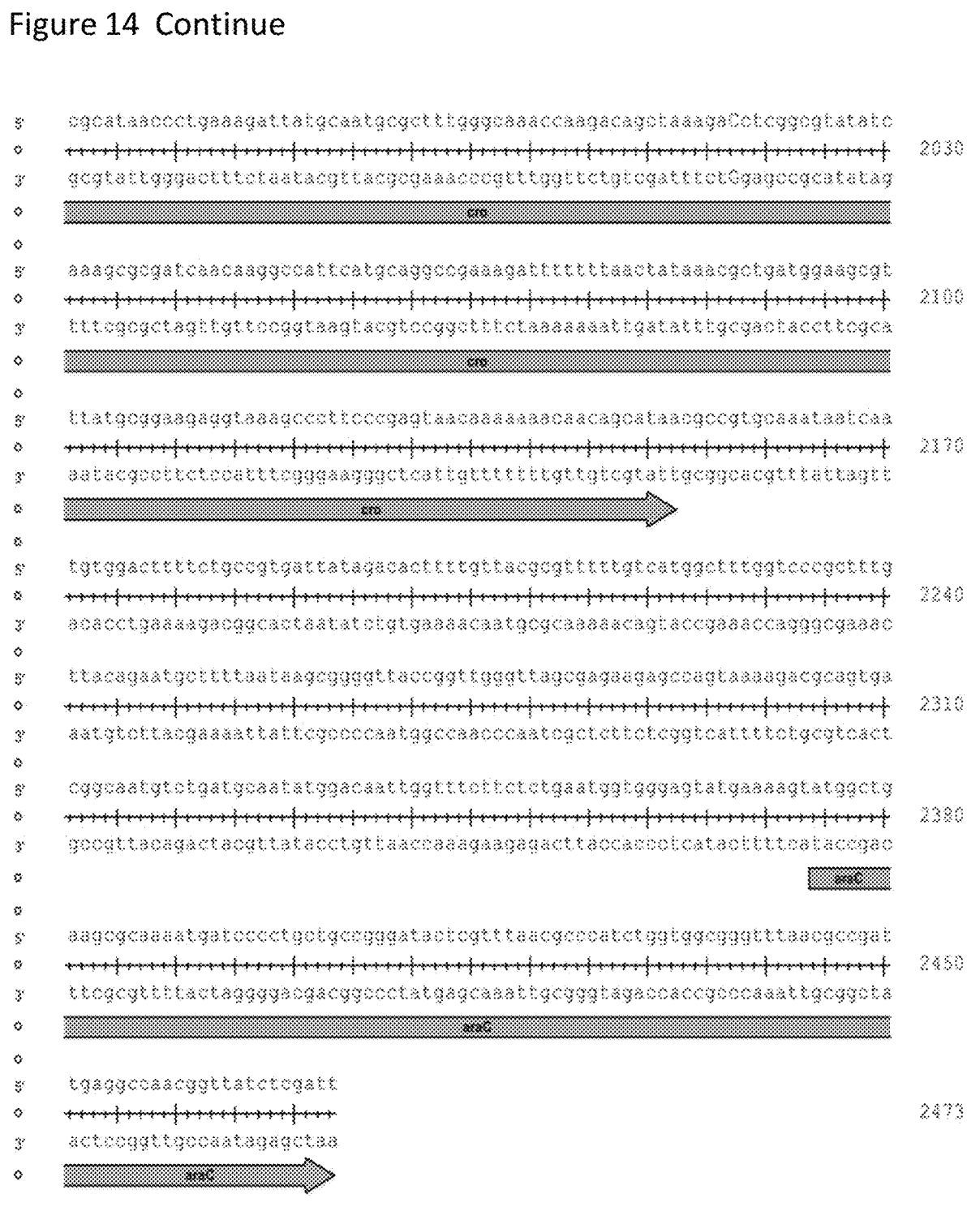

FIG. 14 shows the DNA sequence (SEQ ID NO: 7) of a representative trigger element having a tetracycline response element comprising tetR and the tetA promoter element upstream of the Cro coding sequence.

Figure 15:
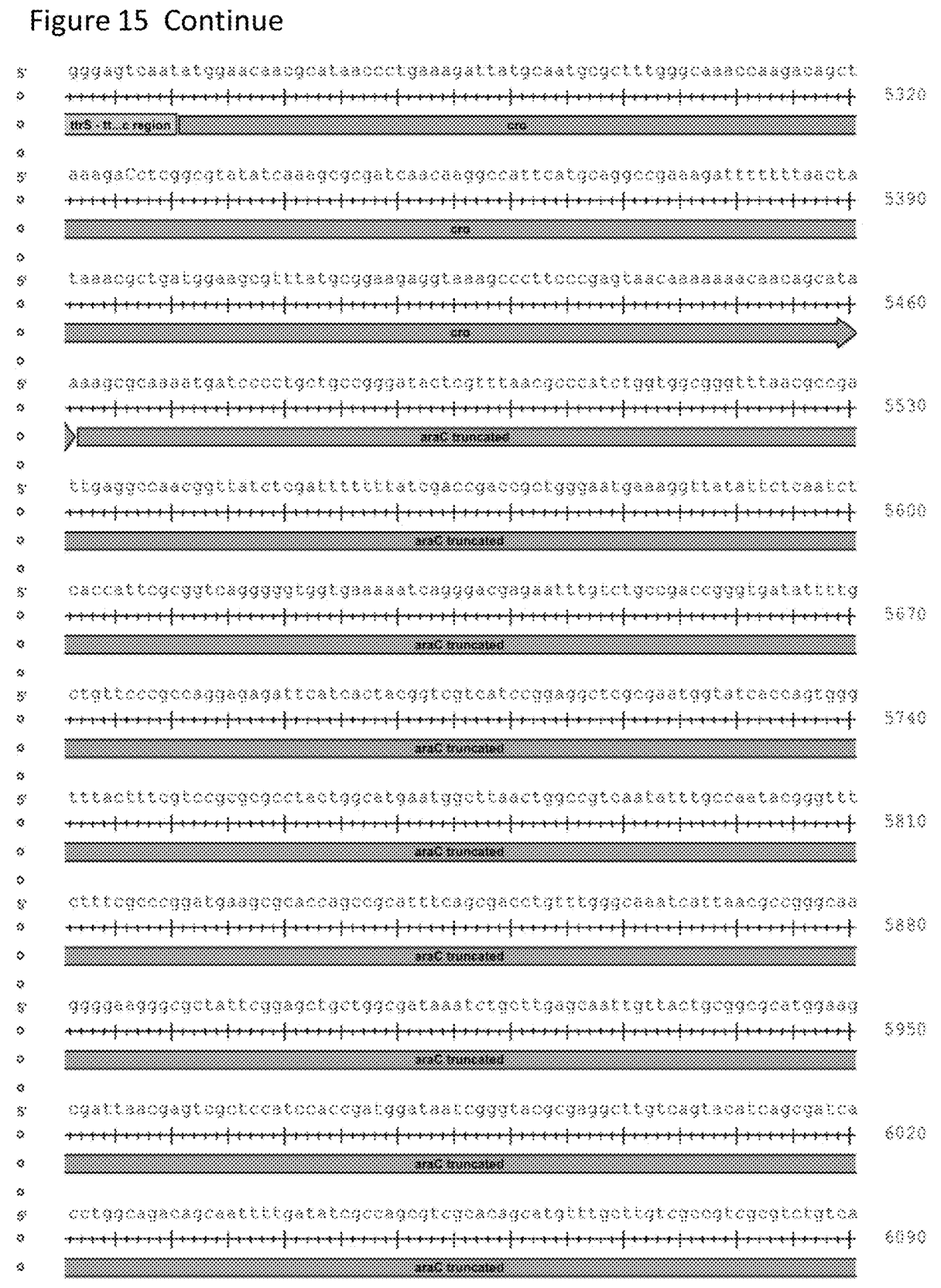
Figure 15:
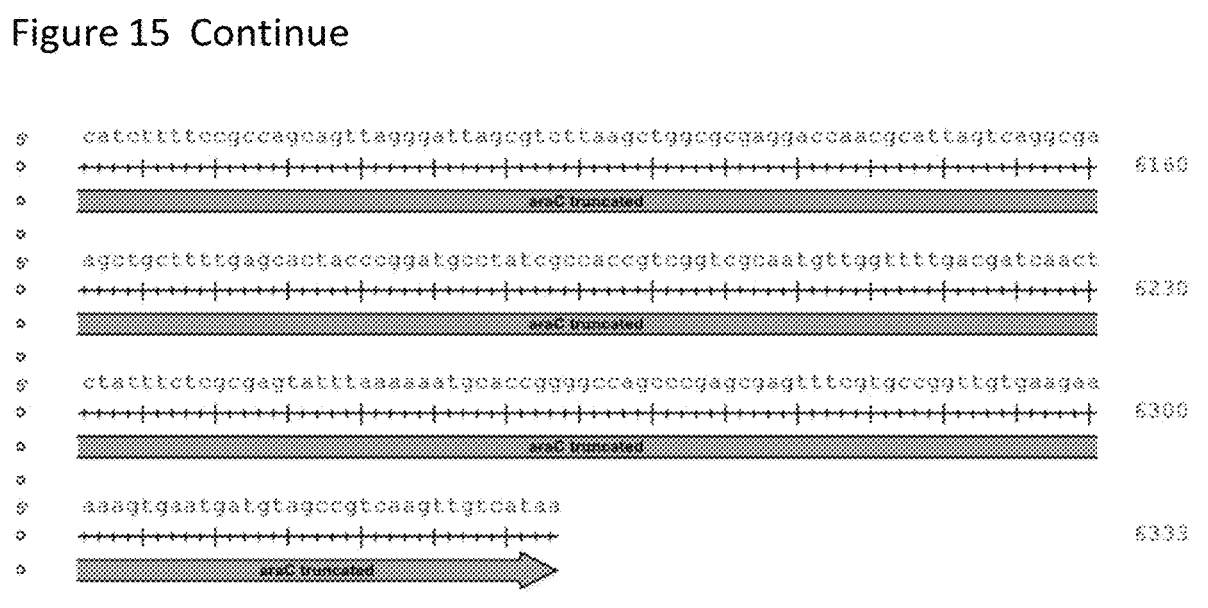

FIG. 15 shows the DNA sequence (SEQ ID NO: 13) of a representative trigger element having a tetrathionate response element comprising ttrR, ttrS (transcriptional regulators), and the ttrB promoter upstream of the Cro coding sequence.

FIG. 16 shows the DNA sequence (SEQ ID NO: 14) of a representative trigger element having a sdiA response element comprising PsidA (promoter sidA) element upstream of the Cro coding sequence.

Figure 20:
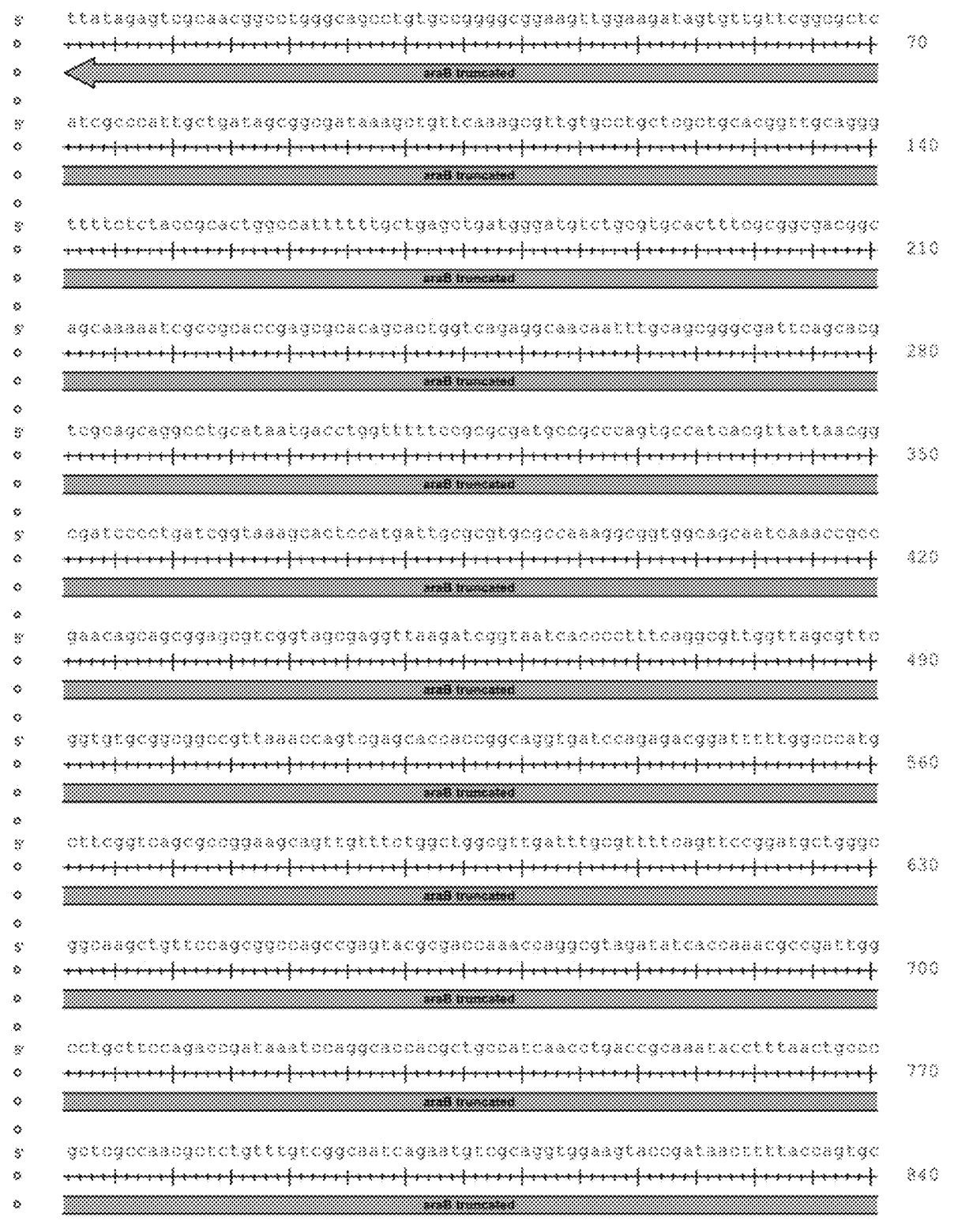
Figure 20:
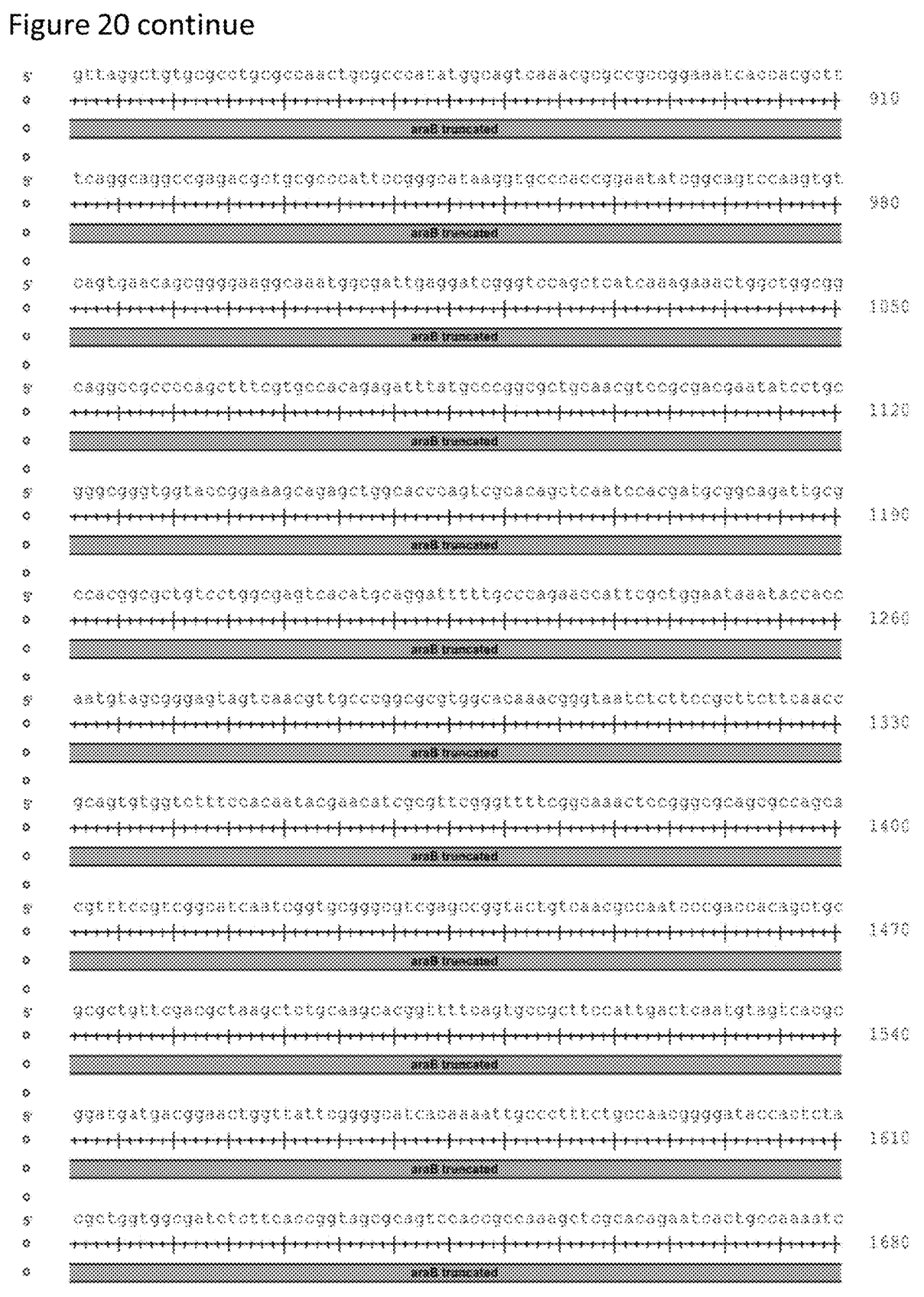
Figure 20:
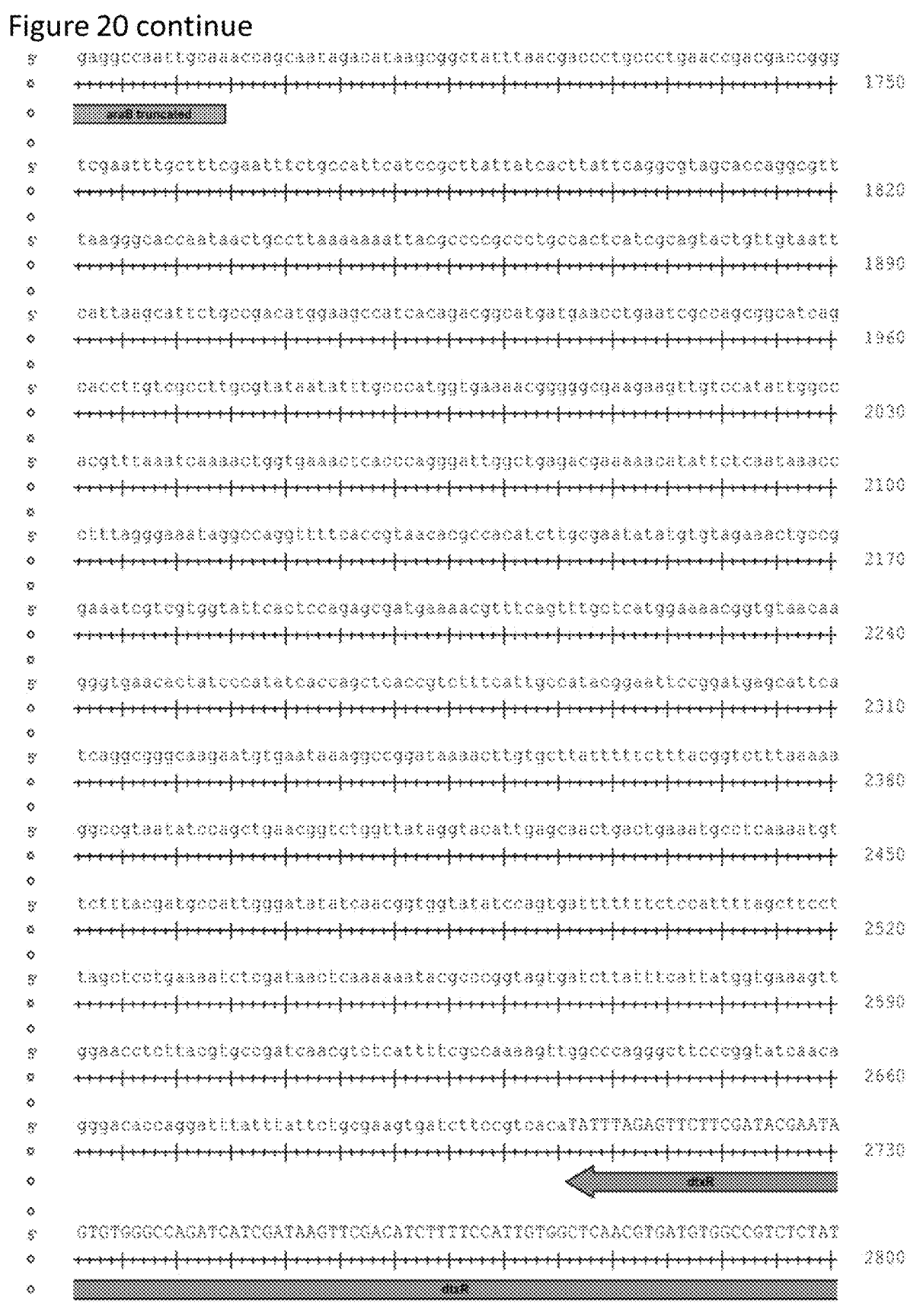
Figure 20:
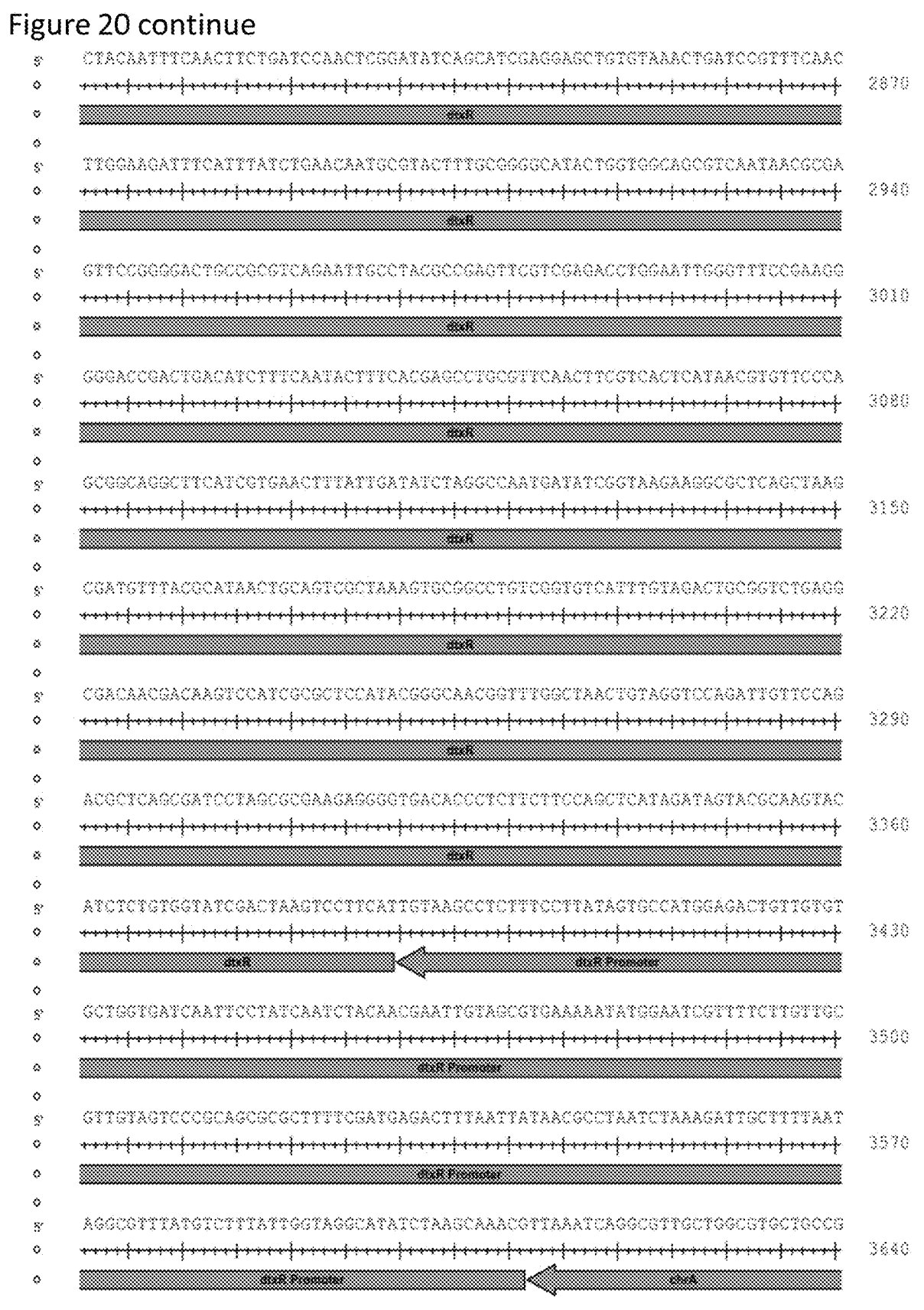

FIG. 20 shows the DNA sequence (SEQ ID NO: 18) of a representative trigger element having a Heme response element (hmuO) comprising dtxR, chrA, chrS and the hmuO promoter element upstream of the Cro coding sequence. hmuO is a cancer responsive element. dtxR, chrA and chrS are transcriptional regulators of the hmuO promoter. In the presence of heme, this minimal system result in the activation of the hmuO promoter, thus triggering the downstream memory element.

Figure 21:
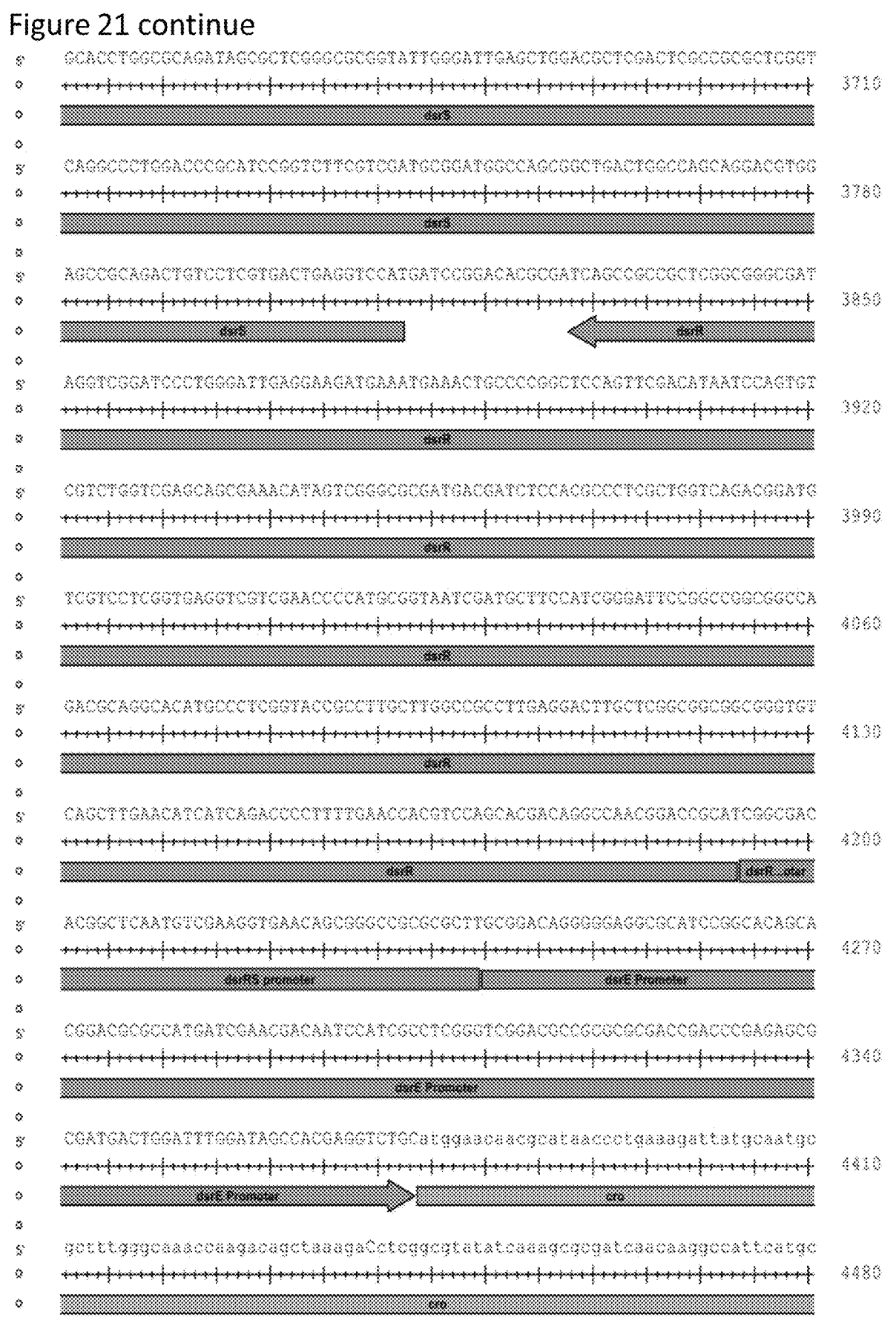
Figure 21:
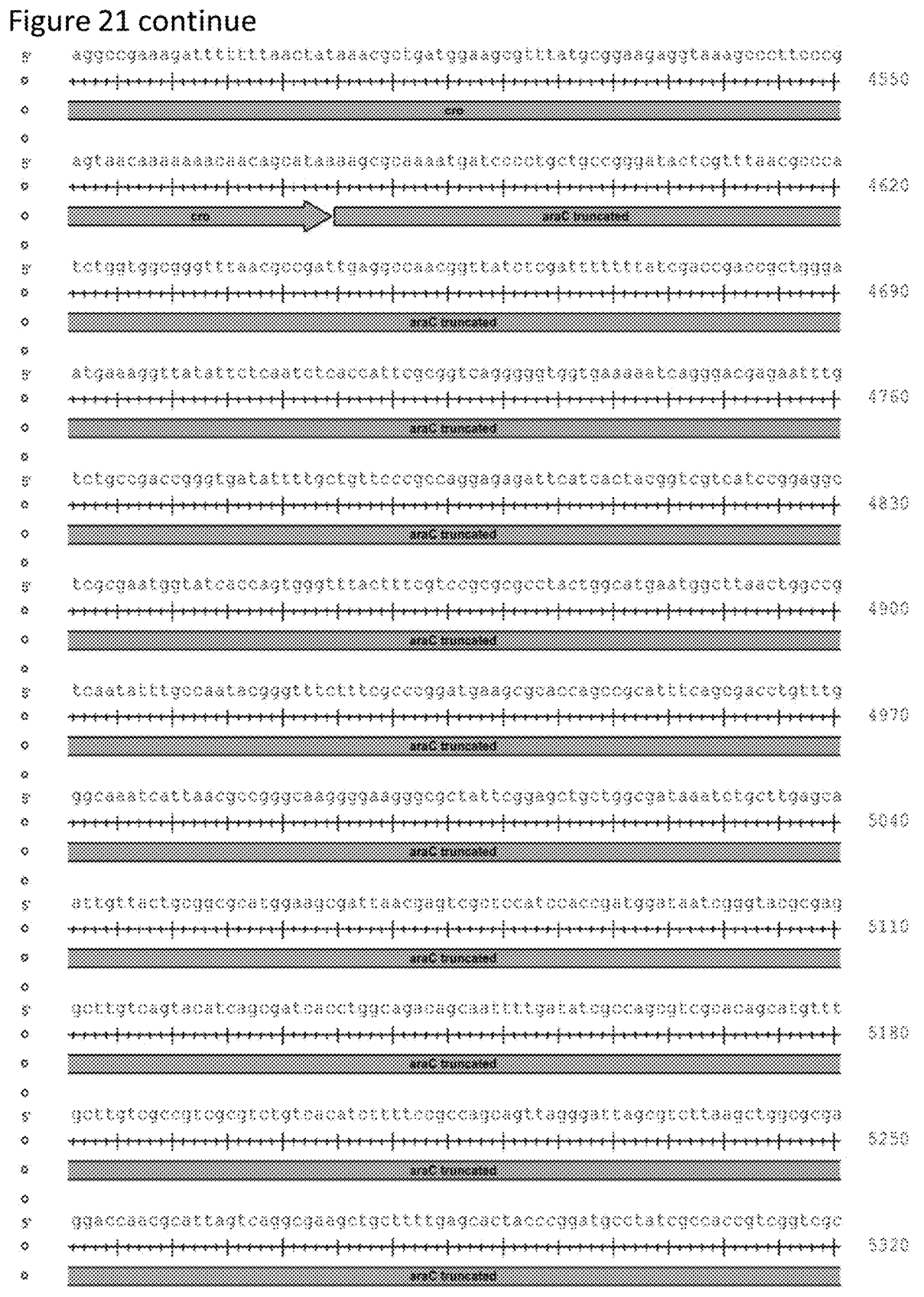

FIG. 21 shows the DNA sequence (SEQ ID NO: 19) of a representative trigger element having a hydrogen sulphide response element ($H_2S$ RE) comprising dsrS, dsrR and the dsrE promoter element upstream of the Cro coding sequence. drsS and dsrR are transcriptional regulators of the dsrE promoter such that in the presence or absence of hydrogen sulfide, the dsrE promoter is activate or repressed, respectively. The activated dsrE promoter will trigger the downstream memory element.

DETAILED DESCRIPTION OF THE INVENTION

Figure 2A:
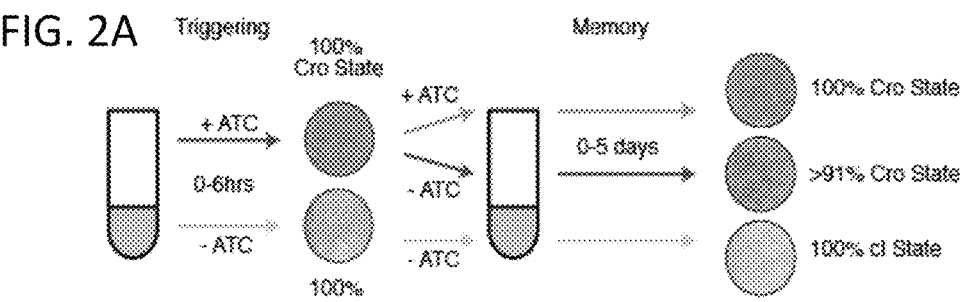
FIGS. 2A-2D shows that engineered bacteria sense and remember ATC exposure in vitro.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Molecular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of the present disclosure are based on genetic engineered *Escherichia coli* and gut coliform bacteria having genome integrated genetic memory circuits that can accurately senses specific environmental conditions in the gut long after the initial stimulus has been removed. The inventors showed that *Escherichia coli* engineered with a synthetic, compact genetic switch can sense antibiotic exposure during passage through the mouse gut. Further, the inventors showed that the engineered bacteria accurately senses, remembers and reports on the specific environmental conditions in the mouse gut, long after the initial stimulus has been removed; long after the removal of the stimulus. The inventors also showed that the designed genetic memory circuit can be transferred to a murine gut coliform bacterium, retaining the same stability and switching properties as in *E. coli* K12 in vitro and in vivo, and surviving among the gut microbiome in the absence of antibiotic selection. This work lays the foundation for the use of synthetic genetic circuits as living diagnostics and therapeutics.

Therefore, specific genetic engineered bacteria can be designed for diagnostic and/or prognosis purposes, to monitor, indicate and/or report certain environmental conditions of interest in the gut without resorting to invasive endoscopy, colonoscopy and/or flexible sigmoidoscopy. Furthermore, specific genetic engineered bacteria can be designed for delivery of therapeutics to the gut when certain environmental conditions of interest occur in the gut.

Accordingly, in one embodiment, provided herein is an engineered unicellular organism comprising a memory circuit comprising a bacteriophage-reporter element-based memory element comprising two antagonistic transcription factors or gene regulatory factors; and an inducible transcription factor-based trigger element which produces a triggering transcription factor upon induction, wherein the triggering transcription factor is operably linked to an inducible promoter, wherein the inducible promoter is responsive to a stimulus, and wherein the memory circuit is integrated into the genome of the organism. The reporter element of memory element comprises a reporter gene that is operably-linked to the one of the two antagonistic transcription factors of the memory element. In the absence of the stimulus that can induce the inducible transcription factor-based trigger element, the memory element is in the OFF state wherein the reporter element does not transcribe the reporter gene. In the presence of the stimulus, the inducible transcription factor-based trigger element is induced to produce the triggering transcription factor which turns the memory element to the ON state wherein the reporter element transcribes the reporter gene.

In one embodiment, the bacteriophage-reporter element-based memory element comprises two antagonistic transcription factors or gene regulatory factors and a reporter element. For example, the lambda phage-based cI/Cro. In one embodiment, each of the two antagonistic transcription factors or gene regulatory factors is operably linked to a respective promoter, wherein the function of each promoter is inhibited by the transcription factor or gene regulatory factor that is not operably-linked to it. In one embodiment, the reporter element comprises a reporter gene which is operably-linked to the one of the two antagonistic transcription factors of the memory element. In one embodiment, the triggering transcription factor is one of the two antagonistic transcription factors comprising the memory element.

In one embodiment, provided herein is an engineered unicellular organism such as a bacterium, wherein the organism comprises a memory circuit comprising a lambda phage-based cI/Cro-reporter gene-based memory element, and an inducible Cro-based or cI-based trigger element, wherein the lambda phage-based cI/Cro regulates the expression of the reporter gene encompassed within the memory element, wherein Cro or cI in the trigger element is operably linked to an inducible promoter, wherein the inducible promoter is responsive to a trigger agent, and wherein the memory circuit is integrated into the genome of the organism. In one embodiment, the trigger agent is an indicator of a particular environmental condition of interest in the colon of a subject. For example, the condition is inflammation or cancer. In one embodiment, the subject is a mammal, for example, a primate mammal, a human.

In one embodiment, provided herein is an engineered unicellular organism such as a bacterium, wherein the organism comprises a memory circuit comprising a lambda phage-based cI/Cro-reporter gene-based memory element, and an inducible Cro-based or cI-based trigger element, wherein the lambda phage-based cI/Cro regulates the expression of the reporter gene encompassed within the memory element, wherein Cro or cI in the trigger element is operably linked to an inducible promoter, wherein the inducible promoter is responsive to a trigger agent, and wherein the memory circuit is integrated into the genome of the organism, wherein the engineered unicellular organism can sense a trigger element selected from the group consisting of hydrogen peroxide, hydrogen sulfide, NO, quoram signal of pathogenic *E. coli*, elastase, heme, iron, superoxide and tetrathionate.

In another embodiment, provided herein is a method of detecting a target in the colon or the gastrointestinal tract in a subject, the method comprising (a) administering an engineered unicellular organism such as a bacterium to the subject, wherein the organism having a memory circuit comprising a lambda phage-based cI/Cro-reporter gene-based memory element, and an inducible Cro-based or cI-based trigger element, wherein the lambda phage-based cI/Cro regulates the expression of the reporter gene encompassed within the memory element, wherein Cro or cI in the trigger element is operably linked to an inducible promoter, wherein the inducible promoter is responsive to the target, (b) collecting a sample of fecal matter from the subject after a period of time after the administration step; and (c) measuring the expression of the reporter gene from the memory element of the circuit in the engineered bacterium wherein the detectable expression of the reporter gene indicates the presence of the target. In one embodiment, the presence of the target in the colon indicates a particular condition in the colon. In one embodiment, the detectable expression of the reporter gene indicates the presence of a condition in the colon or the gastrointestinal tract of the subject.

In some embodiments, the raw data from the reporter gene comes in the form of either a fluorescent protein or an enzyme that will react with chemical precursors to produce colored pigments or fluorescent compounds. In either case, the "activated" organisms in a fecal sample can be detected directly by sensitive techniques such as flow-cytometry or microscopy or by eye if the engineered bacteria in the fecal matter are cultured for 12 hours and then examined. To culture the bugs for analysis, the fecal sample is solubilized, dilute, and then spread on soft agar plates with antibiotics. These plates are grown at 37 degree Celcius in normal atmosphere for 12-16 hours for colonies to develop. In general, at least 100 colonies of one type of engineered organism would need to be counted to get an accurate percentage of switched versus unswitched bacteria. In order to get this count, it may be necessary to plate multiple dilutions to get the appropriate plated colony density. For direct analysis, the fecal sample is analyzed directly by flow-cytometry.

For example, the raw data is interpreted as a comparison. The number of activated colonies is counted in the test subject and also a healthy subject as a control. Activation of the memory system and reporter genes in response to tetrathionate exposure is established by comparing the percentage of colored engineered organisms in the presence or absence of tetrathionate or healthy versus infected individuals. However, once the background levels of reporter gene activation in the absence of tetrathionate (or infection) are known, it is no longer necessary to perform "negative control" assays to effectively diagnose the presence of tetrathionate in the gut.

Similarly, the false positive rate of the engineered organisms is established in the absence of the environmental stimulus or in healthy individuals, an effective diagnosis can be made without additional controls. These negative controls would account for normal levels of the compound or environmental signal that are present in healthy individuals and possible leaky expression of the reporter element. Once the background levels of reporter gene activation are established for each of these reporter systems, the only relevant controls are related to the quality of the reagents or equipment used to analyze the engineered organisms in the fecal sample.

In another embodiment, provided herein is a method of detecting for cancer in the colon or the gastrointestinal tract in a subject in need thereof, the method comprising (a) administering an engineered unicellular organism such as a bacterium to the subject, wherein the organism has a memory circuit comprising a lambda phage-based cI/Cro-reporter gene-based memory element, and an inducible Cro-based or cI-based trigger element, wherein the lambda phage-based cI/Cro regulates the expression of a reporter gene encompassed within the memory element, wherein Cro or cI in the trigger element is operably linked to an inducible promoter, wherein the inducible promoter is responsive to a symptom or biomarker that is known to occur when colorectal cancer is present; (b) collecting a sample of fecal matter from the subject after a period of time after the administration step; and (c) measuring the expression of the reporter gene from the memory element of the circuit in the engineered bacteria wherein the detectable expression of the reporter gene indicates the presence of the trigger agent and the likelihood of cancer in the colon or the gastrointestinal tract of the subject.

Specific examples of sensors organism that might be useful for detecting cancer are trigger systems linked to the oxyRS, soxRS, dsrI, ttrRS, sidA, ompC, hmuO, sodB, and vpsA bacterial gene promoters. To directly detect colon cancer, engineered unicellular organisms that will sense hydrogen peroxide (oxyRS), hydrogen sulfide (soxRS, dsrE), tetrathionate (ttrRS), bacterial quorum signals (sidA), elastase (ompC), heme (hmuO), iron (sodB), and biofilm formation (vpsA) are used.

Different cancers have different biomarkers. For example, elastase is frequently used as a biomarker of pancreatic cancer; if heme, iron, or biofilms are detected, then colorectal adenoma is suspected; if tetrathionate, then a *Salmonella* infection; if hydrogen sulfide, then dyregulation of the microbiota and *F. nucleatum* and *B. wadsworthia*; etc. These later markers represent risk factors for colorectal cancer. Thus, different biomarkers can be used to indicate different diagnosis.

At a minimum, detecting elastase (ompC) would be necessary for pancreatic cancer diagnosis. Heme (humO) and an increase in gut iron levels (sodB) would be indicative of blood in the stool which could be caused by colorectal adenoma or another serious complication. Bacterial biofilms (vpsA) are strongly associated with colorectal cancer but not a direct diagnosis. Detecting Tetrathionate (ttrRS) is necessary for *Salmonella* diagnosis. Detecting bacterial quorum signals (sidA) is necessary for pathogenic *E. coli* diagnosis. Detecting hydrogen sulfide (soxRS, dsrE) would be strongly associated with a dysregulation of gut microbes, specifically *F. nucleatum* and *B. wadsworthia* which are a risk factor for colorectal cancer.

To sense the presence of hydrogen peroxide and gut inflammation, engineered organisms with oxyRS responsive gene promoters will be linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

To sense the presence of hydrogen sulfide in the gut lumen produced by dysregulated gut microbes such as *F. nucleatum* and *B. wadsworthia*, engineered organisms with soxRS or dsrE responsive gene promoters will be linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

The activity levels of the trigger elements that sense the various triggering or inducing agent describing (e.g. ttrB, dsrE, sdiA) are correlated with the amount of chemical or biological disease signature present. However, switching of the memory element occurs only once an activity threshold of the environmental trigger is surpassed. In practice, this means that in situations with intermediate levels of trigger activation, a percentage of the engineered organisms will switch to the "On" state while the rest do not. Therefore, the inventors can establish the levels of disease biomarker present by determining the percentage of switch versus unswitched bacteria for a given trigger and compare that to the background percentage in healthy individuals. In a multi-organism administration, this becomes slightly more complicated because the switched versus unswitched bacteria are first sorted and then the individual triggers identified by PCR or DNA sequencing.

In one embodiment, the activity levels of the trigger elements is at least two standard deviations or more above background for a positive diagnosis, ie. confirming the presence of the gut condition that is correlated with the triggering agent.

To sense the presence of tetrathionate caused by pathogenic Salmonella invading the gut, engineered organisms with ttrRS responsive gene promoters will be linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

To sense the presence of quorum signals from pathogenic E. coli invading the gut lumen, engineered organisms with the sidA responsive gene promoter will be linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

To sense the presence of elastase in the gut lumen, engineered organisms with the ompC gene promoter will be linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

To sense the presence of heme in the gut lumen, engineered organisms with the hmuO gene promoter will be linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

To sense the presence of iron in the gut lumen, engineered organisms with the sodB gene promoter will be linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

To sense the presence of biofilm in the gut lumen, engineered organisms with the vpsA gene promoter will be linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

In one embodiment, the reporter gene in the different engineered unicellular organisms is the same for each case sensing type of organism. The reporter gene functions to give a preliminary diagnosis to the individual that a potentially serious gut illness is evident. This diagnosis will depend on an implicit comparison to reporter gene levels observed in healthy individuals. After the preliminary diagnosis, the activated organisms can be separated from unactivated organisms in a fecal sample based on the expression of the reporter gene. Once the organisms have been sorted and pooled into active and inactive fractions, the specific identities of the sensors can be determined by PCR or DNA sequencing of the microbes. The identities of the active versus inactive sensors can then be correlated with a specific disease such as colorectal cancer.

In one embodiment, one can assess the overall population of E. coli or Pseudomonas sp. in the colon with engineered organisms capable of sensing chemical compounds called auto-inducers that are involved in quorum sensing systems in these organisms. E. coli and Pseudomonas constantly secrete auto-inducer compounds (E. coli produce autoinducer-2 and Pseudomonas sp produce N-3-oxododecanoyl-homoserine lactone) at low levels so that when these bacterial populations expand, the amount of auto-inducer present also increases. Our engineered organism detects and remember these autoinducer compounds which results in switching of the memory element. As a diagnosis of cancer, we would measure the percentage of switched organisms from a fecal sample and compare this to the percentage observed in healthy individuals.

In another embodiment, provided herein is a method of detecting an enteric pathogenic bacterial infection in the colon or the gastrointestinal tract in a subject in need thereof, the method comprising (a) administering an engineered unicellular organism such as a bacterium to the subject, wherein the bacteria have a memory circuit comprising a lambda phage-based cI/Cro-reporter gene-based memory element, and an inducible Cro-based or cI-based trigger element, wherein the lambda phage-based cI/Cro regulates the expression of a reporter gene within the memory element, wherein Cro or cI in the trigger element is operably linked to an inducible promoter, wherein the inducible promoter is responsive to a symptom or biomarker that is known to occur when a pathogenic bacteria in the colon or the gastrointestinal tract; (b) collecting a sample of fecal matter from the subject after a period of time after the administration step; and (c) measuring the expression of the reporter gene from the memory element of the circuit in the engineered bacteria wherein the detectable expression of the reporter gene indicates the presence of the trigger agent and the presence of pathogenic bacterial infection in the colon or the gastrointestinal tract of the subject.

In some embodiments, the symptom or biomarker that is known to occur when a pathogenic bacteria in the colon include but is not limited to sdiA (regulatory protein SdiA) and enterotoxins secreted by the enteric pathogenic bacteria. For example, verotoxins or Shiga-like toxins from enterohaemorrhagic *E. coli* (EHEC). Non-exclusive and non-limiting examples of enteric pathogenic bacteria include *E. coli* (EHEC, EIEC, EAEC), *Shigella* sp., *Salmonella* sp., *Campylobacter* sp., *Yersinia* sp., *Aeromonas* sp., *Plesiomonas* sp., and *Clostridium difficile*.

To sense dysregulation of gut microbes such as *F. nucleatum* and *B. wadsworthia*, engineer organisms that sense the presence of hydrogen sulfide in the gut lumen are used. Hydrogen sulfide will be detected via the soxRS or dsrE responsive gene promoters linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

To sense the presence of pathogenic *Salmonella* invading the gut, engineer organisms that detect tetrathionate via ttrRS responsive gene promoters are used. These gene promoters will be linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

To sense the presence of pathogenic *E. coli* invading the gut lumen, engineer organisms that detect quorum signals specific to invasive *E. coli* via sidA responsive gene promoters are used. These gene promoters will be linked to the cro antirepressor or cI dominant negative transcription factors in the trigger element. Activation of these trigger elements will repress synthesis of the cI repressor and activate synthesis of the cro anti-repressor in the memory element. The cro and switching of the downstream memory element to the "ON" state and concomitant production of the reporter gene.

In another embodiment, provided herein is a method of detecting inflammation in the colon or the gastrointestinal tract in a subject in need thereof, the method comprising administering an engineered unicellular organism such as a bacterium described herein to a subject, wherein the inducible promoter within the inducible trigger element is responsive to a symptom or biomarker that is known to occur when inflammation is present; (b) collecting a sample of fecal matter from the subject after a period of time after the administration step; and (c) measuring the expression of the reporter gene from the memory element of the circuit in the engineered bacteria wherein the detectable expression of the reporter gene indicates the presence of the trigger agent and the likelihood of inflammation in the colon or the gastrointestinal tract of the subject.

In some embodiments, the symptom or biomarker that is known to occur during inflammation in the gut includes but is not limited to ROS, NO, tetrathionate, H2S, calprotectin or lactoferrin. Non-limiting stimulus for the trigger element for detecting inflammation would be ttrRS, soxRS, and oxyRS.

Hydrogen peroxide, nitric oxide (NO), and superoxide are all products of the immune inflammatory response but not necessarily from the same source or mechanism. Therefore, each of these compounds is a marker of inflammation individually and would most likely be present all at the same time.

In another embodiment, provided herein is a method of distinguishing colitis from Crohn's disease in the colon in a subject in need thereof, the method comprising: (a) administering a first engineered unicellular organism such as a bacterium described herein to a subject, wherein the inducible promoter within the first engineered unicellular organism is responsive to a symptom or biomarker that is known to occur when inflammation is present; administering a second engineered unicellular organism such as a bacterium described herein to a subject, wherein the inducible promoter within the second engineered unicellular organism is responsive to a symptom or biomarker that is known to occur when a pathogenic bacteria in the colon; (b) collecting a sample of fecal matter from the subject after a period of time after the administration step; and (c) measuring the expression of the reporter gene from the memory element of the circuit in the first and second engineered unicellular organisms. The presence of inflammation in the colon caused by infection with a pathogenic bacterium such as *Salmonella* can be distinguished here from a patient suffering from Crohn's if both administered unicellular bacteria are activated during passage through the patient's gut. In a different case, the presence of inflammation and elevated levels of *B. wadsworthia* is strongly correlated with Crohn's patients.

Crohn's disease is an inflammatory bowel disease that often leads to colitis and is typically diagnosed only when alternative diagnoses have been excluded and a colonoscopy reveals characteristic granulomas. Our engineered organisms will be capable of discriminating diagnosis such as detecting infectious bacteria, microbial or antibiotic induced dysbiosis (hydrogen sulfide, *F. nucleatum, B. wadswortia*), pancreatic and colorectal cancer—all of which would be extremely useful in reaching an accurate diagnosis.

In another embodiment, provided herein is a method of monitoring the efficacy of a therapy for a colon or the gastrointestinal tract condition in a subject comprising performing a method comprising an engineered unicellular organism such as a bacterium at a first time point; performing a method comprising an engineered unicellular organism such as a bacterium described herein at a second time point, wherein the method in the first time point and second time point are the same and the second time point is after administering at least one therapy; comparing the expression of the reporter gene from the first time point with that of the second time point, wherein a decrease in the expression of the reporter gene is indication of effective therapy and wherein an increase or no change in the expression of the reporter gene is indication of ineffective therapy.

In some embodiments, the decrease of the expression or action of reporter gene at the second time point is by at least 2.5%, at least 5%, at least 7.5%, at least 10%, at least 20%, at least 30%, at least 40%, at least 50%, at least 60%, at least 70%, at least 80%, at least 90%, up to and including 100% compared to the expression or action of reporter gene at the second time point.

For example, a subject has been diagnosed with ulcerative colitis and the subject is started an immune suppression drug therapy to help regulate the immune system. Prior to the start of the therapy, the subject is given a formulation comprising engineered unicellular organisms such as an engineered bacterium described herein. The bacterium is designed to detect inflammation in the gut by detecting at least ROS, NO, tetrathionate, $H_2S$, calprotectin or lactoferrin by way of the stimulus of at least ttrRS, soxRS, or oxyRS on the inducible promoter in the trigger element. A fecal sample is taken one day and/or two days after taking the formulation. The fecal samples are tested and the protein expression of the reporter gene within the memory element of the engineered unicellular organisms indicates the level or status of inflammation in the gut of the subject prior to the therapy. The therapy is then start for one or two months and a formulation comprising engineered unicellular organisms as administered is given. Again, a fecal sample is taken one day and/or two days after taking the formulation. The fecal samples are tested and the protein expression of the reporter gene within the memory element of the engineered unicellular organisms indicates the level or status of inflammation in the gut of the subject during to the therapy. The protein expressions of the reporter gene obtained prior to the therapy and during the therapy are compared. When there is a decrease in the protein expression of the reporter gene during the therapy when compared to prior the start of the therapy, this indicates that the therapy is effective in reducing inflammation in the gut of the subject.

During the course of the therapy, the subject can be periodically monitored by the described method over time, i.e., periodically administer the formulation comprising engineered unicellular organisms such as an engineered bacterium described herein and collecting fecal samples thenafter and measuring the protein expression levels of the reporter gene encompassed within the engineered unicellular organisms. For example, administer the formulation every two months intervals and take subsequent fecal sample. The newest protein expression of the reporter gene is to be compared with that prior to the start of the therapy and also with the immediate previous protein expression of the reporter gene. The therapy continues to be effective if the newest protein expression of the reporter gene is decrease compared to that prior to start of the therapy and the newest protein expression of the reporter gene is decrease or unchanged compared to that of the immediate previous protein expression of the reporter gene.

In another embodiment, provided herein is a composition comprising an engineered unicellular organism such as an engineered bacterium described herein. In one embodiment, one or more types of engineered unicellular organisms comprise the composition. In one embodiment, the composition is formulated for oral administration into a subject.

In another embodiment, provided herein is a pharmaceutical composition comprising an engineered unicellular organisms such as an engineered bacterium described herein and a pharmaceutically acceptable carrier.

In another embodiment, provided herein is an enteric formulation comprising an engineered unicellular organism such as an engineered bacterium described herein.

In one embodiment, the pharmaceutical composition is an enteric formulation.

In one aspect, this disclosure relates to the use of engineered bacteria described herein for detecting cancer in the colon or the gastrointestinal tract in a subject.

In another aspect, this disclosure relates to the use of engineered unicellular organisms such as an engineered bacterium described herein for detecting pathogenic bacterial infection in the colon or the gastrointestinal tract in a subject.

In another aspect, this disclosure relates to the use of engineered unicellular organisms such as an engineered bacterium described herein for detecting inflammation in the colon or the gastrointestinal tract in a subject.

In another aspect, this disclosure relates to the use of engineered unicellular organisms such as an engineered bacterium described herein for distinguishing colitis from Crohn's disease in the colon or the gastrointestinal tract in a subject.

In another aspect, this disclosure relates to the use of engineered unicellular organisms such as an engineered bacterium described herein for monitoring the efficacy of a therapy for a colon or a gastrointestinal tract condition in a subject.

In one embodiment of the engineered bacterium, the memory circuit in maintained in the unicellular organisms such as an engineered bacterium without any antibiotic or metabolite selection.

In one embodiment, the engineered bacteria described herein are lyophilized and used in any methods, compositions, pharmaceutical compositions or formulation.

In one embodiment of any engineered unicellular organism such as an engineered bacterium described, the memory circuit comprises the lambda phage sequences of cI and Cro. These are antagonistic transcription factors. In one embodiment of any engineered bacterium described, the memory circuit comprises the lambda phage sequences of $P_L$, $O_L$, cI and Cro. In other embodiments, the memory circuit also comprises a reporter gene that is operably linked with Cro. In one embodiment, in the OFF state, the Cro/cI of memory circuit mutually exclude the expression of each other, consequently, the reporter gene is not expressed. In the ON state, there is insufficient cI to repress the expression of CRO in the memory circuit. When Cro is then expressed, so is the reporter gene.

In one embodiment of any engineered unicellular organisms such as an engineered bacterium described, the memory circuit further comprises the lambda phage sequences rexA and rexB. In one embodiment of any engineered unicellular organism such as an engineered bacterium described, the memory circuit comprises the lambda phage sequences of PL, OL, rexA, rexB, cI and Cro. In one embodiment of any memory circuit in any engineered unicellular organisms such as an engineered bacterium described, the lambda phage PL, OL, rexA, rexB, cI and Cro sequences are arranged in the following order: PL, OL, rexA, rexB, cI and Cro. In one embodiment, PL, OL, rexA, rexB, cI and Cro sequences are arranged in the normal prophage orientation. Examples of a lambda phage-based cI/Cro-reporter gene-based memory element is described in the Example section and shown in FIGS. 1A and 1B. The nucleic acid sequences for lambda phage, PL, OL, rexA, rexB, cI and Cro are described in Example section and shown in FIG. 6.

In one embodiment, the trigger element is a Cro-based trigger element. The inducible promoter of this trigger element is operably-linked to Cro and drives the expression of Cro under permissible conditions. When induced in the present of a target, drives the expression of Cro, a repressor protein. Excessive amount of CRO inhibits the expression of the cI repressor protein in the memory element, thereby permitting the expression the operably-linked reporter gene.

In one embodiment, the trigger element is a cI-based trigger element. The inducible promoter of this trigger element is operably-linked to cI and drives the expression of cI under permissible conditions. In one embodiment, the cI coding nucleic acid is a mutant cI coding sequence that codes for an engineered mutant form of cI that is a dominant negative protein. The dominant negative CI mutant protein that binds wild-type cI and prevents wild-type cI from binding to DNA. When the inducible promoter is induced in the present of a target, the inducible promoter drives the expression of the expression of the engineered mutant form of cI. This relieves repression of cI in the memory element and leads to expression of CRO from the memory element, which activates the memory state. The reporter gene in the memory element gets expressed.

In one embodiment, the trigger element comprises an inducible promoter. In one embodiment, the inducible promoter is responsive to the target or a stimulus. In one embodiment, the inducible promoter is responsive to the target or a stimulus by way of the RE in the promoter. For example, an inducible promoter having a responsive element (RE) described in Table 3. For example, an inducible promoter having a tetracycline responsive element (RE) is responsive to tetracycline. Therefore, in the presence of tetracycline, engineered unicellular bacteria having such a TRE inducible promoter that is operably linked to a trigger transcription factor would express the trigger transcription factor which in turn would consequently lead to the expression of the reporter gene encompassed in the memory element when the memory element switches from the OFF state to the ON state as a result of the expression of the trigger transcription factor in the presence of tetracycline.

In one embodiment, the memory element and the trigger element are integrated into the genome of the bacteria. In one embodiment, the memory element and the trigger element are spread throughout the genome and not within 90,000 bases of each other. In one embodiment, the trigger element is integrated in the Ara operon and that the memory element is integrated in the mph operon.

In one embodiment, the reporter gene is selected from a group consisting of β-galactosidase (LacZ), chloramphenicol acetyltransferase (CAT), neomycin phosphotransferase (G418), bacteria luciferase (LuxAB), fluorescent protein (FP), alkaline phosphatase (PhoA), and p-glucuronidase (GUS), and leptin. In some embodiments, the FP is selected from green fluorescent protein, yellow fluorescent protein, red fluorescent protein, cyan fluorescent protein, blue fluorescent protein, Far-red fluorescent protein, true-red fluorescent protein, and infra-red fluorescent protein.

In one embodiment, the inducible promoter is responsive to tetracycline. In other embodiments the inducible promoter is responsive to but not limited to tetrathionate, reactive oxygen species such as hydrogen peroxide, nitric oxide, and superoxide, undesirable pathogenic bacteria such as E. coli NC101, S. typhimurium, B. wadswortia, F. nucleatum and $H_2S$.

In another embodiment, provided herein is a method of detecting a target in the colon of a subject, the method comprising administering engineered bacteria described herein to the subject, wherein the inducible promoter is responsive to the target or a stimulus.

In one embodiment, the target is an indicator of a condition in the colon. In one embodiment, more than one target indicates a condition in the colon. In one embodiment, a combination of targets is used to indicate a condition in the colon.

In one embodiment, the method further comprises collecting a sample of fecal matter from the subject after administering the engineered bacteria to the subject.

In one embodiment, the method further comprises measuring for the expression of the reporter gene in the sample of fecal matter wherein the detectable expression of the reporter gene indicates the presence of the target and the presence of the condition in the colon of the subject.

In one embodiment, the method further comprises selecting a subject for detecting. In one embodiment, the subject selected for any of the methods exhibits the following symptoms: diarrhea, rectal bleeding, urgent need to move bowels, abdominal cramps and pain, sensation of incomplete evacuation, constipation (can lead to bowel obstruction), fever, loss of appetite, weight loss, fatigue night sweats and loss of normal menstrual cycle.

In one embodiment, the subject has or is at risk of developing a colon condition. For example, having a family history of colorectal cancer or the subject is a Jews of European descent (Ashkenazi Jews), an African Americans and Hispanic.

In one embodiment, the subject at risk of developing a colon condition exhibits at least one of the following symptoms: diarrhea, rectal bleeding, urgent need to move bowels, abdominal cramps and pain, sensation of incomplete evacuation, constipation (can lead to bowel obstruction), fever, loss of appetite, weight loss, fatigue, night sweats and loss of normal menstrual cycle.

In one embodiment, the target is selected from the group consisting of tetrathionate, reactive oxygen species, H2S, sdiA, heme, elastase, bacteria enterotoxins, calprotectin and lactoferrin.

In one embodiment, the stimulus is the inducer described in Table 3 or the target of interest in Table 4.

In one embodiment, the colon condition is selected from the group consisting of cancer, inflammation, and pathogenic bacterial infection, inflammatory bowel disease (IBD) such as Crohn's disease, colitis, and diabetes.

Crohn's disease and ulcerative colitis are both major categories of Inflammatory Bowel Diseases (IBD). IBD affects an estimated 1.4 million Americans. These chronic diseases tend to run in families and they affect males and females equally. While IBD can affect anyone, caucasians are more likely than other ethnic groups to have IBD. The diseases are especially prevalent in Jews of European descent (Ashkenazi Jews). African Americans and Hispanics in the United States are increasingly affected.

Crohn's disease is a chronic inflammatory condition of the gastrointestinal tract and may affect any part from the mouth to the anus.

Ulcerative colitis is a chronic inflammatory condition limited to the colon, otherwise known as the large intestine.

In one embodiment, the cancer in the colon of a subject is colorectal cancer.

In some embodiments, the symptoms or biomarkers that are known to occur when cancer is present in the colon or the symptoms or biomarkers that are known to be associated with the presence of cancer in the colon include but are not limited to inflammation, hydrogen sulfite gas (H2S) and specific bacteria. Non-limiting exemplary colorectal cancer-associated bacteria include F. nucleatum, B. wadsworthia, pathogenic E. coli, Streptococcus bovis, and Salmonella sp. For example, the method of detecting for cancer in a subject comprises determining the combination of presences of inflammation, $H_2S$ (hydrogen sulfide gas) and specific bacteria that are known to be present and associated with colon cancer.

In one embodiment of any methods described, the presence of inflammation can be determined by detecting the presence of calprotectin and/or lactoferrin. These are substances that are released by white blood cells. A hallmark of inflammation is an influx of white blood cells to the location of inflammation. Therefore, calprotectin and lactoferrin are indicators of the presence of white blood cells which in turn are indicators of inflammation. Accordingly, calprotectin and lactoferrin are the targets to be detected in the colon for the purpose of determining whether there is inflammation in the colon. In one embodiment, the inducible promoter of trigger element of the engineered bacterium described herein is responsive to calprotectin. In one embodiment, the inducible promoter of trigger element of the engineered bacterium described herein is responsive to lactoferrin. The detectable presence of calprotectin and/or lactoferrin activates the inducible promoter of trigger element of the engineered unicellular organism such as a bacterium and leads to expression of the repressor CRO or mutant form of the CI protein. These repressor proteins in turn lead to the expression of the reporter gene of the memory element of the engineered unicellular organism such as a bacterium. Therefore, the detectable presence of calprotectin and/or lactoferrin as indicated by the expression of the reporter gene of the memory element of the engineered unicellular organism such as a bacterium would indicate positive inflammation in the colon.

In some embodiments of any methods described, the inducible promoter of trigger element of the engineered bacterium described herein is responsive to $H_2S$. The detectable presence of H2S in the colon activates the inducible promoter of trigger element of the engineered unicellular organism such as a bacterium and leads to expression of the repressor CRO or mutant CI protein. These repressor proteins in turn lead to the expression of the reporter gene of the memory element of the engineered unicellular organism such as a bacterium. Therefore, in this aspect, the expression of the reporter gene indicates the presence of detectable $H_2S$ in the colon.

In one embodiment of any one method of detecting for colorectal cancer in a subject, more than one type of genetic engineered bacterium can be administered to the subject. For example, if the subject is suspected of having colon cancer or is at high risk of developing such cancer, the subject can be administered three different types of genetic engineered bacterium, a first type for detecting the presence of inflammation in the colon, a second type for detecting $H_2S$ in the colon, and a third type for detecting a cancer-associated bacteria in the colon. When the reporter genes of all three types of genetic engineered bacteria are positive, ie., expressed the reporter gene from the memory element of each type of engineered bacteria administered, this indicates that inflammation, $H_2S$ and a cancer-associated bacteria have been detected in the colon of the subject. When there is positive presence of all three: inflammation, $H_2S$ and a cancer-associated bacteria, it indicates the likelihood of the presence colon cancer in the subject.

It is also envisioned that the methods described herein can be used as prophylaxis, for monitoring for the development of a colon condition of interest. For example, for colitis flare up or colon cancer.

Formulation and Application

In some embodiments, the genetic engineered unicellular organism such as a bacterium described herein can be incorporated into a variety of formulations for administration in accordance with the methods disclosed. For example, a simple formulation can incorporate the genetic engineered bacteria described herein with an excipient combined in solution, then frozen and lyophilized. The resulting powder can be formulated in a capsule, sachet, pill, and the like, and may further be formulated to comprise an enteric coating. In some embodiments, the formulations can comprise one or more types of genetic engineered bacteria wherein each type "senses" the presence or absence of a different type of target.

In one embodiment, the genetic engineered unicellular organism such as a bacterium described herein are formulated into pharmaceutical compositions by combination with appropriate, pharmaceutically acceptable carriers or diluents, and are formulated into preparations in solid, semi-solid, or liquid forms, such as tablets, capsules, powders, granules, solutions, gels, and microspheres. As such, administration of the genetic engineered bacteria described herein can be achieved by oral administration.

For oral preparations, the genetic engineered unicellular organism such as a bacterium described herein can be used alone or in combination with appropriate additives to make tablets, powders, granules or capsules, for example, with conventional additives, such as lactose, mannitol, corn starch or potato starch; with binders, such as microcrystalline cellulose, cellulose derivatives, acacia, corn starch or gelatins; with disintegrants, such as corn starch, potato starch or croscarmellose sodium; with lubricants, such as talc or magnesium stearate; and if desired, with diluents, buffering agents, moistening agents, preservatives, colorants, and flavoring agents.

For enteral administration, a composition can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet can be made by compression or molding, optionally with one or more accessory ingredients. Compressed tablets can be prepared by compressing in a suitable machine the active compound in a free-flowing form, e.g., a powder or granules, optionally mixed with accessory ingredients, e.g., binders, lubricants, inert diluents, surface active or dispersing agents. Molded tablets can be made by molding in a suitable machine, a mixture of the powdered active compound with any suitable carrier.

A syrup or suspension can be made by adding the genetic engineered bacteria described herein to a concentrated, aqueous solution of a sugar, e.g., sucrose, to which can also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for oral administration can be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethylammonio-1-propanesulfonate), Big-CHAPS (N, N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate.

In one embodiment, the formulations comprising one or more genetic engineered unicellular organism such as a bacterium described herein and the oral formulations comprise enteric coatings are formulated so that the genetic engineered unicellular organism such as a bacterium described herein is delivered to the intestinal tract. Enteric formulations are often used to protect an active ingredient from the strongly acid contents of the stomach. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

As regards formulations for administering the genetic engineered unicellular organism such as a bacterium described herein, one particularly useful embodiment is a tablet formulation comprising the genetic engineered unicellular organism such as a bacterium described herein with an enteric polymer casing. An example of such a preparation can be found in WO2005/021002. The active material in the core can be present in a micronized or solubilized form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropyl-cellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, colouring agents, flavours etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microstalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The genetic engineered unicellular organism such as a bacterium described herein preferably comprises between 10 and 50% of the weight of the core, more preferably between 15 and 35% of the weight of the core (calculated as free base equivalent). The core can contain any therapeutically suitable dosage level of the active ingredient, but preferably contains up to 150 mg as free base of the active ingredient. Particularly preferably, the core contains 20, 30, 40, 50, 60, 80 or 100 mg as free base of the active ingredient. The active ingredient can be present as the free base, or as any pharmaceutically acceptable salt. If the active ingredient is present as a salt, the weight is adjusted such that the tablet contains the desired amount of active ingredient, calculated as free base of the salt. Preferably, the active ingredient is present as a hydrochloride salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional cross-linking agents such as epichlorohydrin, dichlorohydrin or 1, 2-, 3, 4-diepoxybutane. The casing can also include starch and/or dextrin.

Preferred enteric coating materials are the commercially available EUDRAGIT enteric polymers such as EUDRAGIT L, EUDRAGIT S and EUDRAGIT NE used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or CITROFLEX or CITROFLEX A2. Non-aqueous plasticisers include these, and also diethyl and dibutyl phtalate and dibutyl sebacate. A preferred plasticiser is triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticiser and up to around 50 wt % of anti-tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876.

In an example, lactose monohydrate, microcrystalline cellulose, the active ingredient—e. g. the genetic engineered bacteria, the hydroxypropyl methyl cellulose and half of the croscarmellose sodium are screened into a 10 Litre Fielder high-shear blender (any suitable high shear blender could be used) and blended for 5 minutes at 300 rpm with the chopper off. The mixture is then granulated by the addition of about 750 ml water whilst continuing to blend. The granules are dried in a Glatt 3/5 fluid bed drier, screened by Comil into a Pharmatec 5 Litre bin blender and then blended with any lactose anhydrous given in the formula plus the remainder of the croscarmellose sodium over 5 minutes at 20 rpm. Magnesium stearate is screened into the blender and the mixing process continued for a further 1 minute at 10 rpm. The lubricated mix is compressed using a Riva Piccolla rotary tablet press fitted with 9.5 mm round normal convex punches (any suitable tablet press could be used). The sealcoat, and subsequently the enteric coat, are applied by spraying of an aqueous suspension of the coat ingredients in a Manesty 10 coater using parameters for the coating process as recommended by the manufacturers of the coating polymers (again, any suitable coater could be used).

Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) J Control Release 71(3):307-18. Other enteric-coated preparations of this sort can be prepared by one skilled in the art, using these materials or their equivalents.

The compositions can be formulated as a sustained release composition. For example, sustained-release means or delivery devices are known in the art and include, but are not limited to, sustained-release matrices such as biodegradable matrices or semi-permeable polymer matrices in the form of shaped articles, e.g., films, or microcapsules that comprise the genetic engineered bacteria described herein A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of polylactide, polyglycolide, or polylactide co-glycolide (co-polymers of lactic acid and glycolic acid).

Sustained-release matrices include polylactides (U.S. Pat. No. 3,773,919, EP 58,481), copolymers of L-glutamic acid and gamma-ethyl-L-glutamate (U. Sidman et al., Biopolymers 22:547-556 (1983)), poly (2-hydroxyethyl methacrylate) (R. Langer et al., J. Biomed Mater. Res. 15:167-277 (1981), and R. Langer, Chem. Tech. 12:98-105 (1982)), ethylene vinyl acetate (R. Langer et al., Id.) or poly-D-(+3-hydroxybutyric acid (EP 133,988). Sustained-release compositions also include liposomally entrapped one or more genetic engineered bacteria described herein. Such liposomes can be prepared by methods known per se: DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy. Other biodegradable polymers and their use are described, for example, in detail in Brem et al. (1991, J. Neurosurg. 74:441-446). For examples of sustained release compositions, see U.S. Pat. No. 3,773,919, EP 58,481A, U.S. Pat. No. 3,887,699, EP 158,277A, Canadian Patent No. 1176565, U. Sidman et al., Biopolymers 22:547 (1983) and R. Langer et al., Chem. Tech. 12:98 (1982).

Methods for preparing liposomes and microspheres for administration to a patient are known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

Preferred micro particles are those prepared from biodegradable polymers, such as polyglycolide, polylactide and copolymers thereof. Those of skill in the art can readily determine an appropriate carrier system depending on various factors, including the desired rate of drug release and the desired dosage.

Formulations are typically provided in a unit dosage form, where the term "unit dosage form," refers to physically discrete units suitable as unitary dosages for the subjects, each unit containing a predetermined quantity of the genetic engineered bacteria described herein in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents that are inherently nontoxic and nontherapeutic, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2 dimethylaminoethanol, 2 diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol.

In one embodiment, other ingredients may be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA, and sugar alcohols such as mannitol or sorbitol.

The present invention can be defined in any of the following numbered paragraphs:

1. An engineered bacteria comprising a memory circuit comprising: a bacteriophage-based cI/Cro-reporter gene-based memory element; and an inducible Cro-based trigger element, wherein Cro is operably linked to an inducible promoter, and wherein the inducible promoter is responsive to a trigger agent, wherein the memory circuit is integrated into the genome of the bacteria.
2. The engineered bacteria of paragraph 1, wherein the memory circuit in maintained in the bacteria without antibiotic selection.
3. The engineered bacteria of paragraph 1 or 2, wherein the memory circuit comprises the lambda phage sequences of cI and Cro.
4. The engineered bacteria of paragraph 1, 2 or 3, wherein the reporter gene is selected from a group consisting of β-galactosidase (LacZ), chloramphenicol acetyltransferase (CAT), neomycin phosphotransferase (G418), bacteria luciferase (LuxAB), green fluorescent protein (GFP), alkaline phosphatase (PhoA), and p-glucuronidase (GUS).
5. The engineered bacteria of any one of paragraphs 1-4, wherein the inducible promoter is responsive to tetracycline, tetrathionate, reactive oxygen species, diA and hydrogen sulfite gas ($H_2S$).
6. A method of detecting a target in the gastrointestinal tract or colon of a subject, the method comprising administering an engineered bacterium of any one paragraphs 1-5 to the subject, wherein the inducible promoter is responsive to the target.
7. The method of paragraph 6, wherein the target is an indicator of a condition in the gastrointestinal tract or colon.
8. The method of paragraph 6 or 7 further comprising collecting a sample of fecal matter from the subject after administering the engineered bacteria to the subject.
9. The method of paragraph 6, 7 or 8 further comprising measuring for the expression of the reporter gene in the sample of fecal matter wherein the detectable expression of the reporter gene indicates the presence of the target and the presence of the condition in the gastrointestinal tract or colon of the subject.
10. The method of any one of paragraphs 6-9 further comprising selecting a subject for detecting.
11. The method of any one of paragraphs 6-10, wherein the subject has or is at risk of developing a gastrointestinal tract or colon condition.
12. The method of any one of paragraphs 6-11, wherein the target is selected from the group consisting of tetrathionate, reactive oxygen species, H2S, sdiA, bacteria enterotoxins, calprotectin and lactoferrin.
13. The method of any one of paragraphs 7-12, wherein the gastrointestinal tract or colon condition is cancer, inflammation, pathogenic bacterial infection, inflammatory bowel disease (IBD) such as Crohn's disease, colitis, and diabetes.
14. A method of detecting a target in the gastrointestinal tract or colon in a subject, the method comprising: (a) administering an engineered bacteria of any one of paragraphs 1-5 to the subject, wherein the inducible promoter is responsive to the target; (b) collecting a sample of fecal matter from the subject after a period of time after step a; and (c) measuring the expression of the reporter gene from the memory element of the circuit in the engineered bacteria wherein the detectable expression of the reporter gene indicates the presence of the target and the presence of the condition in the gastrointestinal tract or colon of the subject.
15. The method of paragraph 14, wherein the target is an indicator of a condition in the gastrointestinal tract or colon.
16. The method of paragraph 14 or 15 further comprising selecting a subject for detecting.
17. The method of paragraph 14, 15 or 16, wherein the subject has or is at risk of developing a gastrointestinal tract or colon condition.
18. The method of any one of paragraphs 14-17, wherein target is selected from the group consisting of tetrathionate, reactive oxygen species, H2S, sdiA, bacteria enterotoxins, calprotectin and lactoferrin.
19. The method of any one of paragraphs 15-18, wherein the gastrointestinal tract or colon condition is cancer, inflammation, pathogenic bacterial infection, inflammatory bowel disease (IBD) such as Crohn's disease, colitis, and diabetes.
20. A method of detecting for cancer in the gastrointestinal tract or colon in a subject in need thereof, the method comprising: (a) administering an engineered bacteria of any one of paragraphs 1-5, wherein the inducible promoter is responsive a symptom or biomarker that is known to occur when colorectal cancer is present; (b) collecting a sample of fecal matter from the subject after a period of time after step a; and (c) measuring the expression of the reporter gene from the memory element of the circuit in the engineered bacteria wherein the detectable expression of the reporter gene indicates the presence of the a symptom or biomarker that is known to occur when colorectal cancer is present and the likelihood of cancer in the gastrointestinal tract or colon of the subject.

21. A method of detecting pathogenic bacterial infection in the gastrointestinal tract or colon in a subject in need thereof, the method comprising: (a) administering an engineered bacteria of any one of paragraphs 1-5, wherein the inducible promoter is responsive a symptom or biomarker that is known to occur when as an enteric pathogenic bacterium is present; (b) collecting a sample of fecal matter from the subject after a period of time after step a; and (c) measuring the expression of the reporter gene from the memory element of the circuit in the engineered bacteria wherein the detectable expression of the reporter gene indicates the presence of the symptom or biomarker that is known to occur when as an enteric pathogenic bacterium is present and the presence of pathogenic bacterial infection in the gastrointestinal tract or colon of the subject.

22. A method of detecting inflammation in the gastrointestinal tract or colon in a subject in need thereof, the method comprising: (a) administering an engineered bacteria of any one of paragraphs 1-5, wherein the inducible promoter is responsive a symptom or biomarker that is known to occur when inflammation is present; (b) collecting a sample of fecal matter from the subject after a period of time after step a; and (c) measuring the expression of the reporter gene from the memory element of the circuit in the engineered bacteria wherein the detectable expression of the reporter gene indicates the presence of the a symptom or biomarker that is known to occur when inflammation is present symptom or biomarker that is known to occur when inflammation is present and the likelihood of inflammation in the gastrointestinal tract or colon of the subject.

23. A method of distinguishing colitis from Crohn's disease in the colon in a subject in need thereof, the method comprising: (a) administering a first engineered bacteria of any one of paragraphs 1-5 to a subject, wherein the inducible promoter is responsive to a symptom or biomarker that is known to occur when inflammation is present; (b) administering a second engineered bacteria of any one of claims 1-5 to a subject, wherein the inducible promoter is responsive to a symptom or biomarker that is known to occur when a pathogenic bacteria in the colon; (c) collecting a sample of fecal matter from the subject after a period of time after the administration steps; and (d) measuring the expressions of the reporter genes from the memory element of the circuit in the first and second engineered bacteria.

24. A method of monitoring the efficacy of a therapy for a gastrointestinal tract or colon condition in a subject comprising: (a) performing a method of any one of paragraphs 6-22 at a first time point; (b) performing a method of any one of paragraphs 6-22 at a second time point, wherein the method in the first time point and second time point are the same and the second time point is after administering at least one therapy; (c) comparing the expression of the reporter gene from the first time point with that of the second time point, wherein a decrease in the expression of the reporter gene is indication of effective therapy and wherein an increase or no change in the expression of the reporter gene is indication of ineffective therapy.

25. A formulation comprising engineered bacteria of any one of paragraphs 1-5.

26. Use of engineered bacteria of any one of paragraphs 1-5 for detecting cancer in the gastrointestinal tract or colon in a subject.

27. Use of engineered bacteria of any one of paragraphs 1-5 for detecting pathogenic bacterial infection in the gastrointestinal tract or colon in a subject.

28. Use of engineered bacteria of any one of paragraphs 1-5 for detecting inflammation in the gastrointestinal tract or colon in a subject.

29. Use of engineered bacteria of any one of paragraphs 1-5 for distinguishing colitis from Crohn's disease in the gastrointestinal tract or colon in a subject.

30. Use of engineered bacteria of any one of paragraphs 1-5 for monitoring the efficacy of a therapy for a gastrointestinal tract or colon condition in a subject.

31. An engineered unicellular organism comprising a memory circuit comprising: (a) a bacteriophage-reporter element-based memory element comprising two antagonistic transcription factors or gene regulatory factors; and (b) an inducible transcription factor-based trigger element, wherein the triggering transcription factor is operably linked to an inducible promoter, and wherein the inducible promoter is responsive to a stimulus, and wherein the memory circuit is integrated into the genome of the organism.

32. The engineered unicellular organism of paragraph 31, wherein the memory circuit is maintained in the organism without antibiotic selection.

33. The engineered unicellular organism of paragraph 31 or 32, wherein the memory circuit comprises antagonistic transcription factors.

34. The engineered unicellular organism of paragraph 31, 32 or 33, wherein the antagonistic transcription factors are cI and Cro.

35. The engineered unicellular organism of any one of paragraphs 31-34, wherein the reporter element comprise a reporter gene selected from a group consisting of β-galactosidase (LacZ), chloramphenicol acetyltransferase (CAT), neomycin phosphotransferase (G418), bacteria luciferase (LuxAB), a fluorescent protein (FP), alkaline phosphatase (PhoA), and p-glucuronidase (GUS) or the reporter element comprise a genomic rearrangement detectable by PCR such as deletions or inversions.

36. The engineered unicellular organism of any one of paragraphs 31-35, wherein the inducible promoter is responsive to an environmental marker, wherein the environmental marker is selected from the group consisting of a small molecule or endogenous two-component systems or gene-regulatory networks, and wherein the a small molecule is tetracycline, tetrathionate, reactive oxygen species, heme, iron, elastase, or hydrogen sulfide gas ($H_2S$).

37. A method of detecting a stimulus in a multicellular organism, the method comprising administering an engineered unicellular organism of any one of paragraphs 31-36 to the subject, wherein the inducible promoter is responsive to the stimulus.

38. The method of paragraph 37, wherein the stimulus is an indicator of a condition in the subject.

39. The method of paragraph 37 or 38, wherein the condition is caused by the microbiota.

40. The method of paragraph 37, 38 or 39 further comprising collecting a biological sample of matter from the subject after administering the engineered unicellular organism to the subject.

41. The method of any one of paragraphs 37-40 further comprising measuring for the expression of the reporter element in the subject's biological sample wherein the expression or action of the reporter element indicates the presence of the stimulus and the presence of the condition in the subject.

42. The method of any one of paragraphs 37-41 further comprising selecting a subject for detecting.

43. The method of any one of paragraphs 37-42, wherein the subject has or is at risk of developing a condition caused by the microbiota.

44. The method of any one of paragraphs 37-43, wherein the stimulus is a small molecule stimulus, an endogenous 2-component signaling system, or a gene regulatory network, wherein the small molecule stimulus is selected from the group consisting tetrathionate, reactive oxygen species, $H_2S$, bacterial enterotoxins, calprotectin and lactoferrin.

45. The method of any one of paragraphs 37-44, wherein the condition is a disease related to the microbiota and is selected from the group consisting of cancer, inflammation, pathogenic bacterial infection, inflammatory bowel disease (IBD), Crohn's disease, colitis, rheumatoid arthritis, and diabetes.

46. A method of detecting a stimulus in the subject, the method comprising: (a) administering an engineered unicellular organism of any one of paragraphs 31-36 to the subject, wherein the inducible promoter is responsive to the stimulus; (b) collecting a sample from the subject after a period of time after step a; and (c) measuring the expression or action of a reporter element indicating the state of the memory element of the circuit in the engineered unicellular organism wherein the detectable expression or action of the reporter element indicates the presence of the stimulus and the presence of a condition caused by microbiota in the subject.

47. The method of paragraph 46, wherein the stimulus is an indicator of a condition in the subject.

48. The method of paragraph 46 or 47 further comprising selecting a subject for detecting.

49. The method of paragraph 46, 47 or 48, wherein the subject has or is at risk of developing a condition caused by the microbiota.

50. The method of any one of paragraphs 46-49, wherein the target is an environmental stimulus is a small molecule or protein or an endogenous 2-component signaling systems, or a gene regulatory network, wherein the small molecule or protein is selected from the group consisting of tetrathionate, reactive oxygen species, H2S, bacterial enterotoxins, calprotectin and lactoferrin, and wherein the gene regulatory network is sidA.

51. The method of paragraph 46, wherein the condition is a disease related to the microbiota such as cancer, inflammation, pathogenic bacterial infection, inflammatory bowel disease (IBD), Crohn's disease, colitis, rheumatoid arthritis, and diabetes.

52. A method of detecting for cancer in the gastrointestinal tract or colon in a subject in need thereof, the method comprising: (a) administering an engineered unicellular organism of any one of paragraphs 31-36, wherein the inducible promoter is responsive a symptom or biomarker that is known to occur when colorectal cancer is present; (b) collecting a biological sample from the subject after a period of time after step a; and (c) measuring the expression of the reporter element from the memory element of the circuit in the engineered unicellular organism wherein the detectable expression or action of the reporter element indicates the presence of the a symptom or biomarker that is known to occur when colorectal cancer is present and the likelihood of cancer in the gastrointestinal tract or colon of the subject.

53. A method of detecting pathogenic bacterial infection in the gastrointestinal tract or colon in a subject in need thereof, the method comprising: (a) administering an engineered unicellular organism of any one of paragraphs 31-36, wherein the inducible promoter is responsive a symptom or biomarker that is known to occur when as an enteric pathogenic bacterium is present; (b) collecting a biological sample of from the subject after a period of time after step a; and (c) measuring the expression of or action of the reporter element indicating the state of the memory element of the circuit in the engineered unicellular organism wherein the detectable expression of the reporter element indicates the presence of the symptom or biomarker that is known to occur when as an enteric pathogenic bacterium is present and the presence of pathogenic bacterial infection in the gastrointestinal tract or colon of the subject.

54. A method of detecting inflammation in the gastrointestinal tract or colon in a subject in need thereof, the method comprising: (a) administering an engineered unicellular bacteria of any one of paragraphs 31-36, wherein the inducible promoter is responsive a symptom or biomarker that is known to occur when inflammation is present; (b) collecting a biological sample of from the subject after a period of time after step a; and (c) measuring the expression or action of the reporter element from the memory element of the circuit in the engineered unicellular organism wherein the detectable expression or action of the reporter element indicates the presence of the a symptom or biomarker that is known to occur when inflammation is present and the likelihood of inflammation in the gastrointestinal tract or colon of the subject.

55. A method of distinguishing colitis from Crohn's disease in the gastrointestinal tract or colon in a subject in need thereof, the method comprising: (a) administering an engineered unicellular organism of any one of paragraphs 31-36 to a subject, wherein the inducible promoter is responsive to a symptom or biomarker that is known to occur when inflammation is present; (b) administering a second engineered unicellular bacteria of any one claims 31-36 to a subject, wherein the inducible promoter is responsive to a symptom or biomarker that is known to occur when a pathogenic bacteria in the colon; (c) collecting a biological sample from the subject after a period of time after the administration steps; and (d) measuring the expression or action of the reporter element from the memory element of the circuit in the first and second engineered unicellular organism.

56. A method of monitoring the efficacy of a therapy for a gastrointestinal tract or colon condition in a subject comprising: (a) performing a method of any one of paragraphs 37-54 at a first time point; (b) performing a method of any one of paragraphs 37-54 at a second time point, wherein the method in the first time point and second time point are the same and the second time point is after administering at least one therapy; (c) comparing the expression or action of the reporter element from the first time point with that of the second time point, wherein a decrease in the expression or action of the reporter element indication of effective therapy and wherein an increase or no change in the expression of the reporter element is indication of ineffective therapy.

57. A formulation comprising engineered unicellular organism of any one of paragraphs 31-36.

58. Use of engineered unicellular organism of any one of paragraphs 31-36 for detecting cancer in the gastrointestinal tract or colon in a subject.
59. Use of engineered unicellular organism of any one of paragraphs 31-36 for detecting pathogenic bacterial infection in the gastrointestinal tract or colon in a subject.
60. Use of engineered unicellular organism of any one of paragraphs 31-36 for detecting inflammation in the gastrointestinal tract or colon in a subject.
61. Use of engineered unicellular organism of any one of paragraphs 31-36 for distinguishing colitis from Crohn's disease in the gastrointestinal tract or colon in a subject.
62. Use of engineered unicellular organism of any one of paragraphs 31-36 for monitoring the efficacy of a therapy for a gastrointestinal tract or colon condition in a subject.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

Example

Materials and Methods

Artificial gene-based memory systems have been constructed using bi-stable transcriptional switches to permanently record transient environmental signals transmitted either directly through one of the transcription factors in the switch, or indirectly through a distinct trigger element 8-10. To engineer a bacterium that could record an environmental signal in the mammalian gut, the investigators set the following design specifications: (1) the initial 'non-memory' state should be highly stable, only failing as a result of mutation of the system; (2) the 'memory' state should also be highly stable; (3) the engineered elements should be integrated into the chromosome rather than on plasmids to minimize the chance of loss; and (4) the engineered elements should not impose a detectable fitness burden on the host (illustrated in FIG. 1A).

The inventors used the well-characterized cI/cro genetic switch from bacteriophage lambda[11-13] to construct a memory element for the circuit. Natural selection has already tuned the repressed cI state to be so stable that in an induction-deficient cI$^{ind}$-lysogen, the repressor state only fails due to spontaneous mutation of cI and not to fluctuations in cI protein levels[14]. The presence of a lambda prophage causes little burden on the bacterial host as only 100-200 cI monomers per cell are present in a lysogen[15].

To construct a memory element that reproduces the elements of cI regulation, the investigators inserted a DNA fragment from phage lambda from the left operator (OL) including the rexAB genes, cI, and cro upstream of lacZ; replacing lacI. The construct lacks the N coding sequence, and the terminal 'A' of the Cro stop codon is followed by the initial 'A' in the LacZ start codon. This construct should thus reproduce exactly the elements of cI expression, including the interaction between the OL-OR operator sites[16] and the natural downstream genes and terminators of the cI transcript, which may influence mRNA stability. The junction between Cro and LacZ is not natural; other junctions tested with elements of the natural post-cro terminator tR1 resulted in a memory element in which the cro state could not be maintained (FIG. 1B, FIG. 6A-6D). Previously, it has been observed that when a lambda prophage is integrated in single-copy, the cro state is unstable and spontaneously reverts to the cI state[8,9]; in these constructs lambda N is not expressed and the cro transcripts terminate at tR1. Because PAS 132 (FIG. 6.) does not contain the natural cro terminator sequences, and reads directly into lacZ, the degradation half-life of the engineered transcript may correspond more closely to the longer N-anti-terminated cro transcript, which may be more stable and lead to higher levels of Cro expression.

E. coli were further engineered to contain a trigger element driving Cro expression (FIG. 1C, FIG. 6E). FIG. 6E shows the tetP-Cro trigger element embodiment disclosed in the example section. This element consists of a chloramphenicol-resistance cassette, a tetR-tetP segment from Tn10 that includes the divergent tetracycline promoters, and the cro gene transcribed from the tetA promoter. This segment was inserted into the MG1655 genome at base 70165, in a CAP binding site between araB and araC promoters to minimize aberrant read-through from external promoters. The Tn10 tetracycline repressor is particularly sensitive to ATC, such that a low dose of 100 ng/ml ATC will cause full de-repression of the promoter without inhibiting growth of tetracycline-sensitive E. coli.

The wild-type-tetA promoter (tetP) (an inducible promoter) was placed upstream of Cro, and the minimal genetic elements that form the lambda transcriptional switch were integrated into the bacterial genome. Lambda switches from lysogenic to lytic state when the concentration of cI falls below about 10% of its steady-state value in a lysogen[17]. This leads to de-repression of the PR promoter and the expression of Cro. When Cro levels reach approximately 100 molecules per cell, the activity of the PRM promoter decreases[17]. In the presence of Cro-mediated PRM repression, about four cell divisions are required for cI to be diluted enough to switch from the cI state to the cro state[8,12,16]. Therefore, the investigators expected that if tetP is induced via anhydrotetracycline (ATC) for four consecutive cell divisions the memory element will switch from the cI state to the cro state, which the investigators could monitor by LacZ expression.

Figure 2B:
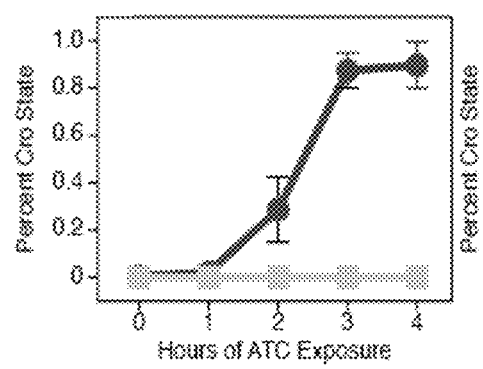
Figure 2C:
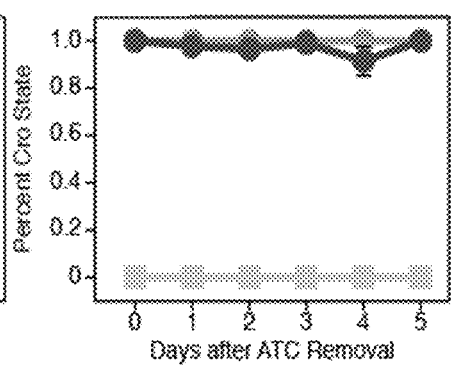
Figure 2D:
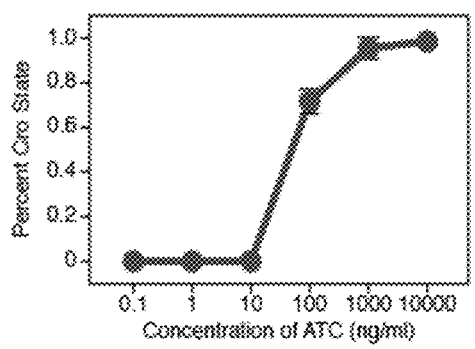

The genetic circuit consisting of the cI/cro switch from the lambda prophage and the tetP trigger was capable of sensing and recording exposure to antibiotics (FIG. 2A). When these engineered E. coli were exposed to ATC they stably switched from the cI state to the cro state after less than 4 hours in cells grown in M9 glucose medium (FIG. 2B). This switching time is consistent with our memory element design in which Cro expression from the trigger element to represses further cI expression, and cI concentrations are reduced by dilution over the course of about 4 cell divisions. After ATC removal, the memory element remained in the cro state for at least 5 days of sub-culturing in M9 medium, representing about 150 cell divisions (FIG. 2C). The Tn10 tetracycline repressor used in our trigger element is particularly sensitive to ATC, such that a low dose of 100 ng/ml ATC will cause full de-repression of the promoter without inhibiting growth of tetracycline-sensitive E. coli (FIG. 2D).

Figure 7:
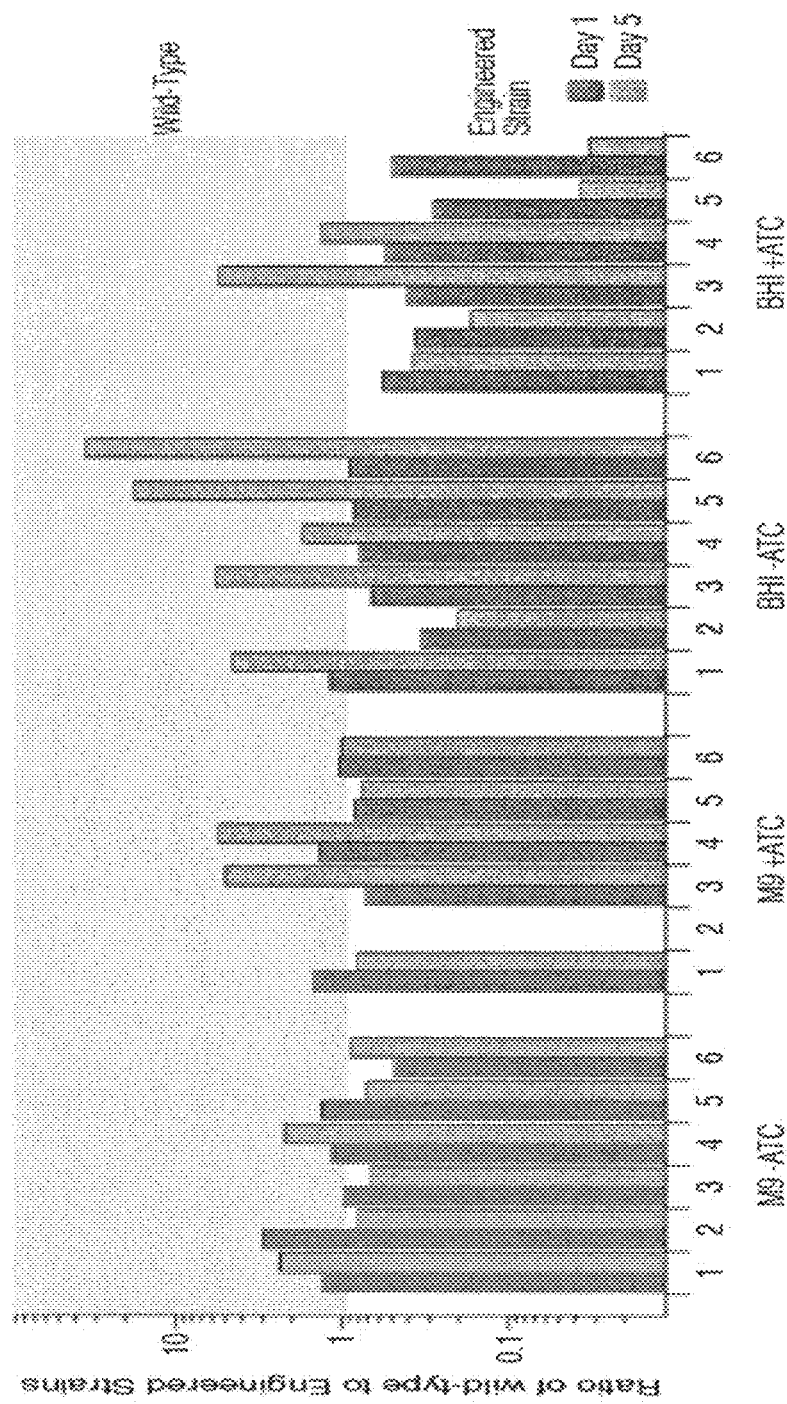
FIG. 7 shows the estimation of the fitness cost of the memory circuit.

The trigger and memory elements were not deleterious to growth of E. coli, as inferred from competitive growth experiments in mixed cultures with the parental strain of E. coli. FIG. 7 shows the estimation of the fitness cost of the memory circuit. To compare the fitness cost of the trigger/memory system used herein, strain PAS 132 and MG1655 rpsL(Lys42Arg) were grown in mixed cultures for many generations as follows. For both strains, six cultures from six isolated colonies of each strain were grown overnight in either M9 0.5% glucose as a representative poor medium or BHI medium as a rich medium without lactose. These cultures were diluted 1000-fold and pairwise-combined to create six mixed cultures of approximately equal numbers of each strain were generated for the following four conditions: M9 glucose, M9 glucose+100 ng/ml ATC, BHI, and BHI+ 100 ng/ml ATC. The cultures were titered on M9 glucose Xgal IPTG plates immediately after the initial mixing and after 5 days of daily 1000-fold dilution and aerobic growth at 37° C., representing about 50 cell divisions or more. The parental MG1655 rpsL strain forms intensely blue colonies on the indicator plates, while the engineered strain forms white or light-blue colonies, depending on its epigenetic state. The results indicate that in each mixed culture, one strain sometimes would outgrow the other, but there was no consistent bias against the strain bearing the trigger and memory elements. The hypothesis is that, given the number of cell divisions, a mutant cell could arise that would have a growth advantage in the particular growth conditions used[18]. Such a mutation could arise in either cell type, and would lead to overgrowth of that genotype. These results indicate that the fitness cost of the memory and trigger elements, regardless of epigenetic state, is low. Bars indicate the ratio of MG1655 to PAS 132 in a single mixed culture.

Multiple independent mixed cultures, each with an initial ratio of about 1:1 *E. coli* MG1655 and PAS 132 were sub-cultured with and without ATC for about 50 cell divisions, and titered on indicator plates to distinguish the two strains. The change in ratios of parent cells to engineered cells varied from culture to culture but did not show a consistent overgrowth of parental cells (FIG. 7). This observation indicates that a spontaneous mutation enhancing growth under the conditions tested was arising in one strain or the other, and outgrowing the culture[18]. Any fitness effect due to our engineered elements appears to be weaker than this subtle effect. These observations indicate that mutational loss of the engineered elements would not be strongly selected, regardless of the epigenetic state of the memory element, and should not confound quantitation of switching experiments.

Figure 3A:
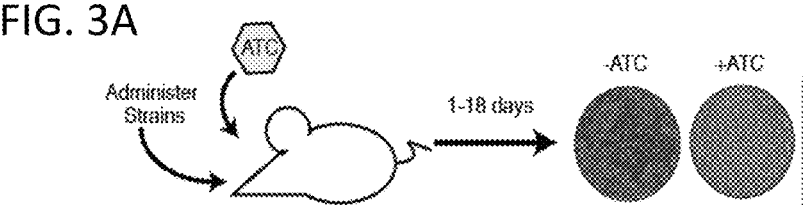
FIGS. 3A-3D shows that engineered bacteria record, remember and report ATC exposure from the mammalian gut.
Figure 3B:
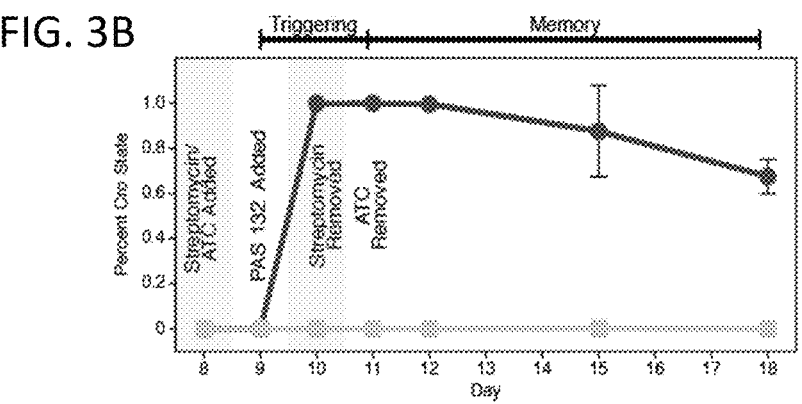
Figure 3C:
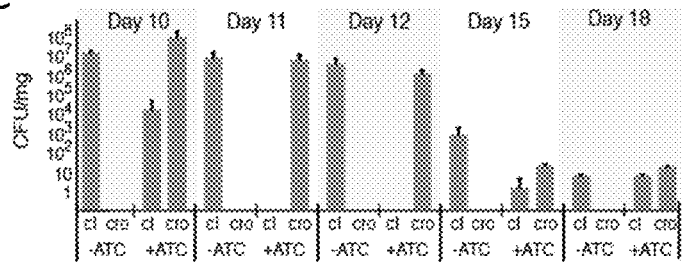
Figure 3D:
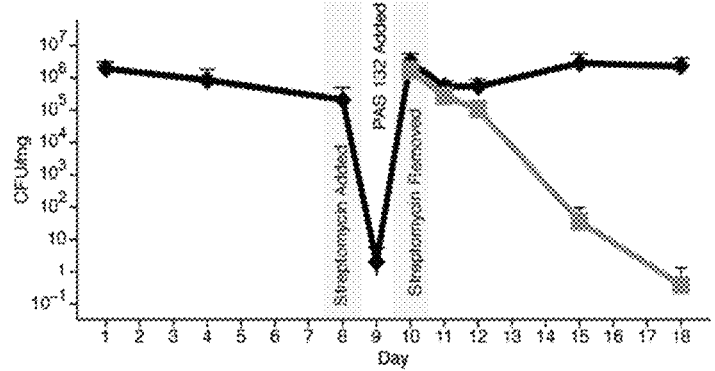

PAS 132 was capable of ATC detection in the mammalian gut (FIG. 3A). ATC is the target or stimulus that induces the inducible tetP promoter. To detect bacteria containing genetic circuits after passage through the mouse gut, the memory strain was engineered to contain a mutation in the rpsL gene (FIG. 8), conferring resistance to streptomycin at concentrations >300 µg/ml[19]. Female Balb/C mice were given streptomycin (0.5 mg/ml in drinking water) to allow colonization by PAS 132; some mice also received ATC (0.1 mg/ml) in drinking water. About $10^7$ bacteria were administered by oral gavage. Fecal samples were collected and titered on MacConkey lactose indicator plates with streptomycin to select for PAS 132, and on Brain-Heart Infusion plates (anaerobic) to determine culturable counts. All of PAS 132 isolated from mice that were given ATC stably switched from the cI state to the cro state within 1 day of exposure (FIG. 3B). The culturable endogenous gut flora began recolonizing the gut as soon as the streptomycin treatment ended (FIG. 3C, 3D). The titer of the engineered bacteria decreased slowly thereafter (FIG. 3C, 3D).

PAS 132 remembered ATC exposure in mice for more than a week after termination of ATC treatment. The inventors confirmed that 100% of the engineered bacteria sensed ATC in the mouse gut and switched to the cro state within 24 hours of ATC exposure (FIG. 3B), after which ATC was removed from the drinking water. The surviving PAS 132 maintained a stable cro memory state after more than a week in the mouse gut without further exposure to ATC (FIG. 3B).

Figure 9A:
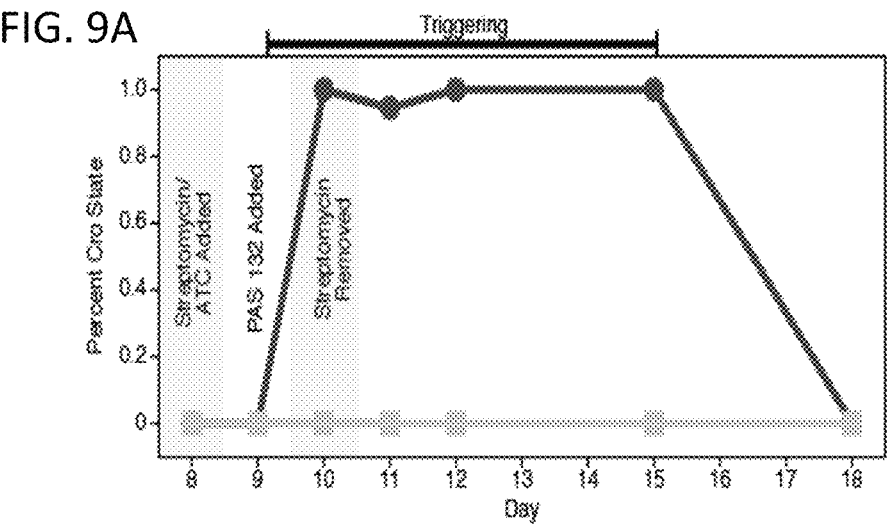
FIGS. 9A and 9B show some additional in vivo experiments with the described embodiment of a genetically engineered bacteria. Mice were given ATC when indicated (0.1 mg/ml) and streptomycin in drinking water (0.5 mg/ml) to allow colonization by engineered strains. PAS 132 cells were administered to the mice via oral gavage.
Figure 9B:
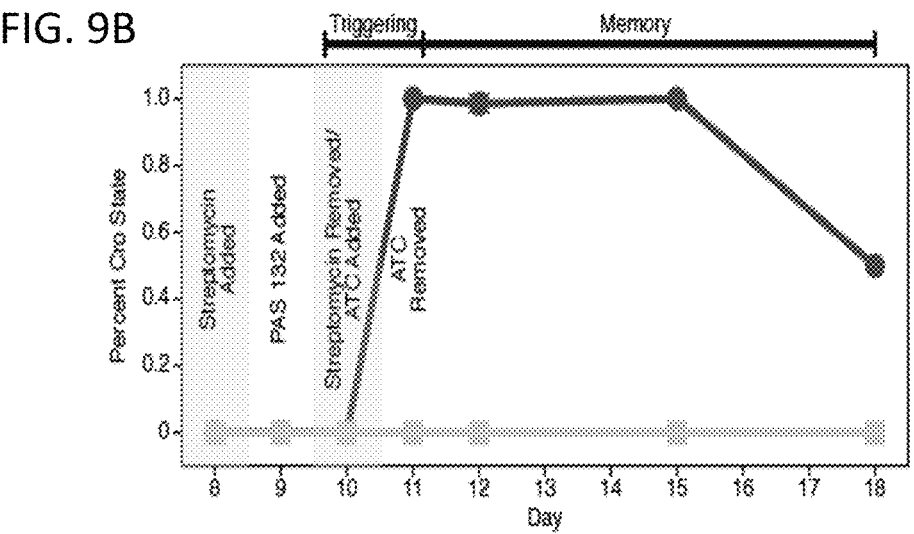
Figure 10A:
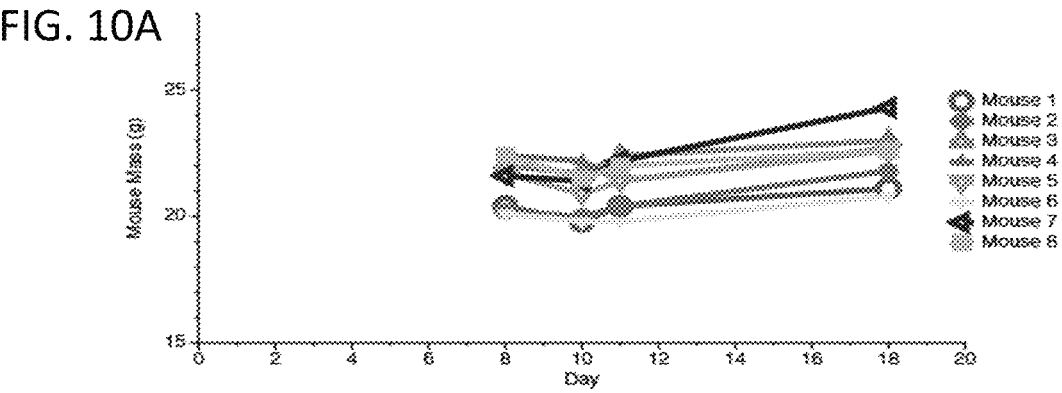
FIG. 10A-10D shows use of the embodiments of genetic engineered bacteria having memory circuit to monitoring mouse health. Mice were weighed on the indicated days in order to monitor their health. A drop in total body mass >20% would indicate that there was a potential health concern. From day 1 to day 18 of all in vivo experiments, all of the mice showed a net gain in total body mass. This indicated that administering two drugs, streptomycin and ATC, as well as our engineered bacteria did not adversely affect mouse health.
Figure 10B:
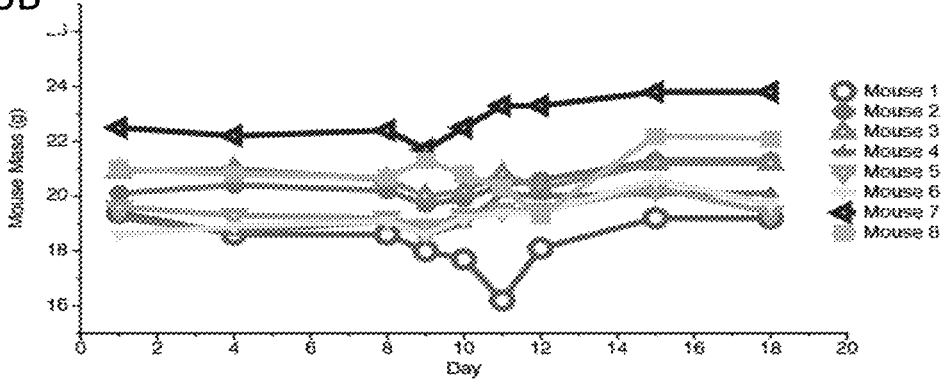
Figure 10C:
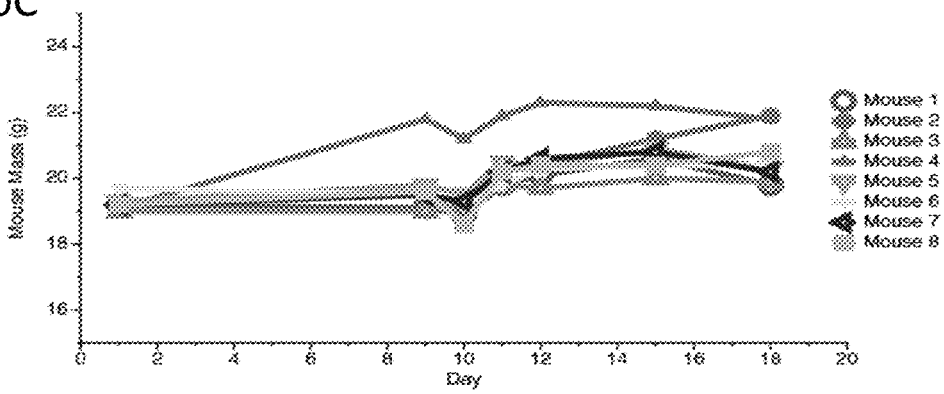
Figure 10D:
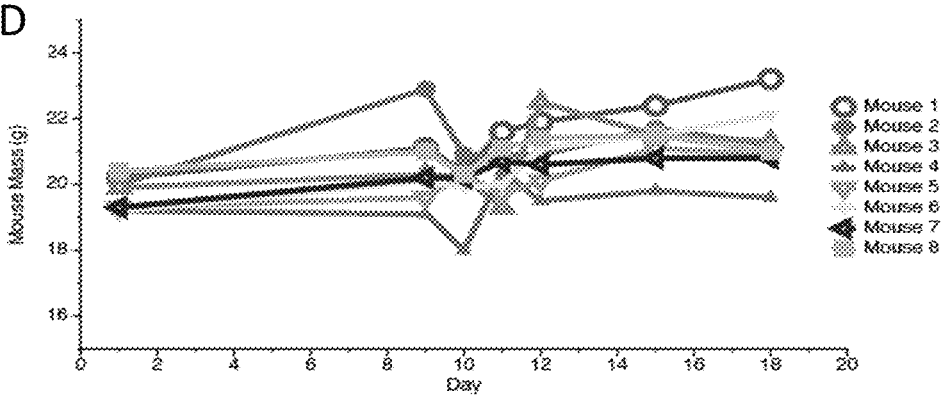
Figure 12A:
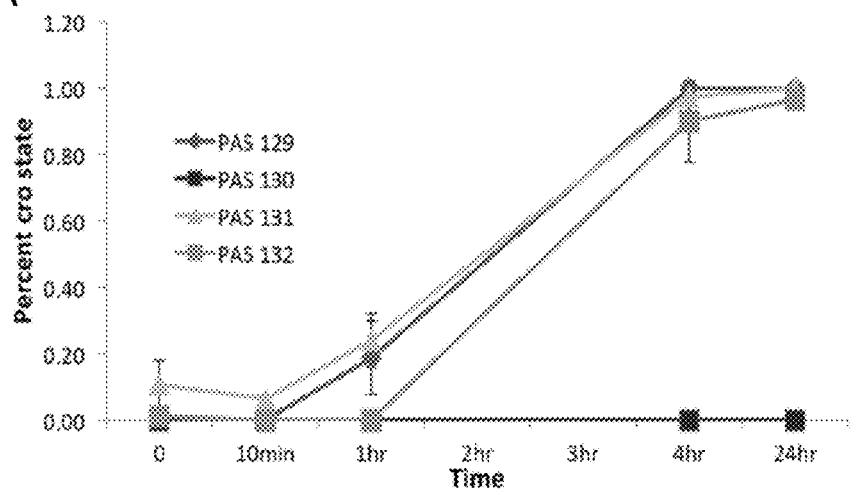
FIGS. 12A-12B show the identification of a memory element with optimal switching properties.
Figure 12B:
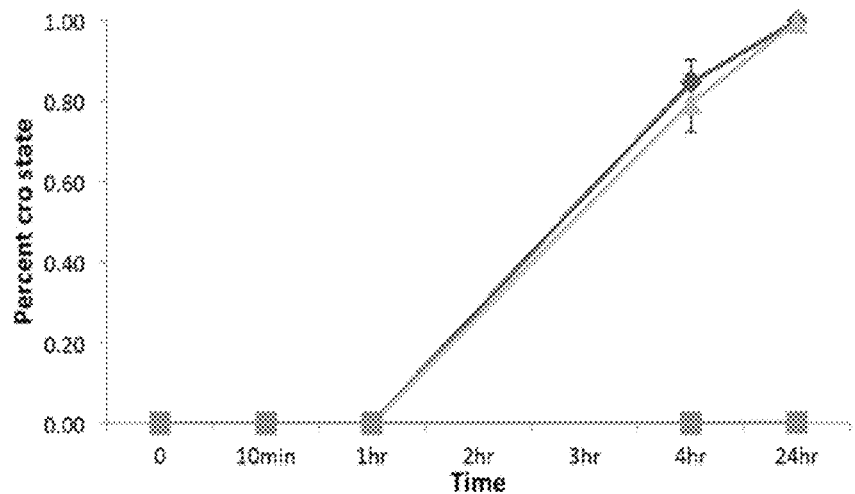

In separate in vivo experiments, mice were not given ATC until PAS 132 was allowed to colonize the mouse gut and streptomycin was removed. Again PAS 132 switched from the cI state to the cro state within 24 hours and remembered ATC exposure throughout the remaining time course (FIG. 9). This indicates that PAS 132 that have already colonized the gut are able to record subsequent changes to their environment. Mouse health was not affected by antibiotic treatment, or administration of PAS 132 (FIG. 10), which demonstrates that the engineered bacteria are not toxic to their host. After ATC removal there was not sufficient ATC in the gut or fecal samples to activate the memory circuit. Tetracycline (Tc) is undetectable in the serum, kidneys, and liver of female mice after less than 8 hours of administration[20]. Therefore the ATC was likely cleared from the mouse when the inventors evaluated our engineered bacteria for memory.

Figure 4A:
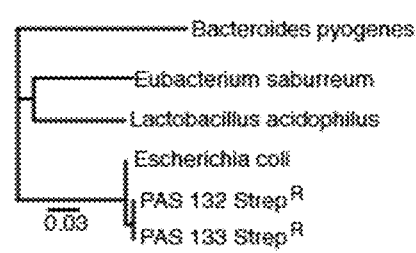
FIGS. 4A-4D show the memory behavior of an endogenous murine E. coli strain engineered to contain the memory circuit.
Figure 4B:
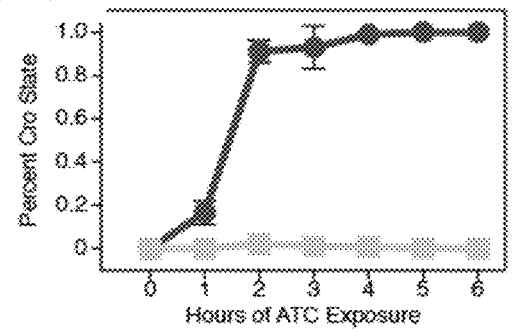
Figure 11:
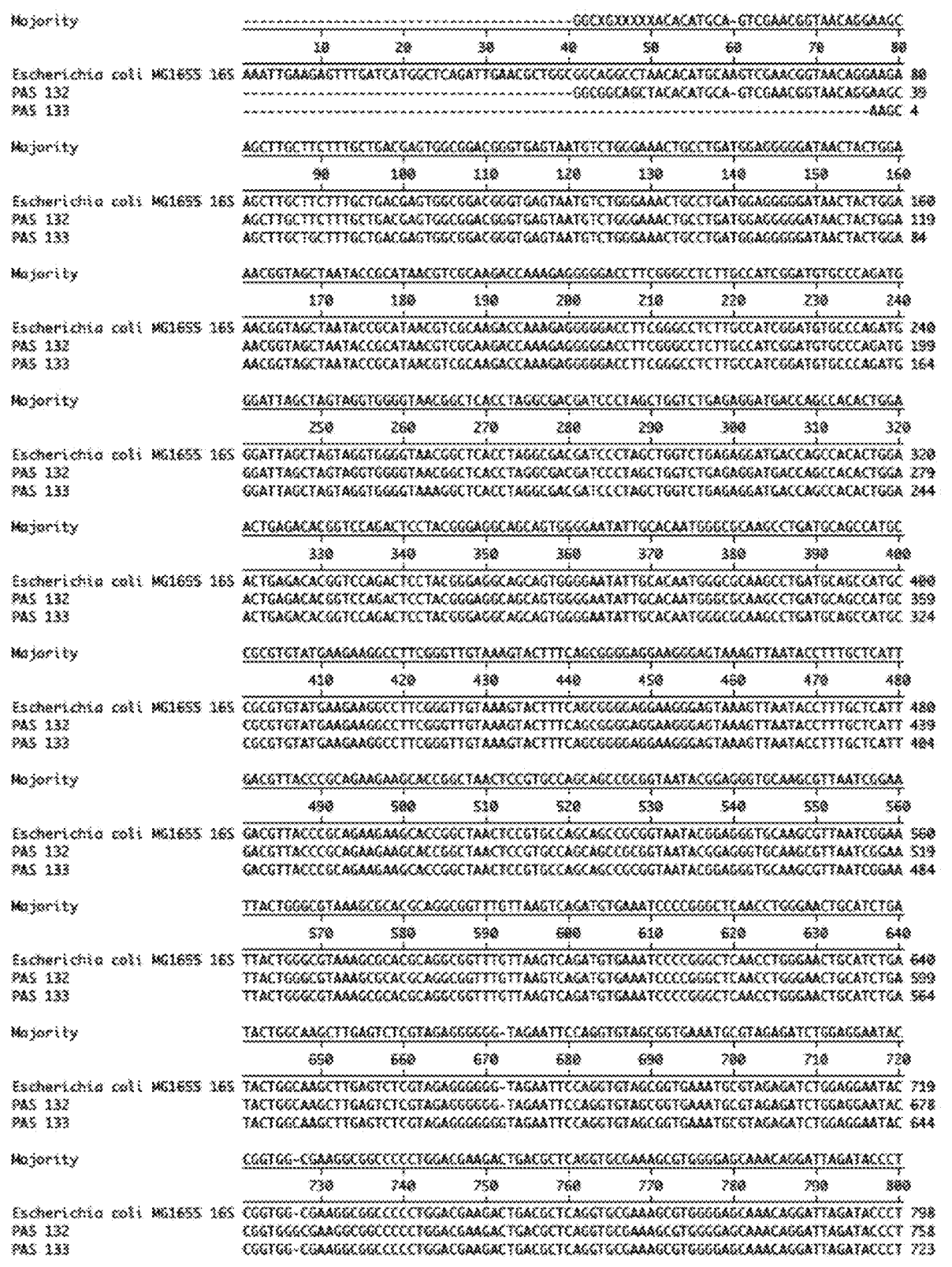
Figure 11:
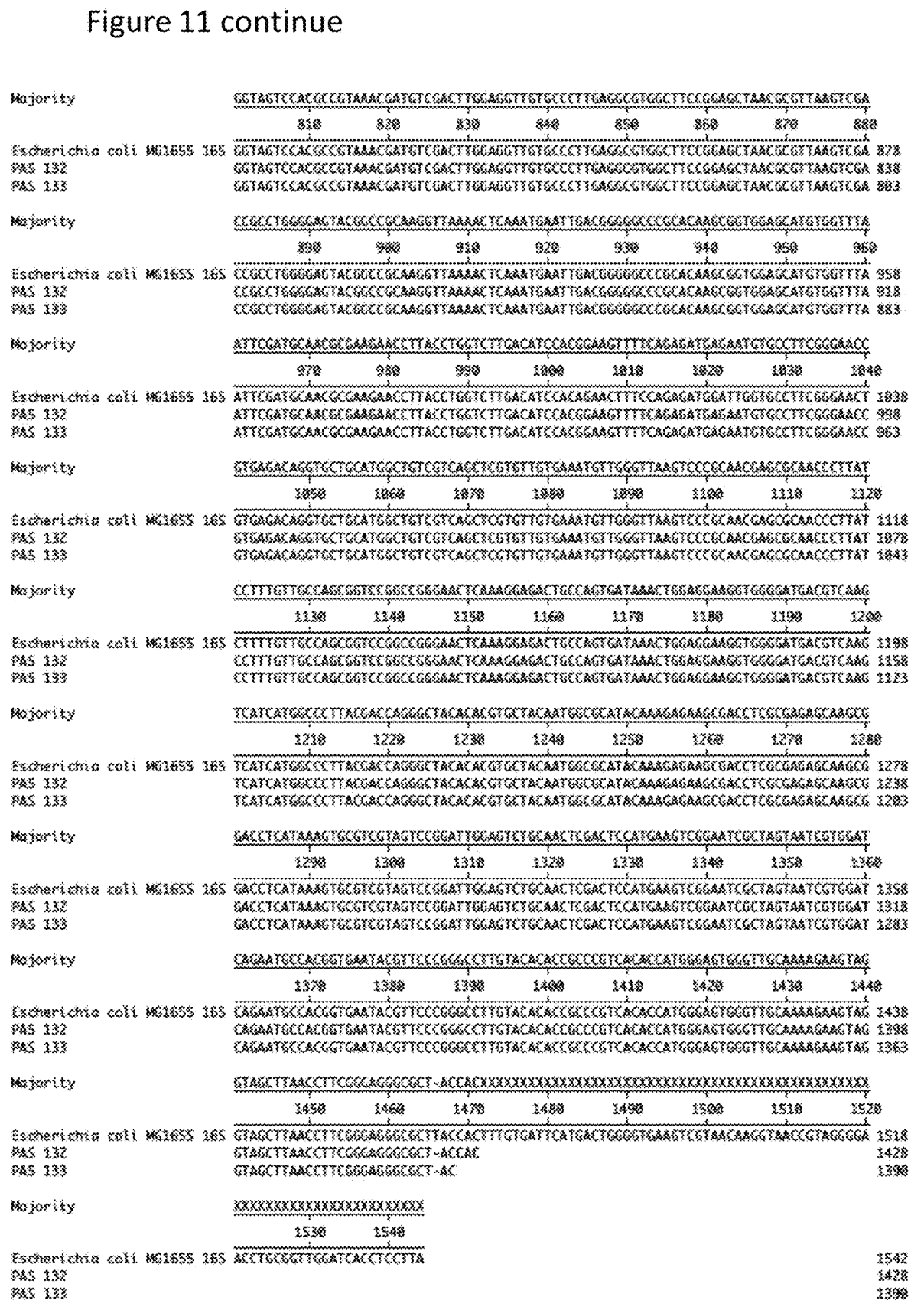

The genetic memory circuit functioned essentially identically in an uncharacterized coliform bacterium from the mouse gut. The inventors isolated a microbe from a mouse fecal sample that fermented lactose on MacConkey Lactose plates, and confirmed that its 16S ribosomal RNA gene sequences matched that of *E. coli* (FIG. 4A, FIG. 11). P1vir transduction was used to insert the memory circuit, trigger and streptomycin resistance mutation into this isolate from natural gut flora, termed NGF-1. The engineered NGF-1 (PAS 133) behaved similarly to the engineered K12 strain, PAS 132 in vitro registering ATC exposure within 4 hours (FIG. 4B).

Figure 4C:
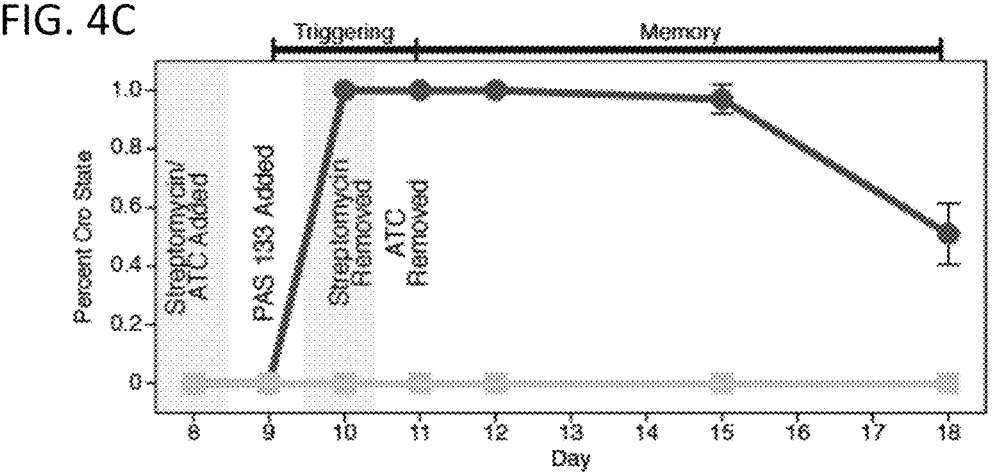
Figure 4D:
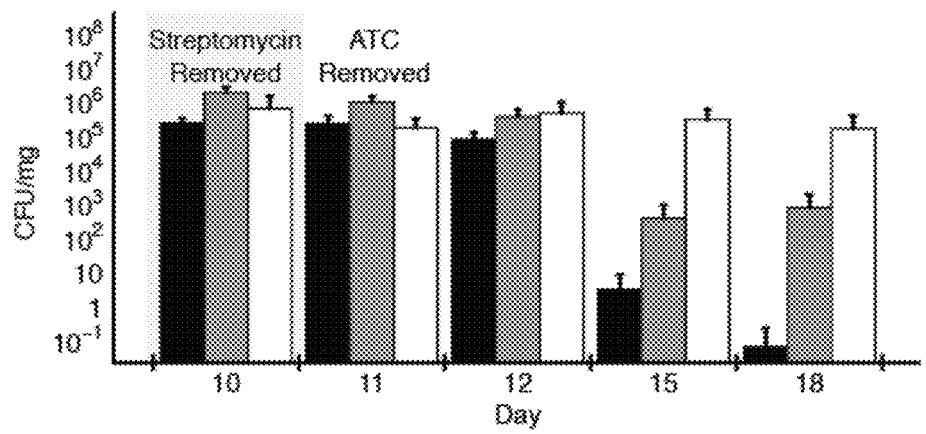
Figure 5A:
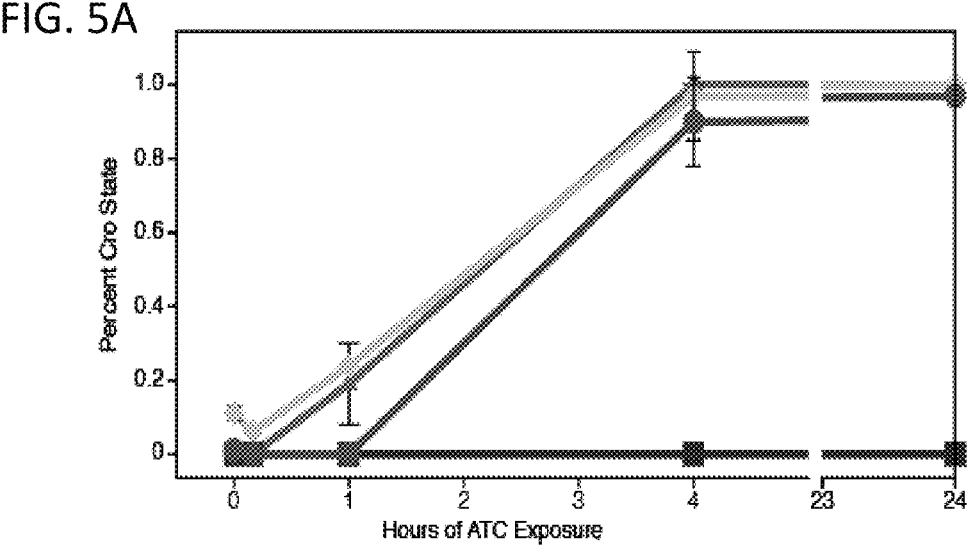
FIGS. 5A-5B shows the identification of a memory element with optimal switching properties. About 10 candidate memory elements with the general structure shown in FIG. 1b were constructed by recombineering into strain TB10, which automatically sets the element into the cI state. Upon removal of the prophage remnant in TB10 by P1 transduction, several of these elements showed frequent spontaneous switching to the cro state and were not characterized further. Four elements (11-14) were characterized in detail. Elements 11 and 13 contain the cIts857 ind1 allele; 12 and 14 have cIind1. Elements 11 and 12 contain the cro-cII intergenic region while in elements 13 and 14 the lacZ ATG immediately follows the cro stop codon (TAA ATG).
Figure 5B:
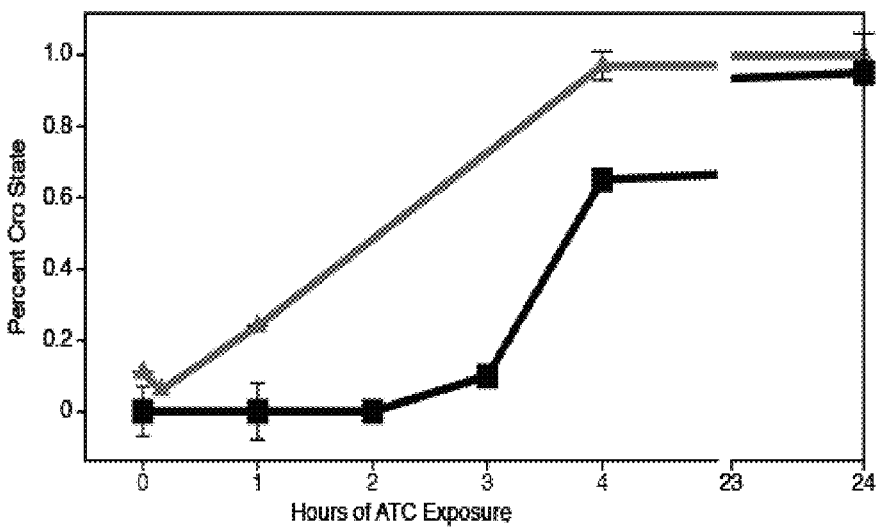
Figure 6A:
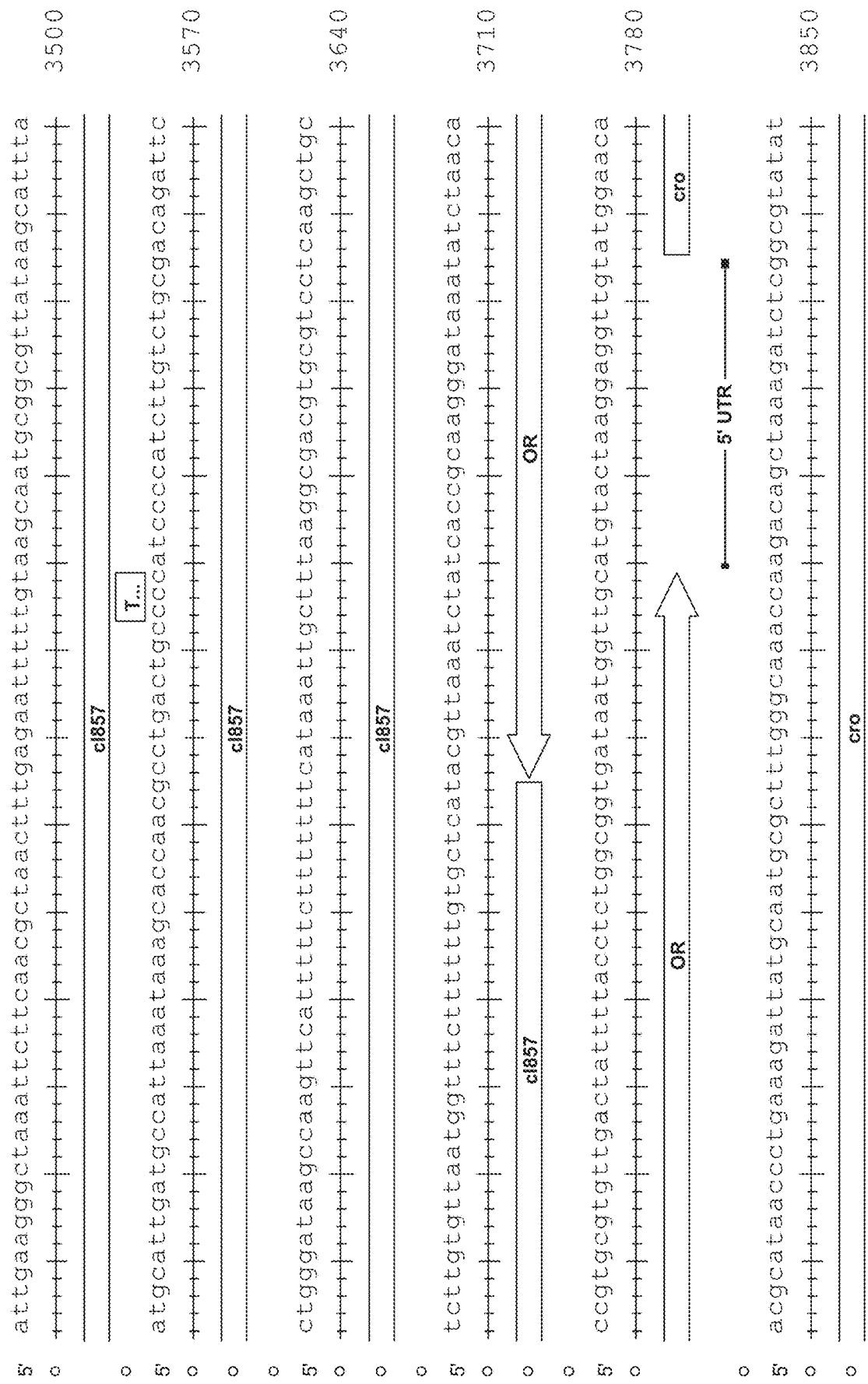
Figure 6A:
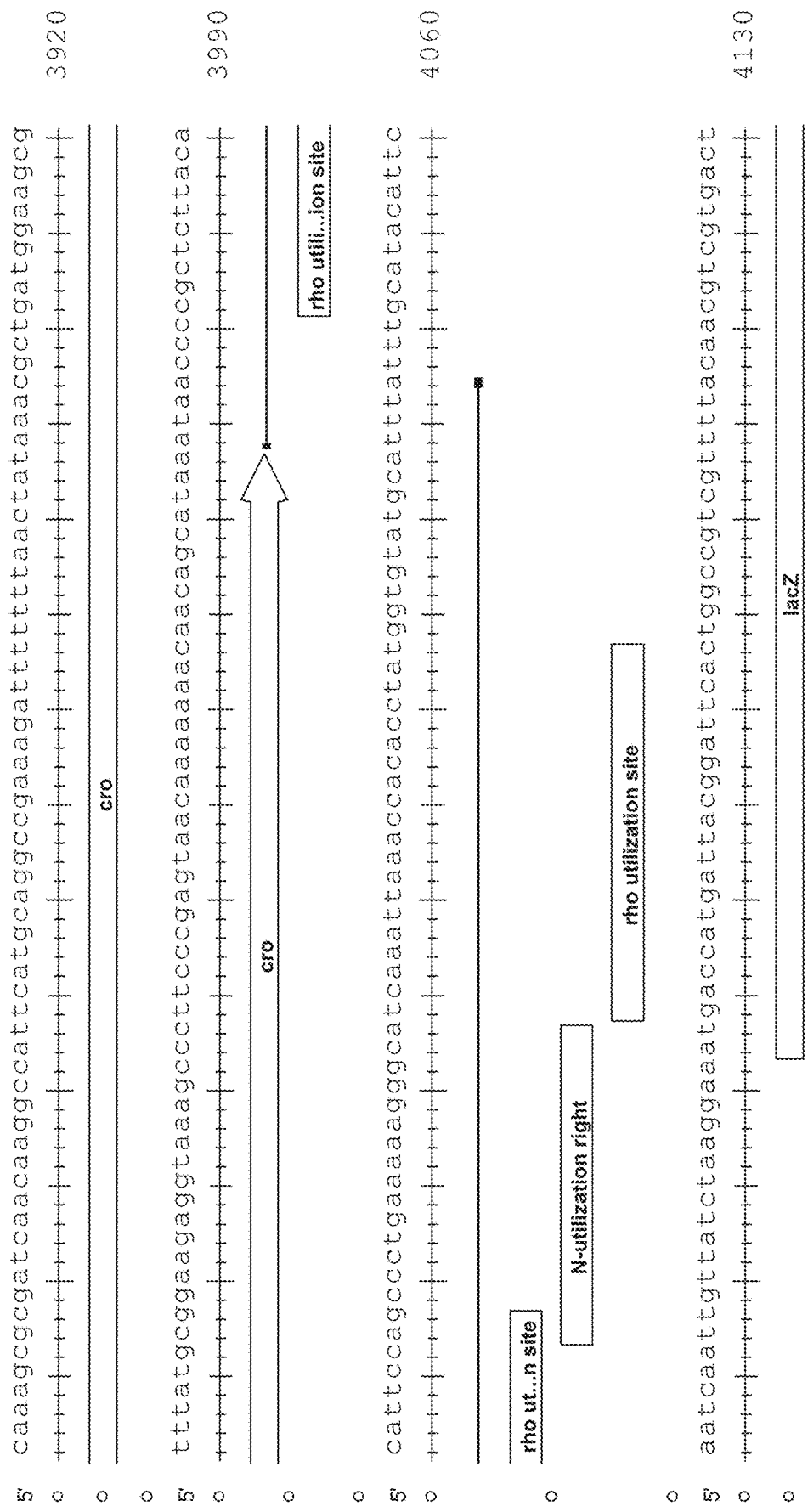
Figure 6B:
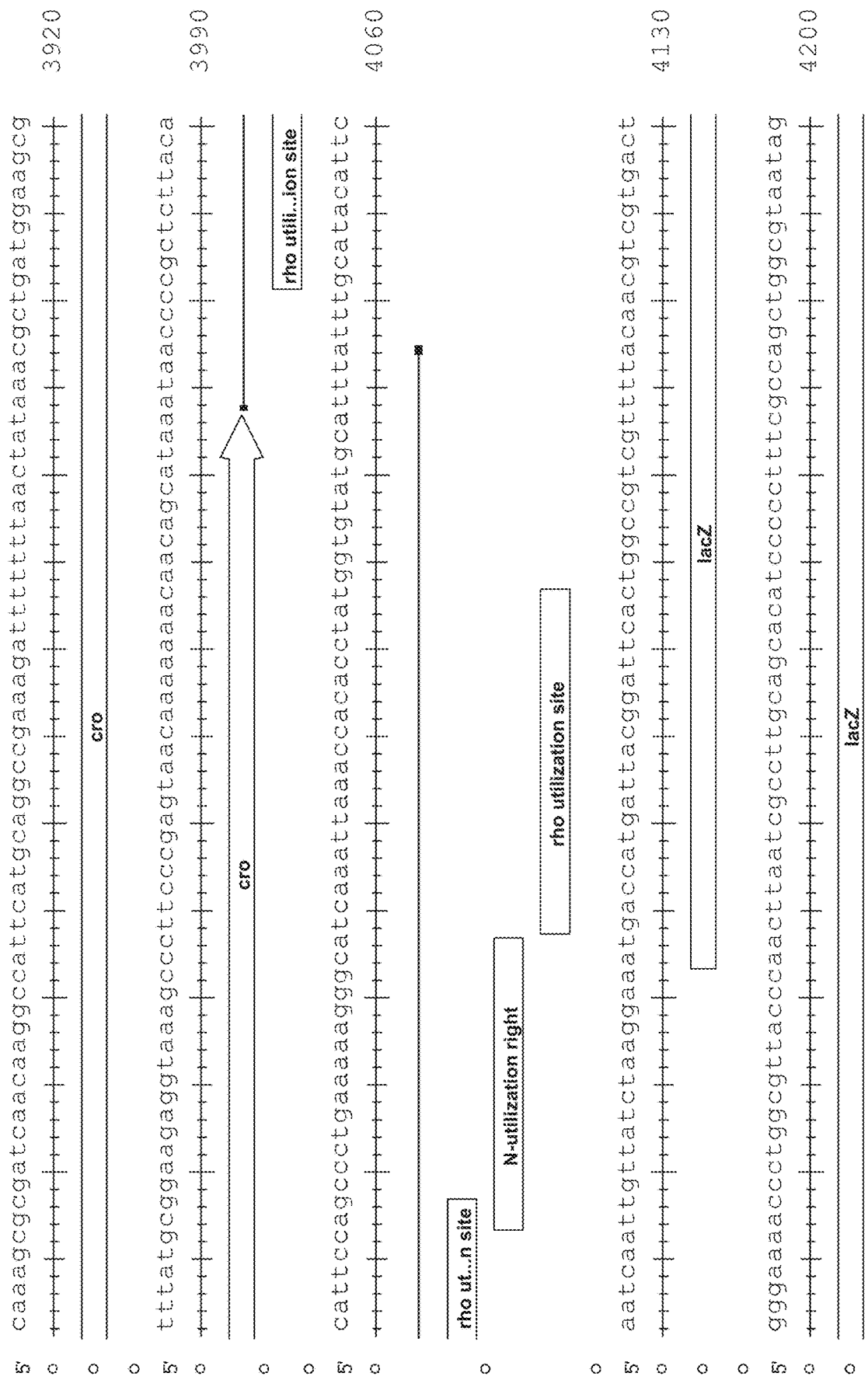
Figure 6C:
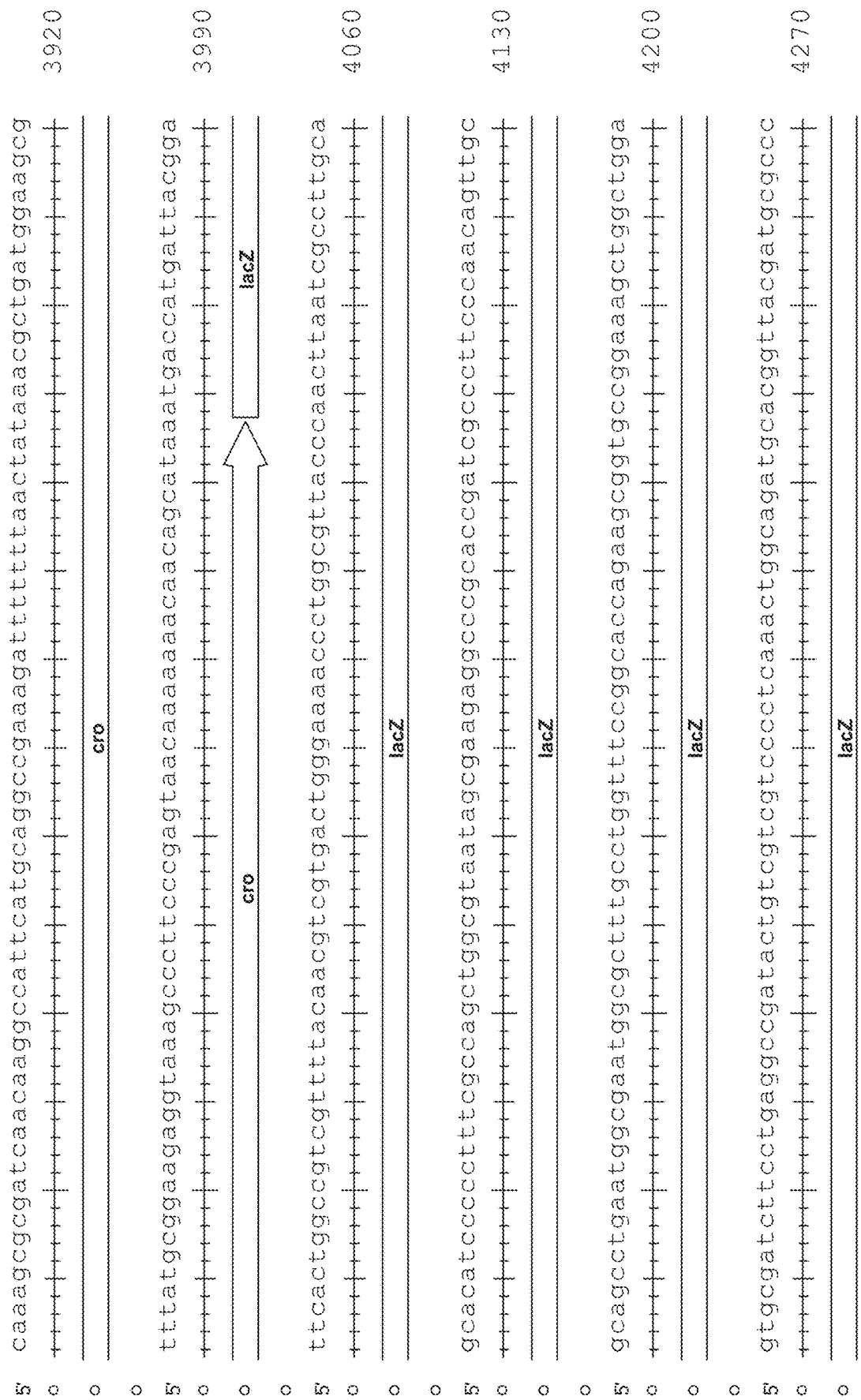
Figure 6C:
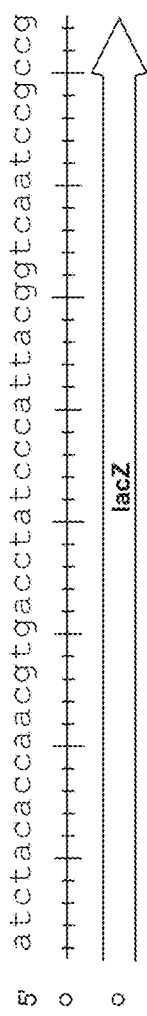
Figure 6D:
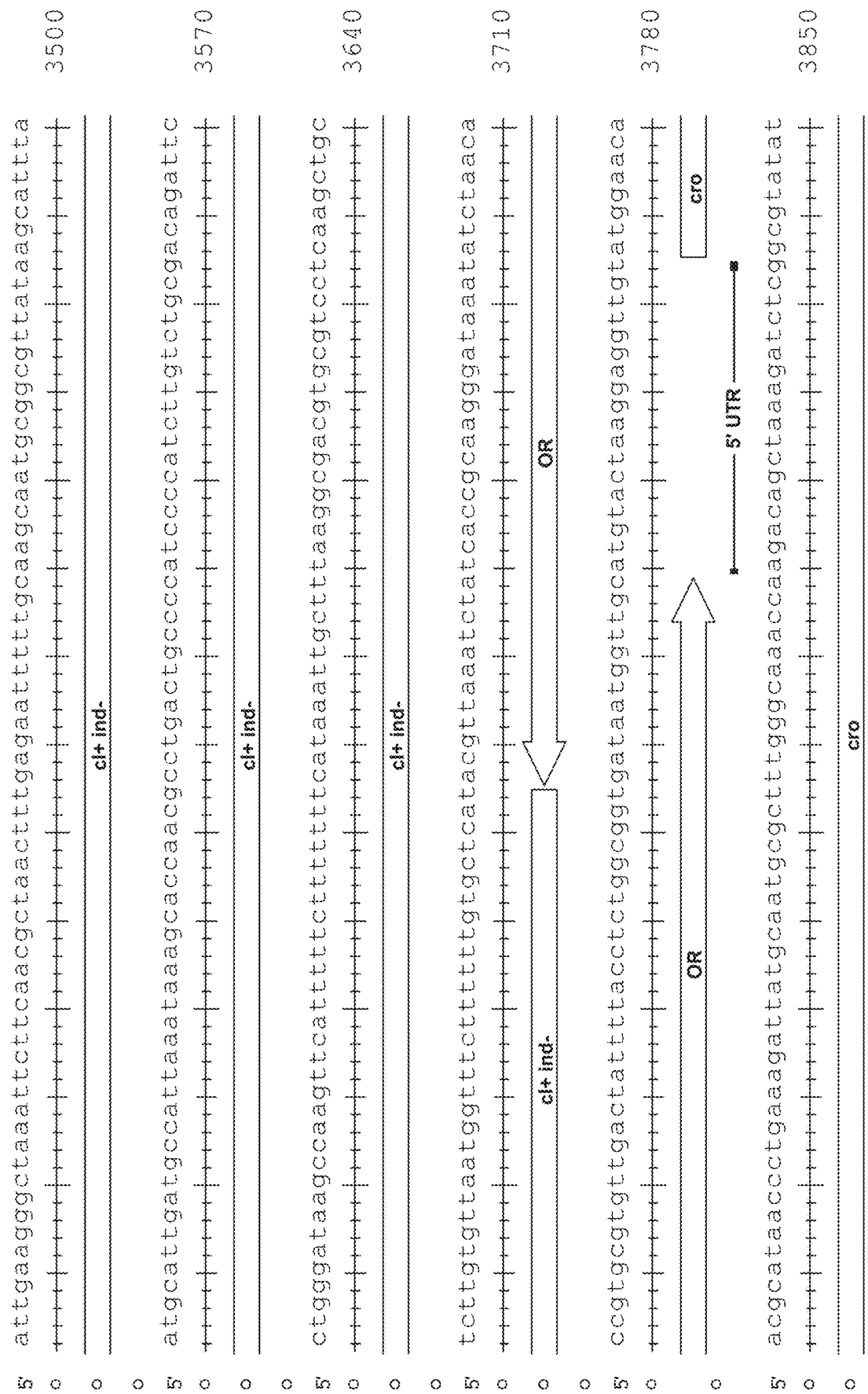
Figure 6D:
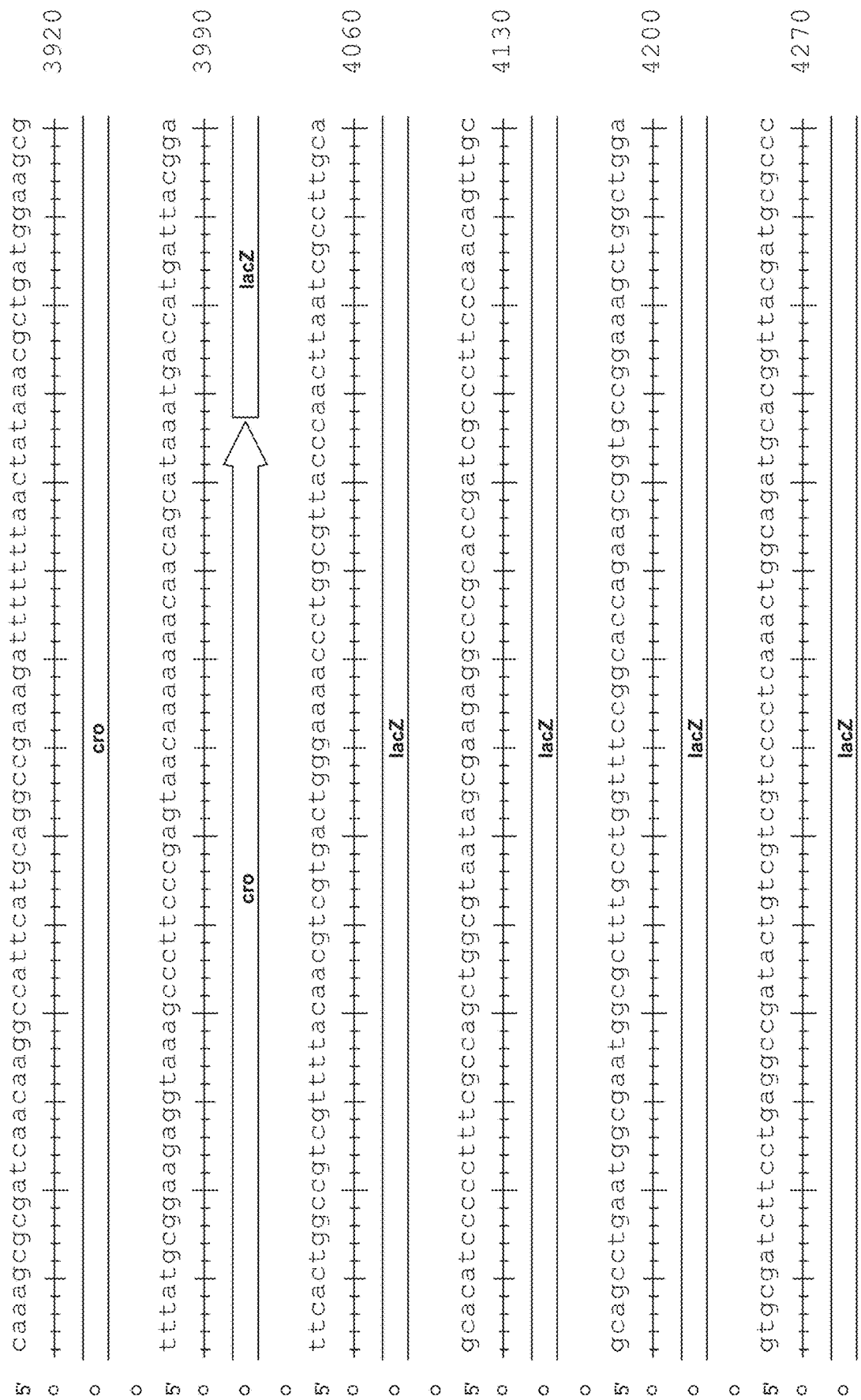
Figure 6D:
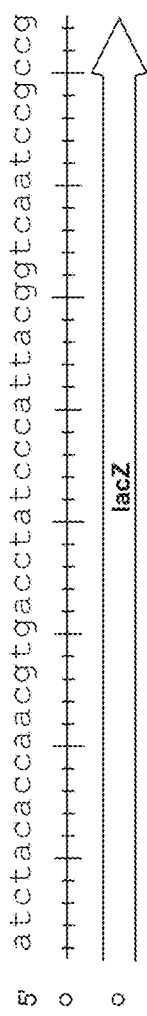

PAS 133 sensed and remembered exposure to ATC in the mouse gut. About $10^7$ PAS 133 bacteria were administered to female Balb/C mice, and treated as described above. Cells were then collected and analyzed as above for LacZ expression on lactose indicator streptomycin plates. PAS 133 detected ATC exposure within 1 day, and remembered exposure of mice to ATC for more than 7 days after ATC withdrawal (FIG. 4C). Moreover, PAS 133 remained stable within the mouse gut flora longer than PAS 132, the engineered K12 strain. Although the inventors administered roughly equal amounts of PAS 132, the K12 strain and PAS 133, the NGF-1 strain, after only 1 day in the mouse, the inventors recovered 10-fold more PAS 133 per mg of fecal sample (FIG. 4D). Between 5 and 8 days in the mice, the PAS 133 population stabilized to around 1000 colony-forming units (CFUs) per mg of fecal sample. The stable population level of PAS 133 was comparable to the coliform titers in most of the pre-treated 10 week-old mice we obtained from Charles River Labs over the course of these experiments. In contrast, PAS 132, the K12 strain was almost completely outcompeted by the natural gut flora after 5 days. This indicated that the quantitative function of the memory circuit is maintained in an uncharacterized wild bacterial strain, indicating that synthetic-biological elements of this type may be broadly useful.

The ability to engineer natural bacteria to report on the environment within the gut should have enormous implications and demonstrates the fundamental power of synthetic biology. In the long term, it may be possible to use synthetically engineered bacteria as non-invasive probiotic diagnostics for disease states or for targeted therapeutic delivery[21]. For example, various disease states release molecules that can be sensed by bacteria, such as reactive oxygen species that may represent inflammatory states, or quorum signals that may indicate the presence of undesirable types of bacteria. The system described is sufficiently modular that the trigger and memory circuits could be readily re-engineered to respond to different stimuli such as inflammation, environmental toxins, tumors, or parasites in the gut. In combination with additional genetic circuits, cells could be designed to report on when a particular event occurred or emit a therapeutic. The inventors also indicate that the similarity to probiotics may make the engineered bacteria more palatable as compared to other therapies based on genetic modifications.

Figure 13A:
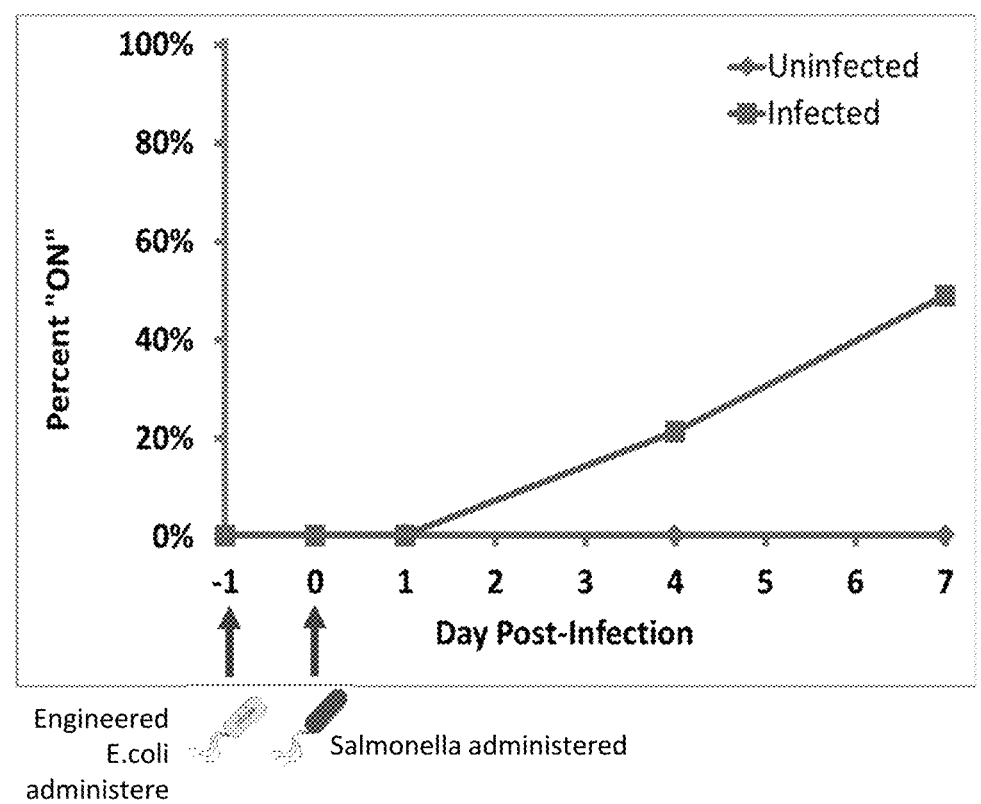
FIG. 13A shows that engineered bacteria that were ingested by mice can sense *Salmonella* infection in the murine gut within 4-7 day after initial infection.
Figure 13B:
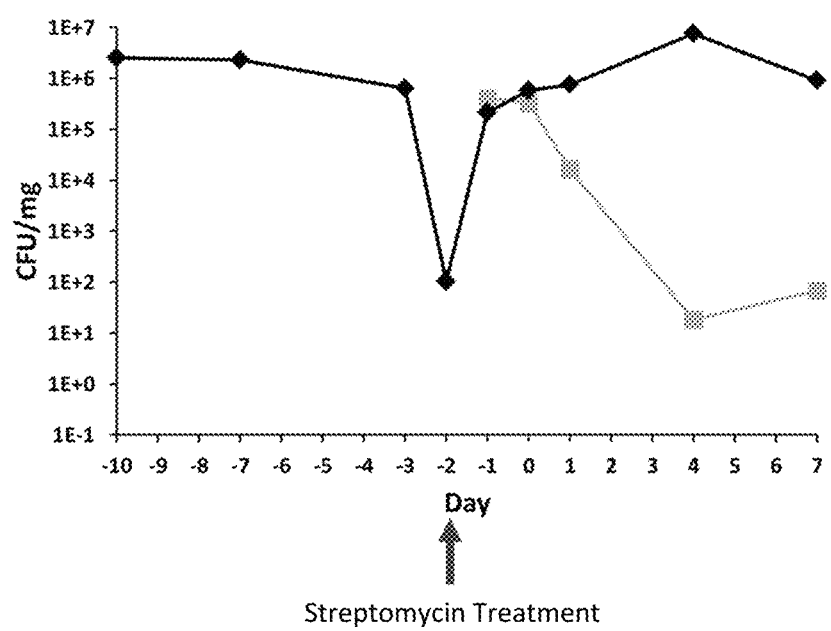
FIG. 13B shows that total endogenous gut flora began recolonizing the gut of mice as soon as the streptomycin treatment ended, after the single dose of streptomycin. Diamond symbol represents total endogenous culturable gut flora, square symbol represents the engineered *E. Coli* SKE09.
Figure 17:
FIG. 17 shows the DNA sequence (SEQ ID NO: 15) of a representative trigger element having a Sox response element comprising PsodA (promoter sox) element upstream of the Cro coding sequence.
Figure 18:
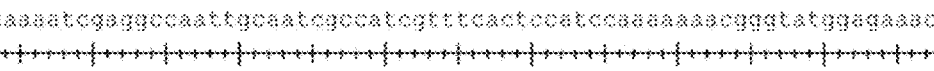
FIG. 18 shows the DNA sequence (SEQ ID NO: 16) of a representative trigger element having a reactive oxygen species (ROS) response element comprising katG promoter element upstream of the Cro coding sequence. The response element is to reactive oxygen species (ROS) that are products of inflammation. The ROS responsive element is the katG promoter.
Figure 19:
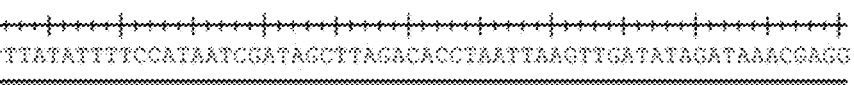
FIG. 19 shows the DNA sequence (SEQ ID NO: 17) of a representative trigger element having a tetracycline response element comprising tetR and the tetA promoter element upstream of the mutant cI coding sequence. "cIDN" is a mutant form of the lamda cI repressor that does not bind DNA.
Figure 22:
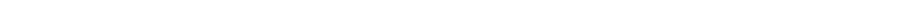
FIG. 22 shows the DNA sequence (SEQ ID NO: 20) of a representative trigger element having a elastase response element (PopmC), another cancer responsive element. The response element comprises opmC promoter (PopmC) element upstream of the Cro coding sequence. In this case, *E. coli* already has transcriptional regulation machinery to activate the opmC promoter. In the presence of elastase, the ompC promoter senses elastase and the promoter will trigger the downstream memory element when activated.

FIG. 13A shows that engineered bacteria that were ingested by mice can sense *Salmonella* infection in the murine gut within 4-7 days after initial infection. The WT lab strain of *E. coli* was engineered with the tetrathionate responsive element and the genetic memory circuit by P1vir phage transduction and named SKE09. SKE09 was administered to mice 1 day before infecting the mice with *Salmonella* and was capable of sensing infection of the mammalian gut (FIG. 13A). Tetrathionate is the target or stimulus that induces the inducible ttrB promoter via transcriptional regulation by the ttrR and ttrS two-component system. Female Balb/C mice were given streptomycin (0.5 mg/ml in drinking water) to allow colonization by SKE09. About $10^7$ bacteria were administered by oral gavage. Fecal samples were collected and titered on MacConkey lactose indicator plates with streptomycin to select for SKE09, and on Brain-Heart Infusion plates (anaerobic) to determine culturable counts. 20% and 49% of all SKE09 isolated from mice in the presence of a *Salmonella* infection were stably switched from the cI state to the cro state at day 4 and 7 of exposure, respectively (FIG. 13A). The culturable endogenous gut flora began recolonizing the gut as soon as the streptomycin treatment ended (FIG. 13B). The titer of the engineered bacteria decreased slowly thereafter (FIG. 13B).

The references cited herein and throughout the specification are incorporated herein by reference.

REFERENCES

1 Kau, A. L., Ahern, P. P., Griffin, N. W., Goodman, A. L. & Gordon, J. I. Human nutrition, the gut microbiome and the immune system. Nature 474, 327-336, doi:10.1038/nature10213 (2011).

2 Costello, E. K., Stagaman, K., Dethlefsen, L., Bohannon, B J & Relman, D. A. The application of ecological theory toward an understanding of the human microbiome. Science 336, 1255-1262, doi:10.1126/science.1224203 (2012).

3 Modi, S. R., Lee, H. H., Spina, C. S. & Collins, J. J. Antibiotic treatment expands the resistance reservoir and ecological network of the phage metagenome. Nature 499, 219-222, doi:10.1038/nature12212 (2013).

4 Burrill, D. R., Inniss, M. C., Boyle, P. M. & Silver, P. A. Synthetic memory circuits for tracking human cell fate. Genes & development 26, 1486-1497, doi:10.1101/gad.189035.112 (2012).

5 Moon, T. S., Lou, C., Tamsir, A., Stanton, B. C. & Voigt, C. A. Genetic programs constructed from layered logic gates in single cells. Nature 491, 249-253, doi:10.1038/nature11516 (2012).

6 Bonnet, J., Yin, P., Ortiz, M. E., Subsoontorn, P. & Endy, D. Amplifying genetic logic gates. Science 340, 599-603, doi:10.1126/science.1232758 (2013).

7 Siuti, P., Yazbek, J. & Lu, T. K. Synthetic circuits integrating logic and memory in living cells. Nature biotechnology 31, 448-452, doi:10.1038/nbt.2510 (2013).

8 Neubauer, Z. & Calef, E. Immunity Phase-shift in Defective Lysogens: Non-mutational Hereditary Change of Early Regulation of lambda Prophage. Journal of molecular biology 51, 1-13 (1970).

9 Toman, Z., Dambly-Chaudiere, C., Tenenbaum, L. & Radman, M. A system for detection of genetic and epigenetic alterations in *Escherichia coli* induced by DNA-damaging agents. Journal of molecular biology 186, 97-105 (1985).

10 Gardner, T. S., Cantor, C. R. & Collins, J. J. Construction of a genetic toggle switch in *Escherichia coli*. Nature 403, 339-342, doi:10.1038/35002131 (2000).

11 Ptashne, M., Jeffrey A, Johnson A. D., Maurer R., Meyer B. J., Pabo C. O., Roberts T. M., Sauer R. T. How the lambda Repressor and Cro Work. Cell 19 (1980).

12 Shea, M. A. & Ackers, G. K. The OR control system of bacteriophage lambda. A physical-chemical model for gene regulation. Journal of molecular biology 181, 211-230 (1985).

13 Arkin, A., Ross, J. & McAdams, H. H. Stochastic kinetic analysis of developmental pathway bifurcation in phage lambda-infected *Escherichia coli* cells. Genetics 149, 1633-1648 (1998).

14 Gimble, F. S. & Sauer, R. T. Mutations in bacteriophage lambda repressor that prevent RecA-mediated cleavage. Journal of bacteriology 162, 147-154 (1985).

15 Reichardt, L. & Kaiser, A. D. Control of lambda Repressor Synthesis. Proceedings of the National Academy of Sciences of the United States of America 68, 2185-2189 (1971).

16 Dodd, I. B., Perkins, A. J., Tsemitsidis, D. & Egan, J. B. Octamerization of lambda CI repressor is needed for effective repression of P(RM) and efficient switching from lysogeny. Genes & development 15, 3013-3022, doi:10.1101/gad.937301 (2001).

17 Bailone A, L. A., and Devoret R. Inactivation of Prophage lambda Repressor in Vivo. Journal of molecular biology 131, 553-572 (1979).

18 Novick, A. & Szilard, L. Experiments with the Chemostat on spontaneous mutations of bacteria. Proceedings of the National Academy of Sciences of the United States of America 36, 708-719 (1950).

19 Foucault, M. L., Thomas, L., Goussard, S., Branchini, B. R. & Grillot-Courvalin, C. In vivo bioluminescence imaging for the study of intestinal colonization by *Escherichia coli* in mice. Applied and environmental microbiology 76, 264-274, doi:10.1128/AEM.01686-09 (2010).

20 Bocker, R., Warnke, L. & Estler, C. J. Blood and organ concentrations of tetracycline and doxycycline in female mice. Comparison to males. Arzneimittelforschung 34, 446-448 (1984).

21 Hasty, J. Engineered microbes for therapeutic applications. ACS synthetic biology 1, 438-439, doi:10.1021/sb300105b (2012).

22 Higuchi, R., Krummel, B. & Saiki, R. K. A general method of in vitro preparation and specific mutagenesis of DNA fragments: study of protein and DNA interactions. Nucleic acids research 16, 7351-7367 (1988).

23 Datsenko, K. A. & Wanner, B. L. One-step inactivation of chromosomal genes in Escherichia coli K-12 using PCR products. Proceedings of the National Academy of Sciences of the United States of America 97, 6640-6645, doi:10.1073/pnas.120163297 (2000).

24 Thomason, L. et al. Recombineering: genetic engineering in bacteria using homologous recombination. Current protocols in molecular biology/edited by Frederick M. Ausubel . . . [et al.] Chapter 1, Unit 1 16, doi:10.1002/0471142727.mb0116s78 (2007).

25 Timms, A. R., Steingrimsdottir, H., Lehmann, A. R. & Bridges, B. A. Mutant sequences in the rpsL gene of Escherichia coli B/r: mechanistic implications for spontaneous and ultraviolet light mutagenesis. Molecular & general genetics: MGG 232, 89-96 (1992).

26 Springer, B. et al. Mechanisms of streptomycin resistance: selection of mutations in the 16S rRNA gene conferring resistance. Antimicrobial agents and chemotherapy 45, 2877-2884, doi:10.1128/AAC.45.10.2877-2884.2001 (2001).

27 Miller, J. H. Experiments in molecular genetics. (Cold Spring Harbor Laboratory, 1972).

28 Weisburg, S., Barns, S. M., Pelletier, D. A. & Lane, D. J. 16S Ribosomal DNA Amplification for Phylogenetic Study. Journal of bacteriology 173, 697-703 (1991).

29 Sanger, F., Coulson, A. R., Hong, G. F., Hill, D. F. & Petersen, G. B. Nucleotide Sequence of Bacteriophage lambda DNA. Journal of molecular biology 162, 729-773 (1982).

30 Blattner, F. R. The Complete Genome Sequence of Escherichia coli K-12. Science 277, 1453-1462, doi:10.1126/science.277.5331.1453 (1997).

TABLE 1

Strains used in this study.

| Strain | Host Organism | Trigger | Memory | rpsL | Source |
|---|---|---|---|---|---|
| PAS 129 | MG1655 | araB::CAM$^R$-tetP->cro | mphR::Kan$^R$-O$_L$-rexBA-cI$^{ts857}$-P$_{RM}$-O$_R$-P$_R$-cro-tR1::lacZ | + | This Study |
| PAS 130 | MG1655 | araB::CAM$^R$-tetP->cro | mphR::Kan$^R$-O$_L$-rexBA-cI$^{ind-}$-P$_{RM}$-O$_R$-P$_R$-cro-tR1::lacZ | + | This Study |
| PAS 131 | MG1655 | araB::CAM$^R$-tetP->cro | mphR::Kan$^R$-O$_L$-rexBA-cI$^{ts857}$-P$_{RM}$-O$_R$-P$_R$-cro::lacZ | + | This Study |
| PAS 132 | MG1655 | araB::CAM$^R$-tetP->cro | mphR::Kan$^R$-O$_L$-rexBA-cI$^{ind-}$-P$_{RM}$-O$_R$-P$_R$-cro::lacZ | Lys42Arg | This Study |
| PAS 133 | NGF-1 | araB::CAM$^R$-tetP->cro | mphR::Kan$^R$-O$_L$-rexBA-cI$^{ind-}$-P$_{RM}$-O$_R$-P$_R$-cro::lacZ | Lys42Arg | This Study |
| TB10 | MG1655 | | Lambda cI$^{ts857}$ prophage remnant for recombineering | | 23 |

TABLE 2

List of Reporter genes in the memory element

| Reporter gene | Source of gene or information for one skilled in the art to genetically construct the cI/Cro-Reporter memory element, ie, where to find this reporter gene |
|---|---|
| β-galactosidase (LacZ) | |
| chloramphenicol acetyltransferase (CAT) | |
| neomycin phosphotransferase (G418) | |
| bacteria luciferase (LuxAB) | |
| fluorescent protein (FP) | Gert-Jan Kremers, et al, Fluorescent proteins at a glance, 2011 J. Cell Sci 124, 157-160. |
| alkaline phosphatase (PhoA) | |
| p-glucuronidase (GUS) | |
| bacterial specific toxins | |
| (microcins) microcin 24 and microcin E492 | |
| leptin (a therapeutic protein). | |

TABLE 3

Inducers (agent) of the inducible promoter and the respective responsive elements

| Inducer | Responsive element (RE) in an inducible promoter |
|---|---|
| tetracycline | Tetracycline responsive element (TRE) |
| Tetrathionate | ttrRS |
| reactive oxygen species-give specific examples | oxyR and soxRS |
| E. coli quorum signals | sdiA |
| H$_2$S -hydrogen sulfide | dsr operon |

TABLE 4

List of targets to be detected in the colon

| Target of interest | Inducer or stimulus of the trigger element | Condition indicated by target |
|---|---|---|
| inflammation | oxyRS, soxRS, ttrRS | Colon cancer |
| H$_2$S | dsr operon | Colon cancer |
| F. nucleatum, | H2S levels; dsr operon | Colon cancer |
| B. wadsworthia | H2S levels; dsr operon | Colon cancer |
| pathogenic E. coli, | SdiA | Colon cancer |
| Salmonella sp. | ttrRS, SdiA | Colon cancer |
| Hydrogen Peroxide | ttrRS, soxRS, oxyRS | Inflammation |
| Nitric Oxide | ttrRS, soxRS, oxyRS | Inflammation |
| Superoxide | ttrRS, soxRS, oxyRS | Inflammation |
| Tetrathionate | ttrRS | Inflammation |

What is claimed is:

1. A method of detecting a target in the gastrointestinal tract or colon in a subject, the method comprising:
 a. administering to a subject engineered bacteria comprising a memory circuit comprising:
  i. a bacteriophage-based a/Cro-reporter gene-based memory element comprising:
   i) a bacteriophage gene sequence of a;
   ii) a bacteriophage gene sequence of Cro; and
   iii) a reporter gene,
  wherein the c/and the Cro are arranged in a genetic toggle switch,
  and wherein the reporter gene is arranged downstream and operably linked to Cro;
  ii. an inducible Cro-based trigger element comprising:
   iv) a bacteriophage gene sequence of a second Cro sequence distinct from the Cro sequence in the memory element; and
   v) an inducible promoter,
  wherein the second Cro sequence is operably linked to the inducible promoter, and
  wherein the inducible promoter is responsive to a trigger agent, wherein the memory circuit is integrated into the genome of the bacteria,
  wherein the inducible promoter is responsive to a target;
 b. collecting a sample of fecal matter from the subject after a period of time after step a; and
 c. measuring the expression of the reporter gene from the memory element of the circuit in the engineered bacteria, wherein detectable expression of the reporter gene indicates the presence of the target, which is indicative of the presence of a condition in the gastrointestinal tract or colon of the subject.

2. The method of claim 1, further comprising selecting a subject to be administered the engineered bacteria in step (a).

3. The method of claim 1, wherein the subject has or is at risk of developing a gastrointestinal tract or colon condition.

4. The method of claim 1, wherein the target is selected from the group consisting of tetrathionate, reactive oxygen species, H2S, sdiA, bacteria enterotoxins, calprotectin and lactoferrin.

5. The method of claim 1, wherein the gastrointestinal tract or colon condition is cancer, inflammation, pathogenic bacterial infection, inflammatory bowel disease (IBD), Crohn's disease, colitis, or diabetes.

6. The method of claim 1, wherein the target is a colorectal cancer biomarker.

7. The method of claim 6, wherein the presence of the colorectal cancer biomarker indicates the presence of cancer in the colon of the subject.

8. The method of claim 1, wherein the target is a biomarker that is known to occur when enteric pathogenic bacterium is present.

9. The method of claim 1, wherein the target is a biomarker that is known to occur when inflammation is present.

10. The method of claim 9, wherein the presence of the biomarker that is known to occur with inflammation is indicative of the presence of inflammation in the gastrointestinal tract or colon of the subject.

* * * * *